(12) United States Patent
Chabot et al.

(10) Patent No.: US 10,900,060 B2
(45) Date of Patent: Jan. 26, 2021

(54) METHOD OF PRODUCING TERPENES OR TERPENOIDS

(71) Applicant: DEINOVE, Grabels (FR)

(72) Inventors: Nicolas Chabot, Montpellier (FR); Sandra Castang, Castelnau le Lez (FR); Philippe Bauchart, Grabels (FR); Jean-Paul Leonetti, Castelnau le Lez (FR)

(73) Assignee: DEINOVE, Grabels (FR)

( * ) Notice: Subject to any disclaimer, the term of this patent is extended or adjusted under 35 U.S.C. 154(b) by 0 days.

(21) Appl. No.: 15/317,994

(22) PCT Filed: Jun. 15, 2015

(86) PCT No.: PCT/EP2015/063335
§ 371 (c)(1),
(2) Date: Dec. 12, 2016

(87) PCT Pub. No.: WO2015/189428
PCT Pub. Date: Dec. 17, 2015

(65) Prior Publication Data
US 2017/0121749 A1   May 4, 2017

(30) Foreign Application Priority Data
Jun. 13, 2014   (EP) .................... 14305907

(51) Int. Cl.
*C12P 23/00* (2006.01)
*C12P 5/00* (2006.01)
(Continued)

(52) U.S. Cl.
CPC ............. *C12P 23/00* (2013.01); *C12N 1/20* (2013.01); *C12N 9/1022* (2013.01); *C12N 15/52* (2013.01); *C12P 5/007* (2013.01); *C12Y 202/01007* (2013.01); *C12Y 205/0101* (2013.01); *C12Y 205/01001* (2013.01); *C12Y 301/07003* (2013.01); *C12Y 402/03* (2013.01); *C12Y 503/03002* (2013.01); *C12Y 505/01019* (2013.01)

(58) Field of Classification Search
None
See application file for complete search history.

(56) References Cited

U.S. PATENT DOCUMENTS

| | | | |
|---|---|---|---|
| 7,659,097 B2* | 2/2010 | Renninger | C12P 5/007 435/157 |
| 2004/0268436 A1* | 12/2004 | Cheng | C12N 9/0083 800/278 |

FOREIGN PATENT DOCUMENTS

| | | |
|---|---|---|
| JP | 2006-515174 | 5/2006 |
| JP | 2009-538139 | 11/2009 |

(Continued)

OTHER PUBLICATIONS

UniProt Accession No. Q1IXX1_DEIGO, published Jun. 13, 2006.*
(Continued)

*Primary Examiner* — Richard C Ekstrom
(74) *Attorney, Agent, or Firm* — Saliwanchik, Lloyd & Eisenschenk

(57) ABSTRACT

The present invention relates to a recombinant *Deinococcus* bacterium exhibiting enhanced 2-C-methyl-D-erythritol 4-phosphate/1-deoxy-D-xylulose 5-phosphate (MEP/DXP) pathway, and its use for producing terpene or terpenoid compounds.

19 Claims, 14 Drawing Sheets
Specification includes a Sequence Listing.

(51) Int. Cl.
*C12N 1/20* (2006.01)
*C12N 9/10* (2006.01)
*C12N 15/52* (2006.01)

(56) References Cited

FOREIGN PATENT DOCUMENTS

| WO | WO 2004/056975 | 7/2004 |
|---|---|---|
| WO | WO 2005/079183 | 9/2005 |
| WO | WO 2007/139924 | 12/2007 |
| WO | WO 2012/052171 | 4/2012 |

OTHER PUBLICATIONS

UniProt Accession No. A0A016QL59_9DEI0, published Jun. 11, 2014 (Year: 2014).*

Blanchard, L. et al. "Characterization of a lysine-to-glutamic acid mutation in a conservative sequence of farnesyl diphosphate synthase from *Saccharomyces cerevisiae*" *Gene*, Mar. 30, 1993, pp. 185-189, vol. 125, No. 2.

Bouvier, F. et al. "Biogenesis, molecular regulation and function of plant isoprenoids" *Progress in Lipid Research*, Nov. 1, 2005, pp. 357-429, vol. 44, No. 6.

Kang, M.-J. et al. "Enhancement of Lycopene Production in *Escherichia coli* by Optimization of the Lycopene Synthetic Pathway" *Journal of Microbiology and Biotechnology*, Aug. 2005, pp. 880-886, vol. 15, No. 4.

Liu, C. et al. "Identification and characterization of the geranylgeranyl diphosphate synthase in *Deinococcus radiodurans*" *Letters in Applied Microbiology*, Nov. 14, 2013, pp. 219-224, vol. 58, No. 3.

Tian, B. et al. "Carotenoid 3',4'-desaturase is involved in carotenoid biosynthesis in the radioresistant bacterium *Deinococcus radiodurans*" *Microbiology*, Dec. 1, 2008, pp. 3697-3706, vol. 154, No. 12.

Tian, B. et al. "Cartenoid biosynthesis in extremophilic Deinoccus-Thermus bacteria" *Trends in Microbiology*, Nov. 1, 2010, pp. 512-520, vol. 18, No. 11.

Vallabhaneni, R. et al. "The carotenoid dioxygenase gene family in maize, sorghum, and rice" *Archives of Biochemistry and Biophysics*, Dec. 1, 2010, pp. 104-111, vol. 504, No. 1.

Xue, J. et al. "Enhancing Isoprene Production by Genetic Modification of the 1-Deoxy-D-Xylulose-5-Phosphate Pathway in *Bacillus subtilis*" *Applied and Environmental Microbiology*, Apr. 1, 2011, pp. 2399-2405, vol. 77, No. 7.

Yuan, L. Z. et al. "Chromosomal promoter replacement of the isoprenoid pathway for enhancing carotenoid production in *E. coli*" *Metabolic Engineering*, Jan. 1, 2006, pp. 79-90, vol. 8, No. 1.

Database Embase [Online] Accession No. EMB-2005407789, "Enhancement of lycopene production in *Escherichia coli* by optimization of the lycopene synthetic pathway" Aug. 2005, pp. 1-2, XP-002730044.

Written Opinion in International Application No. PCT/EP2015/063335, dated Aug. 26, 2015, pp. 1-10.

* cited by examiner

SEQUENCE LISTING

<160> NUMBER OF SEQ ID NOS: 73

<210> SEQ ID NO 1
<211> LENGTH: 1902
<212> TYPE: DNA
<213> ORGANISM: Deinococcus geothermalis

<400> SEQUENCE: 1

```
atgagtgagc caactgccaa cctccagcct gccagccgca ccccgctgct ggaccgggtg      60
aatggcccgg aagacctcaa acggctcgga cgcgaccagc tacccccagct cgctgccgaa    120
ctgcgcgagg agatcgtgcg ggtctgctcg gtagggggt tacatctcgc cagctctctg     180
ggcgcgaccg acctaatcgt ggcgctacat tacgtgctgc attcgccgcg cgaccgcatt    240
ctgttcgacg tggggcatca ggcctacgcc acaagatgc tcacgggccg ccgccacctg     300
atgcacaccg tcaagaagga gggcgggctg tcgggcttca ccaaggtgag cgagtccgaa    360
cacgacgcca tcacggtggg ccatgccagc acctccctcg ccaatgcgct gggcatggcg    420
cttgcacggg acgctttggg acaggattac aaggtggctg ccgtgatcgg ggacggctcg    480
ctgacgggcg gcatggcgct ggcggcgctg aataccatcg ggaccctggg gcggcgaatg    540
ctcattgtgc ttaacgacaa cgagatgagc atcagcgaga acgtggggc catcaaccgc    600
ttcatgcggg gtctccaggt gcagaagtgg ttccaggagg cgaggaagc cgggaaaaag    660
gccgtgcagg cggtcagcaa gccgctcgcc aacttgatga gccgcgccaa gagttccacg    720
cggcactttt tcgatcccgc cagtgtcaat ccctttgccg cgatgggcgt gcgctatgtg    780
ggaccggtgg acggccacaa cgtgcaggaa ttggtgtggc tgatcgagcg gctggtcgac    840
ctcgatgggc cgaccattct gcacgtcgtc accaaaaagg gcaagggcct gagctacgcc    900
gaggccgacc cgatcaaatg gcatggcccg ggcaagtttg acccggcgac gggtgagtcg    960
gtgcccagca atgcctactc gtggagcagc gcctttggag acgcggtgac cgagcttgca   1020
cggctggacc cccgtacctt tgtgatcacg cccgcgatgc gcgagggcag cggcctggtg   1080
cgctacagcc aggttcaccc ccaccgttac ctggatgtcg gtatcgcgga ggacgtggcc   1140
gtcaccacgg ccgccggaat ggcgcttcag gggatgcggc ccatcgtggc gatctactcc   1200
actttcctgc aacgcgccta cgatcaggtg ctgcacgacg tcgccatcga gaatctgaac   1260
gtgaccttcg ccatcgaccg tgggggcatc gtgggcgcag acggagccac ccacaacggc   1320
gtcttcgacc tgagttacct gcgctcgatt ccgaatgtcg gcattggcct gccgaaggac   1380
gccgccgagc tgcgcgggat gctgaagtat gcccaggagc atgctggccc cttcgccatc   1440
cgctatccgc gcggcaacgt ggaacgcgtg ccggaaggca cctggccgga gctgaggtgg   1500
ggcacctggg aacgcttgca agacggcgac gacgtggtga ttctggcggg aggcaaggcg   1560
ctggagtacg cgctgaaggc cgcccgcgac ctccccggcg tgggcgtggt gaatgcccgt   1620
ttcgtgaagc cgctcgacca aggatgctg cgcgaggtgc cgaccaaagc ccgcgcactg   1680
gtcacggtgg aggacaacac ggtcgtcggt gggttcggaa gtgccgtcct ggaagccctc   1740
agcgcgctgg ggctgagaac cccggtgcgg gttctcggca tccccgacgc gtttcaggat   1800
cacgcgaccg tagagagcgt gcatgcccgt gcggggattg acgcgcctgc catccgcacg   1860
gtcctggccc aacttggcgt ggacgtgccg ctggaggtct ag                       1902
```

<210> SEQ ID NO 2
<211> LENGTH: 633
<212> TYPE: PRT
<213> ORGANISM: Deinococcus geothermalis

<400> SEQUENCE: 2

```
Met Ser Glu Pro Thr Ala Asn Leu Gln Pro Ala Ser Arg Thr Pro Leu
1               5                   10                  15

Leu Asp Arg Val Asn Gly Pro Glu Asp Leu Lys Arg Leu Gly Arg Asp
            20                  25                  30

Gln Leu Pro Gln Leu Ala Ala Glu Leu Arg Glu Ile Val Arg Val
        35                  40                  45

Cys Ser Val Gly Gly Leu His Leu Ala Ser Ser Leu Gly Ala Thr Asp
    50                  55                  60

Leu Ile Val Ala Leu His Tyr Val Leu His Ser Pro Arg Asp Arg Ile
65                  70                  75                  80

Leu Phe Asp Val Gly His Gln Ala Tyr Ala His Lys Met Leu Thr Gly
                85                  90                  95

Arg Arg His Leu Met His Thr Val Lys Lys Glu Gly Gly Leu Ser Gly
            100                 105                 110

Phe Thr Lys Val Ser Glu Ser Glu His Asp Ala Ile Thr Val Gly His
            115                 120                 125

Ala Ser Thr Ser Leu Ala Asn Ala Leu Gly Met Ala Leu Ala Arg Asp
130                 135                 140

Ala Leu Gly Gln Asp Tyr Lys Val Ala Ala Val Ile Gly Asp Gly Ser
145                 150                 155                 160

Leu Thr Gly Gly Met Ala Leu Ala Ala Leu Asn Thr Ile Gly Asp Leu
                165                 170                 175

Gly Arg Arg Met Leu Ile Val Leu Asn Asp Asn Glu Met Ser Ile Ser
            180                 185                 190

Glu Asn Val Gly Ala Ile Asn Arg Phe Met Arg Gly Leu Gln Val Gln
            195                 200                 205

Lys Trp Phe Gln Glu Gly Glu Glu Ala Gly Lys Lys Ala Val Gln Ala
210                 215                 220

Val Ser Lys Pro Leu Ala Asn Leu Met Ser Arg Ala Lys Ser Ser Thr
225                 230                 235                 240

Arg His Phe Phe Asp Pro Ala Ser Val Asn Pro Phe Ala Ala Met Gly
                245                 250                 255

Val Arg Tyr Val Gly Pro Val Asp Gly His Asn Val Gln Glu Leu Val
            260                 265                 270

Trp Leu Ile Glu Arg Leu Val Asp Leu Asp Gly Pro Thr Ile Leu His
            275                 280                 285

Val Val Thr Lys Lys Gly Lys Gly Leu Ser Tyr Ala Glu Ala Asp Pro
            290                 295                 300

Ile Lys Trp His Gly Pro Gly Lys Phe Asp Pro Ala Thr Gly Glu Ser
305                 310                 315                 320

Val Pro Ser Asn Ala Tyr Ser Trp Ser Ser Ala Phe Gly Asp Ala Val
                325                 330                 335

Thr Glu Leu Ala Arg Leu Asp Pro Arg Thr Phe Val Ile Thr Pro Ala
                340                 345                 350

Met Arg Glu Gly Ser Gly Leu Val Arg Tyr Ser Gln Val His Pro His
            355                 360                 365

Arg Tyr Leu Asp Val Gly Ile Ala Glu Asp Val Ala Val Thr Thr Ala
            370                 375                 380

Ala Gly Met Ala Leu Gln Gly Met Arg Pro Ile Val Ala Ile Tyr Ser
385                 390                 395                 400

Thr Phe Leu Gln Arg Ala Tyr Asp Gln Val Leu His Asp Val Ala Ile
```

|  | 405 |  |  |  | 410 |  |  |  | 415 |  |  |
|---|---|---|---|---|---|---|---|---|---|---|---|

Glu Asn Leu Asn Val Thr Phe Ala Ile Asp Arg Gly Gly Ile Val Gly
            420                 425                 430

Ala Asp Gly Ala Thr His Asn Gly Val Phe Asp Leu Ser Tyr Leu Arg
        435                 440                 445

Ser Ile Pro Asn Val Gly Ile Gly Leu Pro Lys Asp Ala Ala Glu Leu
    450                 455                 460

Arg Gly Met Leu Lys Tyr Ala Gln Glu His Ala Gly Pro Phe Ala Ile
465                 470                 475                 480

Arg Tyr Pro Arg Gly Asn Val Glu Arg Val Pro Glu Gly Thr Trp Pro
                485                 490                 495

Glu Leu Arg Trp Gly Thr Trp Glu Arg Leu Gln Asp Gly Asp Asp Val
            500                 505                 510

Val Ile Leu Ala Gly Gly Lys Ala Leu Glu Tyr Ala Leu Lys Ala Ala
        515                 520                 525

Arg Asp Leu Pro Gly Val Gly Val Asn Ala Arg Phe Val Lys Pro
    530                 535                 540

Leu Asp Gln Gly Met Leu Arg Glu Val Ala Thr Lys Ala Arg Ala Leu
545                 550                 555                 560

Val Thr Val Glu Asp Asn Thr Val Val Gly Phe Gly Ser Ala Val
                565                 570                 575

Leu Glu Ala Leu Ser Ala Leu Gly Leu Arg Thr Pro Val Arg Val Leu
            580                 585                 590

Gly Ile Pro Asp Ala Phe Gln Asp His Ala Thr Val Glu Ser Val His
        595                 600                 605

Ala Arg Ala Gly Ile Asp Ala Pro Ala Ile Arg Thr Val Leu Ala Glu
    610                 615                 620

Leu Gly Val Asp Val Pro Leu Glu Val
625                 630

<210> SEQ ID NO 3
<211> LENGTH: 1893
<212> TYPE: DNA
<213> ORGANISM: Deinococcus yunweiensis

<400> SEQUENCE: 3

```
atgacatcca gcgacctcgt ccccgttccg cagcgcctgc tcgacgcggt gaactcgccg      60
gacgacctca agaccctgaa gcgcgagcag ctgccgcagg tggcgcagga actccgcgac     120
gagatcgtgc gggtgtgctc ggtgggtggc ctgcacctgg cgtcctcgct gggcgcgacc     180
gacgtgatcg tggcgctgca ctacgtcctg aactcgccgc gtgaccggat tctgttcgat     240
gtgggtcacc aggcctacgc gcacaagatg ctcaccggcc gccgcgagca gatggtcagc     300
gtgaagaagg agggcgggct ctcgggcttc accaaggtca gcgagtcgcc gcacgacgcg     360
atcacggtgg ggcacgccag taccagcctg caaacgcgc tgggcatggc gatggcacgg     420
gacgccctgg ggcaggatta ccacgtggcc gccgtgatcg tgacgggcag cctgaccggc     480
ggcatggccc tggccgccct aaacaccatc ggggacacgc agcgcaagat gctgatcgtc     540
ctgaacgaca cgagatgag catctccgag aacgtggggg ccatgaacaa gttcatgcgt     600
ggcctccagg tgcagaagtg gttccaggag ggcgagggcg cgggcaagaa ggccatgcag     660
gcggtcagcc gccgctcgc caacttcatg agccgcgcca agagcagcac ccggcatttc     720
ttcgaccccg ccagcgtgaa tcccttttgcc accatgggcg tgcgttatgt ggggccagtc     780
gacggacaca acgtgcagga actcgtgtgg ctgctcgaac gcctcgtgga actcgacggg     840
```

```
ccgacgatcc tgcatgtggt gaccaagaag ggcaagggcc tgagctacgc cgaggccgat      900
ccgatctact ggcacggccc cggcaagttc gacccggaga ccggggactt cgtgcccagc      960
aatgcgtact cgtggagcaa cgccttcgga gacgccgtca cggagctggc gaaagccgat     1020
ccccgcacct tcgtgatcac ccccgccatg cgcgagggca cgggctggt cggctacagc      1080 aaggcccatc cgcaccgcta tctggacgtc ggcatcgccg aggaggtcgc tgtgacggcc     1140
gccgccggca tggcccctcca ggggctgcgg cccgtcgtgg cgatctactc caccttcctg    1200
caacgcgcct acgaccaggt gctgcacgac gtcgccattg agcacttgaa cgtcaccttc     1260
gctattgacc gggccgggat cgtcggcgcg acggggcca cccacaacgg cgtcttcgac     1320
ctgagcttcc tgcgctcgat cccaggtgtg cggatcggcc tgcccaagga cgcgaccgag    1380
ctgcgtggca tgctgaagta cgcccaggag caccccggcc ccttcgccat ccgctatccg     1440
cgtggcacca ccgagcgcgt gccagagggc acctggccca ccctggcgtg gggcacgtgg    1500
gagcgcgtga agtccggcga cgacgtggtc atcctggcgg gtggcaaggg cctggagtat    1560
gcccagaagg ccgccgccga cctgcccggc gtgggtgtcg tgaacgcccg tttcgtcaag    1620
ccgcttgacg acgccatgct gcgagaggtg gccggcagtg ctcgcgctat cgtcaccgtc    1680
gaggacaaca ccgtcgtcgg gggatttggc agcgccgtgc tggaggccct gaacgcctgg    1740
ggcctgaccg tgcccgtgcg cgtgctgggc atcccggacg aattccagga acacgccacc    1800
gtggacagcg tgcatgcccg cgccggcatc gacgctcccg ctatccgcac ggtgctggcc    1860
gagcttgggg tggacgtgcc gctgggcgtg taa                                  1893

<210> SEQ ID NO 4
<211> LENGTH: 630
<212> TYPE: PRT
<213> ORGANISM: Deinococcus yunweiensis

<400> SEQUENCE: 4

Met Thr Ser Ser Asp Leu Val Pro Val Pro Gln Arg Leu Leu Asp Ala
1               5                   10                  15

Val Asn Ser Pro Asp Asp Leu Lys Thr Leu Lys Arg Glu Gln Leu Pro
            20                  25                  30

Gln Val Ala Gln Glu Leu Arg Asp Glu Ile Val Arg Val Cys Ser Val
        35                  40                  45

Gly Gly Leu His Leu Ala Ser Ser Leu Gly Ala Thr Asp Val Ile Val
    50                  55                  60

Ala Leu His Tyr Val Leu Asn Ser Pro Arg Asp Arg Ile Leu Phe Asp
65                  70                  75                  80

Val Gly His Gln Ala Tyr Ala His Lys Met Leu Thr Gly Arg Arg Glu
                85                  90                  95

Gln Met Val Ser Val Lys Lys Glu Gly Gly Leu Ser Gly Phe Thr Lys
            100                 105                 110

Val Ser Glu Ser Pro His Asp Ala Ile Thr Val Gly His Ala Ser Thr
        115                 120                 125

Ser Leu Ala Asn Ala Leu Gly Met Ala Met Ala Arg Asp Ala Leu Gly
    130                 135                 140

Gln Asp Tyr His Val Ala Val Ile Gly Asp Gly Ser Leu Thr Gly
145                 150                 155                 160

Gly Met Ala Leu Ala Ala Leu Asn Thr Ile Gly Asp Thr Gln Arg Lys
                165                 170                 175

Met Leu Ile Val Leu Asn Asp Asn Glu Met Ser Ile Ser Glu Asn Val
```

```
                    180                 185                 190
Gly Ala Met Asn Lys Phe Met Arg Gly Leu Gln Val Gln Lys Trp Phe
            195                 200                 205
Gln Glu Gly Glu Gly Ala Gly Lys Lys Ala Met Gln Ala Val Ser Arg
        210                 215                 220
Pro Leu Ala Asn Phe Met Ser Arg Ala Lys Ser Ser Thr Arg His Phe
225                 230                 235                 240
Phe Asp Pro Ala Ser Val Asn Pro Phe Ala Thr Met Gly Val Arg Tyr
                245                 250                 255
Val Gly Pro Val Asp Gly His Asn Val Gln Glu Leu Val Trp Leu Leu
            260                 265                 270
Glu Arg Leu Val Glu Leu Asp Gly Pro Thr Ile Leu His Val Val Thr
        275                 280                 285
Lys Lys Gly Lys Gly Leu Ser Tyr Ala Glu Ala Asp Pro Ile Tyr Trp
    290                 295                 300
His Gly Pro Gly Lys Phe Asp Pro Glu Thr Gly Asp Phe Val Pro Ser
305                 310                 315                 320
Asn Ala Tyr Ser Trp Ser Asn Ala Phe Gly Asp Ala Val Thr Glu Leu
                325                 330                 335
Ala Lys Ala Asp Pro Arg Thr Phe Val Ile Thr Pro Ala Met Arg Glu
            340                 345                 350
Gly Ser Gly Leu Val Gly Tyr Ser Lys Ala His Pro His Arg Tyr Leu
        355                 360                 365
Asp Val Gly Ile Ala Glu Glu Val Ala Val Thr Ala Ala Ala Gly Met
    370                 375                 380
Ala Leu Gln Gly Leu Arg Pro Val Val Ala Ile Tyr Ser Thr Phe Leu
385                 390                 395                 400
Gln Arg Ala Tyr Asp Gln Val Leu His Asp Val Ala Ile Glu His Leu
                405                 410                 415
Asn Val Thr Phe Ala Ile Asp Arg Ala Gly Ile Val Gly Ala Asp Gly
            420                 425                 430
Ala Thr His Asn Gly Val Phe Asp Leu Ser Phe Leu Arg Ser Ile Pro
        435                 440                 445
Gly Val Arg Ile Gly Leu Pro Lys Asp Ala Thr Glu Leu Arg Gly Met
    450                 455                 460
Leu Lys Tyr Ala Gln Glu His Pro Gly Pro Phe Ala Ile Arg Tyr Pro
465                 470                 475                 480
Arg Gly Thr Thr Glu Arg Val Pro Glu Gly Thr Trp Pro Thr Leu Ala
                485                 490                 495
Trp Gly Thr Trp Glu Arg Val Lys Ser Gly Asp Asp Val Val Ile Leu
            500                 505                 510
Ala Gly Gly Lys Gly Leu Glu Tyr Ala Gln Lys Ala Ala Ala Asp Leu
        515                 520                 525
Pro Gly Val Gly Val Val Asn Ala Arg Phe Val Lys Pro Leu Asp Asp
    530                 535                 540
Ala Met Leu Arg Glu Val Ala Gly Ser Ala Arg Ala Ile Val Thr Val
545                 550                 555                 560
Glu Asp Asn Thr Val Val Gly Phe Gly Ser Ala Val Leu Glu Ala
                565                 570                 575
Leu Asn Ala Trp Gly Leu Thr Val Pro Val Arg Val Leu Gly Ile Pro
            580                 585                 590
Asp Glu Phe Gln Glu His Ala Thr Val Asp Ser Val His Ala Arg Ala
        595                 600                 605
```

Gly Ile Asp Ala Pro Ala Ile Arg Thr Val Leu Ala Glu Leu Gly Val
    610                 615                 620

Asp Val Pro Leu Gly Val
625                 630

<210> SEQ ID NO 5
<211> LENGTH: 1908
<212> TYPE: DNA
<213> ORGANISM: Deinococcus radiopugnans

<400> SEQUENCE: 5

| | | | | |
|---|---|---|---|---|
| atgaccgaca | tcaaaaaggc | tgatgggctg | caccteggge | acaagggcac gccgctgctg | 60 |
| gaccgcattg | ccggcccggc | tgacctcaag | aagctctcgc | gcgatcagtt gcccgagctg | 120 |
| agccaggaac | tgcgcgacga | gatcgtgcgg | gtctgctcgg | tgggtgggct gcatctggcg | 180 |
| tcctcgctgg | gggccaccga | cctgatcgtg | gcgctgcatt | acgtgctgaa cagtccgcgt | 240 |
| gaccggattc | tcttcgacgt | gggtcaccag | gcctacgccc | acaagatgct gaccgggcgg | 300 |
| cgggagcaga | tgcacaccgt | caagaaggaa | gtgggctga | gcggctttac caaggtcagc | 360 |
| gagtccgaac | acgacgccat | taccgtgggc | acgccagca | ccagcctggc gaacgcgctg | 420 |
| ggcatggcga | tggcgagaga | cgcgctgggc | caggactatc | aggtggccgc cgtgatcggc | 480 |
| gacggctcgc | tgaccggcgg | gatggcgctg | ccgccctga | acaccatcgg tgacctgcgc | 540 |
| cgcaagatgc | tgatcgtcct | gaacgacaac | gagatgagca | tttccgagaa cgtgggcgcg | 600 |
| atcaacaagt | tcatgcgcgg | cctgcaggtc | cagaagtggt | ttcaggaggg cgagggagcc | 660 |
| gggaacaagg | cggtgcagtc | cctgagcaag | ccgctggccg | atttcatgag ccgtgccaag | 720 |
| agcagcaccc | gccacttctt | cgatccggcc | agcgtcaatc | ccttcgccat gatgggcgtg | 780 |
| cgttatgtcg | gcccggtcga | cggccacaac | gtccaggaac | tggtgtggct gatggaacgg | 840 |
| ctggtggacc | tggacggccc | cacgatcctg | catgtcgtga | cccgcaaggg caagggcctg | 900 |
| agctacgccg | aggccgaccc | gatctactgg | cacggtcccg | gtcaatttga cccggacacc | 960 |
| ggggatttca | aggccagcag | cgcgtactcg | tggagcgccg | cgttcggcga cgccgtgacc | 1020 |
| gaactggcca | aacgcgatcc | gcgtactttc | gtgatcaccc | cggccatgcg cgagggcagc | 1080 |
| gggctggtgg | gctacagccg | ggcgcacccg | caccgttacc | tggacgtggg catcgccgag | 1140 |
| gacgtggccg | tgaccactgc | cgccggcatg | gcgttcaggg | cctgcggcc catcgtggcg | 1200 |
| atctactcca | ccttcctgca | acgcgcctac | gatcaggtgt | tgcacgacgt cgccatcgag | 1260 |
| aacctgaacg | tcaccttcgc | catcgaccgc | gccgggatcg | tggggccga cggctcgacg | 1320 |
| cacaacggcg | tgttcgacct | gagctacctg | cgcagcattc | ccaacgtgcg gatcggcctg | 1380 |
| ccgaaggacg | cccacgagat | gcgcggcatg | ctgaagtacg | cgcaggagca cgacggtccc | 1440 |
| ttcgccatcc | gttacccgcg | cggcaacacg | gtcaaggtgc | ggaaggcac gtggcccacg | 1500 |
| ctggaatggg | gcacgtggga | gcgcgtcaag | gaaggctccg | acgccgtgat cctgccggc | 1560 |
| ggcaaggcgc | tggaatacgc | gcaggcggcg | gcggcggacc | tgcccggcgt cggtgtggtg | 1620 |
| aacgcccgtt | cgtcaagcc | gctggacctg | aacatgctgc | gcgagctggc cggcagcgcc | 1680 |
| cgcacaatca | tcaccgtgga | ggacaacacg | ctggtgggcg | gcttcggcag cgccgtgttg | 1740 |
| gaggccctga | acagcatggg | cttaaaggtg | cccgtgcgga | cgctgggcat tccggacgag | 1800 |
| ttccaggacc | acgccaccgc | cgagagcgtc | cacgcccgcg | ccggcatcga tgcccaggcg | 1860 |
| atccgcaccg | tgctggccga | gcttggggtg | gatgtgcctc | tgggcgtc | 1908 |

<210> SEQ ID NO 6
<211> LENGTH: 636
<212> TYPE: PRT
<213> ORGANISM: Deinococcus radiopugnans

<400> SEQUENCE: 6

```
Met Thr Asp Ile Lys Lys Ala Asp Gly Leu His Leu Gly His Lys Gly
1               5                   10                  15

Thr Pro Leu Leu Asp Arg Ile Ala Gly Pro Ala Asp Leu Lys Lys Leu
            20                  25                  30

Ser Arg Asp Gln Leu Pro Glu Leu Ser Gln Glu Leu Arg Asp Glu Ile
        35                  40                  45

Val Arg Val Cys Ser Val Gly Gly Leu His Leu Ala Ser Ser Leu Gly
50                  55                  60

Ala Thr Asp Leu Ile Val Ala Leu His Tyr Val Leu Asn Ser Pro Arg
65                  70                  75                  80

Asp Arg Ile Leu Phe Asp Val Gly His Gln Ala Tyr Ala His Lys Met
                85                  90                  95

Leu Thr Gly Arg Arg Glu Gln Met His Thr Val Lys Lys Glu Gly Gly
            100                 105                 110

Leu Ser Gly Phe Thr Lys Val Ser Glu Ser Glu His Asp Ala Ile Thr
        115                 120                 125

Val Gly His Ala Ser Thr Ser Leu Ala Asn Ala Leu Gly Met Ala Met
130                 135                 140

Ala Arg Asp Ala Leu Gly Gln Asp Tyr Gln Val Ala Ala Val Ile Gly
145                 150                 155                 160

Asp Gly Ser Leu Thr Gly Gly Met Ala Leu Ala Ala Leu Asn Thr Ile
                165                 170                 175

Gly Asp Leu Arg Arg Lys Met Leu Ile Val Leu Asn Asp Asn Glu Met
            180                 185                 190

Ser Ile Ser Glu Asn Val Gly Ala Ile Asn Lys Phe Met Arg Gly Leu
        195                 200                 205

Gln Val Gln Lys Trp Phe Gln Glu Gly Glu Gly Ala Gly Asn Lys Ala
210                 215                 220

Val Gln Ser Leu Ser Lys Pro Leu Ala Asp Phe Met Ser Arg Ala Lys
225                 230                 235                 240

Ser Ser Thr Arg His Phe Phe Asp Pro Ala Ser Val Asn Pro Phe Ala
                245                 250                 255

Met Met Gly Val Arg Tyr Val Gly Pro Val Asp Gly His Asn Val Gln
            260                 265                 270

Glu Leu Val Trp Leu Met Glu Arg Leu Val Asp Leu Asp Gly Pro Thr
        275                 280                 285

Ile Leu His Val Val Thr Arg Lys Gly Lys Gly Leu Ser Tyr Ala Glu
290                 295                 300

Ala Asp Pro Ile Tyr Trp His Gly Pro Gly Gln Phe Asp Pro Asp Thr
305                 310                 315                 320

Gly Asp Phe Lys Ala Ser Ser Ala Tyr Ser Trp Ser Ala Ala Phe Gly
                325                 330                 335

Asp Ala Val Thr Glu Leu Ala Lys Arg Asp Pro Arg Thr Phe Val Ile
            340                 345                 350

Thr Pro Ala Met Arg Glu Gly Ser Gly Leu Val Gly Tyr Ser Arg Ala
        355                 360                 365

His Pro His Arg Tyr Leu Asp Val Gly Ile Ala Glu Asp Val Ala Val
370                 375                 380
```

```
Thr Thr Ala Ala Gly Met Ala Leu Gln Gly Leu Arg Pro Ile Val Ala
385                 390                 395                 400

Ile Tyr Ser Thr Phe Leu Gln Arg Ala Tyr Asp Gln Val Leu His Asp
                405                 410                 415

Val Ala Ile Glu Asn Leu Asn Val Thr Phe Ala Ile Asp Arg Ala Gly
            420                 425                 430

Ile Val Gly Ala Asp Gly Ser Thr His Asn Gly Val Phe Asp Leu Ser
        435                 440                 445

Tyr Leu Arg Ser Ile Pro Asn Val Arg Ile Gly Leu Pro Lys Asp Ala
    450                 455                 460

His Glu Met Arg Gly Met Leu Lys Tyr Ala Gln Glu His Asp Gly Pro
465                 470                 475                 480

Phe Ala Ile Arg Tyr Pro Arg Gly Asn Thr Val Lys Val Pro Glu Gly
                485                 490                 495

Thr Trp Pro Thr Leu Glu Trp Gly Thr Trp Glu Arg Val Lys Glu Gly
                500                 505                 510

Ser Asp Ala Val Ile Leu Ala Gly Gly Lys Ala Leu Glu Tyr Ala Gln
            515                 520                 525

Ala Ala Ala Ala Asp Leu Pro Gly Val Gly Val Asn Ala Arg Phe
        530                 535                 540

Val Lys Pro Leu Asp Leu Asn Met Leu Arg Glu Leu Ala Gly Ser Ala
545                 550                 555                 560

Arg Thr Ile Ile Thr Val Glu Asp Asn Thr Leu Val Gly Gly Phe Gly
                565                 570                 575

Ser Ala Val Leu Glu Ala Leu Asn Ser Met Gly Leu Lys Val Pro Val
            580                 585                 590

Arg Thr Leu Gly Ile Pro Asp Glu Phe Gln Asp His Ala Thr Ala Glu
        595                 600                 605

Ser Val His Ala Arg Ala Gly Ile Asp Ala Gln Ala Ile Arg Thr Val
    610                 615                 620

Leu Ala Glu Leu Gly Val Asp Val Pro Leu Gly Val
625                 630                 635

<210> SEQ ID NO 7
<211> LENGTH: 1908
<212> TYPE: DNA
<213> ORGANISM: Deinococcus radiopugnans

<400> SEQUENCE: 7
atgaccgaca tcaaaaaggc tgatgggctg cacctcgggc acaagggcac gccgctgctg      60
gaccgcattg ccggcccggc tgacctcaag aagctctcgc gcgatcagtt gcccgagctg     120
agccaggaac tgcgcgacga gatcgtgcgg gtctgctcgg tgggtgggct gcatctggcg     180
tcctcgctgg gggccaccga cctgatcgtg gcgctgcatt acgtgctgaa cagtccgcgt     240
gaccggattc tcttcgacgt gggtcaccag gcctacgccc acaagatgct gaccgggcgg     300
cgggagcaga tgcacaccgt caagaaggaa ggtgggctga gcggctttac caaggtcagc     360
gagtccgaac acgacgccat taccgtgggc cacgccagca ccagcctggc gaacgcgctg     420
ggcatggcga tggcgagaga cgcgctgggc caggactatc aggtggccgc cgtgatcggc     480
gacggctcgc tgaccggcgg gatggcgctg ccgccctga caccatcgg tgacctgcgc     540 cgcaagatgc tgatcgtcct gaacgacaac gagatgagca tttccgagaa cgtgggcgcg     600
atcaacaagt tcatgcgcgg cctgcaggtc cagaagtggt tcaggagggg cgagggagcc     660
```

```
gggaaaaagg cggtgcagtc cctgagcaag ccgctggccg atttcatgag ccgtgccaag    720
agcagcacct gccacttctt cgatccggcc agcgtcaatc ccttcgccat gatgggcgtg    780
cgttatgtcg gcccggtcga cggccacaac gtccaggaac tggtgtggct gatggaacgg    840
ctggtggacc tggacggccc cacgatcctg catgtcgtga cccgcaaggg caagggcctg    900
agctacgccg aggccgaccc gatctactgg cacggtcccg gtcaatttga cccggacacc    960
ggggatttca aggccagcag cgcgtactcg tggagcgccg cgttcggcga cgccgtgacc   1020
gaactggcca aacgcgatcc gcgtactttc gtgatcaccc cggccatgcg cgagggcagc   1080
gggctggtgg gctacagccg ggcgcacccg accgttacc tggacgtggg catcgccgag    1140
gacgtggccg tgaccactgc cgccggcatg gcgttgcagg gcctgcggcc catcgtggcg   1200
atctactcca ccttcctgca acgcgcctac gatcaggtgt gcacgacgt cgccatcgag    1260 aacctgaacg tcaccttcgc catcgaccgc gccgggatcg tggggccga cggctcgacg    1320 cacaacggcg tgttcgacct gagctacctg cgcagcattc ccaacgtgcg gatcggcctg   1380
ccgaaggacg cccacgagat gcgcggcatg ctgaagtacg cgcaggagca cgacggtccc   1440
ttcgccatcc gttacccgcg cggcaacacg gtcaaggtgc cggaaggcac gtggcccacg   1500
ctggaatggg gcacgtggga gcgcgtcaag gaaggctccg acgccgtgat cctggccggc   1560
ggcaaggcgc tggaatacgc gcaggcggcg gcggcggacc tgcccggcgt cggtgtggtg   1620
aacgcccgtt tcgtcaagcc gctggacctg aacatgctgc gcgagctggc cggcagcgcc   1680
cgcacaatca tcaccgtgga ggacaacacg ctggtgggcg gcttcggcag cgccgtgttg   1740
gaggccctga acagcatggg cttaaaggtg cccgtgcgga cgctgggcat tccggacgag   1800
ttccaggacc acgccaccgc cgagagcgtc cacgcccgcg ccggcatcga tgcccaggcg   1860
atccgcaccg tgctggccga gcttggggtg gatgtgcctc tgggcgtc                1908
```

<210> SEQ ID NO 8
<211> LENGTH: 636
<212> TYPE: PRT
<213> ORGANISM: Deinococcus radiopugnans

<400> SEQUENCE: 8

```
Met Thr Asp Ile Lys Lys Ala Asp Gly Leu His Leu Gly His Lys Gly
1               5                   10                  15

Thr Pro Leu Leu Asp Arg Ile Ala Gly Pro Ala Asp Leu Lys Lys Leu
            20                  25                  30

Ser Arg Asp Gln Leu Pro Glu Leu Ser Gln Glu Leu Arg Asp Glu Ile
        35                  40                  45

Val Arg Val Cys Ser Val Gly Gly Leu His Leu Ala Ser Ser Leu Gly
    50                  55                  60

Ala Thr Asp Leu Ile Val Ala Leu His Tyr Val Leu Asn Ser Pro Arg
65                  70                  75                  80

Asp Arg Ile Leu Phe Asp Val Gly His Gln Ala Tyr Ala His Lys Met
                85                  90                  95

Leu Thr Gly Arg Arg Glu Gln Met His Thr Val Lys Lys Glu Gly Gly
            100                 105                 110

Leu Ser Gly Phe Thr Lys Val Ser Glu Ser Glu His Asp Ala Ile Thr
        115                 120                 125

Val Gly His Ala Ser Thr Ser Leu Ala Asn Ala Leu Gly Met Ala Met
    130                 135                 140

Ala Arg Asp Ala Leu Gly Gln Asp Tyr Gln Val Ala Ala Val Ile Gly
145                 150                 155                 160
```

```
Asp Gly Ser Leu Thr Gly Gly Met Ala Leu Ala Ala Leu Asn Thr Ile
            165                 170                 175

Gly Asp Leu Arg Arg Lys Met Leu Ile Val Leu Asn Asp Asn Glu Met
            180                 185                 190

Ser Ile Ser Glu Asn Val Gly Ala Ile Asn Lys Phe Met Arg Gly Leu
            195                 200                 205

Gln Val Gln Lys Trp Phe Gln Glu Gly Glu Ala Gly Lys Lys Ala
            210                 215                 220

Val Gln Ser Leu Ser Lys Pro Leu Ala Asp Phe Met Ser Arg Ala Lys
225                 230                 235                 240

Ser Ser Thr Cys His Phe Phe Asp Pro Ala Ser Val Asn Pro Phe Ala
            245                 250                 255

Met Met Gly Val Arg Tyr Val Gly Pro Val Asp Gly His Asn Val Gln
            260                 265                 270

Glu Leu Val Trp Leu Met Glu Arg Leu Val Asp Leu Asp Gly Pro Thr
            275                 280                 285

Ile Leu His Val Val Thr Arg Lys Gly Lys Gly Leu Ser Tyr Ala Glu
            290                 295                 300

Ala Asp Pro Ile Tyr Trp His Gly Pro Gly Gln Phe Ala Pro Asp Thr
305                 310                 315                 320

Gly Asp Phe Lys Ala Ser Ser Ala Tyr Ser Trp Ser Ala Ala Phe Gly
            325                 330                 335

Asp Ala Val Thr Glu Leu Ala Lys Arg Asp Pro Arg Thr Phe Val Ile
            340                 345                 350

Thr Pro Ala Met Arg Glu Gly Ser Gly Leu Val Gly Tyr Ser Arg Ala
            355                 360                 365

His Pro His Arg Tyr Leu Asp Val Gly Ile Ala Glu Asp Val Ala Val
            370                 375                 380

Thr Thr Ala Ala Gly Met Ala Leu Gln Gly Leu Arg Pro Ile Val Ala
385                 390                 395                 400

Ile Tyr Ser Thr Phe Leu Gln Arg Ala Tyr Asp Gln Val Leu His Asp
            405                 410                 415

Val Ala Ile Glu Asn Leu Asn Val Thr Phe Ala Ile Asp Arg Ala Gly
            420                 425                 430

Ile Val Gly Ala Asp Gly Ser Thr His Asn Gly Val Phe Asp Leu Ser
            435                 440                 445

Tyr Leu Arg Ser Ile Pro Asn Val Arg Ile Gly Leu Pro Lys Asp Ala
            450                 455                 460

His Glu Met Arg Gly Met Leu Lys Tyr Ala Gln Glu His Asp Gly Pro
465                 470                 475                 480

Phe Ala Ile Arg Tyr Pro Arg Gly Asn Thr Val Lys Val Pro Glu Gly
            485                 490                 495

Thr Trp Pro Thr Leu Glu Trp Gly Thr Trp Glu Arg Val Lys Glu Gly
            500                 505                 510

Ser Asp Ala Val Ile Leu Ala Gly Gly Lys Ala Leu Glu Tyr Ala Gln
            515                 520                 525

Ala Ala Ala Ala Asp Leu Pro Gly Val Gly Val Asn Ala Arg Phe
            530                 535                 540

Val Lys Pro Leu Asp Leu Asn Met Leu Arg Glu Leu Ala Gly Ser Ala
545                 550                 555                 560

Arg Thr Ile Ile Thr Val Glu Asp Asn Thr Leu Val Gly Gly Phe Gly
            565                 570                 575
```

```
Ser Ala Val Leu Glu Ala Leu Asn Ser Met Gly Leu Lys Val Pro Val
            580                 585                 590

Arg Thr Leu Gly Ile Pro Asp Glu Phe Gln Asp His Ala Thr Ala Glu
            595                 600                 605

Ser Val His Ala Arg Ala Gly Ile Asp Ala Gln Ala Ile Arg Thr Val
        610                 615                 620

Leu Ala Glu Leu Gly Val Asp Val Pro Leu Gly Val
625                 630                 635

<210> SEQ ID NO 9
<211> LENGTH: 1908
<212> TYPE: DNA
<213> ORGANISM: Deinococcus radiopugnans

<400> SEQUENCE: 9
atgaccgaca tcaaaaaggc tgatgggctg cacctcgggc acaagggcac gccgctgctg      60
gaccgcattg ccggcccggc tgacctcaag aagctctcgc gcgatcagtt gcccgagctg     120
agccaggaac tgcgcgacga gatcgtgcgg gtctgctcgg tgggtgggct gcatctggcg     180
tcctcgctgg ggccaccgga cctgatcgtg gcgctgcatt acgtgctgaa cagtccgcgt     240
gaccggattc tcttcgacgt gggtcaccag gcctacgccc acaagatgct gaccgggcgg     300
cgggagcaga tgcacaccgt caagaaggaa ggtgggctga gcggctttac caaggtcagc     360
gagtccgaac acgacgccat accgtgggc cacgccagca ccagcctggc gaacgcgctg     420
ggcatggcga tggcgagaga cgcgctgggc caggactatc aggtggccgc cgtgatcggc     480
gacggctcgc tgaccggcgg gatggcgctg ccgcccctga caccatcgg tgacctgcgc     540 cgcaagatgc tgatcgtcct gaacgacaac gagatgagca tttccgagaa cgtgggcgcg     600
atcaacaagt tcatgcgcgg cctgcaggtc cagaagtggt tcaggagggg cgagggagcc     660
gggaacaagg cggtgcagtc cctgagcaag ccgctggccg atttcatgag ccgtgccaag     720
agcagcacct gccacttctt cgatccggcc agcgtcaatc ccttcgccat gatgggcgtg     780
cgttatgtcg gccggtcga cggccacaac gtccaggaac tggtgtggct gatggaacgg     840
ctggtggacc tggacggccc cacgatcctg catgtcgtga cccgcaaggg caagggcctg     900
agctacgccg aggccgaccc gatctactgg cacggtcccg gtcaatttga cccggacacc     960
ggggatttca aggccagcag cgcgtactcg tggagcgccg cgttcggcga cgccgtgacc    1020
gaactggcca aacgcgatcc gcgtactttc gtgatcaccc cggccatgcg cgagggcagc    1080
gggctggtgg gctacagccg ggcgcacccc caccgttacc tggacgtggg catcgccgag    1140
gacgtggccg tgaccactgc cgccggcatg gcgttgcagg gcctgcggcc catcgtggcg    1200
atctactcca ccttcctgca acgcgcctac gatcaggtgt tgcacgacgt cgccatcgag    1260
aacctgaacg tcaccttcgc catcgaccgc gccgggatcg tggggccga cggctcgacg    1320 cacaacggcg tgttcgacct gagctacctg cgcagcattc ccaacgtgcg gatcggcctg    1380
ccgaaggacg cccacgagat gcgcggcatg ctgaagtacg cgcaggagca cgacggtccc    1440
ttcgccatcc gttacccgcg cggcaacacg gtcaaggtgc cggaaggcac gtggcccacg    1500
ctggaatggg gcacgtggga gcgcgtcaag gaaggctccg acgccgtgat cctgccggc     1560 ggcaaggcgc tggaatacgc gcaggcggcg gcggcggacc tgcccggcgt cggtgtggtg    1620
aacgcccgtt tcgtcaagcc gctggacctg aacatgctgc gcgagctggc ggcagcgcc     1680 cgcacaatca tcaccgtgga ggacaacacg ctggtgggcg gcttcggcag cgccgtgttg    1740
gaggccctga acagcatggg cttaaaggtg cccgtgcgga cgctgggcat tccggacgag    1800
```

-continued

```
ttccaggacc acgccaccgc cgagagcgtc cacgcccgcg ccggcatcga tgcccaggcg    1860
atccgcaccg tgctggccga gcttggggtg gatgtgcctc tgggcgtc                 1908
```

<210> SEQ ID NO 10
<211> LENGTH: 636
<212> TYPE: PRT
<213> ORGANISM: Deinococcus radiopugnans

<400> SEQUENCE: 10

```
Met Thr Asp Ile Lys Lys Ala Asp Gly Leu His Leu Gly His Lys Gly
1               5                  10                  15

Thr Pro Leu Leu Asp Arg Ile Ala Gly Pro Ala Asp Leu Lys Lys Leu
            20                  25                  30

Ser Arg Asp Gln Leu Pro Glu Leu Ser Gln Glu Leu Arg Asp Glu Ile
        35                  40                  45

Val Arg Val Cys Ser Val Gly Gly Leu His Leu Ala Ser Ser Leu Gly
    50                  55                  60

Ala Thr Asp Leu Ile Val Ala Leu His Tyr Val Leu Asn Ser Pro Arg
65                  70                  75                  80

Asp Arg Ile Leu Phe Asp Val Gly His Gln Ala Tyr Ala His Lys Met
                85                  90                  95

Leu Thr Gly Arg Arg Glu Gln Met His Thr Val Lys Lys Glu Gly Gly
            100                 105                 110

Leu Ser Gly Phe Thr Lys Val Ser Glu Ser Glu His Asp Ala Ile Thr
        115                 120                 125

Val Gly His Ala Ser Thr Ser Leu Ala Asn Ala Leu Gly Met Ala Met
    130                 135                 140

Ala Arg Asp Ala Leu Gly Gln Asp Tyr Gln Val Ala Ala Val Ile Gly
145                 150                 155                 160

Asp Gly Ser Leu Thr Gly Gly Met Ala Leu Ala Ala Leu Asn Thr Ile
                165                 170                 175

Gly Asp Leu Arg Arg Lys Met Leu Ile Val Leu Asn Asp Asn Glu Met
            180                 185                 190

Ser Ile Ser Glu Asn Val Gly Ala Ile Asn Lys Phe Met Arg Gly Leu
        195                 200                 205

Gln Val Gln Lys Trp Phe Gln Glu Gly Glu Gly Ala Gly Asn Lys Ala
    210                 215                 220

Val Gln Ser Leu Ser Lys Pro Leu Ala Asp Phe Met Ser Arg Ala Lys
225                 230                 235                 240

Ser Ser Thr Cys His Phe Phe Asp Pro Ala Ser Val Asn Pro Phe Ala
                245                 250                 255

Met Met Gly Val Arg Tyr Val Gly Pro Val Asp Gly His Asn Val Gln
            260                 265                 270

Glu Leu Val Trp Leu Met Glu Arg Leu Val Asp Leu Asp Gly Pro Thr
        275                 280                 285

Ile Leu His Val Val Thr Arg Lys Gly Lys Gly Leu Ser Tyr Ala Glu
    290                 295                 300

Ala Asp Pro Ile Tyr Trp His Gly Pro Gly Gln Phe Asp Pro Asp Thr
305                 310                 315                 320

Gly Asp Phe Lys Ala Ser Ser Ala Tyr Ser Trp Ser Ala Ala Phe Gly
                325                 330                 335

Asp Ala Val Thr Glu Leu Ala Lys Arg Asp Pro Arg Thr Phe Val Ile
            340                 345                 350
```

Thr Pro Ala Met Arg Glu Gly Ser Gly Leu Val Gly Tyr Ser Arg Ala
            355                 360                 365

His Pro His Arg Tyr Leu Asp Val Gly Ile Ala Glu Asp Val Ala Val
        370                 375                 380

Thr Thr Ala Ala Gly Met Ala Leu Gln Gly Leu Arg Pro Ile Val Ala
385                 390                 395                 400

Ile Tyr Ser Thr Phe Leu Gln Arg Ala Tyr Asp Gln Val Leu His Asp
                405                 410                 415

Val Ala Ile Glu Asn Leu Asn Val Thr Phe Ala Ile Asp Arg Ala Gly
            420                 425                 430

Ile Val Gly Ala Asp Gly Ser Thr His Asn Gly Val Phe Asp Leu Ser
        435                 440                 445

Tyr Leu Arg Ser Ile Pro Asn Val Arg Ile Gly Leu Pro Lys Asp Ala
    450                 455                 460

His Glu Met Arg Gly Met Leu Lys Tyr Ala Gln Glu His Asp Gly Pro
465                 470                 475                 480

Phe Ala Ile Arg Tyr Pro Arg Gly Asn Thr Val Lys Val Pro Glu Gly
                485                 490                 495

Thr Trp Pro Thr Leu Glu Trp Gly Thr Trp Glu Arg Val Lys Glu Gly
            500                 505                 510

Ser Asp Ala Val Ile Leu Ala Gly Gly Lys Ala Leu Glu Tyr Ala Gln
        515                 520                 525

Ala Ala Ala Asp Leu Pro Gly Val Gly Val Val Asn Ala Arg Phe
    530                 535                 540

Val Lys Pro Leu Asp Leu Asn Met Leu Arg Glu Leu Ala Gly Ser Ala
545                 550                 555                 560

Arg Thr Ile Ile Thr Val Glu Asp Asn Thr Leu Val Gly Gly Phe Gly
                565                 570                 575

Ser Ala Val Leu Glu Ala Leu Asn Ser Met Gly Leu Lys Val Pro Val
            580                 585                 590

Arg Thr Leu Gly Ile Pro Asp Glu Phe Gln Asp His Ala Thr Ala Glu
        595                 600                 605

Ser Val His Ala Arg Ala Gly Ile Asp Ala Gln Ala Ile Arg Thr Val
    610                 615                 620

Leu Ala Glu Leu Gly Val Asp Val Pro Leu Gly Val
625                 630                 635

<210> SEQ ID NO 11
<211> LENGTH: 1893
<212> TYPE: DNA
<213> ORGANISM: Deinococcus yunweiensis

<400> SEQUENCE: 11
atgacatcca gcgacctcgt ccccgttccg cagcgcctgc tcgacgcggt gaactcgccg      60
gacgacctca agaccctgaa gcgcgagcag ctgccgcagg tggcgcagga actccgcgac     120
gagatcgtgc gggtgtgctc ggtggtggc ctgcacctgg cgtcctcgct gggcgcgacc     180
gacgtgatcg tggcgctgca ctacgtcctg aactcgccgc gtgaccggat tctgttcgat     240
gtgggtcacc aggcctacgc gcacaagatg ctcaccggcc gccgcgagca gatggtcagc     300
gtgaagaagg agggcgggct ctcgggcttc accaaggtca gcgagtcgcc gcacgacgcg     360
atcacggtgg ggcacgccag taccagcctg gcaaacgcgc tgggcatggc gatggcacgg     420
gacgccctgg gcaggatta ccacgtggcc gccgtgatcg tgacggcag cctgaccggc     480 ggcatggccc tggccgccct aaacaccatc ggggacacgc agcgcaagat gctgatcgtc     540

```
ctgaacgaca acgagatgag catctccgag aacgtggggg ccatgaacaa gttcatgcgt    600
ggcctccagg tgcagaagtg gttccaggag ggcgagggcg cgggcaacaa ggccatgcag    660
gcggtcagcc gcccgctcgc caacttcatg agccgcgcca agagcagcac ccggcatttc    720
ttcgaccccg ccagcgtgaa tccctttgcc accatgggcg tgcgttatgt ggggccagtc    780
gacggacaca acgtgcagga actcgtgtgg ctgctcgaac gcctcgtgga actcgacggg    840
ccgacgatcc tgcatgtggt gaccaagaag ggcaagggcc tgagctacgc cgaggccgat    900
ccgatctact ggcacggccc cggcaagttc gacccggaga ccggggactt cgtgcccagc    960
aatgcgtact cgtggagcaa cgccttcgga gacgccgtca cggagctggc gaaagccgat   1020
ccccgcacct tcgtgatcac ccccgccatg cgcgagggca gcgggctggt cggctacagc   1080
aaggcccatc cgcaccgcta tctggacgtc ggcatcgccg aggaggtcgc tgtgacggcc   1140
gccgccggca tggccctcca ggggctgcgg cccgtcgtgg cgatctactc caccttcctg   1200
caacgcgcct acgaccaggt gctgcacgac gtcgccattg agcacttgaa cgtcaccttc   1260
gctattgacc gggccgggat cgtcggcgcg gacggggcca cccacaacgg cgtcttcgac   1320
ctgagcttcc tgcgctcgat cccaggtgtg cggatcggcc tgcccaagga cgcgaccgag   1380
ctgcgtggca tgctgaagta cgcccaggag caccccggcc ccttcgccat ccgctatccg   1440
cgtggcacca ccgagcgcgt gccagagggc acctggccca ccctggcgtg ggcacgtgg    1500
gagcgcgtga agtccggcga cgacgtggtc atcctggcgg gtggcaaggg cctggagtat   1560
gcccagaagg ccgccgccga cctgcccggc gtgggtgtcg tgaacgcccg tttcgtcaag   1620
ccgcttgacg acgccatgct gcgagaggtg gccggcagtg ctcgcgctat cgtcaccgtc   1680
gaggacaaca ccgtcgtcgg gggatttggc agcgccgtgc tggaggccct gaacgcctgg   1740
ggcctgaccg tgcccgtgcg cgtgctgggc atcccggacg aattccagga acacgccacc   1800
gtggacagcg tgcatgcccg cgccggcatc gacgctcccg ctatccgcac ggtgctggcc   1860
gagcttgggg tggacgtgcc gctgggcgtg taa                                1893
```

<210> SEQ ID NO 12
<211> LENGTH: 630
<212> TYPE: PRT
<213> ORGANISM: Deinococcus yunweiensis

<400> SEQUENCE: 12

```
Met Thr Ser Ser Asp Leu Val Pro Val Pro Gln Arg Leu Leu Asp Ala
1               5                   10                  15

Val Asn Ser Pro Asp Asp Leu Lys Thr Leu Lys Arg Glu Gln Leu Pro
            20                  25                  30

Gln Val Ala Gln Glu Leu Arg Asp Glu Ile Val Arg Val Cys Ser Val
        35                  40                  45

Gly Gly Leu His Leu Ala Ser Ser Leu Gly Ala Thr Asp Val Ile Val
    50                  55                  60

Ala Leu His Tyr Val Leu Asn Ser Pro Arg Asp Arg Ile Leu Phe Asp
65                  70                  75                  80

Val Gly His Gln Ala Tyr Ala His Lys Met Leu Thr Gly Arg Arg Glu
                85                  90                  95

Gln Met Val Ser Val Lys Lys Glu Gly Gly Leu Ser Gly Phe Thr Lys
            100                 105                 110

Val Ser Glu Ser Pro His Asp Ala Ile Thr Val Gly His Ala Ser Thr
        115                 120                 125
```

```
Ser Leu Ala Asn Ala Leu Gly Met Ala Met Ala Arg Asp Ala Leu Gly
    130                 135                 140

Gln Asp Tyr His Val Ala Ala Val Ile Gly Asp Gly Ser Leu Thr Gly
145                 150                 155                 160

Gly Met Ala Leu Ala Ala Leu Asn Thr Ile Gly Asp Thr Gln Arg Lys
                165                 170                 175

Met Leu Ile Val Leu Asn Asp Asn Glu Met Ser Ile Ser Glu Asn Val
                180                 185                 190

Gly Ala Met Asn Lys Phe Met Arg Gly Leu Gln Val Gln Lys Trp Phe
            195                 200                 205

Gln Glu Gly Glu Gly Ala Gly Asn Lys Ala Met Gln Ala Val Ser Arg
210                 215                 220

Pro Leu Ala Asn Phe Met Ser Arg Ala Lys Ser Ser Thr Arg His Phe
225                 230                 235                 240

Phe Asp Pro Ala Ser Val Asn Pro Phe Ala Thr Met Gly Val Arg Tyr
                245                 250                 255

Val Gly Pro Val Asp Gly His Asn Val Gln Glu Leu Val Trp Leu Leu
                260                 265                 270

Glu Arg Leu Val Glu Leu Asp Gly Pro Thr Ile Leu His Val Val Thr
    275                 280                 285

Lys Lys Gly Lys Gly Leu Ser Tyr Ala Glu Ala Asp Pro Ile Tyr Trp
290                 295                 300

His Gly Pro Gly Lys Phe Asp Pro Glu Thr Gly Asp Phe Val Pro Ser
305                 310                 315                 320

Asn Ala Tyr Ser Trp Ser Asn Ala Phe Gly Asp Ala Val Thr Glu Leu
                325                 330                 335

Ala Lys Ala Asp Pro Arg Thr Phe Val Ile Thr Pro Ala Met Arg Glu
            340                 345                 350

Gly Ser Gly Leu Val Gly Tyr Ser Lys Ala His Pro His Arg Tyr Leu
        355                 360                 365

Asp Val Gly Ile Ala Glu Glu Val Ala Val Thr Ala Ala Ala Gly Met
370                 375                 380

Ala Leu Gln Gly Leu Arg Pro Val Val Ala Ile Tyr Ser Thr Phe Leu
385                 390                 395                 400

Gln Arg Ala Tyr Asp Gln Val Leu His Asp Val Ala Ile Glu His Leu
                405                 410                 415

Asn Val Thr Phe Ala Ile Asp Arg Ala Gly Ile Val Gly Ala Asp Gly
                420                 425                 430

Ala Thr His Asn Gly Val Phe Asp Leu Ser Phe Leu Arg Ser Ile Pro
            435                 440                 445

Gly Val Arg Ile Gly Leu Pro Lys Asp Ala Thr Glu Leu Arg Gly Met
        450                 455                 460

Leu Lys Tyr Ala Gln Glu His Pro Gly Pro Phe Ala Ile Arg Tyr Pro
465                 470                 475                 480

Arg Gly Thr Thr Glu Arg Val Pro Glu Gly Thr Trp Pro Thr Leu Ala
                485                 490                 495

Trp Gly Thr Trp Glu Arg Val Lys Ser Gly Asp Asp Val Val Ile Leu
                500                 505                 510

Ala Gly Gly Lys Gly Leu Glu Tyr Ala Gln Lys Ala Ala Ala Asp Leu
            515                 520                 525

Pro Gly Val Gly Val Val Asn Ala Arg Phe Val Lys Pro Leu Asp Asp
530                 535                 540

Ala Met Leu Arg Glu Val Ala Gly Ser Ala Arg Ala Ile Val Thr Val
```

```
545                 550                 555                 560
Glu Asp Asn Thr Val Val Gly Gly Phe Gly Ser Ala Val Leu Glu Ala
                565                 570                 575

Leu Asn Ala Trp Gly Leu Thr Val Pro Val Arg Val Leu Gly Ile Pro
            580                 585                 590

Asp Glu Phe Gln Glu His Ala Thr Val Asp Ser Val His Ala Arg Ala
        595                 600                 605

Gly Ile Asp Ala Pro Ala Ile Arg Thr Val Leu Ala Glu Leu Gly Val
    610                 615                 620

Asp Val Pro Leu Gly Val
625                 630

<210> SEQ ID NO 13
<211> LENGTH: 1893
<212> TYPE: DNA
<213> ORGANISM: Deinococcus yunweiensis

<400> SEQUENCE: 13
atgacatcca gcgacctcgt ccccgttccg cagcgcctgc tcgacgcggt gaactcgccg      60
gacgacctca agaccctgaa gcgcgagcag ctgccgcagg tggcgcagga actccgcgac     120
gagatcgtgc gggtgtgctc ggtgggtggc ctgcacctgg cgtcctcgct gggcgcgacc     180
gacgtgatcg tggcgctgca ctacgtcctg aactcgccgc gtgaccggat tctgttcgat     240
gtgggtcacc aggcctacgc gcacaagatg ctcaccggcc gccgcagca gatggtcagc      300 gtgaagaagg agggcgggct ctcgggcttc accaaggtca gcgagtcgcc gcacgacgcg     360
atcacggtgg ggcacgccag taccagcctg gcaaacgcgc tgggcatggc gatggcacgg     420
gacgccctgg ggcaggatta ccacgtggcc gccgtgatcg tgacggcag cctgaccggc      480 ggcatggccc tggccgccct aaacaccatc ggggacacgc agcgcaagat gctgatcgtc     540
ctgaacgaca acgagatgag catctccgag aacgtggggg ccatgaacaa gttcatgcgt     600
ggcctccagg tgcagaagtg gttccaggag ggcgagggcc gggcaagaa ggccatgcag      660 gcggtcagcc gcccgctcgc caacttcatg agccgcgcca agagcagcac ctgccatttc     720
ttcgaccccg ccagcgtgaa tccctttgcc accatggggcg tgcgttatgt ggggccagtc     780
gacggacaca acgtgcagga actcgtgtgg ctgctcgaac gcctcgtgga actcgacggg     840
ccgacgatcc tgcatgtggt gaccaagaag ggcaagggcc tgagctacgc cgaggccgat     900
ccgatctact ggcacggccc cggcaagttc gaccccggaga ccggggactt cgtgcccagc     960
aatgcgtact cgtggagcaa cgccttcgga gacgccgtca cggagctggc gaaagccgat    1020
ccccgcacct tcgtgatcac ccccgccatg cgcgagggca cgggctggt cggctacagc     1080 aaggcccatc cgcaccgcta tctggacgtc ggcatcgccg aggaggtcgc gtgacggcc     1140 gccgccggca tggccctcca ggggctgcgg cccgtcgtgg cgatctactc caccttcctg    1200
caacgcgcct acgaccaggt gctgcacgac gtcgccattg agcacttgaa cgtcaccttc    1260
gctattgacc gggccgggat cgtcggcgcg gacggggcca cccacaacgg cgtcttcgac    1320
ctgagcttcc tgcgctcgat cccaggtgtg cggatcggcc tgcccaagga cgcgaccgag    1380
ctgcgtggca tgctgaagta cgcccaggag caccccggcc ccttcgccat ccgctatccg    1440
cgtggcacca ccgagcgcgt gccagagggc acctggccca ccctggcgtg ggcacgtgg     1500 gagcgcgtga gtccggcga cgacgtggtc atcctggcgg gtggcaaggg cctggagtat    1560
gcccagaagg ccgccgccga cctgcccggc gtgggtgtcg tgaacgcccg tttcgtcaag    1620
```

```
ccgcttgacg acgccatgct gcgagaggtg gccggcagtg ctcgcgctat cgtcaccgtc    1680
gaggacaaca ccgtcgtcgg gggatttggc agcgccgtgc tggaggccct gaacgcctgg    1740
ggcctgaccg tgcccgtgcg cgtgctgggc atcccggacg aattccagga acacgccacc    1800
gtggacagcg tgcatgcccg cgccggcatc gacgctcccg ctatccgcac ggtgctggcc    1860
gagcttgggg tggacgtgcc gctgggcgtg taa                                 1893

<210> SEQ ID NO 14
<211> LENGTH: 630
<212> TYPE: PRT
<213> ORGANISM: Deinococcus yunweiensis

<400> SEQUENCE: 14

Met Thr Ser Ser Asp Leu Val Pro Val Pro Gln Arg Leu Leu Asp Ala
1               5                   10                  15

Val Asn Ser Pro Asp Asp Leu Lys Thr Leu Lys Arg Glu Gln Leu Pro
            20                  25                  30

Gln Val Ala Gln Glu Leu Arg Asp Glu Ile Val Arg Val Cys Ser Val
        35                  40                  45

Gly Gly Leu His Leu Ala Ser Ser Leu Gly Ala Thr Asp Val Ile Val
    50                  55                  60

Ala Leu His Tyr Val Leu Asn Ser Pro Arg Asp Arg Ile Leu Phe Asp
65                  70                  75                  80

Val Gly His Gln Ala Tyr Ala His Lys Met Leu Thr Gly Arg Arg Glu
                85                  90                  95

Gln Met Val Ser Val Lys Lys Glu Gly Gly Leu Ser Gly Phe Thr Lys
            100                 105                 110

Val Ser Glu Ser Pro His Asp Ala Ile Thr Val Gly His Ala Ser Thr
        115                 120                 125

Ser Leu Ala Asn Ala Leu Gly Met Ala Met Ala Arg Asp Ala Leu Gly
    130                 135                 140

Gln Asp Tyr His Val Ala Ala Val Ile Gly Asp Gly Ser Leu Thr Gly
145                 150                 155                 160

Gly Met Ala Leu Ala Ala Leu Asn Thr Ile Gly Asp Thr Gln Arg Lys
                165                 170                 175

Met Leu Ile Val Leu Asn Asp Asn Glu Met Ser Ile Ser Glu Asn Val
            180                 185                 190

Gly Ala Met Asn Lys Phe Met Arg Gly Leu Gln Val Gln Lys Trp Phe
        195                 200                 205

Gln Glu Gly Glu Gly Ala Gly Lys Lys Ala Met Gln Ala Val Ser Arg
    210                 215                 220

Pro Leu Ala Asn Phe Met Ser Arg Ala Lys Ser Ser Thr Cys His Phe
225                 230                 235                 240

Phe Asp Pro Ala Ser Val Asn Pro Phe Ala Thr Met Gly Val Arg Tyr
                245                 250                 255

Val Gly Pro Val Asp Gly His Asn Val Gln Glu Leu Val Trp Leu Leu
            260                 265                 270

Glu Arg Leu Val Glu Leu Asp Gly Pro Thr Ile Leu His Val Val Thr
        275                 280                 285

Lys Lys Gly Lys Gly Leu Ser Tyr Ala Glu Ala Asp Pro Ile Tyr Trp
    290                 295                 300

His Gly Pro Gly Lys Phe Asp Pro Glu Thr Gly Asp Phe Val Pro Ser
305                 310                 315                 320

Asn Ala Tyr Ser Trp Ser Asn Ala Phe Gly Asp Ala Val Thr Glu Leu
```

```
                325                 330                 335
Ala Lys Ala Asp Pro Arg Thr Phe Val Ile Thr Pro Ala Met Arg Glu
            340                 345                 350
Gly Ser Gly Leu Val Gly Tyr Ser Lys Ala His Pro Arg Tyr Leu
        355                 360                 365
Asp Val Gly Ile Ala Glu Glu Val Ala Val Thr Ala Ala Gly Met
    370                 375                 380
Ala Leu Gln Gly Leu Arg Pro Val Val Ala Ile Tyr Ser Thr Phe Leu
385                 390                 395                 400
Gln Arg Ala Tyr Asp Gln Val Leu His Asp Val Ala Ile Glu His Leu
                405                 410                 415
Asn Val Thr Phe Ala Ile Asp Arg Ala Gly Ile Val Gly Ala Asp Gly
            420                 425                 430
Ala Thr His Asn Gly Val Phe Asp Leu Ser Phe Leu Arg Ser Ile Pro
        435                 440                 445
Gly Val Arg Ile Gly Leu Pro Lys Asp Ala Thr Glu Leu Arg Gly Met
    450                 455                 460
Leu Lys Tyr Ala Gln Glu His Pro Gly Pro Phe Ala Ile Arg Tyr Pro
465                 470                 475                 480
Arg Gly Thr Thr Glu Arg Val Pro Glu Gly Thr Trp Pro Thr Leu Ala
                485                 490                 495
Trp Gly Trp Glu Arg Val Lys Ser Gly Asp Asp Val Val Ile Leu
            500                 505                 510
Ala Gly Gly Lys Gly Leu Glu Tyr Ala Gln Lys Ala Ala Ala Asp Leu
        515                 520                 525
Pro Gly Val Gly Val Val Asn Ala Arg Phe Val Lys Pro Leu Asp Asp
    530                 535                 540
Ala Met Leu Arg Glu Val Ala Gly Ser Ala Arg Ala Ile Val Thr Val
545                 550                 555                 560
Glu Asp Asn Thr Val Val Gly Gly Phe Gly Ser Ala Val Leu Glu Ala
                565                 570                 575
Leu Asn Ala Trp Gly Leu Thr Val Pro Val Arg Val Leu Gly Ile Pro
            580                 585                 590
Asp Glu Phe Gln Glu His Ala Thr Val Asp Ser Val His Ala Arg Ala
        595                 600                 605
Gly Ile Asp Ala Pro Ala Ile Arg Thr Val Leu Ala Glu Leu Gly Val
    610                 615                 620
Asp Val Pro Leu Gly Val
625                 630

<210> SEQ ID NO 15
<211> LENGTH: 1893
<212> TYPE: DNA
<213> ORGANISM: Deinococcus yunweiensis

<400> SEQUENCE: 15
atgacatcca gcgacctcgt ccccgttccg cagcgcctgc tcgacgcggt gaactcgccg      60
gacgacctca agaccctgaa gcgcgaggag ctgccgcagg tggcgcagga actccgcgac     120
gagatcgtgc gggtgtgctc ggtggtggc ctgcacctgg cgtcctcgct gggcgcgacc     180
gacgtgatcg tggcgctgca ctacgtcctg aactcgccgc gtgaccggat tctgttcgat     240
gtgggtcacc aggcctacgc gcacaagatg ctcaccggcc gccgcgagca gatggtcagc     300
gtgaagaagg agggcgggct ctcgggcttc accaaggtca gcgagtcgcc gcacgacgcg     360
```

```
atcacggtgg ggcacgccag taccagcctg gcaaacgcgc tgggcatggc gatggcacgg      420
gacgccctgg ggcaggatta ccacgtggcc gccgtgatcg gtgacggcag cctgaccggc      480
ggcatggccc tggccgccct aaacaccatc ggggacacgc agcgcaagat gctgatcgtc      540
ctgaacgaca acgagatgag catctccgag aacgtggggg ccatgaacaa gttcatgcgt      600
ggcctccagg tgcagaagtg gttccaggag ggcgagggcg cgggcaacaa ggccatgcag      660
gcggtcagcc gcccgctcgc caacttcatg agccgcgcca agagcagcac ctgccatttc      720
ttcgaccccg ccagcgtgaa tccctttgcc accatgggcg tgcgttatgt ggggccagtc      780
gacggacaca acgtgcagga actcgtgtgg ctgctcgaac gcctcgtgga actcgacggg      840
ccgacgatcc tgcatgtggt gaccaagaag ggcaagggcc tgagctacgc cgaggccgat      900
ccgatctact ggcacggccc cggcaagttc gacccggaga ccggggactt cgtgcccagc      960
aatgcgtact cgtggagcaa cgccttcgga gacgccgtca cggagctggc gaaagccgat     1020
ccccgcacct tcgtgatcac ccccgccatg cgcgagggca gcgggctggt cggctacagc     1080
aaggcccatc cgcaccgcta tctggacgtc ggcatcgccg aggaggtcgc tgtgacggcc     1140
gccgccggca tggccctcca ggggctgcgg cccgtcgtgg cgatctactc caccttcctg     1200
caacgcgcct acgaccaggt gctgcacgac gtcgccattg agcacttgaa cgtcaccttc     1260
gctattgacc gggccgggat cgtcggcgcg gacggggcca cccacaacgg cgtcttcgac     1320
ctgagcttcc tgcgctcgat cccaggtgtg cggatcggcc tgcccaagga cgcgaccgag     1380
ctgcgtggca tgctgaagta cgcccaggag caccccggcc ccttcgccat ccgctatccg     1440
cgtggcacca ccgagcgcgt gccagagggc acctggccca cctggcgtg gggcacgtgg     1500
gagcgcgtga agtccggcga cgacgtggtc atcctggcgg gtggcaaggg cctggagtat     1560
gcccagaagg ccgccgccga cctgcccggc gtgggtgtcg tgaacgcccg tttcgtcaag     1620
ccgcttgacg acgccatgct gcgagaggtg gccggcagtg ctcgcgctat cgtcaccgtc     1680
gaggacaaca ccgtcgtcgg gggatttggc agcgccgtgc tggaggccct gaacgcctgg     1740
ggcctgaccg tgcccgtgcg cgtgctgggc atcccggacg aattccagga acacgccacc     1800
gtggacagcg tgcatgcccg cgccggcatc gacgctcccg ctatccgcac ggtgctggcc     1860
gagcttgggg tggacgtgcc gctgggcgtg taa                                 1893
```

```
<210> SEQ ID NO 16
<211> LENGTH: 630
<212> TYPE: PRT
<213> ORGANISM: Deinococcus yunweiensis

<400> SEQUENCE: 16
```

Met Thr Ser Ser Asp Leu Val Pro Val Pro Gln Arg Leu Leu Asp Ala
1               5                   10                  15

Val Asn Ser Pro Asp Asp Leu Lys Thr Leu Lys Arg Glu Gln Leu Pro
            20                  25                  30

Gln Val Ala Gln Glu Leu Arg Asp Glu Ile Val Arg Val Cys Ser Val
        35                  40                  45

Gly Gly Leu His Leu Ala Ser Ser Leu Gly Ala Thr Asp Val Ile Val
    50                  55                  60

Ala Leu His Tyr Val Leu Asn Ser Pro Arg Asp Arg Ile Leu Phe Asp
65                  70                  75                  80

Val Gly His Gln Ala Tyr Ala His Lys Met Leu Thr Gly Arg Arg Glu
                85                  90                  95

Gln Met Val Ser Val Lys Lys Glu Gly Gly Leu Ser Gly Phe Thr Lys

```
                100             105              110
Val Ser Glu Ser Pro His Asp Ala Ile Thr Val Gly His Ala Ser Thr
            115                 120                 125
Ser Leu Ala Asn Ala Leu Gly Met Ala Met Ala Arg Asp Ala Leu Gly
            130                 135                 140
Gln Asp Tyr His Val Ala Val Ile Gly Asp Gly Ser Leu Thr Gly
145                 150                 155                 160
Gly Met Ala Leu Ala Ala Leu Asn Thr Ile Gly Asp Thr Gln Arg Lys
                165                 170                 175
Met Leu Ile Val Leu Asn Asp Asn Glu Met Ser Ile Ser Glu Asn Val
                180                 185                 190
Gly Ala Met Asn Lys Phe Met Arg Gly Leu Gln Val Gln Lys Trp Phe
                195                 200                 205
Gln Glu Gly Glu Gly Ala Gly Asn Lys Ala Met Gln Ala Val Ser Arg
            210                 215                 220
Pro Leu Ala Asn Phe Met Ser Arg Ala Lys Ser Ser Thr Cys His Phe
225                 230                 235                 240
Phe Asp Pro Ala Ser Val Asn Pro Phe Ala Thr Met Gly Val Arg Tyr
                245                 250                 255
Val Gly Pro Val Asp Gly His Asn Val Gln Glu Leu Val Trp Leu Leu
            260                 265                 270
Glu Arg Leu Val Glu Leu Asp Gly Pro Thr Ile Leu His Val Val Thr
            275                 280                 285
Lys Lys Gly Lys Gly Leu Ser Tyr Ala Glu Ala Asp Pro Ile Tyr Trp
            290                 295                 300
His Gly Pro Gly Lys Phe Asp Pro Glu Thr Gly Asp Phe Val Pro Ser
305                 310                 315                 320
Asn Ala Tyr Ser Trp Ser Asn Ala Phe Gly Asp Ala Val Thr Glu Leu
                325                 330                 335
Ala Lys Ala Asp Pro Arg Thr Phe Val Ile Thr Pro Ala Met Arg Glu
                340                 345                 350
Gly Ser Gly Leu Val Gly Tyr Ser Lys Ala His Pro His Arg Tyr Leu
            355                 360                 365
Asp Val Gly Ile Ala Glu Glu Val Ala Val Thr Ala Ala Ala Gly Met
            370                 375                 380
Ala Leu Gln Gly Leu Arg Pro Val Val Ala Ile Tyr Ser Thr Phe Leu
385                 390                 395                 400
Gln Arg Ala Tyr Asp Gln Val Leu His Asp Val Ala Ile Glu His Leu
                405                 410                 415
Asn Val Thr Phe Ala Ile Asp Arg Ala Gly Ile Val Gly Ala Asp Gly
                420                 425                 430
Ala Thr His Asn Gly Val Phe Asp Leu Ser Phe Leu Arg Ser Ile Pro
            435                 440                 445
Gly Val Arg Ile Gly Leu Pro Lys Asp Ala Thr Glu Leu Arg Gly Met
            450                 455                 460
Leu Lys Tyr Ala Gln Glu His Pro Gly Pro Phe Ala Ile Arg Tyr Pro
465                 470                 475                 480
Arg Gly Thr Thr Glu Arg Val Pro Glu Gly Thr Trp Pro Thr Leu Ala
                485                 490                 495
Trp Gly Thr Trp Glu Arg Val Lys Ser Gly Asp Asp Val Val Ile Leu
                500                 505                 510
Ala Gly Gly Lys Gly Leu Glu Tyr Ala Gln Lys Ala Ala Ala Asp Leu
            515                 520                 525
```

```
Pro Gly Val Gly Val Val Asn Ala Arg Phe Val Lys Pro Leu Asp Asp
        530                 535                 540

Ala Met Leu Arg Glu Val Ala Gly Ser Ala Arg Ala Ile Val Thr Val
545                 550                 555                 560

Glu Asp Asn Thr Val Val Gly Gly Phe Gly Ser Ala Val Leu Glu Ala
                565                 570                 575

Leu Asn Ala Trp Gly Leu Thr Val Pro Val Arg Val Leu Gly Ile Pro
            580                 585                 590

Asp Glu Phe Gln Glu His Ala Thr Val Asp Ser Val His Ala Arg Ala
        595                 600                 605

Gly Ile Asp Ala Pro Ala Ile Arg Thr Val Leu Ala Glu Leu Gly Val
    610                 615                 620

Asp Val Pro Leu Gly Val
625                 630
```

<210> SEQ ID NO 17
<211> LENGTH: 684
<212> TYPE: DNA
<213> ORGANISM: Deinococcus geothermalis

<400> SEQUENCE: 17

```
gtgaccagcg tctgcttcct ggccggccgc accgccgccc tgattcccgc tgccgggtcc      60
ggcacccgcc tgggccgcgg gcccaaggcc tttgtcgagg tggcgggcca agcctcctg     120
gcacgcagcg tggctgccct tgcgccctgg gtggacgaag tgctcgtggc gctgccggag    180
ggcttccctc ttccgccggg ccttcccgcg caggctatcc tgggcggcac gacccggcag    240
gagagcgtgt ggcggctgct gcacgcgacc acagcggacg tggtgctcgt ccacgacgcg    300
gcgcggccct tcctgccggg gcggtggtc acggcgctcc ttgaggccgt gtccgagacc     360
ggcgccgcca ccgccgccct gccggtggcc gacaccctgg tgcgaggcga gcggggcagg    420
tgggcggacc tcgtcccgcg cgaggacctc tgggctgtgc agacgccgca aggtttccgc    480
cgtgcgttgc tgctgcgggc acacgcagcg gcgcgggcgg agggcttcgg cgccacagac    540
gacgcaggcc tgatcgcgcg gctgggcctc ccggtgaggc tggtgcctgg cgacgcccgg    600
ctcttcaagg tcaccactcc cggcgacctt gcgcttgcgc aggcggtggc ggcagtgtgg    660
gatgctacgt gtgatgcccc ctga                                          684
```

<210> SEQ ID NO 18
<211> LENGTH: 227
<212> TYPE: PRT
<213> ORGANISM: Deinococcus geothermalis

<400> SEQUENCE: 18

```
Val Thr Ser Val Cys Phe Leu Ala Gly Arg Thr Ala Ala Leu Ile Pro
1               5                   10                  15

Ala Ala Gly Ser Gly Thr Arg Leu Gly Arg Gly Pro Lys Ala Phe Val
            20                  25                  30

Glu Val Ala Gly Gln Ser Leu Leu Ala Arg Ser Val Ala Ala Leu Ala
        35                  40                  45

Pro Trp Val Asp Glu Val Leu Val Ala Leu Pro Glu Gly Phe Pro Leu
    50                  55                  60

Pro Pro Gly Leu Pro Ala Gln Ala Ile Leu Gly Gly Thr Thr Arg Gln
65                  70                  75                  80

Glu Ser Val Trp Arg Leu Leu His Ala Thr Thr Ala Asp Val Val Leu
                85                  90                  95
```

Val His Asp Ala Ala Arg Pro Phe Leu Pro Gly Ala Val Thr Ala
            100                 105                 110

Leu Leu Glu Ala Val Ser Glu Thr Gly Ala Ala Thr Ala Leu Pro
        115                 120                 125

Val Ala Asp Thr Leu Val Arg Gly Glu Arg Gly Arg Trp Ala Asp Leu
130                 135                 140

Val Pro Arg Glu Asp Leu Trp Ala Val Gln Thr Pro Gln Gly Phe Arg
145                 150                 155                 160

Arg Ala Leu Leu Leu Arg Ala His Ala Ala Arg Ala Glu Gly Phe
                165                 170                 175

Gly Ala Thr Asp Asp Ala Gly Leu Ile Ala Arg Leu Gly Leu Pro Val
            180                 185                 190

Arg Leu Val Pro Gly Asp Ala Arg Leu Phe Lys Val Thr Thr Pro Gly
        195                 200                 205

Asp Leu Ala Leu Ala Gln Ala Val Ala Ala Val Trp Asp Ala Thr Cys
    210                 215                 220

Asp Ala Pro
225

<210> SEQ ID NO 19
<211> LENGTH: 699
<212> TYPE: DNA
<213> ORGANISM: Deinococcus yunweiensis

<400> SEQUENCE: 19
gtgagcggtt cgtcctccac cgactccacc gacaccgccg cggcgctgat tcccgccgcc     60
ggggcgggca cgcgtctggg tctggggccg aaggcttacc tgagtgtgaa cggccgcagc    120
ctgctgcgtc gcagtatcga cgcactgctc ccgcacgtgg acgaggtgat cgtggccctg    180
cccgccggcc tgccgcccag cgctggatca gagctggcgg acgtccgggt gatcgtgggc    240
ggcgcgacgc ggcaggacac ggtgtatgcc ctgttgcagg ccacggcggc cgccacgtc     300 ctgatccacg atgccgcccg gcccttcctg ggggccgcga ccatccacgc cctgctggcc    360
gccgtgcgcg agactggagc cgcgaccgcc gcgctgccgg tggccgacac cctggtgagg    420
gccacgccgg gtggcgagtg gctccagggc gtgccccgcg atcacctgtg ggccgtgcag    480
accccccagg cgttccggcg gctggagctg ctggccgcgc acgagcaggc ccgcgccgac    540
ggccacgccg ccaccgacga cgcgggcctg ctcgcccggc aggggcatcc ggtgcggctg    600
gtgcccggcg acgcccggct gttcaaggtg accacgcccg ccgacctgcc cctggctcag    660
gcggttgccc gggtgtggga tgctgatgac catgcctga                          699

<210> SEQ ID NO 20
<211> LENGTH: 232
<212> TYPE: PRT
<213> ORGANISM: Deinococcus yunweiensis

<400> SEQUENCE: 20

Val Ser Gly Ser Ser Ser Thr Asp Ser Thr Asp Thr Ala Ala Ala Leu
1               5                   10                  15

Ile Pro Ala Ala Gly Ala Gly Thr Arg Leu Gly Leu Gly Pro Lys Ala
            20                  25                  30

Tyr Leu Ser Val Asn Gly Arg Ser Leu Leu Arg Arg Ser Ile Asp Ala
        35                  40                  45

Leu Leu Pro His Val Asp Glu Val Ile Val Ala Leu Pro Ala Gly Leu
    50                  55                  60

Pro Pro Ser Ala Gly Ser Glu Leu Ala Asp Val Arg Val Ile Val Gly
65                  70                  75                  80

Gly Ala Thr Arg Gln Asp Thr Val Tyr Ala Leu Leu Gln Ala Thr Ala
                85                  90                  95

Ala Arg His Val Leu Ile His Asp Ala Ala Arg Pro Phe Leu Gly Ala
            100                 105                 110

Ala Thr Ile His Ala Leu Leu Ala Ala Val Arg Glu Thr Gly Ala Ala
            115                 120                 125

Thr Ala Ala Leu Pro Val Ala Asp Thr Leu Val Arg Ala Thr Pro Gly
    130                 135                 140

Gly Glu Trp Leu Gln Gly Val Pro Arg Asp His Leu Trp Ala Val Gln
145                 150                 155                 160

Thr Pro Gln Ala Phe Arg Arg Leu Glu Leu Leu Ala Ala His Glu Gln
                165                 170                 175

Ala Arg Ala Asp Gly His Ala Ala Thr Asp Ala Gly Leu Leu Ala
            180                 185                 190

Arg Gln Gly His Pro Val Arg Leu Val Pro Gly Asp Ala Arg Leu Phe
    195                 200                 205

Lys Val Thr Thr Pro Ala Asp Leu Pro Leu Ala Gln Ala Val Ala Arg
    210                 215                 220

Val Trp Asp Ala Asp Asp His Ala
225                 230

<210> SEQ ID NO 21
<211> LENGTH: 492
<212> TYPE: DNA
<213> ORGANISM: Deinococcus geothermalis

<400> SEQUENCE: 21
atgacccctt ccccctccc ctaccgcatc ggctacggag aagacgcgca ccgcctgacc      60
gaggggcgag cgttggtgct gggcggcgta cctatccccc acgccgaacg cggcgcggtc    120
gcgcacagtg acggggacgc cgtgctgcac gcgctggctg acgcgctgct ttcgggcatg    180
agcctgggcg acatcgggca gtattacccc gacaccgacc ctgcccacgc ggggctggac    240
tcgcgggtga ttctggccga cagcctggcg ctggtgcgcg agtggaagta cgttccggca    300
aacgtcgcgc tggtgatcac cctcgaccgc cccaaattgg ggccgctgcg cgccgacatc    360
gcccgcaacg tggctgccct gctgggcctg aatgaaacgg aggtagggt gagcttcaag    420 acctccgagg cctggcgcc tgagcatgtg caggtacggg tcacggtgct gctgcggcgg    480
gtggaggggt ga                                                       492

<210> SEQ ID NO 22
<211> LENGTH: 163
<212> TYPE: PRT
<213> ORGANISM: Deinococcus geothermalis

<400> SEQUENCE: 22

Met Thr Pro Ser Pro Leu Pro Tyr Arg Ile Gly Tyr Gly Glu Asp Ala
1               5                   10                  15

His Arg Leu Thr Glu Gly Arg Ala Leu Val Leu Gly Gly Val Pro Ile
            20                  25                  30

Pro His Ala Glu Arg Gly Ala Val Ala His Ser Asp Gly Asp Ala Val
        35                  40                  45

Leu His Ala Leu Ala Asp Ala Leu Leu Ser Gly Met Ser Leu Gly Asp
    50                  55                  60

Ile Gly Gln Tyr Tyr Pro Asp Thr Asp Pro Ala His Ala Gly Leu Asp
65                  70                  75                  80

Ser Arg Val Ile Leu Ala Asp Ser Leu Ala Leu Val Arg Glu Trp Lys
                85                  90                  95

Tyr Val Pro Ala Asn Val Ala Leu Val Ile Thr Leu Asp Arg Pro Lys
            100                 105                 110

Leu Gly Pro Leu Arg Ala Asp Ile Ala Arg Asn Val Ala Ala Leu Leu
            115                 120                 125

Gly Leu Asn Glu Thr Glu Val Gly Val Ser Phe Lys Thr Ser Glu Gly
            130                 135                 140

Leu Ala Pro Glu His Val Gln Val Arg Val Thr Val Leu Leu Arg Arg
145                 150                 155                 160

Val Glu Gly

<210> SEQ ID NO 23
<211> LENGTH: 495
<212> TYPE: DNA
<213> ORGANISM: Deinococcus yunweiensis

<400> SEQUENCE: 23
atggttccca cccttcccta ccgcatcggc tacggcgagg acgcccaccg gctggaggcc      60
gggcggcccc tgatcctggg cggcgtgccc gtgccggagt cccccacgg cgcggtggcc     120 cacagcgacg gcgacgccgt gctgcacgcg gtcgcggacg cgctgctgtc ggggctggcg     180
ctgggcgata tcgggcagta cttccccgac acggccgccg agtggcacgg cctggactcg     240
cgggtgatcg tggcgcgggc gctggagctg gtgcgggaac gcggctacgg accggtcaat     300
gtggctctgg tggtcacgct ggatcgcccg aagctggggc gctgcgggc cgacattgcc     360 cgcagcgtgg cggccctgct gaccctgccg gacaccgagg tcggcgtgag cttcaagacc     420
tccgagggcc tggccccgc ccacgtgcag gtgcgcgtga cagccctgct ggcccggacg     480
gagaccgccg ggtga                                                     495

<210> SEQ ID NO 24
<211> LENGTH: 164
<212> TYPE: PRT
<213> ORGANISM: Deinococcus yunweiensis

<400> SEQUENCE: 24

Met Val Pro Thr Leu Pro Tyr Arg Ile Gly Tyr Gly Glu Asp Ala His
1               5                   10                  15

Arg Leu Glu Ala Gly Arg Pro Leu Ile Leu Gly Gly Val Pro Val Pro
                20                  25                  30

Glu Ser Pro His Gly Ala Val Ala His Ser Asp Gly Asp Ala Val Leu
            35                  40                  45

His Ala Val Ala Asp Ala Leu Leu Ser Gly Leu Ala Leu Gly Asp Ile
        50                  55                  60

Gly Gln Tyr Phe Pro Asp Thr Ala Ala Glu Trp His Gly Leu Asp Ser
65                  70                  75                  80

Arg Val Ile Val Ala Arg Ala Leu Glu Leu Val Arg Glu Arg Gly Tyr
                85                  90                  95

Gly Pro Val Asn Val Ala Leu Val Val Thr Leu Asp Arg Pro Lys Leu
            100                 105                 110

Gly Pro Leu Arg Ala Asp Ile Ala Arg Ser Val Ala Ala Leu Leu Thr
            115                 120                 125

Leu Pro Asp Thr Glu Val Gly Val Ser Phe Lys Thr Ser Glu Gly Leu
130                 135                 140

Ala Pro Ala His Val Gln Val Arg Val Thr Ala Leu Leu Ala Arg Thr
145                 150                 155                 160

Glu Thr Ala Gly

<210> SEQ ID NO 25
<211> LENGTH: 1275
<212> TYPE: DNA
<213> ORGANISM: Deinococcus geothermalis

<400> SEQUENCE: 25

```
atgccccgc  ccgtccgcgt  aaactggccg  cgtatgagga  ccacgcgccg  tcagaccgtg     60
accacctggg  tcgggaatgt  tcctgtgggg  agtgcgcacc  ccattgtcgt  gcagtccatg    120
acgaataccg  acaccgcgaa  tgctgaggca  accgcccttc  aggttgcgca  gcttgcgcgg    180
gccgggtcgg  agattgtgcg  tgtgaccgtc  aatacccgcg  aggccgccgc  cgcccttccc    240
gaaatcgtgg  cccgcctgca  cgacttgggt  ttggatgtgc  cctggtgggg  ggatttccac    300
tacaacggcc  atctcctgct  gcgcgagtat  cccgagacgg  cgcggctgct  cgccaagtac    360
cgcatcaacc  ccggcaatgt  gggtgctggg  cagcaccacg  acgccaactt  cgctaccatg    420
atcgaggttg  ccaaggaatt  cggtaaaccg  gttcgcatcg  gcgtgaactg  gggcagcctc    480
gaccagcagg  tgctcgcccg  gttgatggac  gagaacgccc  ggcggggcag  ccccaagtcc    540
ggcaccgacg  tgatgatcga  cgcgatggtc  accagcgccc  tggaaagcgc  cgcgtacgcc    600
gaggggctgg  gcctcccgca  cgacaagatc  atcatctcgg  tcaaggtcag  ctccgctccc    660
gaactgtggc  aggtgtaccg  tcagctcgcg  ccgctgtgcg  actatcccct  ccacctcggc    720
ctgaccgaag  cggggatggg  catgaagggc  atggtgcgt   ccagcgtggc  cctcgctccc    780
ctgctcagcg  aggggatcgg  ggacaccatc  cgcgtttccc  tgaccctga  accggcgcc    840
ccccgcaagc  tggaggtgga  ggtcgcgcaa  cagattctcc  agagcctggg  cctccggcag    900
tttctcccgc  aggtcacctc  ctgtcccggc  tgcgggcgca  ccacctccac  cttctttcag    960
gaactcgccc  gcaagattca  ggactacatc  cgtgacgcga  tgcccgaatg  gaaggcgaag   1020
tatcccggtg  tcgaggacat  gcaggtcgcc  gtgatgggct  gcatcgtcaa  tggccccggc   1080
gagagcaagc  acgccaacat  cggcatctcg  ctgcccggca  ccggcgaaga  ccccgcgca    1140
cccgtctacc  aagacggcaa  gctgctgacc  accctgagag  gcccgcgcat  tgccgaggac   1200
tttcaggaat  tgcttgaaaa  gtacgtggaa  gaacgctatg  acacaaaatc  cgcccacaca   1260
acagtccagg  agtga                                                       1275
```

<210> SEQ ID NO 26
<211> LENGTH: 424
<212> TYPE: PRT
<213> ORGANISM: Deinococcus geothermalis

<400> SEQUENCE: 26

Met Pro Pro Pro Val Arg Val Asn Trp Pro Arg Met Arg Thr Thr Arg
1               5                   10                  15

Arg Gln Thr Val Thr Thr Trp Val Gly Asn Val Pro Val Gly Ser Ala
                20                  25                  30

His Pro Ile Val Val Gln Ser Met Thr Asn Thr Asp Thr Ala Asn Ala
            35                  40                  45

Glu Ala Thr Ala Leu Gln Val Ala Gln Leu Ala Arg Ala Gly Ser Glu
        50                  55                  60

Ile Val Arg Val Thr Val Asn Thr Arg Glu Ala Ala Ala Leu Pro
65                  70                  75                  80

Glu Ile Val Ala Arg Leu His Asp Leu Gly Leu Asp Val Pro Leu Val
            85                  90                  95

Gly Asp Phe His Tyr Asn Gly His Leu Leu Arg Glu Tyr Pro Glu
        100                 105                 110

Thr Ala Arg Leu Leu Ala Lys Tyr Arg Ile Asn Pro Gly Asn Val Gly
        115                 120                 125

Ala Gly Gln His His Asp Ala Asn Phe Ala Thr Met Ile Glu Val Ala
130                 135                 140

Lys Glu Phe Gly Lys Pro Val Arg Ile Gly Val Asn Trp Gly Ser Leu
145                 150                 155                 160

Asp Gln Gln Val Leu Ala Arg Leu Met Asp Glu Asn Ala Arg Arg Gly
                165                 170                 175

Ser Pro Lys Ser Gly Thr Asp Val Met Ile Asp Ala Met Val Thr Ser
            180                 185                 190

Ala Leu Glu Ser Ala Ala Tyr Ala Glu Gly Leu Gly Leu Pro His Asp
        195                 200                 205

Lys Ile Ile Ile Ser Val Lys Val Ser Ser Ala Pro Glu Leu Trp Gln
210                 215                 220

Val Tyr Arg Gln Leu Ala Pro Leu Cys Asp Tyr Pro Leu His Leu Gly
225                 230                 235                 240

Leu Thr Glu Ala Gly Met Gly Met Lys Gly Met Val Ala Ser Ser Val
                245                 250                 255

Ala Leu Ala Pro Leu Leu Ser Glu Gly Ile Gly Asp Thr Ile Arg Val
            260                 265                 270

Ser Leu Thr Pro Glu Pro Gly Ala Pro Arg Lys Leu Glu Val Glu Val
        275                 280                 285

Ala Gln Gln Ile Leu Gln Ser Leu Gly Leu Arg Gln Phe Leu Pro Gln
290                 295                 300

Val Thr Ser Cys Pro Gly Cys Gly Arg Thr Thr Ser Thr Phe Phe Gln
305                 310                 315                 320

Glu Leu Ala Arg Lys Ile Gln Asp Tyr Ile Arg Asp Ala Met Pro Glu
                325                 330                 335

Trp Lys Ala Lys Tyr Pro Gly Val Glu Asp Met Gln Val Ala Val Met
            340                 345                 350

Gly Cys Ile Val Asn Gly Pro Gly Glu Ser Lys His Ala Asn Ile Gly
        355                 360                 365

Ile Ser Leu Pro Gly Thr Gly Glu Asp Pro Arg Ala Pro Val Tyr Gln
370                 375                 380

Asp Gly Lys Leu Leu Thr Thr Leu Arg Gly Pro Arg Ile Ala Glu Asp
385                 390                 395                 400

Phe Gln Glu Leu Leu Glu Lys Tyr Val Glu Glu Arg Tyr Gly His Lys
                405                 410                 415

Ser Ala His Thr Thr Val Gln Glu
            420

<210> SEQ ID NO 27
<211> LENGTH: 1263
<212> TYPE: DNA
<213> ORGANISM: Deinococcus yunweiensis

<400> SEQUENCE: 27
ctggaatggc ggaagttcca gatgacgacc cgccggcaga ccgtgaccgt ggacgtgggc    60

```
ggcgtgccca tcggcagcgc ccacccatc gtcgtgcaga gcatgaccaa caccgacacc    120
gccgacgccg agggcaccgc gatccagatc gcgcaactgg cccgcgctgg cagcgagatc    180
gtgcgcgtca ctgtgaacac ccgtgaggca gccgccgcca tccccgagat cgtcgcccgg    240
ctcgccgagg tcggcctgag cgttcccatc gtcggggact ccactacaa cggacacatc     300 ctgctgcgtg aatttcctga cggcgcggg ctgctcgcca agtaccgcat caaccccggc     360
aatgtcggcg cgggccagca ccacgacgcg aacttcgcca ccatgatcga agtcgccaag    420
gagtacgaca agccggtgcg gatcggtgtg aactggggca gtctggatca gcaggtgctc    480
gcccgcctga tggacgagaa gcggcgcgcg gcagccccca gagcgggac cgacgtcatg     540 atcgacgcga tggtcgtgtc ggcgctggaa tcagccgcgt atgccgagga actgggcctg    600
gcgcacgaca agatcctgat ctcagtgaag gtgagcagcg ctcccgaact gtggcaggtc    660
taccggcaac tcgcgccgct gtgcgactac cccctgcacc tgggcctgac cgaggctggt    720
atgggcatga aggcatcgt ggcgtcgtcc gtggccctgg ctccgctgct caccgagggc    780
atcggcgaca ccatccgcgt gagcctgacc ccggaaccgg gcgcgagccg caagctggag    840
gtcgaggtcg cacagcagat gctccagagc ctggggctgc gccagtttct cccgcaggtc    900
accagttgcc ccggctgtgg gcgcaccacc agtgtgttct tcaggaact ggcgcagaag    960 attcaggact acatacgcga cacgatgccg gactggaaac agaagtaccc cggtgtcgag   1020
gacatgcagg tcgccgtgat gggctgcatc gtgaacggcc ccggtgagag caagcacgcc   1080
aacatcggca tttctctgcc cggcactggg gaagacccc cgcccccggt gtatcaggac    1140
ggcaagctgc tgacgaccct cagaggcccc cggatcgccg aggacttcca ggccctgatg    1200
gagaagtacg tcgaggaacg gtacgggcac gccgcgcagg ccccggcgtc aacgctggtc    1260
taa                                                                 1263
```

<210> SEQ ID NO 28
<211> LENGTH: 420
<212> TYPE: PRT
<213> ORGANISM: Deinococcus yunweiensis

<400> SEQUENCE: 28

```
Leu Glu Trp Arg Lys Phe Gln Met Thr Thr Arg Arg Gln Thr Val Thr
1               5                   10                  15

Val Asp Val Gly Gly Val Pro Ile Gly Ser Ala His Pro Ile Val Val
            20                  25                  30

Gln Ser Met Thr Asn Thr Asp Thr Ala Asp Ala Glu Gly Thr Ala Ile
        35                  40                  45

Gln Ile Ala Gln Leu Ala Arg Ala Gly Ser Glu Ile Val Arg Val Thr
    50                  55                  60

Val Asn Thr Arg Glu Ala Ala Ala Ile Pro Glu Ile Val Ala Arg
65                  70                  75                  80

Leu Ala Glu Val Gly Leu Ser Val Pro Ile Val Gly Asp Phe His Tyr
                85                  90                  95

Asn Gly His Ile Leu Leu Arg Glu Phe Pro Glu Thr Ala Arg Leu Leu
            100                 105                 110

Ala Lys Tyr Arg Ile Asn Pro Gly Asn Val Gly Ala Gly Gln His His
        115                 120                 125

Asp Ala Asn Phe Ala Thr Met Ile Glu Val Ala Lys Glu Tyr Asp Lys
    130                 135                 140

Pro Val Arg Ile Gly Val Asn Trp Gly Ser Leu Asp Gln Gln Val Leu
```

```
            145                 150                 155                 160
        Ala Arg Leu Met Asp Glu Asn Ala Ala Ala Gly Ser Pro Lys Ser Gly
                        165                 170                 175

Thr Asp Val Met Ile Asp Ala Met Val Val Ser Ala Leu Glu Ser Ala
                        180                 185                 190

Ala Tyr Ala Glu Glu Leu Gly Leu Ala His Asp Lys Ile Leu Ile Ser
                        195                 200                 205

Val Lys Val Ser Ser Ala Pro Glu Leu Trp Gln Val Tyr Arg Gln Leu
                        210                 215                 220

Ala Pro Leu Cys Asp Tyr Pro Leu His Leu Gly Leu Thr Glu Ala Gly
        225                 230                 235                 240

Met Gly Met Lys Gly Ile Val Ala Ser Ser Val Ala Leu Ala Pro Leu
                        245                 250                 255

Leu Thr Glu Gly Ile Gly Asp Thr Ile Arg Val Ser Leu Thr Pro Glu
                        260                 265                 270

Pro Gly Ala Ser Arg Lys Leu Glu Val Glu Val Ala Gln Gln Met Leu
                        275                 280                 285

Gln Ser Leu Gly Leu Arg Gln Phe Leu Pro Val Thr Ser Cys Pro
        290                 295                 300

Gly Cys Gly Arg Thr Thr Ser Val Phe Phe Gln Glu Leu Ala Gln Lys
        305                 310                 315                 320

Ile Gln Asp Tyr Ile Arg Asp Thr Met Pro Asp Trp Lys Gln Lys Tyr
                        325                 330                 335

Pro Gly Val Glu Asp Met Gln Val Ala Val Met Gly Cys Ile Val Asn
                        340                 345                 350

Gly Pro Gly Glu Ser Lys His Ala Asn Ile Gly Ile Ser Leu Pro Gly
                        355                 360                 365

Thr Gly Glu Asp Pro Arg Ala Pro Val Tyr Gln Asp Gly Lys Leu Leu
                        370                 375                 380

Thr Thr Leu Arg Gly Pro Arg Ile Ala Glu Asp Phe Gln Ala Leu Met
        385                 390                 395                 400

Glu Lys Tyr Val Glu Glu Arg Tyr Gly His Ala Ala Gln Ala Pro Ala
                        405                 410                 415

Ser Thr Leu Val
                420

<210> SEQ ID NO 29
<211> LENGTH: 1041
<212> TYPE: DNA
<213> ORGANISM: Deinococcus geothermalis

<400> SEQUENCE: 29
gtgaccgacc ccgacccgaa cgctgccgcg cccacaggcc tcccggcacg caagctgcgg      60
catcttgaag cctgtctgcg cccggaaagt cagtacatgg gcgtgactac cgggctggag     120
cgggtgccct ggccttaccg ggcgctccca gagctggacc tggaggcggt ggacctcacg     180
acgaccttcc tgggtcggag actgcgtgcc ccggtgttga ttggagcgat gacgggaggc     240
gcgcagcggg cggaggtcat caatcgcaac ctcgccaccg ccgcggagcg gttgggcatc     300
gggatgatgt tgggtcaca gcgagtgatg ctggagcgcc tgaagcagc ggtcagcttt      360 cgcgtgcgcg acgtggcccc cggtgtactg ctgctgggaa atctcggagc ggcacagttt     420
ctgctggggt acggcgtgtc cgaggccgag cggcggtgc gggcggtgga ggcagacggc      480
ctcgccatcc atctcaaccc gctgcaagaa gccatgcagg ccggtgggga cacgcgctgg     540
```

-continued

```
cgaggtctcg cggcgcggct ggccgaggtg gtgcccgctc tgccttttcc ggtgattctc    600
aaggaggtgg ggcatggcct ggatccggcc actgtgcaga ccgtggccac ggcgggtttt    660
gcggcgctgg acgtggcggg cgcgggcggt acgagttggg cgcgggttga gcaactggtg    720
cgctacggcg ccgttctcgc gccggacctg tgcgaagtgg gactgcccac cgcaccggcc    780
atcgtggagg cgcgccgggc agctcccgga acacccctga tcgcctccgg gggcatccgc    840
accggtttgg acgcagcgcg tgccctggcc ctcggcgcgc aggtggtggc ggtggctcgg    900
cctctcctcg ctcccgcgct ggagagtgcg gcggcggtag aggcgtggct tgcgcggttc    960
attcacgagc tgcgggtggc gctgtttgtg ggcggcttca ggagtgtgga ggcggtgcgg   1020
ggccggctcg agctggtttg a                                             1041
```

<210> SEQ ID NO 30
<211> LENGTH: 346
<212> TYPE: PRT
<213> ORGANISM: Deinococcus geothermalis

<400> SEQUENCE: 30

```
Val Thr Asp Pro Asp Pro Asn Ala Ala Ala Pro Thr Gly Leu Pro Ala
1               5                   10                  15

Arg Lys Leu Arg His Leu Glu Ala Cys Leu Arg Pro Glu Ser Gln Tyr
            20                  25                  30

Met Gly Val Thr Thr Gly Leu Glu Arg Val Pro Trp Pro Tyr Arg Ala
        35                  40                  45

Leu Pro Glu Leu Asp Leu Glu Ala Val Asp Leu Thr Thr Thr Phe Leu
    50                  55                  60

Gly Arg Arg Leu Arg Ala Pro Val Leu Ile Gly Ala Met Thr Gly Gly
65                  70                  75                  80

Ala Gln Arg Ala Glu Val Ile Asn Arg Asn Leu Ala Thr Ala Ala Glu
                85                  90                  95

Arg Leu Gly Ile Gly Met Met Leu Gly Ser Gln Arg Val Met Leu Glu
            100                 105                 110

Arg Pro Glu Ala Ala Val Ser Phe Arg Val Arg Asp Val Ala Pro Gly
        115                 120                 125

Val Leu Leu Leu Gly Asn Leu Gly Ala Ala Gln Phe Leu Leu Gly Tyr
    130                 135                 140

Gly Val Ser Glu Ala Glu Arg Ala Val Arg Ala Val Glu Ala Asp Gly
145                 150                 155                 160

Leu Ala Ile His Leu Asn Pro Leu Gln Glu Ala Met Gln Ala Gly Gly
                165                 170                 175

Asp Thr Arg Trp Arg Gly Leu Ala Ala Arg Leu Ala Glu Val Val Pro
            180                 185                 190

Ala Leu Pro Phe Pro Val Ile Leu Lys Glu Val Gly His Gly Leu Asp
        195                 200                 205

Pro Ala Thr Val Gln Thr Val Ala Thr Ala Gly Phe Ala Ala Leu Asp
    210                 215                 220

Val Ala Gly Ala Gly Gly Thr Ser Trp Ala Arg Val Glu Gln Leu Val
225                 230                 235                 240

Arg Tyr Gly Ala Val Leu Ala Pro Asp Leu Cys Glu Val Gly Leu Pro
                245                 250                 255

Thr Ala Pro Ala Ile Val Glu Ala Arg Arg Ala Ala Pro Gly Thr Pro
            260                 265                 270

Leu Ile Ala Ser Gly Gly Ile Arg Thr Gly Leu Asp Ala Ala Arg Ala
        275                 280                 285
```

Leu Ala Leu Gly Ala Gln Val Val Ala Val Ala Arg Pro Leu Leu Ala
    290                 295                 300

Pro Ala Leu Glu Ser Ala Ala Val Glu Ala Trp Leu Ala Arg Phe
305                 310                 315                 320

Ile His Glu Leu Arg Val Ala Leu Phe Val Gly Gly Phe Arg Ser Val
                325                 330                 335

Glu Ala Val Arg Gly Arg Leu Glu Leu Val
            340                 345

<210> SEQ ID NO 31
<211> LENGTH: 1053
<212> TYPE: DNA
<213> ORGANISM: Deinococcus yunweiensis

<400> SEQUENCE: 31
gtggacgact cgacgagcgg catccaggca cgcaagatgc accatctcca agcgtgtctg      60
gagccgcaca gccagtacca gacggtcacg accggcctgg acgcggtgcc ctggccgtac     120
cgggcgctgc ccgaggtcga tctgccggcc gtacagctcc agacaagctt cctgggtcgc     180
cggctggccg cccccgtgct gatcggtgcc atgaccggcg gggccgagcg ggcacggatc     240
atcaaccgca atctggcgat ggctgcgcag cgcctgggca tcggcatgat gctcggctcg     300
cagcgcgtca tgctggagcg cccggaggtg accgagacct tccgcgtgcg cgatgtggcc     360
ccggacatcc tgctcgtcgg gaatctgggg gcggcgcagt tcggcctggg ctacggcgcg     420
gccgaggcgc tccgcgccgt acagcagatc gacgccgacg ccctggcgat tcatgccaat     480
ccccttcagg aagccatgca ggctgggggg gacacgcgct ggcggggcct gctggaacgc     540
ctgtcggacg tggtaccagc gctgccgttc ccgacgatcc tgaaggaagt cggacatggg     600
ctggatgtcc acaccgccca cgcggcggcc gacctgggct tcacgcgcct ggatgtggcc     660
ggggccggtg gcacgagctg ggcgcggggtg gagcagctcg tccgctacgg cacggtgcgc     720
tcgccggccc tgtgtgagct gggcatcccg accgcgcggg cctgcgggga cgtgcggggc     780
gccctgcccg gcatgccgct ggtcgcgtcc ggggcatcc gcaccggcct ggacgccgcc     840
cgtgccctgg cgctgggggc gcaggtggtc gccattgccc ggcccctgct ggaaccggca     900
ttggacggcc cggacgcggc cgaggcgtgg ctcgcggcct tcatccacga cctgcggatc     960
gcgctgtttg tcggtggcta cgacagtgtg gacgaggtgc gcccggcgct ggactggccg    1020
ctggtgtcgg gggctgtcag ctctgggctg tga                                 1053

<210> SEQ ID NO 32
<211> LENGTH: 350
<212> TYPE: PRT
<213> ORGANISM: Deinococcus yunweiensis

<400> SEQUENCE: 32

Val Asp Asp Ser Thr Ser Gly Ile Gln Ala Arg Lys Met His His Leu
1               5                   10                  15

Gln Ala Cys Leu Glu Pro His Ser Gln Tyr Gln Thr Val Thr Thr Gly
            20                  25                  30

Leu Asp Ala Val Pro Trp Pro Tyr Arg Ala Leu Pro Glu Val Asp Leu
        35                  40                  45

Pro Ala Val Gln Leu Gln Thr Ser Phe Leu Gly Arg Arg Leu Ala Ala
    50                  55                  60

Pro Val Leu Ile Gly Ala Met Thr Gly Gly Ala Glu Arg Ala Arg Ile
65                  70                  75                  80

```
Ile Asn Arg Asn Leu Ala Met Ala Ala Gln Arg Leu Gly Ile Gly Met
                 85                  90                  95

Met Leu Gly Ser Gln Arg Val Met Leu Glu Arg Pro Glu Val Thr Glu
            100                 105                 110

Thr Phe Arg Val Arg Asp Val Ala Pro Asp Ile Leu Leu Val Gly Asn
        115                 120                 125

Leu Gly Ala Ala Gln Phe Gly Leu Gly Tyr Gly Ala Ala Glu Ala Leu
    130                 135                 140

Arg Ala Val Gln Gln Ile Asp Ala Asp Ala Leu Ala Ile His Ala Asn
145                 150                 155                 160

Pro Leu Gln Glu Ala Met Gln Ala Gly Gly Asp Thr Arg Trp Arg Gly
                165                 170                 175

Leu Leu Glu Arg Leu Ser Asp Val Val Pro Ala Leu Pro Phe Pro Thr
            180                 185                 190

Ile Leu Lys Glu Val Gly His Gly Leu Asp Val His Thr Ala His Ala
        195                 200                 205

Ala Ala Asp Leu Gly Phe Thr Ala Leu Asp Val Ala Gly Ala Gly Gly
    210                 215                 220

Thr Ser Trp Ala Arg Val Glu Gln Leu Val Arg Tyr Gly Thr Val Arg
225                 230                 235                 240

Ser Pro Ala Leu Cys Glu Leu Gly Ile Pro Thr Ala Arg Ala Leu Arg
                245                 250                 255

Asp Val Arg Gly Ala Leu Pro Gly Met Pro Leu Val Ala Ser Gly Gly
            260                 265                 270

Ile Arg Thr Gly Leu Asp Ala Ala Arg Ala Leu Ala Leu Gly Ala Gln
        275                 280                 285

Val Val Ala Ile Ala Arg Pro Leu Leu Glu Pro Ala Leu Asp Gly Pro
    290                 295                 300

Asp Ala Ala Glu Ala Trp Leu Ala Ala Phe Ile His Asp Leu Arg Ile
305                 310                 315                 320

Ala Leu Phe Val Gly Gly Tyr Asp Ser Val Asp Glu Val Arg Pro Ala
                325                 330                 335

Leu Asp Trp Pro Leu Val Ser Gly Ala Val Ser Ser Gly Leu
            340                 345                 350

<210> SEQ ID NO 33
<211> LENGTH: 10
<212> TYPE: DNA
<213> ORGANISM: Artificial Sequence
<220> FEATURE:
<223> OTHER INFORMATION: none
<220> FEATURE:
<221> NAME/KEY: misc_feature
<222> LOCATION: (1)..(10)
<223> OTHER INFORMATION: n is a, c, g, or t

<400> SEQUENCE: 33 nnnnnnnnnn                                                              10

<210> SEQ ID NO 34
<211> LENGTH: 1164
<212> TYPE: DNA
<213> ORGANISM: Deinococcus geothermalis

<400> SEQUENCE: 34
atgaagctga cggttctggg cagtacgggc agtatcggca cgcaggcgct ggaggtggcg        60
cgggaacgcg gctgggagat cggggcgctc gccgcagggc gcaatctcga cctgctggaa      120
```

```
gcgcaggtac gggcgttcca gccgcaggtg gtgagtgtgg cggcggaggt gtacgcgcag    180
gcgcggcagc ggctgtccgg cgtgcgggtg atcgcggacc ccacggaggc ggcggcgctg    240
cccgcagacg tggtcgtcaa cgcgatgagc ggactggttg ggttggcgcc cacgcgggca    300
gcactggaag ctgggcaagc tctggccctg cgacaaaag aggccatggt cacggcagcg     360
cacctgatgt gggaggccgc agccagcggc ggcggctgcc tcgtaccggt cgattcggaa    420
cacaccggca tgtaccagtg cctgaccggc gaggacctcg cggatgtagc cgaactgatt    480
ctgacggcct cgggtggccc cttttgtgac ggcccggcgg acttgagcgg cgtgacgccg    540
gcccaggccc tgaagcatcc ctcgtggaag atgggaccga aggtaacgct ggattccgcc    600
accctgatga acaaggggct ggaggtgatg gagtgcgctt ccctctacgg cttgcccctc    660
tcgcaggtga gcgtcgtcgt gcatccgcag agcatcgtcc acgcggcggt ccgcttccgc    720
gacggcagcc tgaagggaca gttcggaccg accgacatgc gcctggcgat tgcctacgcg    780
atcgacgccg cgccgaccgg aatgcgccgc cccggtgacg tacgcggggc gcggcgcggg    840
cccgaggtgg ccgagcactt gggctggccg ctgcaggga gctgggagtt ccgcgcaccg     900
gacgtggccc gctttccctg cctggatctg gcctaccgcg caggacaggc gggcggcctc    960
ctcccgacag ccctgaacgc ggcggatgag gtggccgtgg aagcctttct ggacggaaga   1020
atcggcttta tggacatccc gcggctgatc gaacgcgtgc tggacgagac gcctgccgga   1080
gcgctgacct gggagacgct gctggagaca gacgcctggg cgcgggcgcg ggcccaggaa   1140
ctgacggtgg gggtacgggc gtga                                          1164
```

<210> SEQ ID NO 35
<211> LENGTH: 387
<212> TYPE: PRT
<213> ORGANISM: Deinococcus geothermalis

<400> SEQUENCE: 35

```
Met Lys Leu Thr Val Leu Gly Ser Thr Gly Ser Ile Gly Thr Gln Ala
1               5                   10                  15

Leu Glu Val Ala Arg Glu Arg Gly Trp Glu Ile Gly Ala Leu Ala Ala
            20                  25                  30

Gly Arg Asn Leu Asp Leu Leu Glu Ala Gln Val Arg Ala Phe Gln Pro
        35                  40                  45

Gln Val Val Ser Val Ala Ala Glu Val Tyr Ala Gln Ala Arg Gln Arg
    50                  55                  60

Leu Ser Gly Val Arg Val Ile Ala Asp Pro Thr Glu Ala Ala Ala Leu
65                  70                  75                  80

Pro Ala Asp Val Val Asn Ala Met Ser Gly Leu Val Gly Leu Ala
                85                  90                  95

Pro Thr Arg Ala Ala Leu Glu Ala Gly Gln Ala Leu Ala Leu Ala Thr
            100                 105                 110

Lys Glu Ala Met Val Thr Ala Ala His Leu Met Trp Glu Ala Ala Ala
        115                 120                 125

Ser Gly Gly Gly Cys Leu Val Pro Val Asp Ser Glu His Thr Gly Met
    130                 135                 140

Tyr Gln Cys Leu Thr Gly Glu Asp Leu Ala Asp Val Ala Glu Leu Ile
145                 150                 155                 160

Leu Thr Ala Ser Gly Gly Pro Phe Cys Asp Gly Pro Ala Asp Leu Ser
                165                 170                 175

Gly Val Thr Pro Ala Gln Ala Leu Lys His Pro Ser Trp Lys Met Gly
```

|     |     |     |     |     | 180 |     |     |     | 185 |     |     |     |     | 190 |
| --- | --- | --- | --- | --- | --- | --- | --- | --- | --- | --- | --- | --- | --- | --- |

Pro Lys Val Thr Leu Asp Ser Ala Thr Leu Met Asn Lys Gly Leu Glu
     195        200       205

Val Met Glu Cys Ala Ser Leu Tyr Gly Leu Pro Leu Ser Gln Val Ser
210        215       220

Val Val Val His Pro Gln Ser Ile Val His Ala Val Arg Phe Arg
225       230       235       240

Asp Gly Ser Leu Lys Gly Gln Phe Gly Pro Thr Asp Met Arg Leu Ala
     245        250       255

Ile Ala Tyr Ala Ile Asp Ala Ala Pro Thr Gly Met Arg Arg Pro Gly
     260        265       270

Asp Val Arg Gly Ala Arg Arg Gly Pro Glu Val Ala Glu His Leu Gly
   275        280       285

Trp Pro Leu Gln Gly Ser Trp Glu Phe Arg Ala Pro Asp Val Ala Arg
   290        295       300

Phe Pro Cys Leu Asp Leu Ala Tyr Arg Ala Gly Gln Ala Gly Gly Leu
305        310       315       320

Leu Pro Thr Ala Leu Asn Ala Ala Asp Glu Val Ala Val Glu Ala Phe
     325        330       335

Leu Asp Gly Arg Ile Gly Phe Met Asp Ile Pro Arg Leu Ile Glu Arg
     340        345       350

Val Leu Asp Glu Thr Pro Ala Gly Ala Leu Thr Trp Glu Thr Leu Leu
   355        360       365

Glu Thr Asp Ala Trp Ala Arg Ala Arg Ala Gln Glu Leu Thr Val Gly
370        375       380

Val Arg Ala
385

<210> SEQ ID NO 36
<211> LENGTH: 1161
<212> TYPE: DNA
<213> ORGANISM: Deinococcus yunweiensis

<400> SEQUENCE: 36

| | | | | | |
| --- | --- | --- | --- | --- | --- |
| atgaaggtca | cggttctggg | cagtacgggc | agtatcggca | cgcaggcgct | cgacgtcgtg | 60 |
| cgggaacgcg | gctggagcgt | gggcacgctc | gcggccgggc | gcaatctgga | tctgctggcg | 120 |
| atccaggtgc | gcgagttcca | gccggacgtc | gtgagcgtgg | acgccagcgt | ctatgctgcc | 180 |
| gcccgcgacc | ttctgccaca | tctgacggtg | attgccgatg | ccgccgaggc | ctctgcccgg | 240 |
| cccgccgacg | tggtcgtgaa | cgccatgagc | ggcctgatcg | gcttgagcc | gacccgtacg | 300 |
| gcgctcctgg | ccggacaggc | cgtggcgctg | gcgaccaagg | aggccatggt | cacggctgcg | 360 |
| cacctgatgt | gggacgccgc | cgcagcgggt | ggggccgcg | tcgtgccggt | cgattccgag | 420 |
| cacaccggcg | tgtaccagtg | cctgaccggc | gagcacatgg | gcgacgtggc | cgaggtgatc | 480 |
| ctgaccgcgt | ccgtggcccc | cttccgggac | ggcccggccg | acctgtcgcg | cgtcacggcc | 540 |
| gcgcaggcgc | tcaggcaccc | gtcgtggacg | atggggccga | aggtgaccat | cgattcctcg | 600 |
| accctgatga | caaggggct | ggaggtcatg | gagtgcgcca | gcctgtacgg | gctgcccatg | 660 |
| actcaggtgg | gcgtggtcat | tcatccacag | agcctgatgc | acgcggcggt | gcgcttccgc | 720 |
| gacggcagcc | tgaaggcgca | gtttggcccg | accgacatgc | gcctgccgat | cgcctacgcc | 780 |
| atggacgcgg | cgcccaccgg | catgaccgc | ccggcgacg | tgcggggagc | gcggcgcggg | 840 |
| ccggaggtcg | ccgggcacgc | gtcatggccc | ctgcgcggcg | aatggcagtt | ccgcgagccc | 900 |

-continued

```
gatctggagc gctttccctg cctggccctg gcgtaccgcg ccggcaccgg gggcggcctg    960
ctgccggtgg ccctgaacgc cgctgatgaa gtggcggtgg acgccttcct ggccgggcga   1020
attggctacc tggacatccc ccgcgtgatc gggggtgtgc tggacgacac cccggccggt   1080
gacctgacgt gggacacgct gcacgccacc gacacctggg cacgcacccg tgcgagtgaa   1140
ctgtgcgggg tgaccgcgtg a                                             1161
```

<210> SEQ ID NO 37
<211> LENGTH: 386
<212> TYPE: PRT
<213> ORGANISM: Deinococcus yunweiensis

<400> SEQUENCE: 37

```
Met Lys Val Thr Val Leu Gly Ser Thr Gly Ser Ile Gly Thr Gln Ala
1               5                   10                  15

Leu Asp Val Val Arg Glu Arg Gly Trp Ser Val Gly Thr Leu Ala Ala
            20                  25                  30

Gly Arg Asn Leu Asp Leu Leu Ala Ile Gln Val Arg Glu Phe Gln Pro
        35                  40                  45

Asp Val Val Ser Val Asp Ala Ser Val Tyr Ala Ala Ala Arg Asp Leu
    50                  55                  60

Leu Pro His Leu Thr Val Ile Ala Asp Ala Ala Glu Ala Ser Ala Arg
65                  70                  75                  80

Pro Ala Asp Val Val Asn Ala Met Ser Gly Leu Ile Gly Leu Glu
                85                  90                  95

Pro Thr Arg Thr Ala Leu Leu Ala Gly Gln Ala Val Ala Leu Ala Thr
            100                 105                 110

Lys Glu Ala Met Val Thr Ala Ala His Leu Met Trp Asp Ala Ala Ala
        115                 120                 125

Ala Gly Gly Gly Arg Val Val Pro Val Asp Ser Glu His Thr Gly Val
    130                 135                 140

Tyr Gln Cys Leu Thr Gly Glu His Met Gly Asp Val Ala Glu Val Ile
145                 150                 155                 160

Leu Thr Ala Ser Gly Gly Pro Phe Arg Asp Gly Pro Ala Asp Leu Ser
                165                 170                 175

Arg Val Thr Ala Ala Gln Ala Leu Arg His Pro Ser Trp Thr Met Gly
            180                 185                 190

Pro Lys Val Thr Ile Asp Ser Ser Thr Leu Met Asn Lys Gly Leu Glu
        195                 200                 205

Val Met Glu Cys Ala Ser Leu Tyr Gly Leu Pro Met Thr Gln Val Gly
    210                 215                 220

Val Val Ile His Pro Gln Ser Leu Met His Ala Ala Val Arg Phe Arg
225                 230                 235                 240

Asp Gly Ser Leu Lys Ala Gln Phe Gly Pro Thr Asp Met Arg Leu Pro
                245                 250                 255

Ile Ala Tyr Ala Met Asp Ala Ala Pro Thr Gly Met Thr Arg Pro Gly
            260                 265                 270

Asp Val Arg Gly Ala Arg Arg Gly Pro Glu Val Ala Gly His Ala Ser
        275                 280                 285

Trp Pro Leu Arg Gly Glu Trp Gln Phe Arg Glu Pro Asp Leu Glu Arg
    290                 295                 300

Phe Pro Cys Leu Ala Leu Ala Tyr Arg Ala Gly Thr Gly Gly Gly Leu
305                 310                 315                 320

Leu Pro Val Ala Leu Asn Ala Ala Asp Glu Val Ala Val Asp Ala Phe
```

```
            325                 330                 335
Leu Ala Gly Arg Ile Gly Tyr Leu Asp Ile Pro Arg Val Ile Gly Gly
            340                 345                 350

Val Leu Asp Asp Thr Pro Ala Gly Asp Leu Thr Trp Asp Thr Leu His
            355                 360                 365

Ala Thr Asp Thr Trp Ala Arg Thr Arg Ala Ser Glu Leu Cys Gly Val
            370                 375                 380

Thr Ala
385

<210> SEQ ID NO 38
<211> LENGTH: 873
<212> TYPE: DNA
<213> ORGANISM: Deinococcus geothermalis

<400> SEQUENCE: 38
atgcccctgg atcccctcac cctgcgtccc ctccacccga gcgaaaccgc cacctatctc    60
gcccctgcca aggtcaatct gggtctcagc gtgcgcggcc tgcgcacaga cggctaccac   120
gaactgcact ccgtcatggt gccgctggtt gtgggagacg aactcgagat cgcagcggcc   180
gacacgctga ccctgcgggt ggaggggcag cattgcccca cgatgagcg caacctggtc    240 taccgggccg cgcgggcgta tctggacgcg gccagggtca gcggcggcgc catgatcacc   300
ctgcgcaagc ggctgcccct ggcttctggc ctgggcggcg cagcagcga tgcggccacc   360 acattgatgg cactggcgcg gctgttccct gctcctgtga acctcccggc gctggccctc   420
acgctgggtg cagatgtgcc gttttttcctg ctcggccagg cggcgctggc caggggggtc  480
ggggaagtgc tcacgccgct gccggtgccg caagtgccgc tggtgctggt caatccgggg   540
gtagaggtca cgcccgcga cgcctatgcc tggctggatg aggaggaagc cttcacgccg   600
ccgctcgatg tggagggcct gctggccgcc ctcaccgccc agcacgagct gcccaccttc   660
aatgctctcc agggcccggt cgccgcgcgc acgcgcccca tccaagctgc cctggccgcc   720
ctctcgagcg caggcctgcg ttcgccgctg atgagcggct caggagcgac ctgttttgcc   780
ctggccgcga gtgacgctca ggcacacgct gctgcgcagg cgctgcaggc acagcacccg   840
gcgtggtggg tggtggcgac gaggacgctg tag                                873

<210> SEQ ID NO 39
<211> LENGTH: 290
<212> TYPE: PRT
<213> ORGANISM: Deinococcus geothermalis

<400> SEQUENCE: 39

Met Pro Leu Asp Pro Leu Thr Leu Arg Pro Leu His Pro Ser Glu Thr
1               5                   10                  15

Ala Thr Tyr Leu Ala Pro Ala Lys Val Asn Leu Gly Leu Ser Val Arg
            20                  25                  30

Gly Leu Arg Thr Asp Gly Tyr His Glu Leu His Ser Val Met Val Pro
        35                  40                  45

Leu Val Val Gly Asp Glu Leu Glu Ile Ala Ala Ala Asp Thr Leu Thr
    50                  55                  60

Leu Arg Val Glu Gly Ala Leu Pro Thr Asp Glu Arg Asn Leu Val
65                  70                  75                  80

Tyr Arg Ala Ala Arg Ala Tyr Leu Asp Ala Ala Arg Val Ser Gly Gly
                85                  90                  95

Ala Met Ile Thr Leu Arg Lys Arg Leu Pro Leu Ala Ser Gly Leu Gly
```

```
              100                 105                 110
Gly Gly Ser Ser Asp Ala Ala Thr Thr Leu Met Ala Leu Ala Arg Leu
            115                 120                 125

Phe Pro Ala Pro Val Asn Leu Pro Ala Leu Ala Leu Thr Leu Gly Ala
        130                 135                 140

Asp Val Pro Phe Phe Leu Leu Gly Gln Ala Ala Leu Ala Gln Gly Val
145                 150                 155                 160

Gly Glu Val Leu Thr Pro Leu Pro Val Pro Gln Val Pro Leu Val Leu
                165                 170                 175

Val Asn Pro Gly Val Glu Val Ser Ala Arg Asp Ala Tyr Ala Trp Leu
            180                 185                 190

Asp Glu Glu Glu Ala Phe Thr Pro Pro Leu Asp Val Glu Gly Leu Leu
        195                 200                 205

Ala Ala Leu Thr Ala Gln His Glu Leu Pro Thr Phe Asn Ala Leu Gln
        210                 215                 220

Gly Pro Val Ala Ala Arg His Ala Pro Ile Gln Ala Ala Leu Ala Ala
225                 230                 235                 240

Leu Ser Ser Ala Gly Leu Arg Ser Pro Leu Met Ser Gly Ser Gly Ala
                245                 250                 255

Thr Cys Phe Ala Leu Ala Ala Ser Asp Ala Gln Ala His Ala Ala Ala
            260                 265                 270

Gln Ala Leu Gln Ala Gln His Pro Ala Trp Trp Val Val Ala Thr Arg
        275                 280                 285

Thr Leu
    290

<210> SEQ ID NO 40
<211> LENGTH: 858
<212> TYPE: DNA
<213> ORGANISM: Deinococcus yunweiensis

<400> SEQUENCE: 40
atgaccatgc ctgacacgct ccccctggc agcaccacgt acttcgcccc cgcgaaggtc      60
aacctgggcc tgagcgtgcg tgccccacgg gccgacggct accacgacct gcacaccctg     120
atggtgccgc tcgcagtcgg cgacgacctg agtgtcgctc cggccgacgc cctgactgtg     180
gaggtgcgcg gagccgacct gcccaccgac tcgcgcaatc tggtgtcccg cgccgcccgt     240
gcgtatctgg acgccgccgg caccgatcag ggcgcccacc tgatcctgca caagcggttg     300
cccatcgcca gcgggcttgg tgggggcagc agcgacgccg cgaccaccct gatggccctg     360
gcccgcctgt accggctgg cctcgacctg catgccctgg cgcgtgtgct gggagccgac     420
gtgcccttct tcctgctggg ccgggcggcc gtggccgagg caccggcga gatcctgacg     480 ccgctgccgg taccgcgcac gccctggtg ctggtcaatc ccggcgtgga ggtcagtgcc     540
cgcgacgcct atcactggct ggacgccgag gagaccttca ccgcgccgct ggacatcgac     600
gcggtgctgg cgaccctggc cgacggccgc ccggtgccgt acctcaatgc gctgcaaggc     660
cccgtcgccg cccggcacgt gcccatccag gaggcgctcc aggccctgtc ggacgctgga     720
ctgcgttccc cgctgatgag cggctcgggc agcacgtgtt ttgccctggc cggcagcgag     780
gatcacgccc atacctgcgc cgaggccatg gctgtccggt accgcagtg gtgggtacag     840 gccaccagca cgctctga                                                   858

<210> SEQ ID NO 41
<211> LENGTH: 285
```

<212> TYPE: PRT
<213> ORGANISM: Deinococcus yunweiensis

<400> SEQUENCE: 41

Met Thr Met Pro Asp Thr Leu Pro Pro Gly Ser Thr Thr Tyr Phe Ala
1               5                   10                  15

Pro Ala Lys Val Asn Leu Gly Leu Ser Val Arg Ala Pro Arg Ala Asp
            20                  25                  30

Gly Tyr His Asp Leu His Thr Leu Met Val Pro Leu Ala Val Gly Asp
        35                  40                  45

Asp Leu Ser Val Ala Pro Ala Asp Ala Leu Thr Val Glu Val Arg Gly
    50                  55                  60

Ala Asp Leu Pro Thr Asp Ser Arg Asn Leu Val Ser Arg Ala Ala Arg
65                  70                  75                  80

Ala Tyr Leu Asp Ala Ala Gly Thr Asp Gln Gly Ala His Leu Ile Leu
                85                  90                  95

His Lys Arg Leu Pro Ile Ala Ser Gly Leu Gly Gly Ser Ser Asp
            100                 105                 110

Ala Ala Thr Thr Leu Met Ala Leu Ala Arg Leu Tyr Pro Ala Gly Leu
            115                 120                 125

Asp Leu His Ala Leu Ala Arg Val Leu Gly Ala Asp Val Pro Phe Phe
130                 135                 140

Leu Leu Gly Arg Ala Ala Val Ala Glu Gly Thr Gly Glu Ile Leu Thr
145                 150                 155                 160

Pro Leu Pro Val Pro Arg Thr Pro Leu Val Leu Val Asn Pro Gly Val
                165                 170                 175

Glu Val Ser Ala Arg Asp Ala Tyr His Trp Leu Asp Ala Glu Glu Thr
            180                 185                 190

Phe Thr Ala Pro Leu Asp Ile Asp Ala Val Leu Ala Thr Leu Ala Asp
        195                 200                 205

Gly Arg Pro Val Pro Tyr Leu Asn Ala Leu Gln Gly Pro Val Ala Ala
    210                 215                 220

Arg His Val Pro Ile Gln Glu Ala Leu Gln Ala Leu Ser Asp Ala Gly
225                 230                 235                 240

Leu Arg Ser Pro Leu Met Ser Gly Ser Gly Ser Thr Cys Phe Ala Leu
                245                 250                 255

Ala Gly Ser Glu Asp His Ala His Thr Cys Ala Glu Ala Met Ala Val
            260                 265                 270

Arg Tyr Pro Gln Trp Trp Val Gln Ala Thr Ser Thr Leu
        275                 280                 285

<210> SEQ ID NO 42
<211> LENGTH: 996
<212> TYPE: DNA
<213> ORGANISM: Deinococcus geothermalis

<400> SEQUENCE: 42
atggttgaac ggattcatct tgccaagccg cgcggcttct gcgcgggcgt ggtgatggcc      60
atccaggcgg tcgaaaaagc cgctcgtacc gaagaccgtc ccgtgacggt ctatcattcc     120
attgtccaca accacaccgt tgtcgagcgg ttggaacagg aacatggcgt gcagtttgtg     180
gagagcctgg acgatctaac agccctcccg aacggcagcg agacggtgat ctttagcgct     240
cacggcatca gccagcggt gcgcgagcgg gcgcgggcct gggcgtgag caccatcgac     300 gcaacctgtc cgctggtgac caaggtccac accgaggcga aaaagtacgc tcgcgagggc     360

-continued

| | |
|---|---|
| tataccatcc tgctgatcgg ggacagcgcg cggcaccagg aagtcatcgg cacacgcggc | 420 |
| gaggcccccg aacagaccat cgtggtgggc gtactgggca aaacgggaga aggactacac | 480 |
| gaccccata ccgtcgaagt acctgatccc gagcgggtgg tggtcctcac gcagacgacc | 540 |
| ctcagtgtgg acgatacccg ccgcaccatc gacatcctga aaacccgctt tccgaagctg | 600 |
| gtgattccac ccagcgaaga tctctgctac gccaccaaga accgccagga ggccgtcaag | 660 |
| gcgatcgctc acaggtcga cgcttttctg gtgctgacca gcactcattc agcaacggg | 720 |
| atgcgcctgc tggaactcgc ccgcgacctg tgcggccggg ccgagcgcct ggaaactgct | 780 |
| gccgacctcg cgcacctcga tctgaccggc gtgcgctcgc tgggcatcac cagtgcagcc | 840 |
| agcacacccg atgatctcgt ccagaaagtg gtcgcccact ccgccggct caatccgaac | 900 |
| cttgaagtca tcgaggaagg cgagtgggaa acatcgagt ccgcgaacc taaaaagatc | 960 |
| gggccggggc aggccctccc ccggacaacg cagtag | 996 |

<210> SEQ ID NO 43
<211> LENGTH: 331
<212> TYPE: PRT
<213> ORGANISM: Deinococcus geothermalis

<400> SEQUENCE: 43

```
Met Val Glu Arg Ile His Leu Ala Lys Pro Arg Gly Phe Cys Ala Gly
1               5                   10                  15

Val Val Met Ala Ile Gln Ala Val Glu Lys Ala Ala Arg Thr Glu Asp
            20                  25                  30

Arg Pro Val Thr Val Tyr His Ser Ile Val His Asn His Thr Val Val
        35                  40                  45

Glu Arg Leu Glu Gln Glu His Gly Val Gln Phe Val Glu Ser Leu Asp
    50                  55                  60

Asp Leu Thr Ala Leu Pro Asn Gly Ser Glu Thr Val Ile Phe Ser Ala
65                  70                  75                  80

His Gly Ile Ser Pro Ala Val Arg Glu Arg Ala Arg Ala Leu Gly Val
                85                  90                  95

Ser Thr Ile Asp Ala Thr Cys Pro Leu Val Thr Lys Val His Thr Glu
            100                 105                 110

Ala Lys Lys Tyr Ala Arg Glu Gly Tyr Thr Ile Leu Leu Ile Gly Asp
        115                 120                 125

Ser Ala Arg His Gln Glu Val Ile Gly Thr Arg Gly Glu Ala Pro Glu
    130                 135                 140

Gln Thr Ile Val Val Gly Val Leu Gly Lys Thr Gly Glu Gly Leu His
145                 150                 155                 160

Asp Pro His Thr Val Glu Val Pro Asp Pro Glu Arg Val Val Val Leu
                165                 170                 175

Thr Gln Thr Thr Leu Ser Val Asp Asp Thr Arg Arg Thr Ile Asp Ile
            180                 185                 190

Leu Lys Thr Arg Phe Pro Lys Leu Val Ile Pro Ser Glu Asp Leu
        195                 200                 205

Cys Tyr Ala Thr Lys Asn Arg Gln Glu Ala Val Lys Ala Ile Ala Pro
    210                 215                 220

Gln Val Asp Ala Phe Leu Val Leu Thr Ser Thr His Ser Ser Asn Gly
225                 230                 235                 240

Met Arg Leu Leu Glu Leu Ala Arg Asp Leu Cys Gly Arg Ala Glu Arg
                245                 250                 255

Leu Glu Thr Ala Ala Asp Leu Ala His Leu Asp Leu Thr Gly Val Arg
```

```
              260                 265                 270
Ser Leu Gly Ile Thr Ser Ala Ala Ser Thr Pro Asp Asp Leu Val Gln
            275                 280                 285

Lys Val Val Ala His Phe Arg Arg Leu Asn Pro Asn Leu Glu Val Ile
        290                 295                 300

Glu Glu Gly Glu Trp Glu Asn Ile Glu Phe Arg Glu Pro Lys Lys Ile
305                 310                 315                 320

Gly Pro Gly Gln Ala Leu Pro Arg Thr Thr Gln
            325                 330
```

<210> SEQ ID NO 44
<211> LENGTH: 1002
<212> TYPE: DNA
<213> ORGANISM: Deinococcus yunweiensis

<400> SEQUENCE: 44

```
atgaccatga ttgaacgcgt gttcctggcc cggccccgtg ggttctgcgc gggggtcgtc    60
atggcgatcc aggcggtcga gcgggctgcc gtgaccgagg agcggccggt gacggtgtac   120
cactccatcg tccacaacca cacggtcgtc gagcggctgt cggcagccca cggagtgcat   180
ttcgtcgagg atctggacgc ggtcgaggcg ctgccccagg gcggcgagac cgtcgtgttc   240
agtgcccacg gcatcagccc gacggtgcgc gagcgggcac gctcactcgg gctggcgacc   300
atcgacgcga cctgcccgct ggtcacgaag gtgcacacag gccaagaa atacgcccgt    360
gagggctaca cgatcctgct gatcggggac agcgcacggc atcaggaggt catcggcacg   420
cggggtgagg ccccggacag caccattctg gtgggcgtgc tcggcaagac cggcgagggc   480
ctgcacgacc cccacaccgt cgaggtgccc gatccgcaga gctggtcgt gctgacccag   540
acgaccctga gcgtggacga cacgcggcgc accgtggaca tcctgaaggc ccggttcccg   600
gcgctggtgg tgccgcccag cgaggatctg tgctacgcca ccaaaaaccg ccaggacgcc   660
gtgaaagcca tcgcgccgca ggtggacgcc ttcctggtac tcaccagcac gcattccagc   720
aacggcatgc gcctgctgga actggctgcc gagacctgcg acgctcgga gcggctggag   780
acggtggccg acctggccgg cattgacctg agcggcgtgc gcagtgtggg gatcacgtcg   840
gccgcgagca caccggacga tctggtgcag gcggtcgtgg cccacttcca gatgctgaac   900
ccggccctgg cggtcatcga ggagggcgag tgggaggaca tcgagttccg cgagccgaag   960
aagatcctgc cgggtgacgc cctgccgcgc acgatgcagt ga                    1002
```

<210> SEQ ID NO 45
<211> LENGTH: 333
<212> TYPE: PRT
<213> ORGANISM: Deinococcus yunweiensis

<400> SEQUENCE: 45

```
Met Thr Met Ile Glu Arg Val Phe Leu Ala Arg Pro Arg Gly Phe Cys
1               5                  10                  15

Ala Gly Val Val Met Ala Ile Gln Ala Val Glu Arg Ala Ala Val Thr
            20                  25                  30

Glu Glu Arg Pro Val Thr Val Tyr His Ser Ile Val His Asn His Thr
        35                  40                  45

Val Val Glu Arg Leu Ser Ala Ala His Gly Val His Phe Val Glu Asp
    50                  55                  60

Leu Asp Ala Val Glu Ala Leu Pro Gln Gly Gly Glu Thr Val Val Phe
65                  70                  75                  80
```

Ser Ala His Gly Ile Ser Pro Thr Val Arg Glu Ala Arg Ser Leu
            85                  90                  95

Gly Leu Ala Thr Ile Asp Ala Thr Cys Pro Leu Val Thr Lys Val His
        100                 105                 110

Thr Glu Ala Lys Lys Tyr Ala Arg Glu Gly Tyr Thr Ile Leu Leu Ile
        115                 120                 125

Gly Asp Ser Ala Arg His Gln Glu Val Ile Gly Thr Arg Gly Glu Ala
    130                 135                 140

Pro Asp Ser Thr Ile Leu Val Gly Val Leu Gly Lys Thr Gly Glu Gly
145                 150                 155                 160

Leu His Asp Pro His Thr Val Glu Val Pro Asp Pro Gln Lys Leu Val
                165                 170                 175

Val Leu Thr Gln Thr Thr Leu Ser Val Asp Asp Thr Arg Arg Thr Val
            180                 185                 190

Asp Ile Leu Lys Ala Arg Phe Pro Ala Leu Val Val Pro Pro Ser Glu
        195                 200                 205

Asp Leu Cys Tyr Ala Thr Lys Asn Arg Gln Asp Ala Val Lys Ala Ile
    210                 215                 220

Ala Pro Gln Val Asp Ala Phe Leu Val Leu Thr Ser Thr His Ser Ser
225                 230                 235                 240

Asn Gly Met Arg Leu Leu Glu Leu Ala Ala Glu Thr Cys Gly Arg Ser
                245                 250                 255

Glu Arg Leu Glu Thr Val Ala Asp Leu Ala Gly Ile Asp Leu Ser Gly
            260                 265                 270

Val Arg Ser Val Gly Ile Thr Ser Ala Ala Ser Thr Pro Asp Asp Leu
        275                 280                 285

Val Gln Ala Val Ala His Phe Gln Met Leu Asn Pro Ala Leu Ala
    290                 295                 300

Val Ile Glu Glu Gly Glu Trp Glu Asp Ile Glu Phe Arg Glu Pro Lys
305                 310                 315                 320

Lys Ile Leu Pro Gly Asp Ala Leu Pro Arg Thr Met Gln
                325                 330

<210> SEQ ID NO 46
<211> LENGTH: 990
<212> TYPE: DNA
<213> ORGANISM: Deinococcus geothermalis

<400> SEQUENCE: 46 atgcacccccg acctgctccc ccgcgtgctg tctctgcttc ccaaccgcgg tgaccgcccg      60
gaactgcgcg ccttctccgc catgctgcgc gactatcccg agcgcggcgg aaagggcatc     120
cgctcggaac tgctgctcgc cagtgcccgc gcccatggcg ccttgcccag cacttcagcc     180
tgggaaggag cgctgtggct cgcggcgggc ctggaactgt tccagaattg ggtgctgatc     240
cacgacgaca tcgaggatga ctcggaggag cgccggggca ggcccgcgct gcaccgcctg     300
tacggcgtgc cggtagccat caatgtgggt gacgccctcc acgcctcgat gtgggccgcc     360
gtccaccgcg cgggggtgcc gggcggcctg aagaattcc tgaacatggt ctggcgcacg      420
gcggagggcc agcacctcga tctcacctgg gtgcaggagc gcagctggaa cctgggcgaa     480
gccgactatc tggcgatggt gcgcctgaaa acggccctgt acacggtggt ggtgccgctg     540
cggctcgggg cactcgccgc cggagtgctc ccggacgagc gctttacggc agcgggcgaa     600
gccctgggcg cggccttcca aattcgcgac gacgtgctga acctggccgg ggatcccgcg     660
aagtacggca aggagatcgg cggcgacctc tgggagggca aacgcacctt gattgtgctg     720

```
cactggctcg cccacgcgcc ggaggagcag cggcaggtct ttctggaaca gatgcgccgg    780
gaccgagcgg acaaggacgc cgccgccatc gcagccatcc accgctggct gctggagagc    840
ggcagcgttc agtacgccca ggcctacgcc gacacacagg cccgcgaagg cctcgcccgc    900
ctgaccgagg cgctggagaa cgcacccgac ccgcaggcgg cgcgggcact cctggcccag    960 ttgcggggc tggcgacgcg cgaagcgtag                                       990
```

```
<210> SEQ ID NO 47
<211> LENGTH: 329
<212> TYPE: PRT
<213> ORGANISM: Deinococcus geothermalis

<400> SEQUENCE: 47
```

```
Met His Pro Asp Leu Leu Pro Arg Val Leu Ser Leu Leu Pro Asn Arg
1               5                   10                  15

Gly Asp Arg Pro Glu Leu Arg Ala Phe Ser Ala Met Leu Arg Asp Tyr
            20                  25                  30

Pro Glu Arg Gly Gly Lys Gly Ile Arg Ser Glu Leu Leu Leu Ala Ser
        35                  40                  45

Ala Arg Ala His Gly Ala Leu Pro Ser Thr Ser Ala Trp Glu Gly Ala
    50                  55                  60

Leu Trp Leu Ala Ala Gly Leu Glu Leu Phe Gln Asn Trp Val Leu Ile
65                  70                  75                  80

His Asp Asp Ile Glu Asp Ser Glu Glu Arg Arg Gly Arg Pro Ala
                85                  90                  95

Leu His Arg Leu Tyr Gly Val Pro Ala Ile Asn Val Gly Asp Ala
            100                 105                 110

Leu His Ala Ser Met Trp Ala Ala Val His Arg Ala Gly Val Pro Gly
        115                 120                 125

Gly Leu Glu Glu Phe Leu Asn Met Val Trp Arg Thr Ala Glu Gly Gln
    130                 135                 140

His Leu Asp Leu Thr Trp Val Gln Glu Arg Ser Trp Asn Leu Gly Glu
145                 150                 155                 160

Ala Asp Tyr Leu Ala Met Val Arg Leu Lys Thr Ala Leu Tyr Thr Val
                165                 170                 175

Val Val Pro Leu Arg Leu Gly Ala Leu Ala Ala Gly Val Leu Pro Asp
            180                 185                 190

Glu Arg Phe Thr Ala Ala Gly Glu Ala Leu Gly Ala Ala Phe Gln Ile
        195                 200                 205

Arg Asp Asp Val Leu Asn Leu Ala Gly Asp Pro Ala Lys Tyr Gly Lys
    210                 215                 220

Glu Ile Gly Gly Asp Leu Trp Glu Gly Lys Arg Thr Leu Ile Val Leu
225                 230                 235                 240

His Trp Leu Ala His Ala Pro Glu Glu Gln Arg Gln Val Phe Leu Glu
                245                 250                 255

Gln Met Arg Arg Asp Arg Ala Asp Lys Asp Ala Ala Ile Ala Ala
            260                 265                 270

Ile His Arg Trp Leu Leu Glu Ser Gly Ser Val Gln Tyr Ala Gln Ala
        275                 280                 285

Tyr Ala Asp Thr Gln Ala Arg Glu Gly Leu Ala Arg Leu Thr Glu Ala
    290                 295                 300

Leu Glu Asn Ala Pro Asp Pro Gln Ala Ala Arg Ala Leu Leu Ala Gln
305                 310                 315                 320
```

Leu Arg Gly Leu Ala Thr Arg Glu Ala
              325

<210> SEQ ID NO 48
<211> LENGTH: 1704
<212> TYPE: DNA
<213> ORGANISM: Ocimum basilicum

<400> SEQUENCE: 48

| | | |
|---|---|---|
| atgtcttgtg cacggatcac cgtaacattg ccgtatcgct ccgcaaaaac atcaattcaa | 60 | |
| cggggaatta cgcattaccc cgcccttata cgcccacgct tctctgcttg cacgcctttg | 120 | |
| gcatcggcga tgcctctaag ttcaactcct ctcatcaacg gggataactc tcagcgtaaa | 180 | |
| aacacacgtc aacacatgga ggagagcagc agcaagagga gagaatatct gctggaggaa | 240 | |
| acgacgcgaa aactgcagag aaacgacacc gaatcggtgg agaaactcaa gcttatcgac | 300 | |
| aacatccaac agttgggaat cggctactat tttgaggacg ccatcaacgc cgtactccgc | 360 | |
| tcgcctttct ccaccggaga agaagacctc ttcaccgctg ctctgcgctt ccgcttgctc | 420 | |
| cgccacaacg gcatcgaaat cagccctgaa atattcctaa aattcaagga cgagagggga | 480 | |
| aaattcgacg aatcggacac gctagggtta ctgagcttgt acgaagcgtc aaatttgggg | 540 | |
| gttgcaggag aagaaatatt ggaggaggct atggagtttg cggaggctcg cctgagacgg | 600 | |
| tcgctgtcag agccggcggc gccgcttcat ggtgaggtgg cgcaagcgct agatgtgccg | 660 | |
| aggcatctga aatggcgag gttggaagcg agacgattca tcgagcagta tggtaaacag | 720 | |
| agcgatcatg atggagatct tttggagctg gcaattttgg attataatca agttcaggct | 780 | |
| caacaccaat ccgaactcac tgaaataatc aggtggtgga aggagctcgg tttggtggat | 840 | |
| aagttgagtt ttgggcgaga cagaccattg gagtgctttt tgtggaccgt ggggctcctc | 900 | |
| ccagagccca gtattcgag cgttagaata gagttggcga aagccatctc tattctctta | 960 | |
| gtgatcgatg atattttcga tacctatgga gagatggatg acctcatcct cttcaccgat | 1020 | |
| gcaattcgaa gatgggatct tgaagcaatg gaggggctcc ctgagtacat gaaaatatgc | 1080 | |
| tacatggcgt tgtacaatac caccaatgaa gtatgctaca agtgctcag ggatactgga | 1140 | |
| cggattgtcc tccttaacct caaatctacg tggatagaca tgattgaagg tttcatggag | 1200 | |
| gaagcaaaat ggttcaatgg tggaagtgca ccaaaattgg aagagtatat agagaatgga | 1260 | |
| gtgtccacgg caggagcata catggctttt gcacacatct tctttctcat aggagaaggt | 1320 | |
| gttacacacc aaaattccca actcttcacc caaaaaccct accccaaggt cttctccgcc | 1380 | |
| gccggccgca ttcttcgcct ctgggatgat ctcggaaccg ccaaggaaga gcaagagcga | 1440 | |
| ggagatctgg cttcgtgcgt gcagttattt atgaaagaga agtcgttgac ggaagaggag | 1500 | |
| gcaagaagtc gcattttgga agagataaaa ggattatgga gggatctgaa tggggaactg | 1560 | |
| gtctacaaca agaatttgcc gttatccata atcaaagtcg cacttaacat ggcgagagct | 1620 | |
| tctcaagttg tgtacaagca cgatcaagac acttattttt caagcgtaga caattatgtg | 1680 | |
| gatgccctct tcttcactca ataa | 1704 | |

<210> SEQ ID NO 49
<211> LENGTH: 567
<212> TYPE: PRT
<213> ORGANISM: Ocimum basilicum

<400> SEQUENCE: 49

Met Ser Cys Ala Arg Ile Thr Val Thr Leu Pro Tyr Arg Ser Ala Lys
1               5                   10                  15

-continued

```
Thr Ser Ile Gln Arg Gly Ile Thr His Tyr Pro Ala Leu Ile Arg Pro
         20                  25                  30

Arg Phe Ser Ala Cys Thr Pro Leu Ala Ser Ala Met Pro Leu Ser Ser
         35                  40                  45

Thr Pro Leu Ile Asn Gly Asp Asn Ser Gln Arg Lys Asn Thr Arg Gln
 50                  55                  60

His Met Glu Glu Ser Ser Lys Arg Glu Tyr Leu Leu Glu Glu
 65                  70                  75                  80

Thr Thr Arg Lys Leu Gln Arg Asn Asp Thr Glu Ser Val Glu Lys Leu
                 85                  90                  95

Lys Leu Ile Asp Asn Ile Gln Gln Leu Gly Ile Gly Tyr Tyr Phe Glu
                100                 105                 110

Asp Ala Ile Asn Ala Val Leu Arg Ser Pro Phe Ser Thr Gly Glu Glu
             115                 120                 125

Asp Leu Phe Thr Ala Ala Leu Arg Phe Arg Leu Leu Arg His Asn Gly
 130                 135                 140

Ile Glu Ile Ser Pro Glu Ile Phe Leu Lys Phe Lys Asp Glu Arg Gly
145                 150                 155                 160

Lys Phe Asp Glu Ser Asp Thr Leu Gly Leu Leu Ser Leu Tyr Glu Ala
                 165                 170                 175

Ser Asn Leu Gly Val Ala Gly Glu Glu Ile Leu Glu Glu Ala Met Glu
             180                 185                 190

Phe Ala Glu Ala Arg Leu Arg Arg Ser Leu Ser Glu Pro Ala Ala Pro
         195                 200                 205

Leu His Gly Glu Val Ala Gln Ala Leu Asp Val Pro Arg His Leu Arg
     210                 215                 220

Met Ala Arg Leu Glu Ala Arg Phe Ile Glu Gln Tyr Gly Lys Gln
225                 230                 235                 240

Ser Asp His Asp Gly Asp Leu Leu Glu Leu Ala Ile Leu Asp Tyr Asn
                 245                 250                 255

Gln Val Gln Ala Gln His Gln Ser Glu Leu Thr Glu Ile Ile Arg Trp
             260                 265                 270

Trp Lys Glu Leu Gly Leu Val Asp Lys Leu Ser Phe Gly Arg Asp Arg
         275                 280                 285

Pro Leu Glu Cys Phe Leu Trp Thr Val Gly Leu Leu Pro Glu Pro Lys
     290                 295                 300

Tyr Ser Ser Val Arg Ile Glu Leu Ala Lys Ala Ile Ser Ile Leu Leu
305                 310                 315                 320

Val Ile Asp Asp Ile Phe Asp Thr Tyr Gly Glu Met Asp Asp Leu Ile
                 325                 330                 335

Leu Phe Thr Asp Ala Ile Arg Arg Trp Asp Leu Glu Ala Met Glu Gly
             340                 345                 350

Leu Pro Glu Tyr Met Lys Ile Cys Tyr Met Ala Leu Tyr Asn Thr Thr
         355                 360                 365

Asn Glu Val Cys Tyr Lys Val Leu Arg Asp Thr Gly Arg Ile Val Leu
     370                 375                 380

Leu Asn Leu Lys Ser Thr Trp Ile Asp Met Ile Glu Gly Phe Met Glu
385                 390                 395                 400

Glu Ala Lys Trp Phe Asn Gly Gly Ser Ala Pro Lys Leu Glu Glu Tyr
                 405                 410                 415

Ile Glu Asn Gly Val Ser Thr Ala Gly Ala Tyr Met Ala Phe Ala His
             420                 425                 430
```

```
Ile Phe Phe Leu Ile Gly Glu Gly Val Thr His Gln Asn Ser Gln Leu
            435                 440                 445
Phe Thr Gln Lys Pro Tyr Pro Lys Val Phe Ser Ala Ala Gly Arg Ile
450                 455                 460
Leu Arg Leu Trp Asp Asp Leu Gly Thr Ala Lys Glu Glu Gln Glu Arg
465                 470                 475                 480
Gly Asp Leu Ala Ser Cys Val Gln Leu Phe Met Lys Glu Lys Ser Leu
                485                 490                 495
Thr Glu Glu Ala Arg Ser Arg Ile Leu Glu Ile Lys Gly Leu
            500                 505                 510
Trp Arg Asp Leu Asn Gly Glu Leu Val Tyr Asn Lys Asn Leu Pro Leu
            515                 520                 525
Ser Ile Ile Lys Val Ala Leu Asn Met Ala Arg Ala Ser Gln Val Val
530                 535                 540
Tyr Lys His Asp Gln Asp Thr Tyr Phe Ser Ser Val Asp Asn Tyr Val
545                 550                 555                 560
Asp Ala Leu Phe Phe Thr Gln
                565
```

```
<210> SEQ ID NO 50
<211> LENGTH: 1239
<212> TYPE: DNA
<213> ORGANISM: Deinococcus geothermalis

<400> SEQUENCE: 50
atgcctgccg cgcccccgt gaccgatgcc ctggtggttg ggggcggccc agcaggtttg      60
gcgttatccg ccgaactcgc ggcgtgtggc ctgcgggtgc ggctgatcgc tccccacccg     120
ccccggccct ttccggcgac ctacggcgcg tggctggagg aactcccgt ctggaccccgt    180
gcctgctgcg ccgacgtgtg gaccgacgtg cgcgcctatt tggatgaacg ccccacgccc    240
ctgctgcgcc catatgtccg gctcgacaat gcccggttgc tggacaccct gctgacccgt    300
gctggaaacg gcctaacctg gaccgttggc agcgtgtgcg ccgcctcacg ggtcggggag    360
gggtgggagg ttcaggggac gcacggcgaa atctggcgcg cccacctggt cgtgacgcg     420
gcgggacaca cgggcagcct gagctgtccc cagcatctgg gcggtccggc tctccagacg    480
gcagttggcc tggtcgcaca cttcgacacg ccaccggtgc cgcctggctc cgccgtgtgg    540
atggattacc gcagctccca cctcgcgcct gccgacctgc acgcggcgcc caccttcctc    600
tacgccctgc atctgggcgg ttcccgctac ctggtggagg aaacgagcct ggtcgctcgg    660
cccgggctgt cccgtccgct gcttgagcaa aggctgcgcg ctcgcctcgc cgcgcaggga    720
acgcttcctc gtgaggtcga gcgggaggaa tgggtcgcct ttcccatgaa cgtgtcggcg    780
cccgccccg accggtgct ggccttcggg tcggcgcgg gtctggtgca tccggtgagc     840
gggtttcagg tggcgggggc actcggcgac gcgccgaaag tcgcgcgggc ggtggcgatg    900
gcgctcgctg cgggcagtcc ggaggccgcc gtgcaggccg gtggcaggc cctctggcct    960
cccgaacgcc gggcggcgcg tgaggtcgcc ctgctggggc tggacgcgct gctggcactc   1020
ccgggcgatc agctcccggc cttcttcgcg gcctttttcc agctgcctgc ccgcgagtgg   1080
cgggcgtttt tggccccca cacgggcgcc ggaaggctgg cccgcgtcat gctgcggcta   1140
tttgcccagg tgcccggccc ggttcgcgcg tccctggccc gtgccgcgct cgcccagagc   1200
catgtgagcg cgcaggcgct gcgagctgcc ctcggatga                          1239
```

```
<210> SEQ ID NO 51
```

```
<211> LENGTH: 412
<212> TYPE: PRT
<213> ORGANISM: Deinococcus geothermalis

<400> SEQUENCE: 51

Met Pro Ala Ala Pro Val Thr Asp Ala Leu Val Val Gly Gly Gly
1               5                   10                  15

Pro Ala Gly Leu Ala Leu Ser Ala Glu Leu Ala Ala Cys Gly Leu Arg
            20                  25                  30

Val Arg Leu Ile Ala Pro His Pro Arg Pro Phe Pro Ala Thr Tyr
        35                  40                  45

Gly Ala Trp Leu Glu Glu Leu Pro Val Trp Thr Arg Ala Cys Cys Ala
    50                  55                  60

Asp Val Trp Thr Asp Val Arg Ala Tyr Leu Asp Glu Arg Pro Thr Pro
65                  70                  75                  80

Leu Leu Arg Pro Tyr Val Arg Leu Asp Asn Ala Arg Leu Leu Asp Thr
                85                  90                  95

Leu Leu Thr Arg Ala Gly Asn Gly Leu Thr Trp Thr Val Gly Ser Val
            100                 105                 110

Cys Ala Ala Ser Arg Val Gly Glu Gly Trp Glu Val Gln Gly Thr His
        115                 120                 125

Gly Glu Ile Trp Arg Ala His Leu Val Val Asp Ala Ala Gly His Thr
130                 135                 140

Gly Ser Leu Ser Cys Pro Gln His Leu Gly Gly Pro Ala Leu Gln Thr
145                 150                 155                 160

Ala Val Gly Leu Val Ala His Phe Asp Thr Pro Val Pro Pro Gly
                165                 170                 175

Ser Ala Val Trp Met Asp Tyr Arg Ser Ser His Leu Ala Pro Ala Asp
            180                 185                 190

Leu His Ala Ala Pro Thr Phe Leu Tyr Ala Leu His Leu Gly Gly Ser
        195                 200                 205

Arg Tyr Leu Val Glu Glu Thr Ser Leu Val Ala Arg Pro Gly Leu Ser
    210                 215                 220

Arg Pro Leu Leu Glu Gln Arg Leu Arg Ala Arg Leu Ala Ala Gln Gly
225                 230                 235                 240

Thr Leu Pro Arg Glu Val Glu Arg Glu Glu Trp Val Ala Phe Pro Met
                245                 250                 255

Asn Val Ser Ala Pro Gly Pro Gly Pro Val Leu Ala Phe Gly Ser Ala
            260                 265                 270

Ala Gly Leu Val His Pro Val Ser Gly Phe Gln Val Ala Gly Ala Leu
        275                 280                 285

Gly Asp Ala Pro Lys Val Ala Arg Ala Val Ala Met Ala Leu Ala Ala
    290                 295                 300

Gly Ser Pro Glu Ala Ala Val Gln Ala Gly Trp Gln Ala Leu Trp Pro
305                 310                 315                 320

Pro Glu Arg Arg Ala Ala Arg Glu Val Ala Leu Leu Gly Leu Asp Ala
                325                 330                 335

Leu Leu Ala Leu Pro Gly Asp Gln Leu Pro Ala Phe Ala Ala Phe
            340                 345                 350

Phe Gln Leu Pro Ala Arg Glu Trp Arg Ala Phe Leu Ala Pro His Thr
        355                 360                 365

Gly Ala Gly Arg Leu Ala Arg Val Met Leu Arg Leu Phe Ala Gln Val
    370                 375                 380

Pro Gly Pro Val Arg Ala Ser Leu Ala Arg Ala Ala Leu Ala Gln Ser
```

```
                385                 390                 395                 400
His Val Ser Ala Gln Ala Leu Arg Ala Ala Leu Gly
                    405                 410

<210> SEQ ID NO 52
<211> LENGTH: 636
<212> TYPE: PRT
<213> ORGANISM: Deinococcus radiopugnans

<400> SEQUENCE: 52

Met Thr Asp Ile Lys Lys Ala Asp Gly Leu His Leu Gly His Lys Gly
1               5                   10                  15

Thr Pro Leu Leu Asp Arg Ile Ala Gly Pro Ala Asp Leu Lys Lys Leu
            20                  25                  30

Ser Arg Asp Gln Leu Pro Glu Leu Ser Gln Glu Leu Arg Asp Glu Ile
        35                  40                  45

Val Arg Val Cys Ser Val Gly Gly Leu His Leu Ala Ser Ser Leu Gly
    50                  55                  60

Ala Thr Asp Leu Ile Val Ala Leu His Tyr Val Leu Asn Ser Pro Arg
65                  70                  75                  80

Asp Arg Ile Leu Phe Asp Val Gly His Gln Ala Tyr Ala His Lys Met
                85                  90                  95

Leu Thr Gly Arg Arg Glu Gln Met His Thr Val Lys Lys Glu Gly Gly
            100                 105                 110

Leu Ser Gly Phe Thr Lys Val Ser Glu Ser Glu His Asp Ala Ile Thr
        115                 120                 125

Val Gly His Ala Ser Thr Ser Leu Ala Asn Ala Leu Gly Met Ala Met
    130                 135                 140

Ala Arg Asp Ala Leu Gly Gln Asp Tyr Gln Val Ala Ala Val Ile Gly
145                 150                 155                 160

Asp Gly Ser Leu Thr Gly Gly Met Ala Leu Ala Ala Leu Asn Thr Ile
                165                 170                 175

Gly Asp Leu Arg Arg Lys Met Leu Ile Val Leu Asn Asp Asn Glu Met
            180                 185                 190

Ser Ile Ser Glu Asn Val Gly Ala Ile Asn Lys Phe Met Arg Gly Leu
        195                 200                 205

Gln Val Gln Lys Trp Phe Gln Glu Gly Glu Gly Ala Gly Lys Lys Ala
    210                 215                 220

Val Gln Ser Leu Ser Lys Pro Leu Ala Asp Phe Met Ser Arg Ala Lys
225                 230                 235                 240

Ser Ser Thr Arg His Phe Phe Asp Pro Ala Ser Val Asn Pro Phe Ala
                245                 250                 255

Met Met Gly Val Arg Tyr Val Gly Pro Val Asp Gly His Asn Val Gln
            260                 265                 270

Glu Leu Val Trp Leu Met Glu Arg Leu Val Asp Leu Asp Gly Pro Thr
        275                 280                 285

Ile Leu His Val Val Thr Arg Lys Gly Lys Gly Leu Ser Tyr Ala Glu
    290                 295                 300

Ala Asp Pro Ile Tyr Trp His Gly Pro Gly Gln Phe Asp Pro Asp Thr
305                 310                 315                 320

Gly Asp Phe Lys Ala Ser Ser Ala Tyr Ser Trp Ser Ala Ala Phe Gly
                325                 330                 335

Asp Ala Val Thr Glu Leu Ala Lys Arg Asp Pro Arg Thr Phe Val Ile
            340                 345                 350
```

Thr Pro Ala Met Arg Glu Gly Ser Gly Leu Val Gly Tyr Ser Arg Ala
            355                 360                 365

His Pro His Arg Tyr Leu Asp Val Gly Ile Ala Glu Asp Val Ala Val
        370                 375                 380

Thr Thr Ala Ala Gly Met Ala Leu Gln Gly Leu Arg Pro Ile Val Ala
385                 390                 395                 400

Ile Tyr Ser Thr Phe Leu Gln Arg Ala Tyr Asp Gln Val Leu His Asp
            405                 410                 415

Val Ala Ile Glu Asn Leu Asn Val Thr Phe Ala Ile Asp Arg Ala Gly
        420                 425                 430

Ile Val Gly Ala Asp Gly Ser Thr His Asn Gly Val Phe Asp Leu Ser
        435                 440                 445

Tyr Leu Arg Ser Ile Pro Asn Val Arg Ile Gly Leu Pro Lys Asp Ala
    450                 455                 460

His Glu Met Arg Gly Met Leu Lys Tyr Ala Gln Glu His Asp Gly Pro
465                 470                 475                 480

Phe Ala Ile Arg Tyr Pro Arg Gly Asn Thr Val Lys Val Pro Glu Gly
            485                 490                 495

Thr Trp Pro Thr Leu Glu Trp Gly Thr Trp Glu Arg Val Lys Glu Gly
        500                 505                 510

Ser Asp Ala Val Ile Leu Ala Gly Gly Lys Ala Leu Glu Tyr Ala Gln
    515                 520                 525

Ala Ala Ala Asp Leu Pro Gly Val Gly Val Val Asn Ala Arg Phe
        530                 535                 540

Val Lys Pro Leu Asp Leu Asn Met Leu Arg Glu Leu Ala Gly Ser Ala
545                 550                 555                 560

Arg Thr Ile Ile Thr Val Glu Asp Asn Thr Leu Val Gly Gly Phe Gly
            565                 570                 575

Ser Ala Val Leu Glu Ala Leu Asn Ser Met Gly Leu Lys Val Pro Val
        580                 585                 590

Arg Thr Leu Gly Ile Pro Asp Glu Phe Gln Asp His Ala Thr Ala Glu
        595                 600                 605

Ser Val His Ala Arg Ala Gly Ile Asp Ala Gln Ala Ile Arg Thr Val
    610                 615                 620

Leu Ala Glu Leu Gly Val Asp Val Pro Leu Gly Val
625                 630                 635

<210> SEQ ID NO 53
<211> LENGTH: 1902
<212> TYPE: DNA
<213> ORGANISM: Artificial Sequence
<220> FEATURE:
<223> OTHER INFORMATION: K219N mutant of the DXP synthase from D.
      geothermalis

<400> SEQUENCE: 53
atgagtgagc caactgccaa cctccagcct gccagccgca cccgctgct ggaccgggtg      60 aatgcccgg aagacctcaa acggctcgga cgcgaccagc taccccagct cgctgccgaa     120
ctgcgcgagg agatcgtgcg ggtctgctcg gtagggggt tacatctcgc cagctctctg     180
ggcgcgaccg acctaatcgt ggcgctacat tacgtgctgc attcgccgcg cgaccgcatt    240
ctgttcgacg tggggcatca ggcctacgcc cacaagatgc tcacgggccg ccgccacctg    300
atgcacaccg tcaagaagga gggcgggctg tcgggcttca ccaaggtgag cgagtccgaa    360
cacgacgcca tcacggtggg ccatgccagc acctccctcg ccaatgcgct gggcatggcg    420

| | |
|---|---|
| cttgcacggg acgctttggg acaggattac aaggtggctg ccgtgatcgg ggacggctcg | 480 |
| ctgacgggcg gcatggcgct ggcggcgctg aataccatcg gggacctggg gcggcgaatg | 540 |
| ctcattgtgc ttaacgacaa cgagatgagc atcagcgaga acgtgggggc catcaaccgc | 600 |
| ttcatgcggg gtctccaggt gcagaagtgg ttccaggagg cgaggaagc cgggaacaag | 660 |
| gccgtgcagg cggtcagcaa gccgctcgcc aacttgatga gccgcgccaa gagttccacg | 720 |
| cggcactttt tcgatcccgc cagtgtcaat ccctttgccg cgatgggcgt gcgctatgtg | 780 |
| ggaccggtgg acgccacaa cgtgcaggaa ttggtgtggc tgatcgagcg gctggtcgac | 840 |
| ctcgatgggc cgaccattct gcacgtcgtc accaaaaagg gcaagggcct gagctacgcc | 900 |
| gaggccgacc cgatcaaatg gcatggcccg ggcaagtttg acccggcgac gggtgagtcg | 960 |
| gtgcccagca atgcctactc gtggagcagc gcctttggag acgcggtgac cgagcttgca | 1020 |
| cggctggacc cccgtacctt tgtgatcacg cccgcgatgc gcgagggcag cggcctggtg | 1080 |
| cgctacagcc aggttcaccc ccaccgttac ctggatgtcg gtatcgcgga ggacgtggcc | 1140 |
| gtcaccacgg ccgccggaat ggcgcttcag gggatgcggc ccatcgtggc gatctactcc | 1200 |
| actttcctgc aacgcgccta cgatcaggtg ctgcacgacg tcgccatcga gaatctgaac | 1260 |
| gtgaccttcg ccatcgaccg tggggcatc gtgggcgcag acgagccac ccacaacggc | 1320 |
| gtcttcgacc tgagttacct gcgctcgatt ccgaatgtcg gcattggcct gccgaaggac | 1380 |
| gccgccagc tgcgcgggat gctgaagtat gcccaggagc atgctggccc cttcgccatc | 1440 |
| cgctatccgc gcggcaacgt ggaacgcgtg ccggaaggca cctggccgga gctgaggtgg | 1500 |
| ggcacctggg aacgcttgca agacggcgac gacgtggtga ttctggcggg aggcaaggcg | 1560 |
| ctggagtacg cgctgaaggc cgcccgcgac ctccccggcg tgggcgtggt gaatgcccgt | 1620 |
| ttcgtgaagc cgctcgacca agggatgctg cgcgaggtgg cgaccaaagc ccgcgcactg | 1680 |
| gtcacggtgg aggacaacac ggtcgtcggt gggttcggaa gtgccgtcct ggaagccctc | 1740 |
| agcgcgctgg ggctgagaac cccggtgcgg gttctcggca tccccgacgc gtttcaggat | 1800 |
| cacgcgaccg tagagagcgt gcatgcccgt gcggggattg acgcgcctgc catccgcacg | 1860 |
| gtcctggccg aacttggcgt ggacgtgccg ctggaggtct ag | 1902 |

<210> SEQ ID NO 54
<211> LENGTH: 633
<212> TYPE: PRT
<213> ORGANISM: Artificial Sequence
<220> FEATURE:
<223> OTHER INFORMATION: K219N mutant of the DXP synthase from D. geothermalis

<400> SEQUENCE: 54

```
Met Ser Glu Pro Thr Ala Asn Leu Gln Pro Ala Ser Arg Thr Pro Leu
1               5                   10                  15

Leu Asp Arg Val Asn Gly Pro Glu Asp Leu Lys Arg Leu Gly Arg Asp
            20                  25                  30

Gln Leu Pro Gln Leu Ala Ala Glu Leu Arg Glu Glu Ile Val Arg Val
        35                  40                  45

Cys Ser Val Gly Gly Leu His Leu Ala Ser Ser Leu Gly Ala Thr Asp
    50                  55                  60

Leu Ile Val Ala Leu His Tyr Val Leu His Ser Pro Arg Asp Arg Ile
65                  70                  75                  80

Leu Phe Asp Val Gly His Gln Ala Tyr Ala His Lys Met Leu Thr Gly
                85                  90                  95
```

-continued

```
Arg Arg His Leu Met His Thr Val Lys Lys Glu Gly Leu Ser Gly
            100                 105                 110

Phe Thr Lys Val Ser Glu Ser Glu His Asp Ala Ile Thr Val Gly His
            115                 120                 125

Ala Ser Thr Ser Leu Ala Asn Ala Leu Gly Met Ala Leu Ala Arg Asp
130                 135                 140

Ala Leu Gly Gln Asp Tyr Lys Val Ala Ala Val Ile Gly Asp Gly Ser
145                 150                 155                 160

Leu Thr Gly Gly Met Ala Leu Ala Ala Leu Asn Thr Ile Gly Asp Leu
                165                 170                 175

Gly Arg Arg Met Leu Ile Val Leu Asn Asp Asn Glu Met Ser Ile Ser
                180                 185                 190

Glu Asn Val Gly Ala Ile Asn Arg Phe Met Arg Gly Leu Gln Val Gln
                195                 200                 205

Lys Trp Phe Gln Glu Gly Glu Glu Ala Gly Asn Lys Ala Val Gln Ala
            210                 215                 220

Val Ser Lys Pro Leu Ala Asn Leu Met Ser Arg Ala Lys Ser Ser Thr
225                 230                 235                 240

Arg His Phe Phe Asp Pro Ala Ser Val Asn Pro Phe Ala Ala Met Gly
                245                 250                 255

Val Arg Tyr Val Gly Pro Val Asp Gly His Asn Val Gln Glu Leu Val
                260                 265                 270

Trp Leu Ile Glu Arg Leu Val Asp Leu Asp Gly Pro Thr Ile Leu His
            275                 280                 285

Val Val Thr Lys Lys Gly Lys Gly Leu Ser Tyr Ala Glu Ala Asp Pro
290                 295                 300

Ile Lys Trp His Gly Pro Gly Lys Phe Asp Pro Ala Thr Gly Glu Ser
305                 310                 315                 320

Val Pro Ser Asn Ala Tyr Ser Trp Ser Ser Ala Phe Gly Asp Ala Val
                325                 330                 335

Thr Glu Leu Ala Arg Leu Asp Pro Arg Thr Phe Val Ile Thr Pro Ala
                340                 345                 350

Met Arg Glu Gly Ser Gly Leu Val Arg Tyr Ser Gln Val His Pro His
            355                 360                 365

Arg Tyr Leu Asp Val Gly Ile Ala Glu Asp Val Ala Val Thr Thr Ala
370                 375                 380

Ala Gly Met Ala Leu Gln Gly Met Arg Pro Ile Val Ala Ile Tyr Ser
385                 390                 395                 400

Thr Phe Leu Gln Arg Ala Tyr Asp Gln Val Leu His Asp Val Ala Ile
                405                 410                 415

Glu Asn Leu Asn Val Thr Phe Ala Ile Asp Arg Gly Gly Ile Val Gly
                420                 425                 430

Ala Asp Gly Ala Thr His Asn Gly Val Phe Asp Leu Ser Tyr Leu Arg
            435                 440                 445

Ser Ile Pro Asn Val Gly Ile Gly Leu Pro Lys Asp Ala Ala Glu Leu
450                 455                 460

Arg Gly Met Leu Lys Tyr Ala Gln Glu His Ala Gly Pro Phe Ala Ile
465                 470                 475                 480

Arg Tyr Pro Arg Gly Asn Val Glu Arg Val Pro Glu Gly Thr Trp Pro
                485                 490                 495

Glu Leu Arg Trp Gly Thr Trp Glu Arg Leu Gln Asp Gly Asp Asp Val
            500                 505                 510

Val Ile Leu Ala Gly Gly Lys Ala Leu Glu Tyr Ala Leu Lys Ala Ala
```

```
            515                 520                 525
Arg Asp Leu Pro Gly Val Gly Val Val Asn Ala Arg Phe Val Lys Pro
    530                 535                 540

Leu Asp Gln Gly Met Leu Arg Glu Val Ala Thr Lys Ala Arg Ala Leu
545                 550                 555                 560

Val Thr Val Glu Asp Asn Thr Val Val Gly Phe Gly Ser Ala Val
                565                 570                 575

Leu Glu Ala Leu Ser Ala Leu Gly Leu Arg Thr Pro Val Arg Val Leu
            580                 585                 590

Gly Ile Pro Asp Ala Phe Gln Asp His Ala Thr Val Glu Ser Val His
        595                 600                 605

Ala Arg Ala Gly Ile Asp Ala Pro Ala Ile Arg Thr Val Leu Ala Glu
    610                 615                 620

Leu Gly Val Asp Val Pro Leu Glu Val
625                 630

<210> SEQ ID NO 55
<211> LENGTH: 1902
<212> TYPE: DNA
<213> ORGANISM: Artificial Sequence
<220> FEATURE:
<223> OTHER INFORMATION: R241C mutant of the DXP synthase from D.
      geothermalis

<400> SEQUENCE: 55
atgagtgagc caactgccaa cctccagcct gccagccgca ccccgctgct ggaccgggtg      60
aatggcccgg aagacctcaa acggctcgga cgcgaccagc taccccagct cgctgccgaa     120
ctgcgcgagg agatcgtgcg ggtctgctcg gtagggggt tacatctcgc cagctctctg      180
ggcgcgaccg acctaatcgt ggcgctacat tacgtgctgc attcgccgcg cgaccgcatt     240
ctgttcgacg tggggcatca ggcctacgcc acaagatgc tcacgggccg ccgccacctg      300
atgcacaccg tcaagaagga gggcgggctg tcgggcttca ccaaggtgag cgagtccgaa     360
cacgacgcca tcacggtggg ccatgccagc acctccctcg ccaatgcgct gggcatggcg     420
cttgcacggg acgctttggg acaggattac aaggtggctg ccgtgatcgg ggacggctcg     480
ctgacgggcg gcatggcgct ggcggcgctg aataccatcg ggacctgggg cggcgaatg      540
ctcattgtgc ttaacgacaa cgagatgagc atcagcgaga acgtgggggc catcaaccgc     600
ttcatgcggg gtctccaggt gcagaagtgg ttccaggagg gcgaggaagc cgggaaaaag     660
gccgtgcagg cggtcagcaa gccgctcgcc aacttgatga ccgcgccaa gagttccacg      720
tgccactttt tcgatcccgc cagtgtcaat cccttttgccg cgatgggcgt gcgctatgtg    780
ggaccggtgg acggccacaa cgtgcaggaa ttggtgtggc tgatcgagcg gctggtcgac    840
ctcgatgggc cgaccattct gcacgtcgtc accaaaaagg gcaagggcct gagctacgcc    900
gaggccgacc cgatcaaatg gcatggcccg gcaagtttg acccggcgac gggtgagtcg     960
gtgcccagca atgcctactc gtggagcagc gcctttggag acgcggtgac cgagcttgca   1020
cggctggacc ccgtacctt tgtgatcacg cccgcgatgc gcgagggcag cggcctggtg    1080
cgctacagcc aggttcaccc ccaccgttac ctggatgtcg gtatcgcgga ggacgtggcc   1140
gtcaccacgg ccgccggaat ggcgcttcag gggatgcggc ccatcgtggc gatctactcc   1200
actttcctgc aacgcgccta cgatcaggtg ctgcacgacg tcgccatcga gaatctgaac   1260
gtgaccttcg ccatcgaccg tggggcatc gtgggcgcag acggagccac ccacaacggc    1320
gtcttcgacc tgagttacct cgcgctcgatt ccgaatgtcg gcattggcct gccgaaggac  1380
```

```
gccgccgagc tgcgcgggat gctgaagtat gcccaggagc atgctggccc cttcgccatc   1440
cgctatccgc gcggcaacgt ggaacgcgtg ccggaaggca cctggccgga gctgaggtgg   1500
ggcacctggg aacgcttgca agacggcgac gacgtggtga ttctggcggg aggcaaggcg   1560
ctggagtacg cgctgaaggc cgcccgcgac ctccccggcg tgggcgtggt gaatgcccgt   1620
ttcgtgaagc cgctcgacca agggatgctg cgcgaggtgg cgaccaaagc ccgcgcactg   1680
gtcacggtgg aggacaacac ggtcgtcggt gggttcggaa gtgccgtcct ggaagccctc   1740
agcgcgctgg ggctgagaac cccggtgcgg gttctcggca tccccgacgc gtttcaggat   1800
cacgcgaccg tagagagcgt gcatgcccgt gcggggattg acgcgcctgc catccgcacg   1860
gtcctggccg aacttggcgt ggacgtgccg ctggaggtct ag                     1902
```

<210> SEQ ID NO 56
<211> LENGTH: 633
<212> TYPE: PRT
<213> ORGANISM: Artificial Sequence
<220> FEATURE:
<223> OTHER INFORMATION: R241C mutant of the DXP synthase from D. geothermalis

<400> SEQUENCE: 56

```
Met Ser Glu Pro Thr Ala Asn Leu Gln Pro Ala Ser Arg Thr Pro Leu
1               5                   10                  15

Leu Asp Arg Val Asn Gly Pro Glu Asp Leu Lys Arg Leu Gly Arg Asp
            20                  25                  30

Gln Leu Pro Gln Leu Ala Ala Glu Leu Arg Glu Glu Ile Val Arg Val
        35                  40                  45

Cys Ser Val Gly Gly Leu His Leu Ala Ser Ser Leu Gly Ala Thr Asp
    50                  55                  60

Leu Ile Val Ala Leu His Tyr Val Leu His Ser Pro Arg Asp Arg Ile
65                  70                  75                  80

Leu Phe Asp Val Gly His Gln Ala Tyr Ala His Lys Met Leu Thr Gly
                85                  90                  95

Arg Arg His Leu Met His Thr Val Lys Lys Glu Gly Gly Leu Ser Gly
            100                 105                 110

Phe Thr Lys Val Ser Glu Ser Glu His Asp Ala Ile Thr Val Gly His
        115                 120                 125

Ala Ser Thr Ser Leu Ala Asn Ala Leu Gly Met Ala Leu Ala Arg Asp
    130                 135                 140

Ala Leu Gly Gln Asp Tyr Lys Val Ala Ala Val Ile Gly Asp Gly Ser
145                 150                 155                 160

Leu Thr Gly Gly Met Ala Leu Ala Ala Leu Asn Thr Ile Gly Asp Leu
                165                 170                 175

Gly Arg Arg Met Leu Ile Val Leu Asn Asp Asn Glu Met Ser Ile Ser
            180                 185                 190

Glu Asn Val Gly Ala Ile Asn Arg Phe Met Arg Gly Leu Gln Val Gln
        195                 200                 205

Lys Trp Phe Gln Glu Gly Glu Glu Ala Gly Lys Lys Ala Val Gln Ala
    210                 215                 220

Val Ser Lys Pro Leu Ala Asn Leu Met Ser Arg Ala Lys Ser Ser Thr
225                 230                 235                 240

Cys His Phe Phe Asp Pro Ala Ser Val Asn Pro Phe Ala Ala Met Gly
                245                 250                 255

Val Arg Tyr Val Gly Pro Val Asp Gly His Asn Val Gln Glu Leu Val
```

```
            260                 265                 270
Trp Leu Ile Glu Arg Leu Val Asp Leu Asp Gly Pro Thr Ile Leu His
        275                 280                 285
Val Val Thr Lys Lys Gly Lys Gly Leu Ser Tyr Ala Glu Ala Asp Pro
    290                 295                 300
Ile Lys Trp His Gly Pro Gly Lys Phe Asp Pro Ala Thr Gly Glu Ser
305                 310                 315                 320
Val Pro Ser Asn Ala Tyr Ser Trp Ser Ala Phe Gly Asp Ala Val
                325                 330                 335
Thr Glu Leu Ala Arg Leu Asp Pro Arg Thr Phe Val Ile Thr Pro Ala
                340                 345                 350
Met Arg Glu Gly Ser Gly Leu Val Arg Tyr Ser Gln Val His Pro His
            355                 360                 365
Arg Tyr Leu Asp Val Gly Ile Ala Glu Asp Val Ala Val Thr Thr Ala
        370                 375                 380
Ala Gly Met Ala Leu Gln Gly Met Arg Pro Ile Val Ala Ile Tyr Ser
385                 390                 395                 400
Thr Phe Leu Gln Arg Ala Tyr Asp Gln Val Leu His Asp Val Ala Ile
                405                 410                 415
Glu Asn Leu Asn Val Thr Phe Ala Ile Asp Arg Gly Ile Val Gly
                420                 425                 430
Ala Asp Gly Ala Thr His Asn Gly Val Phe Asp Leu Ser Tyr Leu Arg
            435                 440                 445
Ser Ile Pro Asn Val Gly Ile Gly Leu Pro Lys Asp Ala Ala Glu Leu
        450                 455                 460
Arg Gly Met Leu Lys Tyr Ala Gln Glu His Ala Gly Pro Phe Ala Ile
465                 470                 475                 480
Arg Tyr Pro Arg Gly Asn Val Glu Arg Val Pro Glu Gly Thr Trp Pro
                485                 490                 495
Glu Leu Arg Trp Gly Thr Trp Glu Arg Leu Gln Asp Gly Asp Asp Val
                500                 505                 510
Val Ile Leu Ala Gly Gly Lys Ala Leu Glu Tyr Ala Leu Lys Ala Ala
            515                 520                 525
Arg Asp Leu Pro Gly Val Gly Val Asn Ala Arg Phe Val Lys Pro
        530                 535                 540
Leu Asp Gln Gly Met Leu Arg Glu Val Ala Thr Lys Ala Arg Ala Leu
545                 550                 555                 560
Val Thr Val Glu Asp Asn Thr Val Val Gly Gly Phe Gly Ser Ala Val
                565                 570                 575
Leu Glu Ala Leu Ser Ala Leu Gly Leu Arg Thr Pro Val Arg Val Leu
                580                 585                 590
Gly Ile Pro Asp Ala Phe Gln Asp His Ala Thr Val Glu Ser Val His
            595                 600                 605
Ala Arg Ala Gly Ile Asp Ala Pro Ala Ile Arg Thr Val Leu Ala Glu
        610                 615                 620
Leu Gly Val Asp Val Pro Leu Glu Val
625                 630

<210> SEQ ID NO 57
<211> LENGTH: 1902
<212> TYPE: DNA
<213> ORGANISM: Artificial Sequence
<220> FEATURE:
<223> OTHER INFORMATION: K219N/R241C mutant of the DXP synthase from D.
      geothermalis
```

<400> SEQUENCE: 57

```
atgagtgagc caactgccaa cctccagcct gccagccgca ccccgctgct ggaccgggtg      60
aatggcccgg aagacctcaa acggctcgga cgcgaccagc taccccagct cgctgccgaa     120
ctgcgcgagg agatcgtgcg ggtctgctcg gtagggggt tacatctcgc cagctctctg      180
ggcgcgaccg acctaatcgt ggcgctacat tacgtgctgc attcgccgcg cgaccgcatt     240
ctgttcgacg tggggcatca ggcctacgcc acaagatgc tcacgggccg ccgccacctg      300
atgcacaccg tcaagaagga gggcgggctg tcgggcttca ccaaggtgag cgagtccgaa     360
cacgacgcca tcacggtggg ccatgccagc acctccctcg ccaatgcgct gggcatggcg     420
cttgcacggg acgctttggg acaggattac aaggtggctg ccgtgatcgg ggacggctcg     480
ctgacgggcg gcatggcgct ggcggcgctg aataccatcg ggacctgggg cggcgaatg      540
ctcattgtgc ttaacgacaa cgagatgagc atcagcgaga acgtggggc catcaaccgc      600
ttcatgcggg tctccaggt gcagaagtgg ttccaggagg cgaggaagc cgggaacaag       660
gccgtgcagg cggtcagcaa gccgctcgcc aacttgatga gccgcgccaa gagttccacg     720
tgccactttt tcgatcccgc cagtgtcaat ccctttgccg cgatgggcgt gcgctatgtg     780
ggaccggtgg acgccacaa cgtgcaggaa ttggtgtggc tgatcgagcg gctggtcgac     840
ctcgatgggc cgaccattct gcacgtcgtc accaaaaagg gcaagggcct gagctacgcc     900
gaggccgacc cgatcaaatg gcatggcccg ggcaagtttg acccggcgac gggtgagtcg     960
gtgcccagca atgcctactc gtggagcagc gcctttggag acgcggtgac cgagcttgca    1020
cggctggacc cccgtacctt tgtgatcacg cccgcgatgc gcgagggcag cggcctggtg    1080
cgctacagcc aggttcaccc ccaccgttac ctggatgtcg gtatcgcgga ggacgtggcc    1140
gtcaccacgg ccgccggaat ggcgcttcag gggatgcggc ccatcgtggc gatctactcc    1200
actttcctgc aacgcgccta cgatcaggtg ctgcacgacg tcgccatcga gaatctgaac    1260
gtgaccttcg ccatcgaccg tggggcatc gtgggcgcag acggagccac ccacaacggc    1320
gtcttcgacc tgagttacct cgctcgatt ccgaatgtcg gcattggcct gccgaaggac     1380
gccgccgagc tgcgcgggat gctgaagtat gcccaggagc atgctggccc cttcgccatc    1440
cgctatccgc gcggcaacgt ggaacgcgtg ccggaaggca cctggccgga gctgaggtgg    1500
ggcacctggg aacgcttgca agacggcgac gacgtggtga ttctggcggg aggcaaggcg    1560
ctggagtacg cgctgaaggc cgcccgcgac ctccccggcg tgggcgtggt gaatgcccgt    1620
ttcgtgaagc gctcgaccc agggatgctg cgcgaggtgg cgaccaaagc ccgcgcactg    1680
gtcacggtgg aggacaacac ggtcgtcggt gggttcggaa gtgccgtcct ggaagccctc    1740
agcgcgctgg ggctgagaac cccggtgcgg gttctcggca tccccgacgc gtttcaggat    1800
cacgcgaccg tagagagcgt gcatgcccgt gcggggattg acgcgcctgc catccgcacg    1860
gtcctggccg aacttggcgt ggacgtgccg ctggaggtct ag                      1902
```

<210> SEQ ID NO 58
<211> LENGTH: 633
<212> TYPE: PRT
<213> ORGANISM: Artificial Sequence
<220> FEATURE:
<223> OTHER INFORMATION: K219N/R241C mutant of the DXP synthase from D. geothermalis

<400> SEQUENCE: 58

Met Ser Glu Pro Thr Ala Asn Leu Gln Pro Ala Ser Arg Thr Pro Leu

-continued

```
1               5                   10                  15
Leu Asp Arg Val Asn Gly Pro Glu Asp Leu Lys Arg Leu Gly Arg Asp
                20                  25                  30
Gln Leu Pro Gln Leu Ala Ala Glu Leu Arg Glu Ile Val Arg Val
                35                  40                  45
Cys Ser Val Gly Gly Leu His Leu Ala Ser Ser Leu Gly Ala Thr Asp
                50                  55                  60
Leu Ile Val Ala Leu His Tyr Val Leu His Ser Pro Arg Asp Arg Ile
65                  70                  75                  80
Leu Phe Asp Val Gly His Gln Ala Tyr Ala His Lys Met Leu Thr Gly
                85                  90                  95
Arg Arg His Leu Met His Thr Val Lys Lys Glu Gly Gly Leu Ser Gly
                100                 105                 110
Phe Thr Lys Val Ser Glu Ser Glu His Asp Ala Ile Thr Val Gly His
                115                 120                 125
Ala Ser Thr Ser Leu Ala Asn Ala Leu Gly Met Ala Leu Ala Arg Asp
                130                 135                 140
Ala Leu Gly Gln Asp Tyr Lys Val Ala Ala Val Ile Gly Asp Gly Ser
145                 150                 155                 160
Leu Thr Gly Gly Met Ala Leu Ala Ala Leu Asn Thr Ile Gly Asp Leu
                165                 170                 175
Gly Arg Arg Met Leu Ile Val Leu Asn Asp Asn Glu Met Ser Ile Ser
                180                 185                 190
Glu Asn Val Gly Ala Ile Asn Arg Phe Met Arg Gly Leu Gln Val Gln
                195                 200                 205
Lys Trp Phe Gln Glu Gly Glu Glu Ala Gly Asn Lys Ala Val Gln Ala
                210                 215                 220
Val Ser Lys Pro Leu Ala Asn Leu Met Ser Arg Ala Lys Ser Ser Thr
225                 230                 235                 240
Cys His Phe Phe Asp Pro Ala Ser Val Asn Pro Phe Ala Ala Met Gly
                245                 250                 255
Val Arg Tyr Val Gly Pro Val Asp Gly His Asn Val Gln Glu Leu Val
                260                 265                 270
Trp Leu Ile Glu Arg Leu Val Asp Leu Asp Gly Pro Thr Ile Leu His
                275                 280                 285
Val Val Thr Lys Lys Gly Lys Gly Leu Ser Tyr Ala Glu Ala Asp Pro
                290                 295                 300
Ile Lys Trp His Gly Pro Gly Lys Phe Asp Pro Ala Thr Gly Glu Ser
305                 310                 315                 320
Val Pro Ser Asn Ala Tyr Ser Trp Ser Ala Phe Gly Asp Ala Val
                325                 330                 335
Thr Glu Leu Ala Arg Leu Asp Pro Arg Thr Phe Val Ile Thr Pro Ala
                340                 345                 350
Met Arg Glu Gly Ser Gly Leu Val Arg Tyr Ser Gln Val His Pro His
                355                 360                 365
Arg Tyr Leu Asp Val Gly Ile Ala Glu Asp Val Ala Val Thr Thr Ala
                370                 375                 380
Ala Gly Met Ala Leu Gln Gly Met Arg Pro Ile Val Ala Ile Tyr Ser
385                 390                 395                 400
Thr Phe Leu Gln Arg Ala Tyr Asp Gln Val Leu His Asp Val Ala Ile
                405                 410                 415
Glu Asn Leu Asn Val Thr Phe Ala Ile Asp Arg Gly Gly Ile Val Gly
                420                 425                 430
```

```
Ala Asp Gly Ala Thr His Asn Gly Val Phe Asp Leu Ser Tyr Leu Arg
            435                 440                 445

Ser Ile Pro Asn Val Gly Ile Gly Leu Pro Lys Asp Ala Ala Glu Leu
    450                 455                 460

Arg Gly Met Leu Lys Tyr Ala Gln Glu His Ala Gly Pro Phe Ala Ile
465                 470                 475                 480

Arg Tyr Pro Arg Gly Asn Val Glu Arg Val Pro Glu Gly Thr Trp Pro
                485                 490                 495

Glu Leu Arg Trp Gly Thr Trp Glu Arg Leu Gln Asp Gly Asp Asp Val
                500                 505                 510

Val Ile Leu Ala Gly Gly Lys Ala Leu Glu Tyr Ala Leu Lys Ala Ala
            515                 520                 525

Arg Asp Leu Pro Gly Val Gly Val Asn Ala Arg Phe Val Lys Pro
            530                 535                 540

Leu Asp Gln Gly Met Leu Arg Glu Val Ala Thr Lys Ala Arg Ala Leu
545                 550                 555                 560

Val Thr Val Glu Asp Asn Thr Val Val Gly Phe Gly Ser Ala Val
                565                 570                 575

Leu Glu Ala Leu Ser Ala Leu Gly Leu Arg Thr Pro Val Arg Val Leu
            580                 585                 590

Gly Ile Pro Asp Ala Phe Gln Asp His Ala Thr Val Glu Ser Val His
            595                 600                 605

Ala Arg Ala Gly Ile Asp Ala Pro Ala Ile Arg Thr Val Leu Ala Glu
            610                 615                 620

Leu Gly Val Asp Val Pro Leu Glu Val
625                 630
```

```
<210> SEQ ID NO 59
<211> LENGTH: 1911
<212> TYPE: DNA
<213> ORGANISM: Deinococcus radiopugnans

<400> SEQUENCE: 59
ttgaccgaca tcaaaaaggc tgatgggctg cacctcgggc acaagggcac gccgctgctg      60
gaccgcattg ccggcccggc tgacctcaag aagctctcgc gcgatcagtt gcccgagctg     120
agccaggaac tgcgcgacga gatcgtgcgg gtctgctcgg tgggtgggct gcatctggcg     180
tcctcgctgg gggccaccga cctgatcgtg gcgctgcatt acgtgctgaa cagtccgcgt     240
gaccggattc tcttcgacgt gggtcaccag gcctacgccc acaagatgct gaccgggcgg     300
cgggagcaga tgcacaccgt caagaaggaa ggtgggctga gcggctttac caaggtcagc     360
gagtccgaac acgacgccat taccgtgggc cacgccagca ccagcctggc gaacgcgctg     420
ggcatggcga tggcgagaga cgcgctgggc caggactatc aggtggccgc cgtgatcggc     480
gacggctcgc tgaccggcgg gatggcgctg ccgcccctga caccatcgg tgacctgcgc     540 cgcaagatgc tgatcgtcct gaacgacaac gagatgagca tttccgagaa cgtgggcgcg     600
atcaacaagt tcatgcgcgg cctgcaggtc cagaagtggt tcaggagggg cgagggagcc     660
gggaaaaagg cggtgcagtc cctgagcaag ccgctggccg atttcatgag ccgtgccaag     720
agcagcaccc gccacttctt cgatccggcc agcgtcaatc ccttcgccat gatgggcgtg     780
cgttatgtcg gccggtcga cggccacaac gtccaggaac tggtgtggct gatgaacgg      840 ctggtggacc tggacggccc cacgatcctg catgtcgtga cccgcaaggg caagggcctg     900
agctacgccg aggccgaccc gatctactgg cacggtcccg gtcaatttga cccggacacc     960
```

```
ggggatttca aggccagcag cgcgtactcg tggagcgccg cgttcggcga cgccgtgacc      1020
gaactggcca aacgcgatcc gcgtactttc gtgatcaccc cggccatgcg cgagggcagc      1080
gggctggtgg gctacagccg ggcgcacccg caccgttacc tggacgtggg catcgccgag      1140
gacgtggccg tgaccactgc cgccggcatg gcgttgcagg gcctgcggcc catcgtggcg      1200
atctactcca ccttcctgca acgcgcctac gatcaggtgt tgcacgacgt cgccatcgag      1260
aacctgaacg tcaccttcgc catcgaccgc gccgggatcg tggggccga cggctcgacg      1320 cacaacggcg tgttcgacct gagctacctg cgcagcattc ccaacgtgcg gatcggcctg      1380
ccgaaggacg cccacgagat gcgcggcatg ctgaagtacg cgcaggagca cgacggtccc      1440
ttcgccatcc gttacccgcg cggcaacacg gtcaaggtgc cggaaggcac gtggcccacg      1500
ctggaatggg gcacgtggga gcgcgtcaag gaaggctccg acgccgtgat cctgccggc      1560 ggcaaggcgc tggaatacgc gcaggcggcg gcggcggacc tgcccggcgt cggtgtggtg      1620
aacgcccgtt tcgtcaagcc gctggacctg aacatgctgc gcgagctggc cggcagcgcc      1680
cgcacaatca tcaccgtgga ggacaacacg ctggtgggcg gcttcggcag cgccgtgttg      1740
gaggccctga acagcatggg cttaaaggtg cccgtgcgga cgctgggcat tccggacgag      1800
ttccaggacc acgccaccgc cgagagcgtc cacgcccgcg ccggcatcga tgcccaggcg      1860
atccgcaccg tgctggccga gcttggggtg gatgtgcctc tgggcgtctg a              1911

<210> SEQ ID NO 60
<211> LENGTH: 1146
<212> TYPE: DNA
<213> ORGANISM: Deinococcus radiopugnans

<400> SEQUENCE: 60
ttgggcagca cgggcagcat cggcacgcag gcgctggatg tggcgcgcga gcgtggctac      60
acggtgacgg cgctggccgc cgggcgcaac ctggcgctgt tgcagcagca ggtgcgtgag      120
tttcgcccgg cgctggtcag cgtggagccg gcggtgtacg ccgaggccaa ggcgctgctg      180
cccggcaccc gcgtaaccgc ccacgtcagc gaggtggcgg ccctgaaagc tgatgtggtg      240
gtcaacgcca tgagcggttt aatcgggctg ccccccaccc gcgccgcact tcaggcgggt      300
caggcggtgg cgctggcgac gaaggaggcg atggtcacgg cggcgggcct gatctgggag      360
gcggcctcgg cgggcggcgg gcgcgtggtc ccggtggact ccgaacacac cggcgtcttc      420
cagtgcctga ccggcgagga catggcggac gtggccgaag tgatcctgac cgcctccggc      480 ggcccccttcc gcgacggccc cgccgatctg gcgggggtga cgcccgcgca ggcgctgaag      540
cacccgtcgt ggagcatggg gccgaaggtg accatcgaca gcgccaccct gatgaacaag      600
gggctggagg tcatggagtg cgccagcctg tacggcctgc cgctgtctgg ggtgggcgtg      660
gtggtccacc gcagagcct gatccacgcg gcggtgcgct tccgcgacgg cagcctcaag      720
gcgcagttcg gccccaccga catgcgcctg ccgattgcct acgccatcga cgccgcgccc      780
accggcatgc agcgccccgg cgacgtgcgg ggtgccagac gcgggccgga ggtggccggg      840
cacctgtcct ggccgatgcg gggcatgtgg gagttccgcg agcccgattt tgaccgcttt      900
ccctgcctgg gcctggccta ccgcgccgga gaggcgggcg gtctgctgcc ggtggccctg      960
aacgcggcgg acgaggtggc agtggaggcg ttcctggccg gcaactgcc gttcatgggt      1020 atccccaggc tgctggagcg ggtgctggac gagacgccgg cgggcgccct gagctgggac      1080
acgctggacg agaccgacgc ctgggcacgc gtgcggggcct gggaactggt ggggatgcgg      1140
```

```
gcgtga                                                          1146
```

<210> SEQ ID NO 61
<211> LENGTH: 381
<212> TYPE: PRT
<213> ORGANISM: Deinococcus radiopugnans

<400> SEQUENCE: 61

| | | | | | | | | | | | | | | | |
|---|---|---|---|---|---|---|---|---|---|---|---|---|---|---|---|
| Leu | Gly | Ser | Thr | Gly | Ser | Ile | Gly | Thr | Gln | Ala | Leu | Asp | Val | Ala | Arg |
| 1 | | | | 5 | | | | | 10 | | | | | 15 | |
| Glu | Arg | Gly | Tyr | Thr | Val | Thr | Ala | Leu | Ala | Ala | Gly | Arg | Asn | Leu | Ala |
| | | | 20 | | | | 25 | | | | | 30 | | | |
| Leu | Leu | Gln | Gln | Gln | Val | Arg | Glu | Phe | Arg | Pro | Ala | Leu | Val | Ser | Val |
| | | 35 | | | | | 40 | | | | 45 | | | | |
| Glu | Pro | Ala | Val | Tyr | Ala | Glu | Ala | Lys | Ala | Leu | Leu | Pro | Gly | Thr | Arg |
| | 50 | | | | | 55 | | | | | 60 | | | | |
| Val | Thr | Ala | His | Val | Ser | Glu | Val | Ala | Ala | Leu | Lys | Ala | Asp | Val | Val |
| 65 | | | | | 70 | | | | | 75 | | | | | 80 |
| Val | Asn | Ala | Met | Ser | Gly | Leu | Ile | Gly | Leu | Ala | Pro | Thr | Arg | Ala | Ala |
| | | | | 85 | | | | | 90 | | | | | 95 | |
| Leu | Gln | Ala | Gly | Gln | Ala | Val | Ala | Leu | Ala | Thr | Lys | Glu | Ala | Met | Val |
| | | | 100 | | | | | 105 | | | | | 110 | | |
| Thr | Ala | Ala | Gly | Leu | Ile | Trp | Glu | Ala | Ala | Ser | Ala | Gly | Gly | Gly | Arg |
| | | | 115 | | | | | 120 | | | | | 125 | | |
| Val | Val | Pro | Val | Asp | Ser | Glu | His | Thr | Gly | Val | Phe | Gln | Cys | Leu | Thr |
| | 130 | | | | | 135 | | | | | 140 | | | | |
| Gly | Glu | Asp | Met | Ala | Asp | Val | Ala | Glu | Val | Ile | Leu | Thr | Ala | Ser | Gly |
| 145 | | | | | 150 | | | | | 155 | | | | | 160 |
| Gly | Pro | Phe | Arg | Asp | Gly | Pro | Ala | Asp | Leu | Gly | Gly | Val | Thr | Pro | Ala |
| | | | | 165 | | | | | 170 | | | | | 175 | |
| Gln | Ala | Leu | Lys | His | Pro | Ser | Trp | Ser | Met | Gly | Pro | Lys | Val | Thr | Ile |
| | | | 180 | | | | | 185 | | | | | 190 | | |
| Asp | Ser | Ala | Thr | Leu | Met | Asn | Lys | Gly | Leu | Glu | Val | Met | Glu | Cys | Ala |
| | | 195 | | | | | 200 | | | | | 205 | | | |
| Ser | Leu | Tyr | Gly | Leu | Pro | Leu | Ser | Gly | Val | Gly | Val | Val | His | Pro | |
| | 210 | | | | | 215 | | | | | 220 | | | | |
| Gln | Ser | Leu | Ile | His | Ala | Ala | Val | Arg | Phe | Arg | Asp | Gly | Ser | Leu | Lys |
| 225 | | | | | 230 | | | | | 235 | | | | | 240 |
| Ala | Gln | Phe | Gly | Pro | Thr | Asp | Met | Arg | Leu | Pro | Ile | Ala | Tyr | Ala | Ile |
| | | | | 245 | | | | | 250 | | | | | 255 | |
| Asp | Ala | Ala | Pro | Thr | Gly | Met | Gln | Arg | Pro | Gly | Asp | Val | Arg | Gly | Ala |
| | | | 260 | | | | | 265 | | | | | 270 | | |
| Arg | Arg | Gly | Pro | Glu | Val | Ala | Gly | His | Leu | Ser | Trp | Pro | Met | Arg | Gly |
| | | 275 | | | | | 280 | | | | | 285 | | | |
| Met | Trp | Glu | Phe | Arg | Glu | Pro | Asp | Phe | Asp | Arg | Phe | Pro | Cys | Leu | Gly |
| | 290 | | | | | 295 | | | | | 300 | | | | |
| Leu | Ala | Tyr | Arg | Ala | Gly | Ala | Gly | Gly | Leu | Leu | Pro | Val | Ala | Leu | |
| 305 | | | | | 310 | | | | | 315 | | | | | 320 |
| Asn | Ala | Ala | Asp | Glu | Val | Ala | Val | Glu | Ala | Phe | Leu | Ala | Gly | Gln | Leu |
| | | | | 325 | | | | | 330 | | | | | 335 | |
| Pro | Phe | Met | Gly | Ile | Pro | Arg | Leu | Leu | Glu | Arg | Val | Leu | Asp | Glu | Thr |
| | | | 340 | | | | | 345 | | | | | 350 | | |
| Pro | Ala | Gly | Ala | Leu | Ser | Trp | Asp | Thr | Leu | Asp | Glu | Thr | Asp | Ala | Trp |
| | | 355 | | | | | 360 | | | | | 365 | | | |

Ala Arg Val Arg Ala Trp Glu Leu Val Gly Met Arg Ala
    370                 375                 380

<210> SEQ ID NO 62
<211> LENGTH: 699
<212> TYPE: DNA
<213> ORGANISM: Deinococcus radiopugnans

<400> SEQUENCE: 62

```
atgagcggcg cctgcctgct gtccggcacc acggcggcgc tgattcccgc cgccggcagc    60
ggcacccgcc tgggcctggg ccacaaggcg ttcgtgacgg tgggcggcct gtccctgctg   120
gcccgcagcg tcgccgccct ggccccgcac gtggacgagg tgctggtggc cctgccggac   180
ggcttggagc ttcccctggg gatcaaggcc cgcgcgattg tcggcggcca gacccgccag   240
gacagcgtgc gccgcctgct gcgcgcgacg gtggccgata ccgtgctggt tcacgacgcg   300
gcgcggcctt tcctgagtgc cgacatcgtc ctcacgctgc tggaggccgt ggcggaaacg   360
ggggcggcga cggtggccct gcccgtcgcc gacacgctgg tggggcagac gcaggcgag   420
atgtggggag cggccgtctc ccgcgagggg ctgtggtcgg tgcagacgcc gcagggcttc   480
cgccgcgaac ggctgctgcg ggcgcacgcg caggcggccg ccgacggaca cgtcgccacc   540
gacgacgcgg gcctgatcgc gcggcagggc ggcgcagtgc ggctggtgcg cggcgacacc   600
cggctgttca aggtgaccac ccccggcgac ctggcgctgg cccaggcgct ggctccggtg   660
tgggacgcgc agatgagcgg gggcggcggc ccggtatga                          699
```

<210> SEQ ID NO 63
<211> LENGTH: 232
<212> TYPE: PRT
<213> ORGANISM: Deinococcus radiopugnans

<400> SEQUENCE: 63

Met Ser Gly Ala Cys Leu Leu Ser Gly Thr Thr Ala Ala Leu Ile Pro
1               5                   10                  15

Ala Ala Gly Ser Gly Thr Arg Leu Gly Leu Gly His Lys Ala Phe Val
            20                  25                  30

Thr Val Gly Gly Leu Ser Leu Leu Ala Arg Ser Val Ala Ala Leu Ala
        35                  40                  45

Pro His Val Asp Glu Val Leu Val Ala Leu Pro Asp Gly Leu Glu Leu
    50                  55                  60

Pro Leu Gly Ile Lys Ala Arg Ala Ile Val Gly Gly Gln Thr Arg Gln
65                  70                  75                  80

Asp Ser Val Arg Arg Leu Leu Arg Ala Thr Val Ala Asp Thr Val Leu
                85                  90                  95

Val His Asp Ala Ala Arg Pro Phe Leu Ser Ala Asp Ile Val Leu Thr
            100                 105                 110

Leu Leu Glu Ala Val Ala Glu Thr Gly Ala Ala Thr Val Ala Leu Pro
        115                 120                 125

Val Ala Asp Thr Leu Val Gly Ala Asp Ala Gly Glu Met Trp Gly Ala
    130                 135                 140

Ala Val Ser Arg Glu Gly Leu Trp Ser Val Gln Thr Pro Gln Gly Phe
145                 150                 155                 160

Arg Arg Glu Arg Leu Leu Arg Ala His Ala Gln Ala Ala Asp Gly
                165                 170                 175

His Val Ala Thr Asp Asp Ala Gly Leu Ile Ala Arg Gln Gly Gly Ala
            180                 185                 190

Val Arg Leu Val Arg Gly Asp Thr Arg Leu Phe Lys Val Thr Thr Pro
            195                 200                 205

Gly Asp Leu Ala Leu Ala Gln Ala Leu Ala Pro Val Trp Asp Ala Gln
        210                 215                 220

Met Ser Gly Gly Gly Pro Val
225                 230

<210> SEQ ID NO 64
<211> LENGTH: 867
<212> TYPE: DNA
<213> ORGANISM: Deinococcus radiopugnans

<400> SEQUENCE: 64

```
atgctggggg gcgtgagcct ccgcaccccc accctgtccc gcaagaccta tctggccccg      60
gccaaggtca atctcggcct gagcgtgcgt gacctgcggg cggatggcta ccacgaactg     120
cacacgctga tggtgctgct tcggtgggg gatgagctgg agattggccc ggcagccacc     180
ctgaccctgg aggtcagcgg ttcagacctg cctgccgatg aacgcaatct ggtgtaccgc     240
gccgcccgcg cctacctgga cgcggcgggg gtggggagg gtgcgttcat caccctgcac     300
aagcgtctgc cgctggcctc cgggctgggc ggcggcagca cgacgcggc caccaccctg     360
atggccctgg cgcggctgta cccgtcgcag gtgtcgctgc cgaactggc gctgagcctg     420
ggcgcggacg tgcccttctt tctgctgggc caggccgccg ccgccgaggg cgtgggcgaa     480
ctgctggtgc cggtgccggt gccgcgcact gcgctggtgc tggtcaatcc gggcgtggag     540
gtcagcgccc gcgacgccta cgcgtggctg gacgacgagg aagcctttac cccggccctg     600
gacgtgggcg cgatcctggc cgcactgggt ggcgagcggg ccgtgcccta ccacaacgcc     660
ctgcaggact gtgtcagtgc ccgccacgcc cccatccgcg aagctctggc cgcgctgggg     720
gcggcgggtc tacgctcccc cctgatgagc ggttcgggca gcacctgctt cgcgctggcc     780
gccaatgatg gcaggctta cgacgccgca cgggccattg ccgccgccca tccggagtgg     840
tgggtccagg cggcccagac gttgtaa                                         867
```

<210> SEQ ID NO 65
<211> LENGTH: 288
<212> TYPE: PRT
<213> ORGANISM: Deinococcus radiopugnans

<400> SEQUENCE: 65

Met Leu Gly Gly Val Ser Leu Arg Thr Pro Thr Leu Ser Arg Lys Thr
1               5                   10                  15

Tyr Leu Ala Pro Ala Lys Val Asn Leu Gly Leu Ser Val Arg Asp Leu
            20                  25                  30

Arg Ala Asp Gly Tyr His Glu Leu His Thr Leu Met Val Leu Leu Ser
        35                  40                  45

Val Gly Asp Glu Leu Glu Ile Gly Pro Ala Ala Thr Leu Thr Leu Glu
    50                  55                  60

Val Ser Gly Ser Asp Leu Pro Ala Asp Glu Arg Asn Leu Val Tyr Arg
65                  70                  75                  80

Ala Ala Arg Ala Tyr Leu Asp Ala Ala Gly Val Gly Glu Gly Ala Phe
                85                  90                  95

Ile Thr Leu His Lys Arg Leu Pro Leu Ala Ser Gly Leu Gly Gly Gly
            100                 105                 110

Ser Ser Asp Ala Ala Thr Thr Leu Met Ala Leu Ala Arg Leu Tyr Pro
        115                 120                 125

```
Ser Gln Val Ser Leu Pro Glu Leu Ala Leu Ser Leu Gly Ala Asp Val
        130                 135                 140

Pro Phe Phe Leu Leu Gly Gln Ala Ala Ala Glu Gly Val Gly Glu
145                 150                 155                 160

Leu Leu Val Pro Val Pro Val Pro Arg Thr Ala Leu Val Leu Val Asn
                    165                 170                 175

Pro Gly Val Glu Val Ser Ala Arg Asp Ala Tyr Ala Trp Leu Asp Asp
                180                 185                 190

Glu Glu Ala Phe Thr Pro Ala Leu Asp Val Gly Ala Ile Leu Ala Ala
            195                 200                 205

Leu Gly Gly Glu Arg Ala Val Pro Tyr His Asn Ala Leu Gln Asp Cys
210                 215                 220

Val Ser Ala Arg His Ala Pro Ile Arg Glu Ala Leu Ala Ala Leu Gly
225                 230                 235                 240

Ala Ala Gly Leu Arg Ser Pro Leu Met Ser Gly Ser Gly Ser Thr Cys
                245                 250                 255

Phe Ala Leu Ala Ala Asn Asp Gly Gln Ala Tyr Asp Ala Ala Arg Ala
            260                 265                 270

Ile Ala Ala Ala His Pro Glu Trp Trp Val Gln Ala Ala Gln Thr Leu
        275                 280                 285

<210> SEQ ID NO 66
<211> LENGTH: 474
<212> TYPE: DNA
<213> ORGANISM: Deinococcus radiopugnans

<400> SEQUENCE: 66
gtggttcgcg tcggttacgg cgaggacgcc caccgactgg cggccggtca ttccctgatt    60
ctaggaggca ttgctgtacc ggacgctgcg ctggggaccg tgcccacag tgacggcgac    120 gccgtgctgc acgcggtggc agacgcgctg ctctcagggg tggcgctggg tgatatcggc    180
gactattttc ccgacaccga tccgctgtgg gctgggctgg attcacgcgc gatcctgggg    240
cgggtgctgg aactggtccg cgagcgcgga tataccccgg tcaacattgc cctggtggtg    300
acgatggaca gccccggct ggggccgctg cgcgcccaga ttgcccgcaa cgtggccgcc    360
ctgctgggcc tgagtgaaag cgaggtgggg gtcagcttca agacctccga ggggctggcc    420
ccggcccatg ttcagacgcg cgtgaccgcg ctgctcacgc agttgcagga ctga         474

<210> SEQ ID NO 67
<211> LENGTH: 157
<212> TYPE: PRT
<213> ORGANISM: Deinococcus radiopugnans

<400> SEQUENCE: 67

Val Val Arg Val Gly Tyr Gly Glu Asp Ala His Arg Leu Ala Ala Gly
1               5                   10                  15

His Ser Leu Ile Leu Gly Gly Ile Ala Val Pro Asp Ala Ala Leu Gly
                20                  25                  30

Thr Val Ala His Ser Asp Gly Asp Ala Val Leu His Ala Val Ala Asp
            35                  40                  45

Ala Leu Leu Ser Gly Val Ala Leu Gly Asp Ile Gly Asp Tyr Phe Pro
        50                  55                  60

Asp Thr Asp Pro Leu Trp Ala Gly Leu Asp Ser Arg Ala Ile Leu Gly
65                  70                  75                  80

Arg Val Leu Glu Leu Val Arg Glu Arg Gly Tyr Thr Pro Val Asn Ile
                85                  90                  95
```

Ala Leu Val Val Thr Met Asp Lys Pro Arg Leu Gly Pro Leu Arg Ala
            100                 105                 110

Gln Ile Ala Arg Asn Val Ala Ala Leu Leu Gly Leu Ser Glu Ser Glu
        115                 120                 125

Val Gly Val Ser Phe Lys Thr Ser Glu Gly Leu Ala Pro Ala His Val
    130                 135                 140

Gln Thr Arg Val Thr Ala Leu Leu Thr Gln Leu Gln Asp
145                 150                 155

<210> SEQ ID NO 68
<211> LENGTH: 1227
<212> TYPE: DNA
<213> ORGANISM: Deinococcus radiopugnans

<400> SEQUENCE: 68

```
atgatccccc gtcgtcagac cgtcaccgcc aacgtgggag gcgtgttaat cggcagcgcc      60
caccccgtcg tcgtgcagag catgaccaac accgacacgg ccaacgccga ggccaccgcc     120
attcaggtgg cgcaactggc ccgtgcgggc agcgaactgg tgcgcgtgac cgtcaacacc     180
cgcgaggccg ccgccgctgt gcccgaactg attgccggc tggaggaggt gggcctgagc      240
gtgcccatcg tgggcgactt ccactacaac ggccacatcc tgctgcgcga gtttcccgaa     300
acggcccgtc tgctcgccaa gtaccgcatc aatcccggca acgtggggc cgggcagcac      360
cacgacgcca acttcgccac catgattgag gtggccaaag agttcgacaa accgtccgc      420
atcggcgtga actggggcag cctggatcag caggtgcttg cgcggctgat ggacgccaac     480
gccgcgaagg gcagccccaa atccggcact gactgtgatg tcgacgcgat ggtggtctcc     540
gcgctggaaa gtgccgccta cgccgaggag ctggggctgg cccacgacaa gatcctgatc     600
tcggtcaagg tgtccagcgc gcccgaactg tggcaggtgt accgccaact ggccgcccag     660
tgtgactacc gctgcacct gggcctgacc gaggcgggca tgggcatgaa aggcatcgtg      720
gcctcatcgg tggccctcgc cccgctgctg accgagggca tcggcgacac catccgcgtg     780
tccctgaccc ccgaacccgg cgcctcgcgc aagctggagg tggaggtggc gcagcagatt     840
ctgcaaagcc tgggcatccg ccagttcgcg ccgcaggtca ccagttgccc cggctgcggg     900
cgcaccacgt ccattttctt tcaggaattg gcgcagaaga tccaggacta catccgcgac     960
accatgcccg actggaaggt caagtatccg ggggtggagg acatgcaggt ggccgtgatg    1020
ggctgcatcg tcaacggccc tggcgagagc aagcacgcca atatcgggat tccctgccc     1080
ggcacgggg aagacccgcg cgccccggtg taccaggacg gcaaactgct gaccaccctg     1140
aaaggcccgc gcattgccga ggagtttcaa gaattgctgg aagcgtacgt agagcggcgg    1200
tatggagaag aacctgtttc gagctga                                        1227
```

<210> SEQ ID NO 69
<211> LENGTH: 408
<212> TYPE: PRT
<213> ORGANISM: Deinococcus radiopugnans

<400> SEQUENCE: 69

Met Ile Pro Arg Arg Gln Thr Val Thr Ala Asn Val Gly Gly Val Leu
1               5                   10                  15

Ile Gly Ser Ala His Pro Val Val Gln Ser Met Thr Asn Thr Asp
            20                  25                  30

Thr Ala Asn Ala Glu Ala Thr Ala Ile Gln Val Ala Gln Leu Ala Arg
        35                  40                  45

Ala Gly Ser Glu Leu Val Arg Val Thr Val Asn Thr Arg Glu Ala Ala
 50                  55                  60

Ala Ala Val Pro Glu Leu Ile Ala Arg Leu Glu Val Gly Leu Ser
 65                  70                  75                  80

Val Pro Ile Val Gly Asp Phe His Tyr Asn Gly His Ile Leu Leu Arg
                     85                  90                  95

Glu Phe Pro Glu Thr Ala Arg Leu Leu Ala Lys Tyr Arg Ile Asn Pro
                100                 105                 110

Gly Asn Val Gly Ala Gly Gln His His Asp Ala Asn Phe Ala Thr Met
                115                 120                 125

Ile Glu Val Ala Lys Glu Phe Asp Lys Pro Val Arg Ile Gly Val Asn
130                 135                 140

Trp Gly Ser Leu Asp Gln Gln Val Leu Ala Arg Leu Met Asp Ala Asn
145                 150                 155                 160

Ala Ala Lys Gly Ser Pro Lys Ser Gly Thr Asp Val Met Ile Asp Ala
                165                 170                 175

Met Val Val Ser Ala Leu Glu Ser Ala Ala Tyr Ala Glu Glu Leu Gly
                180                 185                 190

Leu Ala His Asp Lys Ile Leu Ile Ser Val Lys Val Ser Ser Ala Pro
                195                 200                 205

Glu Leu Trp Gln Val Tyr Arg Gln Leu Ala Ala Gln Cys Asp Tyr Pro
210                 215                 220

Leu His Leu Gly Leu Thr Glu Ala Gly Met Gly Met Lys Gly Ile Val
225                 230                 235                 240

Ala Ser Ser Val Ala Leu Ala Pro Leu Leu Thr Glu Gly Ile Gly Asp
                245                 250                 255

Thr Ile Arg Val Ser Leu Thr Pro Glu Pro Gly Ala Ser Arg Lys Leu
                260                 265                 270

Glu Val Glu Val Ala Gln Gln Ile Leu Gln Ser Leu Gly Ile Arg Gln
                275                 280                 285

Phe Ala Pro Gln Val Thr Ser Cys Pro Gly Cys Gly Arg Thr Thr Ser
290                 295                 300

Ile Phe Phe Gln Glu Leu Ala Gln Lys Ile Gln Asp Tyr Ile Arg Asp
305                 310                 315                 320

Thr Met Pro Asp Trp Lys Val Lys Tyr Pro Gly Val Glu Asp Met Gln
                325                 330                 335

Val Ala Val Met Gly Cys Ile Val Asn Gly Pro Gly Glu Ser Lys His
                340                 345                 350

Ala Asn Ile Gly Ile Ser Leu Pro Gly Thr Gly Glu Asp Pro Arg Ala
                355                 360                 365

Pro Val Tyr Gln Asp Gly Lys Leu Leu Thr Thr Leu Lys Gly Pro Arg
                370                 375                 380

Ile Ala Glu Glu Phe Gln Glu Leu Leu Glu Ala Tyr Val Glu Arg Arg
385                 390                 395                 400

Tyr Gly Glu Glu Pro Val Ser Ser
                405

<210> SEQ ID NO 70
<211> LENGTH: 996
<212> TYPE: DNA
<213> ORGANISM: Deinococcus radiopugnans

<400> SEQUENCE: 70
atggttgagc gcctgtatct ggccaagccg cgaggcttct gcgcgggcgt ggtcatggcc    60

```
atcggcgccg tggagcgcgc cgcgcagacc gaggacaaac ccgtcaccgt ctaccactcg      120
attgtccaca accacaccgt ggtggaccgg ctggcccgag atcacagcgt gcatttcgtg      180
gagaatctgg acgacgtgga agctttgccg gggggcggcg acaccgtggt gttctccgcg      240
cacggcatca gcccgctggt gcgcgaacgg gcgcgggcgc tggggttgag taccatcgac      300
gccacctgcc cgctggtcac caaggtccac accgaggcca agaagtacgc ccgcgagggc      360
cacaccatcc tgctgatcgg cgacagcgcc cagcatcagg aggtgatcgg cacgcgcggc      420
gaggcccccg gaccacaccat tctggtgggc gtgctgggca gagcggtga ggggctgcac       480
gacccgcaca cggtcacggt gccggacccc gaaaagttgg tggtcctgac ccagacgacc      540
ctgagcgtgg acgacacgcg cgcacggtg acattctca aggcccgctt ccgaagctg         600
atcgtgccgc cagcgagga cctgtgctac gccaccaaga accgccagga cgccgtgaaa       660
gccatcgcgc ccaacgtgga cgcctttctg gtcctgacca gcacccactc cagcaacggc      720
atgcgcctgc tggaactggc cgccgagacg tgtgggcggg ccgagcgcct ggaaaacgca      780
gatgatctgg cgggccttga tctgggcggc gtgaaggcca tcggcatcac cagcgcggcc      840
agcaccccg acgatctggt gcaggccgtg gtggcccatt ccgcgccct gaacccgggg        900
ttgcaggtga tcgaggaggg cgagtgggag aacatcgagt tccgcgagcc gaagaagatt      960
ctgccgggtc agcctttgcc gcgcacgatg ggctga                                 996

<210> SEQ ID NO 71
<211> LENGTH: 331
<212> TYPE: PRT
<213> ORGANISM: Deinococcus radiopugnans

<400> SEQUENCE: 71

Met Val Glu Arg Leu Tyr Leu Ala Lys Pro Arg Gly Phe Cys Ala Gly
1               5                   10                  15

Val Val Met Ala Ile Gly Ala Val Glu Arg Ala Ala Gln Thr Glu Asp
            20                  25                  30

Lys Pro Val Thr Val Tyr His Ser Ile Val His Asn His Thr Val Val
        35                  40                  45

Asp Arg Leu Ala Arg Asp His Ser Val His Phe Val Glu Asn Leu Asp
    50                  55                  60

Asp Val Glu Ala Leu Pro Gly Gly Gly Asp Thr Val Val Phe Ser Ala
65                  70                  75                  80

His Gly Ile Ser Pro Leu Val Arg Glu Arg Ala Arg Ala Leu Gly Leu
                85                  90                  95

Ser Thr Ile Asp Ala Thr Cys Pro Leu Val Thr Lys Val His Thr Glu
            100                 105                 110

Ala Lys Lys Tyr Ala Arg Glu Gly His Thr Ile Leu Leu Ile Gly Asp
        115                 120                 125

Ser Ala Gln His Gln Glu Val Ile Gly Thr Arg Gly Glu Ala Pro Asp
    130                 135                 140

His Thr Ile Leu Val Gly Val Leu Gly Lys Ser Gly Glu Gly Leu His
145                 150                 155                 160

Asp Pro His Thr Val Thr Val Pro Asp Pro Glu Lys Leu Val Val Leu
                165                 170                 175

Thr Gln Thr Thr Leu Ser Val Asp Asp Thr Arg Arg Thr Val Asp Ile
            180                 185                 190

Leu Lys Ala Arg Phe Pro Lys Leu Ile Val Pro Ser Glu Asp Leu
        195                 200                 205
```

Cys Tyr Ala Thr Lys Asn Arg Gln Asp Ala Val Lys Ala Ile Ala Pro
            210                 215                 220

Asn Val Asp Ala Phe Leu Val Leu Thr Ser Thr His Ser Ser Asn Gly
225                 230                 235                 240

Met Arg Leu Leu Glu Leu Ala Ala Glu Thr Cys Gly Arg Ala Glu Arg
                245                 250                 255

Leu Glu Asn Ala Asp Asp Leu Ala Gly Leu Asp Leu Gly Val Lys
                260                 265                 270

Ala Ile Gly Ile Thr Ser Ala Ala Ser Thr Pro Asp Asp Leu Val Gln
            275                 280                 285

Ala Val Val Ala His Phe Arg Ala Leu Asn Pro Gly Leu Gln Val Ile
            290                 295                 300

Glu Glu Gly Glu Trp Glu Asn Ile Glu Phe Arg Glu Pro Lys Lys Ile
305                 310                 315                 320

Leu Pro Gly Gln Pro Leu Pro Arg Thr Met Gly
                325                 330

<210> SEQ ID NO 72
<211> LENGTH: 504
<212> TYPE: DNA
<213> ORGANISM: Deinococcus radiopugnans

<400> SEQUENCE: 72
atggtgcagg ctctggaatg gctcgatctg gtagacgaga atgatcaggt ggtcggccag      60
atcacccgtg acgacgcctg ggcacagcgg cgggcagtgc ggatggtcaa cgcctttctg     120
gtcaaccggc gcggtgagct gtggattccg cgccgcaccg cctccaaacg gatgtttccc     180
aactgtctga atatgagcgt gggaggccac gtcgaacgcg gcgaaaccta tctcagcgcc     240
ttcaagcgcg agacgcacga ggaactgaat ctgaacgtgg acgcgctgga ctggcggaaa     300
atcgccgcct tttcgccgtt cgagacggga ctgagcagct tcatgcgcgt ctatgagatc     360
aggactgacg ccgcgcacga cttcaattcc gccgacttca gcgaggcgtg gtggctgacg     420
cccgccgaac tgctggactg gattgaggcg ggcgaaccgg ccaagggtga tctggccgag     480
ctggtgcggc ggtgctttcc atga                                            504

<210> SEQ ID NO 73
<211> LENGTH: 167
<212> TYPE: PRT
<213> ORGANISM: Deinococcus radiopugnans

<400> SEQUENCE: 73

Met Val Gln Ala Leu Glu Trp Leu Asp Leu Val Asp Glu Asn Asp Gln
1               5                   10                  15

Val Val Gly Gln Ile Thr Arg Asp Asp Ala Trp Ala Gln Arg Arg Ala
            20                  25                  30

Val Arg Met Val Asn Ala Phe Leu Val Asn Arg Arg Gly Glu Leu Trp
        35                  40                  45

Ile Pro Arg Arg Thr Ala Ser Lys Arg Met Phe Pro Asn Cys Leu Asn
    50                  55                  60

Met Ser Val Gly Gly His Val Glu Arg Gly Glu Thr Tyr Leu Ser Ala
65                  70                  75                  80

Phe Lys Arg Glu Thr His Glu Glu Leu Asn Leu Asn Val Asp Ala Leu
                85                  90                  95

Asp Trp Arg Lys Ile Ala Ala Phe Ser Pro Phe Glu Thr Gly Leu Ser
                100                 105                 110

```
Ser Phe Met Arg Val Tyr Glu Ile Arg Thr Asp Ala Ala His Asp Phe
        115                 120             125

Asn Ser Ala Asp Phe Ser Glu Ala Trp Trp Leu Thr Pro Ala Glu Leu
    130             135                 140

Leu Asp Trp Ile Glu Ala Gly Glu Pro Ala Lys Gly Asp Leu Ala Glu
145             150                 155                 160

Leu Val Arg Arg Cys Phe Pro
                165
```

METHOD OF PRODUCING TERPENES OR TERPENOIDS

CROSS-REFERENCE TO RELATED APPLICATION

This application is the U.S. national stage application of International Patent Application No. PCT/EP2015/063335, filed Jun. 15, 2015.

FIELD OF THE INVENTION

The present invention relates to the field of microbiology. More particularly, the present invention relates to the field of production of isoprenoid compounds in genetically modified bacteria.

BACKGROUND OF THE INVENTION

Isoprenoids, also referred to as terpenes or terpenoids, are the most diverse class of natural products. Isoprenoids, which contain monoterpenes, sesquiterpenes, diterpenes and triterpenes as well as carotenoids, are the subject of numerous industrial applications, as they are found, for example, in pharmaceuticals, nutraceuticals, flavors, fragrances, cosmetics, colorants and agrichemicals.

Despite the great diversity in isoprenoid compounds, all are biosynthesized from a common C-5 precursor, isopentenyl pyrophosphate (IPP). This precursor can be synthesized via the mevalonate pathway (MEV) or via the non-mevalonate pathway (or 2-C-methyl-D-erythritol 4-phosphate/1-deoxy-D-xylulose 5-phosphate (MEP/DXP) pathway) leading to the formation of IPP and its isomer dimethylallyl pyrophosphate (DMAPP). DMAPP and IPP are then condensed to generate geranyl diphosphate (GPP) which is further converted with IPP into farnesyl diphosphate (FPP). FPP is further condensed with IPP to form geranylgeranyl diphosphate (GGPP). GPP, FPP and GGPP are the precursors of monoterpenes, sesquiterpenes, diterpenes, triterpenes and carotenoids.

Currently, isoprenoids are mainly extracted from plants or produced by chemical synthesis but suffer from low yields and high production costs.

Metabolic engineering of microorganisms offers an alternative and promising approach for the economical production of large amount of isoprenoids from cheap carbon sources. In this respect, a number of isoprenoids have been already produced by recombinant microorganism. *E. coli* and *S. cerevisiae* which can be genetically manipulated very easily, have often been employed as host cells. For example, limonene was produced from a recombinant *E. coli* expressing the GPP synthase gene from grand fir and the (−)-limonene synthase gene from spearmint (Carter et al., 2003), or linalool production was obtained in a recombinant *S. cerevisiae* expressing the (S)-linalool synthase gene from *Clarkia breweri* (Herrero et al., 2008).

Although engineering microorganisms to produce isoprenoids has shown great promise, it has been postulated that the total amount of isoprenoids is limited by the availability of isoprenoid precursors, i.e. IPP and DMAPP. Engineering an increased supply of isoprenoid precursors is thus necessary to increase the production. However, it was observed that genetic manipulations of the complex MEP pathway can impact cellular growth rates and isoprene production, in particular due to accumulation of toxic metabolic intermediates such as IPP or DMAPP (e.g. Sivy et al., 2011) or metabolic burden on the host caused by depletion of pyruvate from the cells (Brown et al., 2010).

SUMMARY OF THE INVENTION

In a first aspect, the present invention provides an isoprenoid overproducing *Deinococcus* bacterium wherein the MEP pathway has been successfully engineered in order to increase the carbon flux to IPP and DMAPP.

The present invention thus relates to a recombinant *Deinococcus* bacterium exhibiting enhanced 2-C-methyl-D-erythritol 4-phosphate/1-deoxy-D-xylulose 5-phosphate (MEP/DXP) pathway, in particular a bacterium wherein at least one enzymatic activity selected from the group consisting of DXP synthase (DXS), DXP reductoisomerase (DXR), IspD, IspE, IspF, IspG, IspH and IPP isomerase activities (IDI), is increased. Preferably, said at least one enzymatic activity is increased by overexpression of at least one gene selected from the group consisting of native, homologous or heterologous dxs, dxr, ispD, ispE, ispF, ispG, ispH and idi genes.

Preferably, the recombinant bacterium of the invention is genetically modified to increase DXS activity and/or IDI activity. In particular, said recombinant bacterium may overexpress a native, homologous or heterologous idi gene and/or overexpress a native, homologous or heterologous dxs gene.

The bacterium of the invention may further exhibit an increased FPP synthase activity. Preferably, this increase is due to the overexpression of a native, homologous or heterologous ispA gene.

Preferably, the ipsA gene encodes a polypeptide selected from the group consisting of
a) a polypeptide comprising all or an active part of the amino acid sequence of SEQ ID NO: 47;
b) a polypeptide having an amino acid sequence having at least 60, 65, 70, 75, 80, 85, 90, 91, 92, 93, 94, 95, 96, 97, 98 or 99% sequence identity to SEQ ID NO: 47;
c) a polypeptide encoded by a nucleotide sequence having at least 60, 65, 70, 75, 80, 85, 90, 91, 92, 93, 94, 95, 96, 97, 98 or 99% sequence identity to SEQ ID NO: 46; or
d) a polypeptide which is encoded by a nucleic acid sequence which is capable of hybridizing under medium/high stringency, preferably high or very high, conditions with (i) the nucleic acid sequence set forth in SEQ ID NO: 46, (ii) its complementary strand, or (iii) a subsequence of (i) or (ii).

Preferably, the FPP synthase further exhibits dimethylallyltransferase activity and/or geranylgeranyl diphosphate synthase activity, more preferably dimethylallyltransferase activity and geranylgeranyl diphosphate synthase activity.

The bacterium of the invention may also further comprise a mutated DXP synthase comprising an asparagine at position corresponding to position 222 of SEQ ID NO:52 and/or a cysteine at position corresponding to position 244 of SEQ ID NO:52, preferably a mutated DXP synthase comprising a cysteine at position corresponding to position 244 of SEQ ID NO: 52. In particular, the recombinant *Deinococcus* bacterium may express a gene encoding R244C mutant of the DXP synthase from *D. radiopugnans* (SEQ ID NO: 8), a gene encoding R238C mutant of the DXP synthase from *D. yunweiensis* (SEQ ID NO: 14), and/or a gene encoding R241C mutant of the DXP synthase from *D. geothermalis* (SEQ ID NO: 56). Preferably, the recombinant *Deinococcus* bacterium expresses an improved (mutated) DXS enzyme and overexpresses a native, homologous or heterologous idi gene.

Preferably, the bacterium of the invention further comprises a gene encoding a heterologous terpene synthase.

The heterologous terpene synthase may be a monoterpene synthase preferably selected from the group consisting of geraniol synthase, 3S-linalool synthase, myrcene synthase, R-linalool synthase, 1,8 cineol synthase, 4S-limonene synthase, R-limonene synthase, (−)-α-pinene synthase, (−)-β-pinene synthase, (−)-endo-fenchol synthase and (−)-α-terpineol synthase. More preferably, the heterologous terpene synthase is a geraniol synthase, a cineol synthase, a limonene synthase or a linalool synthase.

The heterologous terpene synthase may also be a sesquiterpene synthase preferably selected from the group consisting of (+)-epi-alpha-bisabolol synthase, germacrene A synthase, (E,E)-germacrene B synthase, germacrene C synthase, (−)-germacrene D synthase, valencene synthase, (3S, 6E)-nerolidol synthase, epi-cedrol synthase, patchoulol synthase, santalene synthase and δ-cadinene synthase. More preferably, the heterologous sesquiterpene synthase is a (+)-epi-alpha-bisabolol synthase.

The bacterium of the invention may further exhibit a reduced or suppressed lycopene beta-cyclase activity.

In a second aspect, the present invention relates to a recombinant *Deinococcus* bacterium wherein the FPP synthase activity is increased. Preferably, the FPP synthase activity is increased by overexpression of a native, homologous or heterologous ispA gene. Preferably, the ipsA gene encodes a polypeptide selected from the group consisting of
  a) a polypeptide comprising all or an active part of the amino acid sequence of SEQ ID NO: 47;
  b) a polypeptide having an amino acid sequence having at least 60, 65, 70, 75, 80, 85, 90, 91, 92, 93, 94, 95, 96, 97, 98 or 99% sequence identity to SEQ ID NO: 47;
  c) a polypeptide encoded by a nucleotide sequence having at least 60, 65, 70, 75, 80, 85, 90, 91, 92, 93, 94, 95, 96, 97, 98 or 99% sequence identity to SEQ ID NO: 46; or
  d) a polypeptide which is encoded by a nucleic acid sequence which is capable of hybridizing under medium/high stringency, preferably high or very high, conditions with (i) the nucleic acid sequence set forth in SEQ ID NO: 46, (ii) its complementary strand, or (iii) a subsequence of (i) or (ii).

Preferably, the FPP synthase further exhibits dimethylallyltransferase activity and/or geranylgeranyl diphosphate synthase activity, more preferably dimethylallyltransferase activity and geranylgeranyl diphosphate synthase activity.

In a third aspect, the present invention relates to a recombinant *Deinococcus* bacterium comprising a mutated DXP synthase comprising an asparagine at position corresponding to position 222 of SEQ ID NO:52 and/or a cysteine at position corresponding to position 244 of SEQ ID NO:52, preferably a mutated DXP synthase comprising a cysteine at position corresponding to position 244 of SEQ ID NO: 52. In particular, the recombinant *Deinococcus* bacterium may express a gene encoding R244C mutant of the DXP synthase from *D. radiopugnans* (SEQ ID NO: 8), a gene encoding R238C mutant of the DXP synthase from *D. yunweiensis* (SEQ ID NO: 14), and/or a gene encoding R241C mutant of the DXP synthase from *D. geothermalis* (SEQ ID NO: 56).

In a fourth aspect, the present invention relates to a recombinant *Deinococcus* bacterium expressing a gene encoding a heterologous terpene synthase, preferably a geraniol synthase or a (+)-epi-alpha-bisabolol synthase.

In a fifth aspect, the present invention relates to a recombinant *Deinococcus* bacterium wherein the endogenous lycopene beta-cyclase activity is reduced or suppressed.

In a further aspect, the present invention relates to a use of a recombinant *Deinococcus* bacterium of the invention for producing an isoprenoid, preferably a monoterpene, a diterpene, a triterpene, a sesquiterpene or a carotenoid, more preferably a sesquiterpene or a carotenoid. In an embodiment, the isoprenoid is geraniol, geranic acid and/or lycopene. In a particular embodiment, the isoprenoid is a carotenoid, preferably lycopene or another carotenoid compound derived from lycopene, in particular deinoxanthine. The present invention also relates to a method of producing an isoprenoid comprising (i) culturing a recombinant *Deinococcus* bacterium according to the invention under conditions suitable to produce the isoprenoid and optionally (ii) recovering the isoprenoid. Preferably, the isoprenoid is a monoterpene, a diterpene, a triterpene, a sesquiterpene or a carotenoid, more preferably a sesquiterpene or a carotenoid. In an embodiment, the isoprenoid is selected from the group consisting of geraniol, geranic acid and lycopene.

In another aspect, the present invention relates to a use of a recombinant *Deinococcus* bacterium of the invention for producing a geranyl ester. The present invention also relates to a method of producing a geranyl ester comprising (i) culturing a recombinant *Deinococcus* bacterium according to the invention under conditions suitable to produce geraniol and/or geranic acid, (ii) recovering geraniol and/or geranic acid, and (iii) converting geraniol and/or geranic acid into a geranyl ester, and optionally (iv) recovering the geranyl ester. Preferably, the geranyl ester is geranyl isobutyrate or trans-geranyl acetate.

In another aspect, the present invention relates to a use of a recombinant *Deinococcus* bacterium of the invention for producing a damascone, damascenone and/or ionone. The present invention also relates to a method of producing a damascone, damascenone and/or ionone comprising (i) culturing a recombinant *Deinococcus* bacterium according to the invention under conditions suitable to produce geraniol and/or geranic acid, (ii) recovering geraniol and/or geranic acid, and (iii) converting geraniol and/or geranic acid into the damascone, damascenone and/or ionone, and optionally (iv) recovering the damascone, damascenone and/or ionone.

DETAILED DESCRIPTION OF THE INVENTION

Figure 1:
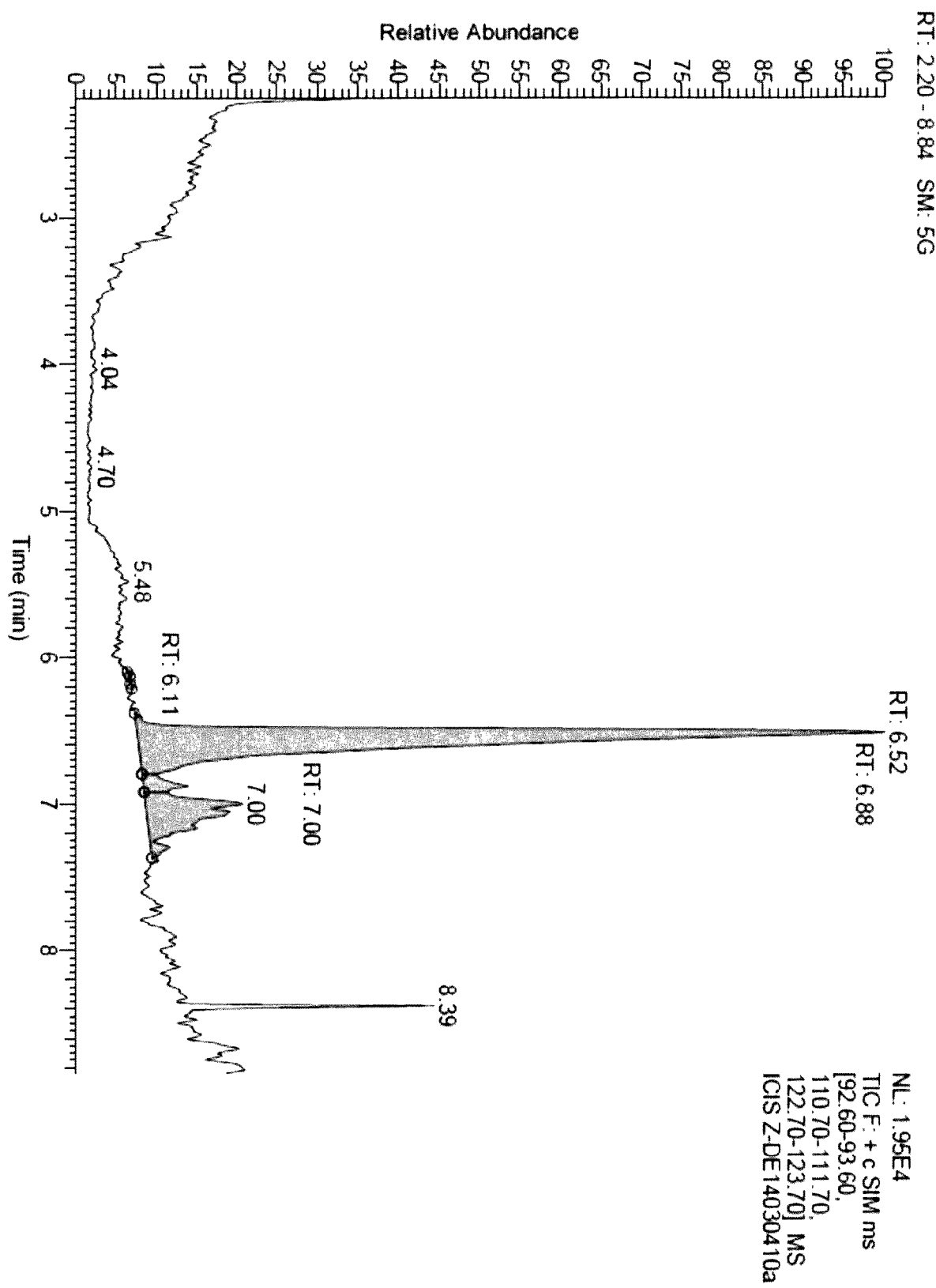
FIG. 1: GCMS analysis of extraction at 24 h of the culture comprising the recombinant *D. geothermalis* bacterium expressing the *Ocimum basilicum* GES.

As indicated, the present invention relates to a *Deinococcus* bacterium genetically modified in order to exhibit improved production of isoprenoids.

In particular, the present application shows that the MEP pathway of *Deinococcus* bacteria can be engineered to increase the carbon flux to IPP and DMAPP. Indeed, the inventors identified several rate-limiting enzymes and showed that these enzymes can be genetically engineered or overexpressed. They observed that isoprenoid production in these recombinant bacteria was significantly increased.

In addition, the inventors herein demonstrated that the production of isoprenoids in *Deinococcus* bacteria can be controlled to promote the production and/or accumulation of compounds of interest. In this respect, they identified and overexpressed the FPP synthase and showed that this overexpression promotes the production of isoprenoids having more than 10 C-atoms, such as diterpenes, triterpenes, sesquiterpenes, and carotenoids, to the detriment of monoterpenes. They also showed that the inactivation of the endogenous lycopene beta-cyclase induces an overproduction of lycopene.

Finally, the present application also demonstrates that *Deinococcus* bacteria, and in particular recombinant *Deinococcus* bacteria as described above, may be efficiently used to produce heterologous isoprenoid compounds via the expression of heterologous terpene synthase.

Definitions

In the context of the invention, the term "*Deinococcus*" includes wild type or natural variant strains of *Deinococcus*, e.g., strains obtained through accelerated evolution, mutagenesis, by DNA-shuffling technologies, or recombinant strains obtained by insertion of eukaryotic, prokaryotic and/or synthetic nucleic acid(s). *Deinococcus* bacteria can designate any bacterium of the genus *Deinococcus*, such as without limitation, *D. geothermalis*, *D. cellulolysiticus*, *D. radiodurans*, *D. proteolyticus*, *D. radiopugnans*, *D. radiophilus*, *D. grandis*, *D. indicus*, *D. frigens*, *D. saxicola*, *D. maricopensis*, *D. marmoris*, *D. deserti*, *D. murrayi*, *D. aerius*, *D. aerolatus*, *D. aerophilus*, *D. aetherius*, *D. alpinitundrae*, *D. altitudinis*, *D. antarcticus*, *D. apachensis*, *D. aquaticus*, *D. aquatilis*, *D. aquiradiocola*, *D. aquivivus*, *D. caeni*, *D. citri*, *D. claudionis*, *D. daejeonensis*, *D. depolymerans*, *D. enclensis*, *D. ficus*, *D. gobiensis*, *D. guangriensis*, *D. guilhemensis*, *D. hohokamensis*, *D. hopiensis*, *D. humi*, *D. misasensis*, *D. navajonensis*, *D. papagonensis*, *D. peraridilitoris*, *D. phoenicis*, *D. pimensis*, *D. piscis*, *D. puniceus*, *D. radiomollis*, *D. radioresistens*, *D. radiotolerans*, *D. reticulitermitis*, *D. roseus*, *D. sahariens*, *D. soli*, *D. sonorensis*, *D. swuensis*, *D. wulumuqiensis*, *D. xibeiensis*, *D. xinjiangensis*, *D. yavapaiensis* or *D. yunweiensis* bacterium, or any combinations thereof. Preferably, the term "*Deinococcus*" refers to *D. geothermalis*, *D. radiopugnans*, *D. yunweiensis* and *D. murrayi*. In some embodiments, the term "*Deinococcus*" refers to mesophile *Deinococcus* bacteria, preferably selected from *D. grandis*, *D. radiodurans*, *D. radiopugnans*, *D. yunweiensis* and *D. aquaticus*. In some other embodiments, the term "*Deinococcus*" refers to thermophile *Deinococcus* bacteria, preferably selected from *D. geothermalis*, *D. murrayi* and *D. maricopensis*. In preferred embodiments, the term "*Deinococcus*" refers to *D. geothermalis*, *D. murrayi*, *D. maricopensis*, *D. grandis*, *D. radiodurans*, *D. radiopugnans*, *D. yunweiensis* and *D. aquaticus*. More preferably, the term "*Deinococcus*" refers to *D. geothermalis*.

The term "recombinant bacterium" or "genetically modified bacterium" designates a bacterium that is not found in nature and which contains a modified genome as a result of either a deletion, insertion or modification of genetic elements. A "recombinant nucleic acid" therefore designates a nucleic acid which has been engineered and is not found as such in wild type bacteria.

The term "gene" designates any nucleic acid encoding a protein. The term gene encompasses DNA, such as cDNA or gDNA, as well as RNA. The gene may be first prepared by e.g., recombinant, enzymatic and/or chemical techniques, and subsequently replicated in a host cell or an in vitro system. The gene typically comprises an open reading frame encoding a desired protein. The gene may contain additional sequences such as a transcription terminator or a signal peptide.

The term "expression cassette" denotes a nucleic acid construct comprising a coding region, i.e. a gene, and a regulatory region, i.e. comprising one or more control sequences, operably linked. Preferably, the control sequences are suitable for *Deinococcus* host cells.

As used herein, the term "expression vector" means a DNA or RNA molecule that comprises an expression cassette. Preferably, the expression vector is a linear or circular double stranded DNA molecule.

The term "operably linked" means a configuration in which a control sequence is placed at an appropriate position relative to a coding sequence, in such a way that the control sequence directs expression of the coding sequence.

The term "control sequences" means nucleic acid sequences necessary for expression of a gene. Control sequences may be native, homologous or heterologous. Well-known control sequences and currently used by the person skilled in the art will be preferred. Such control sequences include, but are not limited to, a leader, polyadenylation sequence, propeptide sequence, promoter, signal peptide sequence, and transcription terminator. Preferably, the control sequences include a promoter and a transcription terminator.

As used herein, the term "native" refers to a genetic element or a protein from the non modified *Deinococcus* bacterium or from a *Deinococcus* bacterium of the same species. The term "homologous" refers to a genetic element or a protein from a *Deinococcus* bacterium of another species than the recombinant *Deinococcus* bacterium. The term "heterologous" refers to a genetic element or a protein from a non *Deinococcus* origin such as other bacteria, microorganisms, plants, viruses, etc. The term "native", "homologous" or "heterologous" may refer to wild-type or mutated genetic element or protein. In some embodiments, these terms refer to genetic elements that are modified, e.g. by mutagenesis, before to be introduced or expressed in the recombinant bacterium of the invention, e.g. to improve one or several characteristics of the encoded protein (e.g. enhanced activity, stability, etc.).

The terms "overexpression", "enhanced expression" and "increase expression" as used herein, are used interchangeably and mean that the expression of a gene or an enzyme is increased compared to a non modified bacterium, e.g. the wild-type bacterium or the corresponding bacterium that has not been genetically modified in order to enhance the MEP/DXP pathway. Increased expression of an enzyme is usually obtained by increasing expression of the gene encoding said enzyme. In embodiments wherein the gene or the enzyme is not naturally present in the bacterium of the invention, i.e. homologous or heterologous gene or enzyme, the terms "overexpression" and "expression" may be used interchangeably.

The term "MEP pathway", "MEP/DXP pathway", "non-mevalonate pathway" or "2-C-methyl-D-erythritol 4-phosphate/1-deoxy-D-xylulose 5-phosphate pathway" as used herein refers to the biosynthetic pathway leading to the formation of IPP and DMAPP from the condensation of pyruvate and D-glyceraldehyde 3-phosphate to 1-deoxy-D-xylulose 5-phosphate (DXP). This pathway involves the following enzymes: 1-deoxy-D-xylulose 5-phosphate synthase (EC 2.2.1.7), 1-deoxy-D-xylulose 5-phosphate reductoisomerase (EC 1.1.1.267), 2-C-methyl-D-erythritol 4-phosphate cytidylyltransferase (EC 2.7.7.60), 4-diphosphocytidyl-2-C-methyl-D-erythritol kinase (EC 2.7.1.148), 2-C-methyl-D-erythritol 2,4-cyclodiphosphate synthase (EC 4.6.1.12), 4-hydroxy-3-methylbut-2-en-1-yl diphosphate synthase (EC 1.17.7.1), 4-hydroxy-3-methylbut-2-enyl diphosphate reductase (EC 1.17.1.2), and isopentenyl-diphosphate delta-isomerase (EC 5.3.3.2).

The terms "isoprenoid," "isoprenoid compound," "terpene," "terpene compound," "terpenoid," and "terpenoid compound" are used interchangeably herein, and refer to any compound that is capable of being derived from IPP. The number of C-atoms present in the isoprenoids is typically evenly divisible by five (e.g., C5, C10, C15, C20, C25, C30 and C40). Irregular isoprenoids and polyterpenes have been reported, and are also included in the definition of "isoprenoid". Isoprenoid compounds include, but are not limited to, monoterpenes, diterpenes, triterpenes, sesquiterpenes, and carotenoids.

The term terpene synthase encompasses enzymes, complexes, and/or groups of enzymes capable of synthesizing an isoprenoid compound, such as a monoterpene, sesquiterpene, diterpene, triterpene or carotenoid, from one or several precursors, in particular from geranyl diphosphate (GPP), farnesyl diphosphate (FPP), geranylgeranyl diphosphate (GGPP), and any combination of two or more of these. Examples of such terpene synthases include, without limitation, monoterpene synthases, diterpene synthases, and sesquiterpene synthases.

The word "pyrophosphate" is used interchangeably herein with "diphosphate".

The term "DXS", "DXP synthase" or "DXPS" refers to the enzyme 1-deoxy-D-xylulose 5-phosphate synthase (EC 2.2.1.7) encoded by the dxs gene which catalyzes the condensation of pyruvate and D-glyceraldehyde 3-phosphate to 1-deoxy-D-xylulose 5-phosphate (DXP). The names of gene product, "DXP synthase", "DXS" or "DXPS", are used interchangeably in this application. The DXP synthase activity can be determined by using a radio-labelled substrate as described by Lois et al. (1998) or any other method known by the skilled person.

The terms "DXP reductoisomerase" or "IspC" or "DXR" refer to the enzyme 1-deoxy-D-xylulose 5-phosphate reductoisomerase (EC 1.1.1.267) encoded by the dxr or ispC gene that catalyzes the simultaneous reduction and isomerization of DXP to 2-C-methyl-D-erythritol-4-phosphate (MEP). The names of the gene, dxr or ispC, are used interchangeably in this application. The names of gene product, DXP reductoisomerase or IspC, are used interchangeably in this application.

The term "MCT" or "IspD" or "CMS" refers to the enzyme 2-C-methyl-D-erythritol 4-phosphate cytidylyltransferase (EC 2.7.7.60) encoded by the ispD gene that catalyzes the formation of 4-diphosphocytidyl-2-C-methyl-D-erythritol (also named 4-(cytidine 5'-diphospho)-2-C-methyl-D-erythritol (CDP-ME)) from CTP (cytidine triphosphate) and 2-C-methyl-D-erythritol 4-phosphate (MEP). The names of gene product, MCT, CMS or IspD are used interchangeably in this application.

The term "CMK" or "IspE" refers to the enzyme 4-diphosphocytidyl-2-C-methyl-D-erythritol kinase, also named 4-(cytidine 5'-diphospho)-2-C-methyl-D-erythritol kinase, (EC 2.7.1.148) encoded by the ispE gene that catalyzes the ATP-dependent phosphorylation of 4-diphosphocytidyl-2C-methyl-D-erythritol (CDP-ME) to 4-diphosphocytidyl-2C-methyl-D-erythritol-2-phosphate (also named 4-(cytidine 5'-diphospho)-2-C-methyl-D-erythritol 2-phosphate (CDP-MEP). The names of gene product, CMK or IspE are used interchangeably in this application.

The term "IspF", "MECDP-synthase", "MECPP-synthase" or "MECPS" or "MCS" refers to the enzyme 2-C-methyl-D-erythritol 2,4-cyclodiphosphate synthase (EC 4.6.1.12) encoded by the ispF gene that catalyzes the conversion of 4-diphosphocytidyl-2-C-methyl-D-erythritol 2-phosphate (CDP-MEP) to 2-C-methyl-D-erythritol 2,4-cyclodiphosphate (ME-CPP or cMEPP) with a corresponding release of cytidine 5-monophosphate (CMP). The names of gene product, IspF, MECDP-synthase, MECPP-synthase, MCS or MECPS are used interchangeably in this application.

The team "IspH" or "IDS" refers to the enzyme 4-hydroxy-3-methylbut-2-enyl diphosphate reductase, also named hydroxymethylbutenyl pyrophosphate reductase, (EC 1.17.1.2) encoded by the ispH gene that converts 1-hydroxy-2-methyl-2-(E)-butenyl 4-diphosphate (HMBPP) into isopentenyl diphosphate (IPP) and dimethylallyl diphosphate (DMAPP).

The term ""IspH" or "IDS" refers to the enzyme 4-hydroxy-3-methylbut-2-enyl diphosphate reductase, also named hydroxymethylbutenyl pyrophosphate reductase, (EC 1.17.1.2) encoded by the ispH gene that converts 1-hydroxy-2-methyl-2-(E)-butenyl 4-diphosphate (HMBPP) into isopentenyl diphosphate (IPP) and dimethylallyl diphosphate (DMAPP).

The term "IDI", "IPP isomerase" or "isopentenyl pyrophosphate isomerase" refers to the enzyme isopentenyl-diphosphate delta-isomerase (EC 5.3.3.2) encoded by the fni or idi gene that catalyzes the 1,3-allylic rearrangement of the homoallylic substrate isopentenyl (IPP) to its allylic isomer, dimethylallyl diphosphate (DMAPP). The names of the gene, fni or idi, are used interchangeably in this application.

The term "mevalonate pathway" or "MEV pathway" is used herein to refer to the biosynthetic pathway that converts acetyl-CoA to IPP. The mevalonate pathway comprises enzymes that catalyze the following steps: (a) condensing two molecules of acetyl-CoA to acetoacetyl-CoA by action of acetyl-CoA C-acetyltransferase (EC 2.3.1.9); (b) condensing acetoacetyl-CoA with acetyl-CoA to form hydroxymethylglutaryl-CoenzymeA (HMG-CoA) by action of hydroxymethylglutaryl-CoA synthase (EC 2.3.3.10); (c) converting HMG-CoA to mevalonate by action of hydroxymethylglutaryl-CoA reductase (NADPH) (EC 1.1.1.34); (d) phosphorylating mevalonate to mevalonate 5-phosphate by action of mevalonate kinase (EC 2.7.1.36); (e) converting mevalonate 5-phosphate to mevalonate 5-pyrophosphate by action of phosphomevalonate kinase (EC 2.7.4.2); and (f) converting mevalonate 5-pyrophosphate to isopentenyl pyrophosphate by action of diphosphomevalonate decarboxylase (EC 4.1.1.33).

The term "IspA", "FDPS", "FPPS" or "FPP synthase" refers to the enzyme farnesyl diphosphate synthase (EC 2.5.1.10, 2.5.1.1) encoded by the ispA gene that catalyzes the sequential condensation of isopentenyl pyrophosphate (IPP) with the allylic pyrophosphates, dimethylallyl pyrophosphate (DMAPP), and then with the resultant geranylpyrophosphate (GPP) to the ultimate product farnesyl pyrophosphate (FPP). Optionally, and in preferred embodiments, this enzyme may also exhibit geranylgeranyl diphosphate synthase activity (2.5.1.29). The names of gene product, IspA, FDPS, FPPS or FPP synthase are used interchangeably in this application.

The term "isoprene synthase" refers to an enzyme that catalyzes the formation of isoprene from dimethylallyl diphosphate (EC 4.2.3.27).

According to the organism, the nomenclature of the above identified enzymes and encoding genes may vary. However, for the sake of clarity, in the present specification, these terms are used independently from the origin of the enzymes or genes.

As used herein, the term "activity" of an enzyme refers to its function and designates in the context of the invention, the reaction that is catalyzed by the enzyme. The enzymatic activity may be measured by any method known by the skilled person.

As used herein, the term "increased activity" or "enhanced activity" or "improved activity" of an enzyme refers to an increased specific catalytic activity, an increased specificity for the substrate, an increased protein or RNA stability and/or an increased intracellular concentration of the enzyme. Preferably, the increased activity is an increased intracellular concentration of the enzyme obtained by overexpressing the gene encoding said enzyme.

The term "apocarotenoid" as used herein refers to organic compounds derived from carotenoids by oxidative cleavage catalyzed by carotenoid cleavage dioxygenases (CCD). Some of the apocarotenoids are essential and valuable constituents of color, flavor, and aroma in edible plants. Examples of apocarotenoid include, but are not limited to, beta-ionone, alpha-ionone, geranylacetone, pseudoionone and beta-damascenone.

As used herein, the term "sequence identity" or "identity" refers to the number (%) of matches (identical amino acid residues) in positions from an alignment of two polypeptide sequences. The sequence identity is determined by comparing the sequences when aligned so as to maximize overlap and identity while minimizing sequence gaps. In particular, sequence identity may be determined using any of a number of mathematical global or local alignment algorithms, depending on the length of the two sequences. Sequences of similar lengths are preferably aligned using a global alignment algorithm (e.g. Needleman and Wunsch algorithm; Needleman and Wunsch, 1970) which aligns the sequences optimally over the entire length, while sequences of substantially different lengths are preferably aligned using a local alignment algorithm (e.g. Smith and Waterman algorithm (Smith and Waterman, 1981) or Altschul algorithm (Altschul et al., 1997; Altschul et al., 2005)). Alignment for purposes of determining percent amino acid sequence identity can be achieved in various ways that are within the skill in the art, for instance, using publicly available computer software available on internet web sites such as http://blast.ncbi.nlm.nih.gov/ or http://www.ebi.ac.uk/Tools/emboss/). Those skilled in the art can determine appropriate parameters for measuring alignment, including any algorithms needed to achieve maximal alignment over the full length of the sequences being compared. For purposes herein, % amino acid sequence identity values refers to values generated using the pair wise sequence alignment program EMBOSS Needle that creates an optimal global alignment of two sequences using the Needleman-Wunsch algorithm, wherein all search parameters are set to default values, i.e. Scoring matrix=BLOSUM62, Gap open=10, Gap extend=0.5, End gap penalty=false, End gap open=10 and End gap extend=0.5.

Genetic Engineering of the MEP Pathway

Among the enzymes involved in the MEP pathway, the inventors identified rate-limiting enzymes and showed that their overexpression results in a significant increase in isoprenoid production.

Accordingly, in a first aspect, the present invention relates to a recombinant *Deinococcus* bacterium exhibiting enhanced 2-C-methyl-D-erythritol 4-phosphate/1-deoxy-D-xylulose 5-phosphate (MEP/DXP) pathway, i.e. a *Deinococcus* bacteria that is genetically modified to have an increased carbon flux to IPP and DMAPP compared to the non modified *Deinococcus* bacterium.

In the recombinant *Deinococcus* bacterium of the invention, the activity of at least one enzyme selected from the group consisting of DXS, DXR, IspD, IspE, IspF, IspG, IspH and IPP isomerase, is increased compared to the non modified bacterium. Preferably, at least two, three, four, five, six or seven of these activities are increased. More preferably, all these activities are increased.

The activity of these enzymes may be increased due to the overexpression of their encoding genes. Thus, in an embodiment, at least one gene selected from the group consisting of dxs, dxr, ispD, ispE, ispF, ispG, ispH and idi genes, is overexpressed. Preferably, at least two, three, four, five, six or seven of these genes are overexpressed. More preferably, all these genes are overexpressed.

To increase the expression of a gene, the skilled person can use any known techniques such as increasing the copy number of the gene in the bacterium, using a promoter inducing a high level of expression of the gene, i.e. a strong promoter, using elements stabilizing the corresponding messenger RNA or modifying Ribosome Binding Site (RBS) sequences and sequences surrounding them.

In an embodiment, the overexpression is obtained by increasing the copy number of the gene in the bacterium. One or several copies of the gene may be introduced into the genome by methods of recombination, known to the expert in the field, including gene replacement. Preferably, an expression cassette comprising the gene is integrated into the genome.

Alternatively, the gene may be carried by an expression vector, preferably a plasmid, comprising an expression cassette with the gene of interest. The expression vector may be present in the bacterium in 1 to 5, 20, 100 or 500 copies, depending on the nature of the origin of replication.

In another embodiment, the overexpression of the gene is obtained by using a promoter inducing a high level of expression of the gene. For instance, the promoter of an endogenous gene may be replaced by a stronger promoter, i.e. a promoter inducing a higher level of expression. The promoters suitable to be used in the present invention are known by the skilled person and can be constitutive or inducible, and native, homologous or heterologous.

Expression cassettes useful in the present invention comprising at least one gene selected from the group consisting of dxs, dxr, ispD, ispE, ispF, ispG, ispH and idi genes, operably linked to one or more control sequences, typically comprising a transcriptional promoter and a transcription terminator, that direct the expression of said gene. Preferably, each expression cassette comprises only one gene operably linked to one or more control sequences. In this case, if several genes are overexpressed, several expression cassettes are used, each of them comprising only one gene. Alternatively, expression cassettes useful in the present invention may comprise an operon comprising (i) at least two genes selected from dxs, dxr, ispD, ispE, ispF, ispG, ispH and idi genes, or (ii) at least one gene selected from dxs, dxr, ispD, ispE, ispF, ispG, ispH and idi genes, and at least another gene, e.g. a gene encoding a terpene synthase or a FPP synthase.

The control sequence may include a promoter that is recognized by the host cell. The promoter contains transcriptional control sequences that mediate the expression of the enzyme. The promoter may be any polynucleotide that shows transcriptional activity in the *Deinococcus* bacterium. The promoter may be a native, homologous or heterologous promoter. Preferred promoters are native or homologous. In this regard, various promoters have been studied and used for gene expression in *Deinococcus* bacteria. Examples of suitable promoters include PtufA and PtufB promoters from the translation elongation factors Tu genes tufA (DR0309) and tufB (DR2050), the promoter of the resU gene located in pI3, the promoter region PgroESL of the groESL operon (Lecointe et al, 2004; Meima et al, 2001), or derivatives of such promoters. Preferably, the promoter is a strong constitutive promoter.

The control sequence may also be a transcription terminator, which is recognized by *Deinococcus* bacteria to terminate transcription. The terminator is operably linked to the 3'-terminus of the gene. Any terminator that is functional in *Deinococcus* bacteria may be used in the present invention such as, for example, the terminator term116 described in Lecointe et al (2004).

Optionally, the expression cassette may also comprise a selectable marker that permits easy selection of recombinant bacteria. Typically, the selectable marker is a gene encoding antibiotic resistance or conferring autotrophy.

In a particular embodiment, the recombinant *Deinococcus* bacterium of the invention comprises: an expression cassette comprising a dxs gene operably linked to a strong constitutive promoter; an expression cassette comprising a dxr gene operably linked to a strong constitutive promoter; an expression cassette comprising a ispD gene operably linked to a strong constitutive promoter; an expression cassette comprising a ispE gene operably linked to a strong constitutive promoter; an expression cassette comprising a ispF gene operably linked to a strong constitutive promoter; an expression cassette comprising a ispG gene operably linked to a strong constitutive promoter; an expression cassette comprising a ispH gene operably linked to a strong constitutive promoter; and/or an expression cassette comprising a idi gene operably linked to a strong constitutive promoter.

These expression cassettes may be integrated into the genome of the bacterium and/or may be maintained in an episomal form into an expression vector. Preferably, the expression cassettes are integrated into the genome of the bacterium. The bacterium of the invention may overexpress (i) dxs (a), dxr (b), ispD (c), ispE (d), ispF (e), ispG (f), ispH (g) or idi (h) gene; (ii) one of the following combinations of two genes: a, b; a, c; a, d; a, e; a, f; a, g; a, h; b, c; b, d; b, e; b, f; b, g; b, h; c, d; c, e; c, f; c, g; c, h; d, e; d, f; d, g; d, h; e, f; e, g; e, h; f, g; f, h and g, h; (iii) one of the following combinations of three genes: a, b, c; a, b, d; a, b, e; a, b, f; a, b, g; a, b, h; a, c, d; a, c, e; a, c, f; a, c, g; a, c, h; a, d, e; a, d, f; a, d, g; a, d, h; a, e, f; a, e, g; a, e, h; a, f, g; a, f, h; a, g, h; b, c, d; b, c, e; b, c, f; b, c, g; b, c, h; b, d, e; b, d, f; b, d, g; b, d, h; b, e, f; b, e, g; b, e, h; b, f, g; b, f, h; b, g, h; c, d, e; c, d, f; c, d, g; c, d, h; c, e, f; c, e, g; c, e, h; c, f, g; c, f, h; c, g, h; d, e, f; d, e, g; d, e, h; d, f, g; d, f, h; d, g, h; e, f, g; e, f, h; e, g, h; and f, g, h; (iv) one of the following combinations of four genes: a, b, c, d; a, b, c, e; a, b, c, f; a, b, c, g; a, b, c, h; a, b, d, e; a, b, d, f; a, b, d, g; a, b, d, h; a, b, e, f; a, b, e, g; a, b, e, h; a, b, f, g; a, b, f, h; a, b, g, h; a, c, d, e; a, c, d, f; a, c, d, g; a, c, d, h; a, c, e, f; a, c, e, g;

a, c, e, h; a, c, f, g; a, c, f, h; a, c, g, h; a, d, e, f; a, d, e, g; a, d, e, h; a, d, f, g; a, d, f, h; a, d, g, h; a, e, f, g; a, e, f, h; a, e, g, h; a, f, g, h; b, c, d, e; b, c, d, f; b, c, d, g; b, c, d, h; b, c, e, f; b, c, e, g; b, c, e, h; b, c, f, g; b, c, f, h; b, c, g, h; b, d, e, f; b, d, e, g; b, d, e, h; b, d, f, g; b, d, f, h; b, d, g, h; b, e, f, g; b, e, f, h; b, e, g, h; b, f, g, h; c, d, e, f; c, d, e, g; c, d, e, h; c, d, f, g; c, d, f, h; c, d, g, h; c, e, f, g; c, e, f, h; c, e, g, h; c, f, g, h; d, e, f, g; d, e, f, h; d, e, g, h; d, f, g, h; and e, f, g, h; (v) one of the following combinations of five genes: a, b, c, d, e; a, b, c, d, f; a, b, c, d, g; a, b, c, d, h; a, b, c, e, f; a, b, c, e, g; a, b, c, e, h; a, b, c, f, g; a, b, c, f, h; a, b, c, g, h; a, b, d, e, f; a, b, d, e, g; a, b, d, e, h; a, b, d, f, g; a, b, d, f, h; a, b, d, g, h; a, b, e, f, g; a, b, e, f, h; a, b, e, g, h; a, b, f, g, h; a, c, d, e, f; a, c, d, e, g; a, c, d, e, h; a, c, d, f, g; a, c, d, f, h; a, c, d, g, h; a, c, e, f, g; a, c, e, f, h; a, c, e, g, h; a, c, f, g, h; a, d, e, f, g; a, d, e, f, h; a, d, e, g, h; a, d, f, g, h; a, e, f, g, h; b, c, d, e, f; b, c, d, e, g; b, c, d, e, h; b, c, d, f, g; b, c, d, f, h; b, c, d, g, h; b, c, e, f, g; b, c, e, f, h; b, c, e, g, h; b, c, f, g, h; b, d, e, f, g; b, d, e, f, h; b, d, e, g, h; b, d, f, g, h; b, e, f, g, h; c, d, e, f, g; c, d, e, f, h; c, d, e, g, h; c, d, f, g, h; c, e, f, g, h; and d, e, f, g, h; (vi) one of the following combinations of six genes: a, b, c, d, e, f; a, b, c, d, e, g; a, b, c, d, e, h; a, b, c, d, f, g; a, b, c, d, f, h; a, b, c, d, g, h; a, b, c, e, f, g; a, b, c, e, f, h; a, b, c, e, g, h; a, b, c, f, g, h; a, b, d, e, f, g; a, b, d, e, f, h; a, b, d, e, g, h; a, b, d, f, g, h; a, b, e, f, g, h; a, c, d, e, f, g; a, c, d, e, f, h; a, c, d, e, g, h; a, c, d, f, g, h; a, c, e, f, g, h; a, d, e, f, g, h; b, c, d, e, f, g; b, c, d, e, f, h; b, c, d, e, g, h; b, c, d, f, g, h; b, c, e, f, g, h; b, d, e, f, g, h; and c, d, e, f, g, h; (vii) one of the following combinations of seven genes: a, b, c, d, e, f, g; a, b, c, d, e, f, h; a, b, c, d, e, g, h; a, b, c, d, f, g, h; a, b, c, e, f, g, h; a, b, d, e, f, g, h; a, c, d, e, f, g, h; and b, c, d, e, f, g, h, or (viii) the combination of the eight genes.

In an embodiment, the bacterium overexpresses at least the ispG gene and optionally one or several of the dxs, dxr, ispD, ispE, ispF, ispH and idi genes.

The overexpressed genes can be native, homologous or heterologous genes.

The dxs gene may be any gene encoding a 1-deoxyxylulose 5-phosphate synthase, preferably a bacterial gene.

In a preferred embodiment, the dxs gene is from a *Deinococcus* bacterium. In particular, the dxs gene may be selected from the group consisting of the dxs genes from *D. geothermalis* (SEQ ID NO: 1; UniProt accession number: Q1IZP0), *D. yunweiensis* (SEQ ID NO: 3), *D. apachensis* (NCBI Accession number: WP_01958600.1), *D. phoenicis* (GenBank: EYB66726.1; NCBI Accession number: WP_034360373.1; UniProt accession number: A0A016QL59), *D. deserti* (NCBI Accession number: WP_012692944.1; GenBank: ACO45821.1; UniProt accession number: C1D1U7), *D. aquatilis* (NCBI Accession number: WP_026298749.1 or WP_019009670.1), *D. wulumuqiensis* (WP_017869298.1), *D. radiodurans* (UniProt accession number: Q9RUB5; NCBI Accession number: WP_010888114.1), *D. gobiensis* (NCBI Accession number: WP_014684923.1; GenBank: AFD25440.1; UniProt accession number: H8GUB6), *D*. sp. 2009 (WP_022801808.1), *D. maricopensis* (NCBI Accession number: WP_013557350.1; UniProt accession number: E8U9V6), *D. peraridilitoris* (NCBI Accession number: WP_015234295.1; UniProt accession number: K9ZXR0), *D. proteolyticus* (NCBI Accession number: WP_013614954.1; UniProt accession number: F0RNL9), *D. radiopugnans* (the sequence encoding the protein set forth in SEQ ID NO: 52; SEQ ID NO: 59), *D. murrayi* (NCBI Accession number: WP_027461316.1), *D. swuensis* (UniProt accession number: A0A0A7KK27; NCBI Accession number: WP_039686512.1), *D. solis* (NCBI Accession number: WP_046842902.1) and *D. ficus* (NCBI Accession number: WP_027461725.1). Preferably, the dxs gene is selected from the group consisting of the dxs genes from *D. geothermalis, D. yunweiensis, D. apachensis, D. phoenicis, D. deserti, D. aquatilis, D. wulumuqiensis, D. radiodurans, D. gobiensis, D*. sp. 2009, *D. maricopensis, D. peraridilitoris, D. proteolyticus* and *D. radiopugnans*. More preferably, the dxs gene is from *D. geothermalis, D. yunweiensis* or *D. radiopugnans*, and even more preferably from *D. yunweiensis* or *D. radiopugnans*. Any polypeptide, preferably from a *Deinococcus* bacterium, having at least 70, preferably 80%, more preferably 90%, sequence identity to any of the polypeptides encoded by those genes, preferably to the polypeptide of SEQ ID NO: 2, 4 or 52, more preferably to the polypeptide of SEQ ID NO: 2 or 4, may be used.

The dxr gene may be any gene encoding a 1-deoxy-D-xylulose 5-phosphate reductoisomerase, preferably a bacterial gene. In a preferred embodiment, the dxr gene is from a *Deinococcus* bacterium. In particular, the dxr gene may be selected from the group consisting of the dxr genes from *D. geothermalis* (SEQ ID NO: 34; UniProt accession number: Q1IZJ1), *D. yunweiensis* (SEQ ID NO: 36), *D. apachensis* (NCBI Accession number: WP_019584825.1), *D. gobiensis* (NCBI Accession number: WP_014685255.1; UniProt accession number: H8GWW6), *D. phoenicis* (UniProt accession number: A0A016QKH6; GenBank: EYB66645.1), *D. radiodurans* (NCBI accession number: WP_10888147.1; UniProt accession number: Q9RU84), *D. wulumuqiensis* (NCBI accession number: WP_017869266.1), *D. deserti* (NCBI accession number: WP_012693383.1; UniProt accession number: C1CVP3), *D*. sp. 2009 (WP_022802132.1), *D. aquatilis* (WP_019009458.1), *D. maricopensis* (NCBI accession number: WP_013557781.1; UniProt accession number: E8UB38), *D. proteolyticus* (NCBI accession number: WP_013614140.1; UniProt accession number: F0RJQ5), *D. peraridilitoris* (NCBI accession number: WP_015237162.1; UniProt accession number: L0A5Z1), *D. swuensis* (UniProt accession number: A0A0A7KF77; GenBank: AIZ44760.1), *D. solis* (WP_046842669.1), *D. marmoris* (WP_029481040.1), *D. ficus* (WP_027462584.1), *D. radiopugnans* (SEQ ID NO: 61) and *D. murrayi* (WP_027460916.1). Preferably, the dxr gene is selected from the group consisting of the dxr genes from *D. geothermalis, D. yunweiensis, D. apachensis, D. gobiensis, D. phoenicis, D. radiodurans, D. wulumuqiensis, D. deserti, D*. sp. 2009, *D. aquatilis, D. maricopensis, D. proteolyticus* and *D. peraridilitoris*. More preferably, the dxr gene is from *D. yunweiensis*. Any polypeptide, preferably from a *Deinococcus* bacterium, having at least 70, preferably 80%, more preferably 90%, sequence identity to any of the polypeptides encoded by those genes, preferably to the polypeptide of SEQ ID NO: 35 or 37, may be used.

The ispD gene may be any gene encoding a 2-C-methyl-D-erythritol 4-phosphate cytidylyltransferase, preferably a bacterial gene. In a preferred embodiment, the ispD gene is from a *Deinococcus* bacterium. In particular, the ispD gene may be selected from the group consisting of the ispD genes from *D. geothermalis* (SEQ ID NO: 17; UniProt accession number: Q1J200), *D. yunweiensis* (SEQ ID NO: 19), *D. apachensis* (NCBI Accession number: WP_019587161.1), *D. phoenicis* (EYB69514.1; UniProt accession number: A0A016QUR2), *D. deserti* (WP_012691946.1; UniProt accession number: C1CXL7), *D. wulumuqiensis* (WP_017871568.1), *D. radiodurans* (WP_010889228.1;

UniProt accession number: Q9RR90), *D.* sp. 2009 (WP_022800717.1), *D. peraridilitoris* (WP_015236716.1; UniProt accession number: L0A4P7), *D. aquatilis* (WP_019010949.1 or WP_026298972.1), *D. maricopensis* (WP_013556207.1; UniProt accession number: E8U6L3), *D. proteolyticus* (WP_013615367.1 or WP_041222801.1; GenBank: ADY26759.1; UniProt accession number: F0RKP7), *D. gobiensis* (WP_014686200.1; GenBank: AFD26720.1; UniProt accession number: H8GV45), *D. marmoris* (WP_029480451.1), *D. soli* (AKH17101.1), *D. swuensis* (UniProt accession number: A0A0A7KL82), *D. misasensis* (WP_034344339.1), *D. radiopugnans* (SEQ ID NO: 63) and *D. murrayi* (GenBank: ACO44823.1; WP_027460458.1). Preferably, the ispD gene is selected from the group consisting of the ispD genes from *D. geothermalis, D. yunweiensis, D. apachensis, D. phoenicis, D. deserti, D. wulumuqiensis, D. radiodurans, D.* sp. 2009, *D. peraridilitoris, D. aquatilis, D. maricopensis, D. proteolyticus* and *D. gobiensis*. More preferably, the ispD gene is from *D. yunweiensis*. Any polypeptide, preferably from a *Deinococcus* bacterium, having at least 70, preferably 80%, more preferably 90%, sequence identity to any of the polypeptides encoded by those genes, preferably to the polypeptide of SEQ ID NO: 18 or 20, may be used.

The ispE gene may be any gene encoding a 4-diphosphocytidyl-2-C-methyl-D-erythritol kinase, preferably a bacterial gene. In a preferred embodiment, the ispE gene is from a *Deinococcus* bacterium. In particular, the ispE gene may be selected from the group consisting of the ispE genes from *D. geothermalis* (SEQ ID NO: 38; UniProt accession number: Q1J201; NCBI accession number: WP 011529330.1), *D. yunweiensis* (SEQ ID NO: 40), *D. phoenicis* (NCBI Accession number: EYB69513.1; UniProt accession number: A0A016QTX2), *D. apachensis* (WP_019587162.1), *D. aquatilis* (WP_019009083.1), *D. maricopensis* (WP_013556206.1; UniProt accession number: E8U6L2; GenBank: ADV66701.1), *D. deserti* (WP_012691947.1; UniProt accession number: C1CXL8), D. sp. 2009 (WP_022800716.1), *D. proteolyticus* (WP_013615364.1; UniProt accession number: F0RKH7), *D. wulumuqiensis* (WP_017871569.1) *D. peraridilitoris* (WP_015236715.1 or WP_022800716.1; UniProt accession number: L0A3E0), *D. gobiensis* (WP_014686199.1; UniProt accession number: H8GV44), *D. radiodurans* (WP_10889229.1; UniProt accession number: Q9RR89), *D. swuensis* (A0A0A7KGN1; GenBank: AIZ45322.1), *D. soli* (AKH17102.1), *D. radiopugnans* (SEQ ID NO: 65) and *D. marmoris* (WP_029480453.1). Preferably, the ispE gene is selected from the group consisting of the ispE genes from *D. geothermalis, D. yunweiensis, D. phoenicis, D. apachensis, D. aquatilis, D. maricopensis, D. deserti,* D. sp. 2009, *D. proteolyticus, D. wulumuqiensis, D. peraridilitoris, D. gobiensis* and *D. radiodurans*. More preferably, the ispE gene is from *D. yunweiensis*. Any polypeptide, preferably from a *Deinococcus* bacterium, having at least 70, preferably 80%, more preferably 90%, sequence identity to any of the polypeptides encoded by those genes, preferably to the polypeptide of SEQ ID NO: 39 or 41, may be used.

The ispF gene may be any gene encoding a 2-C-methyl-D-erythritol 2,4-cyclodiphosphate synthase, preferably a bacterial gene. In a preferred embodiment, the ispF gene is from a *Deinococcus* bacterium. In particular, the ispF gene may be selected from the group consisting of the ispF genes from *D. geothermalis* (SEQ ID NO: 21; UniProt accession number: Q1J2A8; WP_011529223.1), *D. yunweiensis* (SEQ ID NO: 23), *D. phoenicis* (NCBI Accession number: EYB69383.1, WP_034353365.1; UniProt accession number: A0A016QTI4), *D. apachensis* (WP_019587119.1), *D.* sp. 2009 (WP_022800431.1), *D. wulumuqiensis* (WP_017871252.1), *D. maricopensis* (WP_013558001.1; UniProt accession number: E8UBQ8), *D. deserti* (WP_012692194.1; UniProt accession number: C1CZ33), *D. aquatilis* (WP_019009115.1), *D. radiodurans* (WP_010886876.1 UniProt accession number: Q9RXS6), *D. proteolyticus* (WP_013615320.1; UniProt accession number: F0RKD3), *D. gobiensis* (WP_014686259.1; UniProt accession number: H8GVA4), *D. peraridilitoris* (WP_015234905.1), *D. swuensis* (A0A0A7KKV6), *D. radiopugnans* (SEQ ID NO: 67) and *D. murrayi* (WP_027461473.1). Preferably, the ispF gene is selected from the group consisting of the ispF genes from *D. geothermalis, D. yunweiensis, D. phoenicis, D. apachensis, D.* sp. 2009, *D. wulumuqiensis, D. maricopensis, D. deserti, D. aquatilis, D. radiodurans, D. proteolyticus, D. gobiensis* and *D. peraridilitoris*. More preferably, the ispF gene is from *D. yunweiensis*. Any polypeptide, preferably from a *Deinococcus* bacterium, having at least 70, preferably 80%, more preferably 90%, sequence identity to any of the polypeptides encoded by those genes, preferably to the polypeptide of SEQ ID NO: 22 or 24, may be used.

The ispG gene may be any gene encoding a 4-hydroxy-3-methylbut-2-en-1-yl diphosphate synthase, preferably a bacterial gene. In a preferred embodiment, the ispG gene is from a *Deinococcus* bacterium. In particular, the ispG gene may be selected from the group consisting of the ispG genes from *D. geothermalis* (SEQ ID NO: 25), *D. yunweiensis* (SEQ ID NO: 27), *D. apachensis* (NCBI Accession number: WP_019584739.1 or WP_040382265.1), *D. phoenicis* (EYB67750.1), *D. aquatilis* (WP_019008200.1), *D.* sp. 2009 (WP_022801633.1), *D. gobiensis* (WP_014684632.1), *D. radiodurans* (WP_010887031.1), *D. wulumuqiensis* (WP_017871942.1), *D. deserti* (WP_012693251.1), *D. proteolyticus* (WP_013615171.1), *D. maricopensis* (WP_013556907.1; EYB67750.1), *D. peraridilitoris* (WP_015237094.1), *D. radiopugnans* (SEQ ID NO: 69) and *D. murrayi* (WP_027460867.1). Preferably, the ispG gene is selected from the group consisting of the ispG genes from *D. geothermalis, D. yunweiensis, D. apachensis, D. phoenicis, D. aquatilis, D.* sp. 2009, *D. gobiensis, D. radiodurans, D. wulumuqiensis, D. deserti, D. proteolyticus, D. maricopensis* and *D. peraridilitoris*. More preferably, the ispG gene is from *D. yunweiensis*. Any polypeptide, preferably from a *Deinococcus* bacterium, having at least 70, preferably 80%, more preferably 90%, sequence identity to any of the polypeptides encoded by those genes, preferably to the polypeptide of SEQ ID NO: 26 or 28, may be used.

The ispH gene may be any gene encoding a 4-hydroxy-3-methylbut-2-enyl diphosphate reductase, preferably a bacterial gene. In a preferred embodiment, the ispH gene is from a *Deinococcus* bacterium. In particular, the ispH gene may be selected from the group consisting of the ispH genes from *D. geothermalis* (SEQ ID NO: 42), *D. yunweiensis* (SEQ ID NO: 44), *D. phoenicis* (NCBI Accession number: EYB6823.1; WP_034356434.1), *D. apachensis* (WP_019585890.1), *D.* sp. 2009 (WP_022801928.1), *D. gobiensis* (WP_014685178.1), *D. aquatilis* (WP_019007893.1), *D. radiodurans* (WP_10888795.1), *D. deserti* (WP_012693059.1; GeneBank: ACO45936.1), *D. peraridilitoris* (WP_015236935.1), *D. proteolyticus* (WP_013614360.1), *D. maricopensis* (WP_013557691.1), *D. radiopugnans* (SEQ ID NO: 71) and *D. wulumuqiensis* (WP_017869851.1). Preferably, the ispH gene is selected from the group consisting of the ispH genes from *D. geothermalis, D. yunweiensis, D. apachensis, D. phoenicis,*

*D. aquatilis, D.* sp. 2009, *D. gobiensis, D. radiodurans, D. wulumuqiensis, D. deserti, D. proteolyticus, D. maricopensis* and *D. peraridilitoris*. More preferably, the ispH gene is from *D. yunweiensis*. Any polypeptide, preferably from a *Deinococcus* bacterium, having at least 70, preferably 80%, more preferably 90%, sequence identity to any of the polypeptides encoded by those genes, preferably to the polypeptide of SEQ ID NO: 43 or 45, may be used.

The idi gene may be any gene encoding an isopentenyl-diphosphate delta-isomerase, preferably a bacterial gene. In a preferred embodiment, the idi gene is from a *Deinococcus* bacterium. In particular, the idi gene may be selected from the group consisting of the idi genes from *D. geothermalis* (SEQ ID NO: 29), *D. yunweiensis* (SEQ ID NO: 31), *D. apachensis* (NCBI Accession number: WP_019585561.1), *D. phoenicis* (EYB67918.1), *D. aquatilis* (WP_019010639.1 or WP_040380849.1), *D.* sp. 2009 (WP_022802239.1), *D. deserti* (WP_012692934.1), *D. radiodurans* (Q9RVE2.3), *D. maricopensis* (WP_013556085.1) *D. wulumuqiensis* (WP_017870894.1), *D. gobiensis* (WP_014685602.1 or WP_043802116.1), *D. radiopugnans* (SEQ ID NO: 73) and *D. peraridilitoris* (WP_015236653.1). Preferably, the idi gene is selected from the group consisting of the idi genes from *D. geothermalis, D. yunweiensis, D. apachensis, D. phoenicis, D. aquatilis, D.* sp. 2009, *D. gobiensis, D. radiodurans, D. wulumuqiensis, D. deserti, D. maricopensis* and *D. peraridilitoris*. More preferably, the idi gene is from *D. yunweiensis*. Any polypeptide, preferably from a *Deinococcus* bacterium, having at least 70, preferably 80%, more preferably 90%, sequence identity to any of the polypeptides encoded by those genes, preferably to the polypeptide of SEQ ID NO: 30 or 32, may be used.

In a preferred embodiment, the bacterium overexpresses DXS and IDI encoding genes. Preferably, the overexpressed DXS is an improved DXS enzyme as described below.

Improved MEP Enzymes

The dxs, drx, ispD, ispE, ispF, ispG, ispH and idi genes used in the present invention may also encode improved enzymes, i.e. enzymes that possess at least one mutation in their sequence, in comparison with the amino acid sequence of the wild-type enzyme, said mutation leading to an increase of their activity. Such improved enzymes may be obtained according to any techniques known by the skilled person. In particular, improved DXP synthases, more particularly improved *Deinococcus* DXP synthases, may be obtained according to the technique disclosed in the patent application WO 2012/052171.

Thus, in an embodiment, the recombinant *Deinococcus* bacterium comprises a dxs gene encoding an improved DXP synthase, preferably an improved *Deinococcus* DXP synthase, obtained by mutating a DXP synthase in order to obtain an asparagine at position corresponding to position 222 of SEQ ID NO: 52 (or at position corresponding to position 216 of SEQ ID NO: 4 or at position corresponding to position 219 of SEQ ID NO: 2) and/or a cysteine at position corresponding to position 244 of SEQ ID NO: 52 (or at position corresponding to position 238 of SEQ ID NO: 4 or at position corresponding to position 241 of SEQ ID NO: 2). Preferably, the recombinant *Deinococcus* bacterium comprises a dxs gene encoding an improved DXP synthase obtained by mutating a DXP synthase in order to obtain a cysteine at position corresponding to position 244 of SEQ ID NO: 52 (or at position corresponding to position 238 of SEQ ID NO: 4 or at position corresponding to position 241 of SEQ ID NO: 2).

Methods to identify residues corresponding to position 222 or 244 are well known by the skilled person and detailed in the patent application WO 2012/052171. In particular, these residues may be identified using a sequence alignment computer program such as ClustalW, MUSCLE or programs using the Needleman and Wunsch algorithm.

In a preferred embodiment, the recombinant *Deinococcus* bacterium comprises a gene encoding an improved DXP synthase from *D. radiopugnans* having the following substitutions: K222N (SEQ ID NO: 6), R244C (SEQ ID NO: 8) or K222N/R244C (SEQ ID NO: 10). The sequences of the genes encoding these enzymes are presented in SEQ ID NO: 5, 7 and 9, respectively. More preferably, the recombinant *Deinococcus* bacterium comprises a gene encoding R244C mutant of the DXP synthase from *D. radiopugnans* (SEQ ID NO: 8).

In another preferred embodiment, the recombinant *Deinococcus* bacterium comprises a gene encoding an improved DXP synthase from *D. yunweiensis* having the following substitutions: K216N (SEQ ID NO: 12), R238C (SEQ ID NO: 14) or K216N/R238C (SEQ ID NO: 16). The sequences of the genes encoding these enzymes are presented in SEQ ID NO: 11, 13 and 15, respectively. More preferably, the recombinant *Deinococcus* bacterium comprises a gene encoding R238C mutant of the DXP synthase from *D. yunweiensis* (SEQ ID NO: 14).

In a further preferred embodiment, the recombinant *Deinococcus* bacterium comprises a gene encoding an improved DXP synthase from *D. geothermalis* (SEQ ID NO: 2) having the following substitutions: K219N (SEQ ID NO: 54), R241C (SEQ ID NO: 56) or K219N/R241C (SEQ ID NO: 58). More preferably, the recombinant *Deinococcus* bacterium comprises a gene encoding R241C mutant of the DXP synthase from *D. geothermalis*.

The gene encoding the improved DXP synthase may be overexpressed in the recombinant bacterium. Preferably, this gene is integrated in the genome of the bacterium under the control of constitutive or inducible promoter, more preferably under the control of a strong constitutive promoter. This gene can replace the endogenous dxs gene or may be integrated in another place to increase the copy number of the dxs gene.

Thus, in another aspect, the present invention also relates to a recombinant *Deinococcus* bacterium comprising an improved (or mutated) DXP synthase, preferably an improved *Deinococcus* DXP synthase, comprising an asparagine at position corresponding to position 222 of SEQ ID NO:52 and/or a cysteine at position corresponding to position 244 of SEQ ID NO:52. Preferably, the recombinant *Deinococcus* bacterium comprises an improved (or mutated) DXP synthase comprising a cysteine at position corresponding to position 244 of SEQ ID NO:52. The corresponding position can be easily identified by the skilled person using well-known alignment algorithms. In particular, the improved DXP synthase may be any of the improved DXS disclosed above.

Optionally, at least one gene selected from the group consisting of dxs, dxr, ispD, ispE, ispF, ispG, ispH and idi, is overexpressed. Preferably, at least the IDI encoding gene is overexpressed. More preferably, at least one dxs gene and one idi gene are overexpressed.

All embodiments described herein for the other aspects of the invention are also encompassed in this aspect. In particular, the recombinant *Deinococcus* bacterium may further exhibit (i) an enhanced MEP pathway as described above, (ii) a heterologous MEV pathway, (iii) an increase of the FPP synthase activity, (iv) inactivation of the lycopene beta-cyclase and/or (v) expression of a heterologous terpene or isoprene synthase as described herein.

Heterologous MEV Pathway

In another aspect, the recombinant *Deinococcus* bacterium of the invention comprises a heterologous MEV pathway, i.e. expresses heterologous genes encoding hydroxymethylglutaryl-CoA synthase (EC 2.3.3.10), hydroxymethylglutaryl-CoA reductase (NADPH) (EC 1.1.1.34), mevalonate kinase (EC 2.7.1.36), phosphomevalonate kinase (EC 2.7.4.2), and diphosphomevalonate decarboxylase (EC 4.1.1.33).

Preferably, heterologous genes encode enzymes from plants, bacteria or yeasts, more preferably from *Saccharomyces cerevisiae*. In a particular embodiment, the recombinant *Deinococcus* bacterium comprises genes encoding *Saccharomyces cerevisiae* hydroxymethylglutaryl-CoA synthase (Uniprot/Swissprot: P54839), hydroxymethylglutaryl-CoA reductase (NADPH) (Uniprot/Swissprot: P12683), mevalonate kinase (Genbank: NP_013935.1), phosphomevalonate kinase (Genbank: NP_013947.1), and diphosphomevalonate decarboxylase (Genbank: CAA66158.1).

*Deinococcus* bacteria exhibit endogenous acetyl-CoA C-acetyltransferase activity. However, in some embodiment, the recombinant *Deinococcus* bacterium may further comprise a heterologous gene encoding an acetyl-CoA C-acetyltransferase. This gene can replace the endogenous gene or may be integrated in another place to increase the copy number of this gene. This heterologous gene may be from plants, bacteria or yeasts. In a preferred embodiment, the recombinant *Deinococcus* bacterium further comprises a gene encoding a *Saccharomyces cerevisiae* acetyl-CoA C-acetyltransferase (Genbank: NP_015297.1).

All embodiments described herein for the other aspects of the invention are also encompassed in this aspect. In particular, the recombinant *Deinococcus* bacterium may further exhibit (i) an enhanced MEP pathway as described above, optionally with an improved DXP synthase, (ii) an increase of the FPP synthase activity, (iii) inactivation of the lycopene beta-cyclase and/or (iv) expression of a heterologous terpene or isoprene synthase as described herein.

Heterologous Terpene Synthases

The present application also demonstrates that *Deinococcus* bacteria, and in particular recombinant *Deinococcus* bacteria as described above, may be efficiently used to produce heterologous isoprenoid compounds via the expression of heterologous terpene synthases. Thus, in a further aspect, the present invention relates to a recombinant *Deinococcus* bacteria comprising a gene encoding a heterologous terpene synthase.

All embodiments described herein for the other aspects of the invention are also encompassed in this aspect. In particular, the recombinant *Deinococcus* bacterium may further exhibit (i) an enhanced MEP pathway as described above, optionally with an improved DXP synthase, (ii) a heterologous MEV pathway, (iii) an increase of the FPP synthase activity, (iv) inactivation of the lycopene beta-cyclase and/or (v) expression of a heterologous isoprene synthase as described herein.

Preferably, the heterologous terpene synthase is selected from the group consisting of monoterpene synthases, diterpene synthases, triterpene synthases and sesquiterpene synthases, more preferably from monoterpene and sesquiterpene synthases. The recombinant *Deinococcus* bacterium may express one or several heterologous terpene synthases, in particular one or several monoterpene synthases and/or one or several sesquiterpene synthases.

Each heterologous terpene synthase is preferably expressed from an expression cassette as described above, comprising the gene encoding said enzyme and integrated into the genome of the bacterium. Preferably, the gene is under the control of a constitutive promoter, more preferably a strong constitutive promoter.

Heterologous Monoterpene Synthases

In a particular embodiment, the recombinant bacterium of the invention is a *Deinococcus* bacterium modified via the expression of a heterologous monoterpene synthase to produce a monoterpene or monoterpenoid. Example of monoterpene synthases that can be expressed in the recombinant *Deinococcus* bacterium of the invention include, but are not limited to, geraniol synthases (EC 3.1.7.3), linalool synthases such as 3S-linalool synthases (EC 4.2.3.25) and R-linalool synthases (EC 4.2.3.26), 1,8-cineole synthase (EC 4.2.3.108), myrcene synthases (EC 4.2.3.15), 4S-limonene synthases (EC 4.2.3.16), R-limonene synthases (EC 4.2.3.20), α-pinene synthases (EC 4.2.3.119), β-pinene synthases (EC 4.2.3.120), (−)-endo-fenchol synthases (EC 4.2.3.10), and (−)-α-terpineol synthases (EC 4.2.3.111), and any combinations thereof.

In an embodiment, the recombinant bacterium of the invention comprises a gene encoding a heterologous geraniol synthase, i.e. an enzyme that catalyzes the formation of geraniol from geranyl diphosphate. Examples of heterologous geraniol synthases include, but are not limited to, geraniol synthases from *Ocimum basilicum* (SEQ ID NO: 49; GenBank accession number: AAR11765, Zhou et al., 2013; Liu et al., 2013; Lijima et al., 2004), *Valeriana officinalis* (AHE41084, Dong et al., 2013), *Lippia dulcis* (Dong et al., 2013), *Perilla citriodora* (AAY88965; Sugiura et al., 2011), *Perilla frutescens* (ABB30218; Sharkey et al., 2005), *Perilla setoyensis*, (ACN42010.1), *Cinnamomum tenuipilum* (CAD29734), *Phyla dulcis* (ADK62524.1), *Olea europaea* (AFI47926.1), *Vitis vinifera* (ADR74217), *Cicer arietinum* (XP_004487383.1), *Picrorhiza kurrooa* (AHX97739.1), *Citrus jambhiri* (BAM29049.1), *Cinnamomum tenuipile* (CAD29734.2; Yang et al., 2005) and *Catharanthus roseus* (AFD64744.1). Any polypeptide exhibiting a geraniol synthase activity and having at least 70%, 80%, preferably 90%, sequence identity to any of these enzymes may be used, in particular variants of these enzymes having increased catalytic activity, specificity for the substrate, and/or stability. In a particular embodiment, the heterologous geraniol synthase is selected from the group consisting of geraniol synthases from *Ocimum basilicum*, *Valeriana officinalis*, *Phyla dulcis*, *Olea europaea*, *Vitis vinifera*, *Cicer arietinum* and *Catharanthus roseus*. More preferably, the heterologous geraniol synthase is the geraniol synthase of *Ocimum basilicum* (SEQ ID NO: 49), *Cicer arietinum* or *Phyla dulcis*. Even more preferably, the geraniol synthase is the geraniol synthase of *Ocimum basilicum*. The nucleotide sequence of the gene encoding this geraniol synthase may be as set forth in SEQ ID NO: 48.

Optionally, the recombinant bacterium comprising a gene encoding a heterologous geraniol synthase, further comprises a geraniol reductase catalyzing the reduction of geraniol to citronellol (EC 1.6.99.1). Examples of heterologous geraniol reductases include, but are not limited to, the old yellow enzyme 2 (OYE2) from *S. cerevisiae* (Q03558.3) and the homologous from the plant *Hevea brasiliensis*, a 12-oxophytodienoate reductase (OPR), HbOPR (DQ004685.1).

In another embodiment, the recombinant bacterium of the invention comprises a gene encoding a heterologous linalool synthase. The linalool synthase may be a 3S-linalool synthase, i.e. an enzyme that catalyzes the formation of S-linalool from geranyl diphosphate, or a R-linalool synthase, i.e. an enzyme that catalyzes the formation of R-linalool from geranyl diphosphate. Examples of heterologous linalool synthases include, but are not limited to, linalool synthases from *Streptomyces clavuligerus* (Nakano et al., 2011), Lemon Myrtle (Sugiura et al., 2011), *Perilla citriodora* (GenBank accession number AHY39266.1; Sugiura et al., 2011), *Myzus citrate* (Sugiura et al., 2011), *Clarkia breweri* (AAD19838; AAD19840; AAC49395, Rico et al., 2010; Herreo et al., 2008; Dudareva et al., 1996; Pichersky et al., 1995), *Clarkia concinna* (AAD19839), *Lavandula angustifolia* (ABB73045.1; Landmann et al., 2007) *Vitis vinifera* (Martin et al., 2010), *Arabidopsis lyrata* subsp. *lyrata* (EFH62782.1; XP_002886523.1), *Oryza sativa* (EU596453), *Cereus peruvianus* (Sitrit et al., 2004), *Mentha citrata* (AAL99381; Crowell et al., 2002), *Artemisia annua* (AAF13357; AAF13356; Jia et al., 1999), *Ocimum basilicum* (AAV63789; Lijima et al., 2004), *Arabidopsis thaliana* (AA085533; Chen et al., 2003), *Fragaria ananassa* (CAD57081; CAD57106; Aharoni et al., 2004), *Medicago truncatula* (XP_003593502.1), *Antirrhinum majus* (ABR24418), *Lycopersicon esculentum* (AAX69063), *Picea abies* (AAS47693), *Perilla frutescens* var. *hirtella* (ACN42011; Masumoto et al., 2010), *Coriandrum sativum* (AHC54051; Galata et al., 2014), *Cinnamomum osmophloeum* (AFQ20812.1), *Theobroma cacao* (EOY20311.1), *Morus notabilis* (EXC23176.1) and *Coffea Arabica* (Del Terra et al., 2013). Any polypeptide exhibiting a linalool synthase activity and having at least 70%, 80%, preferably 90%, sequence identity to any of these enzymes may be used, in particular variants of these enzymes having increased catalytic activity, specificity for the substrate, and/or stability. In a particular embodiment, the heterologous linalool synthase is selected from the group consisting of linalool synthases from *Clarkia concinna, Medicago truncatula, Perilla frutescens* var. *hirtella, Coriandrum sativum, Lavandula angustifolia, Clarkia breweri, Cinnamomum osmophloeum, Theobroma cacao, Morus notabilis*, and *Coffea Arabica*. More preferably, the heterologous linalool synthase is a linalool synthase of *Perilla frutescens* or *Clarkia breweri*, even more preferably of *Perilla frutescens*.

In an embodiment, the recombinant bacterium of the invention comprises a gene encoding a heterologous myrcene synthase, i.e. an enzyme that catalyzes the formation of myrcene from geranyl diphosphate. Examples of heterologous myrcene synthases include, but are not limited to, myrcene synthases from *Abies grandis* (GenBank accession number: AAB71084), *Antirrhinum majus* (AAO41727; AAO41726), *Arabidopsis thaliana* (NP_189209; AAG09310), *Lycopersicon esculentum* (AAX69064), *Ocimum basilicum* (AAV63791), *Perilla frutescens* (AAF76186), *Picea abies* (AAS47696), *Morus notabilis* (EXB97316.1), *Medicago truncatula* (AES67305.1) and *Quercus ilex* (CAC41012). Any polypeptide exhibiting a myrcene synthase activity and having at least 70%, 80%, preferably 90%, sequence identity to any of these enzymes may be used, in particular variants of these enzymes having increased catalytic activity, specificity for the substrate, and/or stability. In a particular embodiment, the heterologous linalool synthase is selected from the group consisting of myrcene synthases from *Abies grandis, Picea abies, Morus notabilis* and *Medicago truncatula*.

In another embodiment, the recombinant bacterium of the invention comprises a gene encoding a heterologous limonene synthase. The limonene synthase may be a 4S-limonene synthase, i.e. an enzyme that catalyzes the formation of (−)-S-limonene from geranyl diphosphate, or a R-limonene synthase, i.e. an enzyme that catalyzes the formation of (+)-R-limonene from geranyl diphosphate. Examples of heterologous limonene synthases include, but are not limited to, limonene synthases from *Mentha spicata* (GenBank accession number: AAC37366), *Mentha longifolia* (AAD50304.1), *Abies grandis* (AAB70907; AAF61455), *Agastache rugosa* (AAL17636), *Cannabis sativa* (ABI21837), *Citrus limon* (AAM53944; AAM53946), *Citrus unshiu* (BAD27256; BAD27257), *Lavandula angustifolia* (ABB73044), *Perilla frutescens* (AAG31438), *Picea abies* (AAS47694), *Picea sitchensis* (ABA86248) and *Schizonepeta tenuifolia* (AAG01140). Any polypeptide exhibiting a limonene synthase activity and having at least 70%, 80%, preferably 90%, sequence identity to any of these enzymes may be used, in particular variants of these enzymes having increased catalytic activity, specificity for the substrate, and/or stability. In a particular embodiment, the heterologous limonene synthase is from *Mentha spicata* or *Mentha longifolia*, preferably *Mentha iongifolia*.

In another embodiment, the recombinant bacterium of the invention comprises a gene encoding a heterologous cineole synthase. Examples of heterologous cineole synthases include, but are not limited to, cineole synthases from *Streptomyces clavuligerus* (GenBank: EDY47508.1; Nakano et al., 2011), *Solanum lycopersicum* (GenBank: AEM05857.1), *Rosmarinus officinalis* (GenBank: AFZ41794.1), *Salvia fruticosa* (ABH07677.1) and *Arabidopsis thaliana* (AEE77075.1; AEE77074.1). Any polypeptide exhibiting a cineol synthase activity and having at least 70%, 80%, preferably 90%, sequence identity to any of these enzymes may be used, in particular variants of these enzymes having increased catalytic activity, specificity for the substrate, and/or stability. In a particular embodiment, the heterologous cineol synthase is from *Streptomyces clavuligerus*.

Optionally, the recombinant bacterium of the invention comprising a heterologous limonene synthase may further comprise one or several additional enzymes belonging to the pathways converting (i) S-limonene to (−)-carvone, (ii) S-limonene to menthone, menthol, neomenthol or isomenthone, or (iii) R-limonene to (+) carvone. Thus, in a particular embodiment, the recombinant *Deinococcus* bacterium expresses a heterologous limonene synthase and one or several additional heterologous enzymes selected from the groups consisting of (i) (S)-limonene 6-monooxygenase (EC 1.14.13.48) and carveol dehydrogenase (EC 1.1.1.243); (ii) (S)-limonene 3-monooxygenase (EC 1.14.13.47), isopiperitenol dehydrogenase (EC 1.1.1.223), (−)-isopiperitenone reductase (EC1.3.1.82), (+)-cis-isopulegone isomerase, (+)-pulegone reductase (EC 1.3.1.81), (−)-menthol dehydrogenase (EC 1.1.1.207) and (+)-neomenthol dehydrogenase (EC 1.1.1.208); and (iii) (R)-limonene 6-monooxygenase (EC 1.14.13.80) and (+)-trans-carveol dehydrogenase (EC 1.1.1.243).

In another embodiment, the recombinant bacterium of the invention comprises a gene encoding a heterologous pinene synthase. The pinene synthase may be a α-pinene synthase, i.e. an enzyme that catalyzes the formation of α-pinene from geranyl diphosphate, or a β-pinene synthase, i.e. an enzyme that catalyzes the formation of β-pinene from geranyl diphosphate. Examples of heterologous pinene synthases include, but are not limited to, pinene synthases from *Abies grandis* (GenBank accession number: AAB71085), *Artemisia annua* (AAK58723), *Cannabis sativa* (ABI21838), *Citrus limon* (AAM53945), *Citrus unshiu* (BAD27260), *Fragaria vesca* (CAD57092), *Picea abies* (AAS47692), *Picea sitchensis* (AAP72020) and *Pseudotsuga menziesii*

(AAX07267). Any polypeptide exhibiting a pinene synthase activity and having at least 70%, 80%, preferably 90%, sequence identity to any of these enzymes may be used, in particular variants of these enzymes having increased catalytic activity, specificity for the substrate, and/or stability. In a particular embodiment, the heterologous pinene synthase is from *Artemisia annua*.

In an embodiment, the recombinant bacterium of the invention comprises a gene encoding a heterologous (−)-endo-fenchol synthase, i.e. an enzyme that catalyzes the formation of fenchol from geranyl diphosphate. Examples of heterologous (−)-endo-fenchol synthases include, but are not limited to, the (−)-endo-fenchol synthase from *Ocimum basilicum* (GenBank accession number: AAV63790). Any polypeptide exhibiting an endo-fenchol synthase activity and having at least 70%, 80%, preferably 90%, sequence identity to this enzyme may be used, in particular variants of this enzyme having increased catalytic activity, specificity for the substrate, and/or stability.

In an embodiment, the recombinant bacterium of the invention comprises a gene encoding a heterologous (−)-α-terpineol synthase, i.e. an enzyme that catalyzes the formation of α-terpineol from geranyl diphosphate. Examples of heterologous (−)-α-terpineol synthases include, but are not limited to, (−)-α-terpineol synthases from *Vitis vinifera* (GenBank accession number: AAS79351; AAS79352), *Zea mays* (AAL59230; ABR09292), *Santalum album* (ACF24767), *Pinus tadea* (AAO61227) and *Magnolia grandiflora* (ACC66282). Any polypeptide exhibiting an α-terpineol synthase activity and having at least 70%, 80%, preferably 90%, sequence identity to this enzyme may be used, in particular variants of this enzyme having increased catalytic activity, specificity for the substrate, and/or stability. In a particular embodiment, the (−)-α-terpineol synthase is from *Vitis vinifera*.

Heterologous Sesquiterpene Synthases

In another embodiment, the recombinant bacterium of the invention is a *Deinococcus* bacterium modified via the expression of a heterologous sesquiterpene synthase to produce a sesquiterpenoid. Example of sesquiterpene synthases that can be expressed in the recombinant *Deinococcus* bacterium of the invention include, but are not limited to, (+)-epi-alpha-bisabolol synthase (EC 4.2.3.138), germacrene A synthase (EC 4.2.3.23), (E,E)-germacrene B synthase (EC 4.2.3.71), germacrene C synthase (EC 4.2.3.60), (−)-germacrene D synthase (EC 4.2.3.75), valencene synthase (EC 4.2.3.73), (3S, 6E)-nerolidol synthase (EC 4.2.3.48), epi-cedrol synthase (EC 4.2.3.39), patchoulol synthase (EC 4.2.3.70), santalene synthase (EC 4.2.3.50) and δ-cadinene synthase (EC 4.2.3.13).

In an embodiment, the recombinant bacterium of the invention comprises a gene encoding a heterologous (+)-epi-alpha-bisabolol synthase, i.e. an enzyme that catalyzes the formation of (+)-epi-alpha-bisabolol from (2E,6E)-farnesyl diphosphate. Examples of (+)-epi-alpha-bisabolol synthases include, but are not limited to, (+)-epi-alpha-bisabolol synthases from *Streptomyces citricolor* (GenBank accession number: BAL14867.1; Nakano et al., 2011) and *Phyla dulcis* (Attia et al., 2012). Any polypeptide exhibiting (+)-epi-alpha-bisabolol synthase activity and having at least 70%, 80%, preferably 90%, sequence identity to this enzyme may be used, in particular variants of this enzyme having increased catalytic activity, specificity for the substrate, and/or stability. In a particular embodiment, the (+)-epi-alpha-bisabolol synthase is from *Streptomyces citricolor*.

In an embodiment, the recombinant bacterium of the invention comprises a gene encoding a heterologous germacrene A synthase, i.e. an enzyme that catalyzes the cyclization of farnesyl diphosphate (FPP) to the sesquiterpene germacrene A. Examples of heterologous germacrene A synthases include, but are not limited to, germacrene A synthases from *Artemisia annua* (GenBank accession number: ABE03980), *Cichorium intybus* (AAM21658; AAM21659), *Ixeris dentate* (AAL92481), *Lactuca sativa* (AAM11626); AAM11627), *Pogostemon cablin* (AAS86321) and *Solidago Canadensis* (CAC36896). Any polypeptide exhibiting a germacrene A synthase activity and having at least 80%, preferably 90%, sequence identity to this enzyme may be used, in particular variants of this enzyme having increased catalytic activity, specificity for the substrate, and/or stability. In a particular embodiment, the germacrene A synthase is selected from *Artemisia annua* and *Solidago Canadensis*.

In an embodiment, the recombinant bacterium of the invention comprises a gene encoding a heterologous germacrene B synthase, i.e. an enzyme that catalyzes the cyclization of farnesyl diphosphate (FPP) to the sesquiterpene germacrene B. Examples of heterologous germacrene B synthases include, but are not limited to, germacrene B synthase from *Lycopersicon hirsutum* (GenBank accession number: AAG41891). Any polypeptide exhibiting an germacrene B synthase activity and having at least 70%, 80%, preferably 90%, sequence identity to this enzyme may be used, in particular variants of this enzyme having increased catalytic activity, specificity for the substrate, and/or stability.

In an embodiment, the recombinant bacterium of the invention comprises a gene encoding a heterologous germacrene C synthase, i.e. an enzyme that catalyzes the cyclization of farnesyl diphosphate (FPP) to the sesquiterpene germacrene C. Examples of heterologous germacrene C synthases include, but are not limited to, germacrene C synthase from *Lycopersicon esculentum* (GenBank accession number: AAC39432). Any polypeptide exhibiting an germacrene B synthase activity and having at least 70%, 80%, preferably 90%, sequence identity to this enzyme may be used, in particular variants of this enzyme having increased catalytic activity, specificity for the substrate, and/or stability.

In an embodiment, the recombinant bacterium of the invention comprises a gene encoding a heterologous germacrene D synthase, i.e. an enzyme that catalyzes the cyclization of farnesyl diphosphate (FPP) to the sesquiterpene germacrene D. Examples of heterologous germacrene D synthases include, but are not limited to, germacrene D synthases from *Lycopersicon hirsutum* (GenBank accession number: AAG41892), *Ocimum basilicum* (AAV63786), *Pogostemon cablin* (AAS86320, AAS86322), *Populus trichocarpa×Populus deltoides* (AAR99061), *Solidago Canadensis* (AAR31144, AAR31145), *Vitis vinifera* (AAS66357) and *Zingiber officinale* (AAX40665). Any polypeptide exhibiting a germacrene D synthase activity and having at least 70%, 80%, preferably 90%, sequence identity to any of these enzymes may be used, in particular variants of these enzymes having increased catalytic activity, specificity for the substrate, and/or stability.

In an embodiment, the recombinant bacterium of the invention comprises a gene encoding a heterologous valencene synthase, i.e. an enzyme that catalyzes the formation of valencene from farnesyl diphosphate (FPP). Examples of heterologous valencene synthases include, but are not limited to, valencene synthases from *Vitis vinifera* (UniProt accession number Q6Q3H2) and *Citrus sinensis* (Q71MJ3). Any polypeptide exhibiting a valencene synthase activity and having at least 70%, 80%, preferably 90%, sequence identity to any of these enzymes may be used, in particular variants of these enzymes having increased catalytic activity, specificity for the substrate, and/or stability.

In an embodiment, the recombinant bacterium of the invention comprises a gene encoding a heterologous patchoulol synthase, i.e. an enzyme that catalyzes the formation of patchoulol from farnesyl diphosphate (FPP). Examples of heterologous patchoulol synthases include, but are not limited to, patchoulol synthase from *Pogostemon cablin* (UniProt accession number Q49SP3) which produces additional sesquiterpene products, including alpha- and beta-patchoulene, alpha-bulnesene, seychellene, pogostol and alpha-guiaene. Any polypeptide exhibiting a patchoulol synthase activity and having at least 70%, 80%, preferably 90%, sequence identity to this enzyme may be used, in particular variants having increased catalytic activity, specificity for the substrate, and/or stability.

In an embodiment, the recombinant bacterium of the invention comprises a gene encoding a heterologous epi-cedrol synthase, i.e. an enzyme that catalyzes the formation of 8-epi-cedrol from farnesyl diphosphate or geranyl diphosphate. Examples of heterologous epi-cedrol synthases include, but are not limited to, epi-cedrol synthases from *Artemisia annua* (Genbank accession number: AAF80333, CAC08805). Any polypeptide exhibiting a epi-cedrol synthase activity and having at least 70%, 80%, preferably 90%, sequence identity to any of these enzymes may be used, in particular variants having increased catalytic activity, specificity for the substrate, and/or stability.

In an embodiment, the recombinant bacterium of the invention comprises a gene encoding a heterologous (3S, 6E)-nerolidol synthase, i.e. an enzyme that converts farnesyl diphosphate to nerolidol. Examples of heterologous nerolidol synthases include, but are not limited to, nerolidol synthases from *Selaginella moellendorffii* (Uniprot accession number D8RNZ9), *Populus trichocarpa* (F8TWD1), *Medicago truncatula* (Q5UB06), *Fragaria×ananassa* (P0CV94) and *Zea mays* (Degenhardt and Gershenzon, 2000). Any polypeptide exhibiting a nerolidol synthase activity and having at least 70%, 80%, preferably 90%, sequence identity to any of these enzymes may be used, in particular variants of these enzymes having increased catalytic activity, specificity for the substrate, and/or stability. In a particular embodiment, the heterologous nerolidol synthase is selected from *Fragaria×ananassa*.

In an embodiment, the recombinant bacterium of the invention comprises a gene encoding a heterologous santalene synthase, i.e. an enzyme that catalyzes the formation of alpha-santalene, beta-santalene, epi-beta-santalene, endo-beta-bergamotene and/or exo-alpha-bergamotene from farnesyl diphosphate. Examples of heterologous santalene synthases include, but are not limited to, santalene synthase from *Solanum habrochaites* (Uniprot: B8XA41), *Santalum spicatum* (Uniprot: E3W202), *Santalum austrocaledonicum* (Uniprot: E3W203), *Santalum spicatum* (Uniprot: E3W204). Any polypeptide exhibiting a santalene synthase activity and having at least 70%, 80%, preferably 90%, sequence identity to any of these enzymes may be used, in particular variants of these enzymes having increased catalytic activity, specificity for the substrate, and/or stability.

In an embodiment, the recombinant bacterium of the invention comprises a gene encoding a δ-cadinene synthase, i.e. an enzyme that catalyzes the cyclization of trans,trans-farnesyl diphosphate (FPP) to (+)-delta cadinene. Examples of heterologous δ-cadinene synthases include, but are not limited to, δ-cadinene synthases from *Gossypium hirsutum* (GenBank accession number: AAF74977, AAC12784), *Gossypium arboretum* (GenBank accession number CAA65289, Uniprot Q39761) and *Helianthus annuus* (Q4U3F6). Any polypeptide exhibiting a δ-cadinene synthase activity and having at least 70%, 80%, preferably 90%, sequence identity to any of these enzymes may be used, in particular variants of these enzymes having increased catalytic activity, specificity for the substrate, and/or stability. In a particular embodiment, the heterologous δ-cadinene synthase is selected from *Gossypium arboretum*.

Heterologous Isoprene Synthases

In another aspect, the present invention also relates to a recombinant *Deinococcus* bacterium comprising a gene encoding a heterologous isoprene synthase.

All embodiments described herein for the other aspects of the invention are also encompassed in this aspect. In particular, the recombinant *Deinococcus* bacterium may further exhibit (i) an enhanced MEP pathway as described above, optionally with an improved DXP synthase, (ii) a heterologous MEV pathway, (iii) an increase of the FPP synthase activity, (iv) inactivation of the lycopene beta-cyclase and/or (v) expression of a heterologous terpene synthase as described herein.

In a preferred embodiment, the recombinant *Deinococcus* bacterium comprising a gene encoding a heterologous isoprene synthase, overexpresses at least one gene selected from the group consisting of dxs, dxr, ispD, ispE, ispF and ispG, preferably overexpresses the dxs, dxr, ispD, ispE, ispF and ispG genes.

The heterologous isoprene synthase may be any enzyme catalysing the formation of isoprene from dimethylallyl diphosphate. Examples of isoprene synthases include, but are not limited to, isoprene synthases from *Bacillus subtilis* (Hess et al. 2013), *Populus alba* (Lv et al. 2013; Yang et al. 2012; Uniprot: Q50L36), *Populus tremuloides* (Uniprot: Q7XAS7), *Pueraria montana* (Whited et al., 2010; Miller et al., 2001; Sharkey et al., 2005) and *Quercus robur* (Lehning et al., 1999).

Farnesyl Diphosphate Synthase

In addition, the inventors herein demonstrated that the production of isoprenoids in *Deinococcus* bacteria can be controlled to promote the production and/or accumulation of compounds of interest. In this respect, they identified an enzyme of *Deinococcus geothermalis* exhibiting a farnesyl diphosphate synthase activity (EC 2.5.1.10), dimethylallyl-transtransferase activity (EC 2.5.1.1) and geranylgeranyl diphosphate synthase activity (EC 2.5.1.29) and observed that overexpression of this enzyme promotes the production of isoprenoids having more than 10 C-atoms, such as diterpenes, triterpenes, sesquiterpenes, and carotenoids, to the detriment of monoterpenes.

Thus, in a further aspect, the present invention relates to an isolated polypeptide having a farnesyl diphosphate synthase activity, which polypeptide is selected from the group consisting of a) a polypeptide comprising all or an active part of the amino acid sequence of SEQ ID NO: 47;

b) a polypeptide having an amino acid sequence having at least 60, 65 70, 75, 80, 85, 90, 91, 92, 93, 94, 95, 96, 97, 98 or 99% sequence identity to SEQ ID NO: 47, preferably at least 70, 75, 80, 85, 90, 91, 92, 93, 94, 95, 96, 97, 98 or 99% sequence identity to SEQ ID NO: 47;

c) a polypeptide encoded by a nucleotide sequence having at least 60, 65, 70, 75, 80, 85, 90, 91, 92, 93, 94, 95, 96, 97, 98 or 99% sequence identity to SEQ ID NO: 46, preferably at least 70, 75, 80, 85, 90, 91, 92, 93, 94, 95, 96, 97, 98 or 99% sequence identity to SEQ ID NO: 46; or d) a polypeptide which is encoded by a nucleic acid sequence which is capable of hybridizing under medium/high stringency, preferably high or very high, conditions with (i) the nucleic acid sequence set forth in SEQ ID NO: 46, (ii) its complementary strand, or (iii) a subsequence of (i) or (ii).

Preferably, the polypeptide of the invention further exhibits dimethylallyltranstransferase (EC 2.5.1.1) and/or geranylgeranyl diphosphate synthase (EC 2.5.1.29) activities, more preferably dimethylallyltranstransferase and geranylgeranyl diphosphate synthase activities.

Suitable experimental conditions for determining hybridization between a nucleotide probe and a homologous DNA or RNA sequence involve presoaking of the filter containing the DNA fragments or RNA to hybridize in 5×SSC (Sodium chloride/Sodium citrate) for 10 min, and prehybridization of the filter in a solution of 5×SSC, 5×Denhardt's solution, 0.5% SDS and 100 µg/ml of denatured sonicated salmon sperm DNA, followed by hybridization in the same solution containing a concentration of 10 ng/ml of a random-primed $^{32}$P-dCTP-labeled (specific activity >1×10$^9$ cpm/µg) probe for 12 hours at ca. 45° C. (Feinberg and Vogelstein, 1983). For various stringency conditions the filter is then washed twice for 30 minutes in 2×SSC, 0.5% SDS and at least 55° C. (low stringency), more preferably at least 60° C. (medium stringency), still more preferably at least 65° C. (medium/high stringency), even more preferably at least 70° C. (high stringency), and even more preferably at least 75° C. (very high stringency).

The present invention also relates to a nucleic acid encoding a polypeptide of the invention. The nucleic acid can be DNA (cDNA or gDNA), RNA, or a mixture of the two. It can be in single stranded form or in duplex form or a mixture of the two. It can comprise modified nucleotides, comprising for example a modified bond, a modified purine or pyrimidine base, or a modified sugar. It can be prepared by any method known to one skilled in the art, including chemical synthesis, recombination, and mutagenesis. The nucleic acid according to the invention may be deduced from the sequence of the polypeptide according to the invention and codon usage may be adapted according to the host cell in which the nucleic acid shall be transcribed. These steps may be carried out according to methods well known to one of skill in the art and some of which are described in the reference manual Sambrook et al. (Sambrook et al., 2001).

The present invention further relates to an expression cassette comprising a nucleic acid encoding a polypeptide according to the invention, operably linked to one or more control sequences that direct the expression of said nucleic acid in a suitable host cell under conditions compatible with the control sequences.

The control sequence may include a promoter that is recognized by the host cell. The promoter contains transcriptional control sequences that mediate the expression of the enzyme. The promoter may be any polynucleotide that shows transcriptional activity in the *Deinococcus* bacterium, in particular a wild-type, mutated, degenerated or synthetic promoter. The promoter may be a native, homologous or heterologous promoter. Preferred promoters are native or homologous. In this regard, various promoters have been studied and used for gene expression in *Deinococcus* bacteria. Examples of suitable promoters include PtufA and PtufB promoters from the translation elongation factors Tu genes tufA (DR0309) and tufB (DR2050), the promoter of the resU gene located in pI3, the promoter region PgroESL of the groESL operon (Lecointe et al, 2004; Meima et al, 2001), or derivatives of such promoters.

The control sequence may also be a transcription terminator, which is recognized by *Deinococcus* bacteria to terminate transcription. The terminator is operably linked to the 3'-terminus of the gene. Any terminator that is functional in *Deinococcus* bacteria may be used in the present invention (Lecointe et al, 2004).

Optionally, the expression cassette may also comprise a selectable marker that permits easy selection of recombinant bacteria. Typically, the selectable marker is a gene encoding antibiotic resistance or conferring autotrophy.

The present invention also relates to an expression vector comprising a nucleic acid or an expression cassette according to the invention. Said expression vector may be used to transform a host cell, preferably *Deinococcus* host cells, and enable the expression of the nucleic acid of the invention in said cell. The choice of the vector will typically depend on the compatibility of the vector with the host cell into which the vector is to be introduced. The vector may be an autonomously replicating vector, i.e., a vector that exists as an extra-chromosomal entity, the replication of which is independent of chromosomal replication, e.g., a plasmid, an extra-chromosomal element, a mini-chromosome, or an artificial chromosome. The vector may contain any means for assuring self-replication. Alternatively, the vector may be one that, when introduced into the host cell, is integrated into the genome and replicated together with the chromosome(s) into which it has been integrated.

The vector preferably comprises one or more selectable markers that permit easy selection of host cells comprising the vector. A selectable marker is a gene the product of which provides for biocide or viral resistance, resistance to heavy metals, prototrophy to auxotrophy, and the like.

The vector preferably comprises an element that permits integration of the vector into the host cell's genome or autonomous replication of the vector in the cell independent of the genome. When integration into the host cell genome occurs, integration of the sequences into the genome may rely on homologous or non-homologous recombination. On one hand, the vector may contain additional polynucleotides for directing integration by homologous recombination at a precise location into the genome of the host cell. These additional polynucleotides may be any sequence that is homologous with the target sequence in the genome of the host cell. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

The methods for selecting these elements according to the host cell in which expression is desired, are well known to one of skill in the art. The vectors may be constructed by the classical techniques of molecular biology, well known to one of skill in the art.

The present invention further relates to the use of a nucleic acid, an expression cassette or an expression vector according to the invention to transform, transfect or transduce a cell, preferably a *Deinococcus* bacterium. The present invention also relates to a host cell, preferably a *Deino-*

*coccus* bacterium, comprising a nucleic acid, a cassette or an expression vector according to the invention.

The host cell may be transformed, transfected or transduced in a transient or stable manner. An expression cassette or vector of the invention is introduced into a host cell so that the cassette or vector is maintained as a chromosomal integrant or as a self-replicating extra-chromosomal vector as described earlier. The term "host cell" also encompasses any progeny of a parent host cell that is not identical to the parent host cell due to mutations that occur during replication.

The nucleic acid, expression cassette or expression vector according to the invention may be introduced into the host cell by any method known by the skilled person, such as electroporation, conjugation, transduction, competent cell transformation, protoplast transformation, protoplast fusion, biolistic "gene gun" transformation, PEG-mediated transformation, lipid-assisted transformation or transfection, chemically mediated transfection, lithium acetate-mediated transformation, liposome-mediated transformation, Optionally, more than one copy of a nucleic acid, cassette or vector of the present invention may be inserted into the host cell.

As mentioned above, the inventors observed that overexpression of the FPP synthase promotes the production of isoprenoids having more than 10 C-atoms, such as diterpenes, triterpenes, sesquiterpenes, and carotenoids, to the detriment of monoterpenes.

Thus, the present invention thus also relates to a recombinant *Deinococcus* bacterium wherein the FPP synthase activity is increased. Preferably, the FPP synthase activity is increased by overexpression of a native, homologous or heterologous gene encoding a FPP synthase, i.e. a ispA gene. Gene overexpression may be obtained as described above.

The overexpressed FPP synthase may be any heterologous FPP synthase. Examples of heterologous FPP synthases include, but are not limited to, FPP synthases from *Saccharomyces cerevisiae* (Uniprot Q12051) or from *E. coli* (Uniprot P22939). In a particular embodiment, the recombinant bacterium of the invention expresses the FPP synthase from *E. coli*.

In a preferred embodiment, the overexpressed FPP synthase is from a *Deinococcus* bacterium. In particular, the overexpressed FPP synthase is a polypeptide of the invention as described above and having a farnesyl diphosphate synthase activity, preferably farnesyl diphosphate synthase, dimethylallyltranstransferase and geranylgeranyl diphosphate synthase activities. Preferably, the overexpressed FPP synthase is a FPP synthase from *D. geothermalis*, in particular a FPP synthase having all or part of the amino acid sequence set forth in SEQ ID NO: 47.

Alternatively, the farnesyl diphosphate synthase, dimethylallyltranstransferase and geranylgeranyl diphosphate synthase activities may be carried out by separate polypeptides and the increased activities may result from the overexpression of separate encoding genes.

The inventors also showed that the substitution K170G in the FPP synthase set forth in SEQ ID NO: 47 induced a redirection of the carbon flux toward GPP and thus toward production of monoterpenes. Indeed, the K170G mutation in the FPPS allows GPP release for monoterpene biosynthesis (Blanchard and Karst, 1993; Fischer et. al, 2011). Thus, when production of a monoterpene such as geraniol is desired, the endogenous FPP synthase may be replaced by the K170G mutant. In the present document, the following terminology is used to designate a substitution: K170G denotes that amino acid residue at position 170 of SEQ ID NO: 47 (lysine, K) is changed to a glycine (G).

Thus, the present invention also relates to a polypeptide of the invention wherein the lysine residue at position corresponding to position 170 in SEQ ID NO: 47 is substituted with a glycine (the corresponding position can be easily identified by the skilled person using well-known alignment algorithms), a nucleic acid encoding said polypeptide, an expression cassette or vector comprising said nucleic acid and a recombinant *Deinococcus* bacterium expressing said mutated FPP synthase. Preferably, said recombinant bacterium also expresses a heterologous terpene synthase, preferably a monoterpene synthase. This recombinant is preferably used to produce monoterpenes.

All embodiments described herein for the other aspects of the invention are also encompassed in this aspect. In particular, the recombinant *Deinococcus* bacterium may further exhibit (i) an enhanced MEP pathway as described above, optionally with an improved DXP synthase, (ii) a heterologous MEV pathway, (iii) inactivation of the lycopene beta-cyclase and/or (iv) expression of a heterologous terpene or isoprene synthase as described herein.

Inactivation of the Endogenous Lycopene Beta-Cyclase

The inventors also showed that the inactivation of the endogenous lycopene beta-cyclase induces an overproduction/accumulation of lycopene.

Thus, in another aspect, the present invention relates to a recombinant *Deinococcus* bacterium wherein the endogenous lycopene beta-cyclase activity is reduced or suppressed.

The lycopene beta-cyclase (EC 5.5.1.19) catalyzes the reaction from lycopene to beta-carotene via the intermediate gamma-carotene. Examples of lycopene beta-cyclases include, but are not limited to, lycopene beta-cyclases of *D. geothermalis* having the amino acid sequence set forth in SEQ ID NO 51, *D. phoenicis* (Genbank accession number: EYB66908), *D. apachensis* (WP_019585057), *D. aquatilis* (WP_019008078), *D. gobiensis* (WP_014685779), *D. wulumuqiensis* (WP_017870547), *D. maricopensis* (WP_013556733) and *D. radiodurans* (WP_010887447).

The gene encoding the lycopene beta-cyclase may also be easily identified based on homology with the nucleic acid encoding the lycopene beta-cyclase of *D. geothermalis* (SEQ ID NO: 50).

The lycopene beta-cyclase activity may be reduced or suppressed using any method known by the skilled person. Preferably, the gene encoding the lycopene beta-cyclase is inactivated by any method known by the skilled person, for example by deletion of all or part of this gene, by introducing a nonsense codon, a cassette, a gene or a mutation inducing a frameshift. In a preferred embodiment, the gene encoding the lycopene beta-cyclase is deleted.

In a particular embodiment, genes encoding phytoene synthase (EC 2.5.1.32) and phytoene desaturase (EC 1.3.99.28) are overexpressed in order to increase lycopene production. Genes may be native, homologous or heterologous genes, preferably native or homologous genes.

In another particular embodiment, the recombinant bacterium having reduced or suppressed lycopene beta-cyclase activity, and optionally overexpressing genes encoding phytoene synthase and phytoene desaturase, further comprises a gene encoding a heterologous carotenoid cleavage dioxygenase (CCD) catalysing the formation of apocarotenoids from lycopene.

In another particular embodiment, the recombinant bacterium having reduced or suppressed lycopene beta-cyclase activity, and optionally overexpressing genes encoding phytoene synthase and phytoene desaturase, further comprises a gene encoding a heterologous lycopene epsilon cyclase (EC 5.5.1.18) catalysing the formation of δ-carotene from lycopene and optionally a gene encoding a heterologous carotenoid cleavage dioxygenase (CCD) catalysing the formation of apocarotenoids from δ-carotene.

Examples of carotenoid cleavage dioxygenases include, but are not limited to, CCD disclosed in the article of Auldridge et al. (2006) such as CCD from *Arabidopsis thaliana*, *Rubus idaeus* and *Zea mais*.

All embodiments described herein for the other aspects of the invention are also encompassed in this aspect. In particular, the recombinant *Deinococcus* bacterium may further exhibit (i) an increase of the FPP synthase activity and (ii) an enhanced MEP pathway as described above, optionally with an improved DXP synthase as described above, (iii) a heterologous MEV pathway and/or (iv) expression of a heterologous terpene or isoprene synthase as described above.

Method of Producing an Isoprenoid Compound

In a further aspect, the present invention relates to a use of a recombinant *Deinococcus* bacterium as described above for producing a terpene or terpenoid compound. The present invention also relates to a method of producing a terpene or terpenoid comprising (i) culturing a recombinant *Deinococcus* bacterium according to the invention under conditions suitable to produce the terpene or terpenoid and optionally (ii) recovering the terpene or terpenoid.

The terpene or terpenoid compound may be any terpene or terpenoid compound produced by a recombinant *Deinococcus* bacterium as described above.

In an embodiment, the recombinant *Deinococcus* bacterium of the invention is used to produce isoprenoids having more than 10 C atoms, such as carotenoid compounds (C40). In particular, the present invention relates to a method of producing a carotenoid compound comprising (i) culturing a recombinant *Deinococcus* bacterium according to the invention under conditions suitable to produce the carotenoid compound and optionally (ii) recovering the carotenoid compound. The carotenoid compound may be lycopene or any other carotenoid compound derived from lycopene, preferably deinoxanthine. In a particular embodiment, the recombinant *Deinococcus* bacterium overexpresses FPP synthase, preferably *Deinococcus* FPP synthase and more preferably a FPP synthase of the invention as described above.

In an embodiment, the recombinant *Deinococcus* bacterium comprises a heterologous terpene synthase as described above and may produce a terpene or terpenoid compound selected from the group consisting of geraniol, (+)-linalool, (−)-linalool, S-limonene, R-limonene, α-pinene, β-pinene, fenchol, terpineol, (−)-carvone, (+)-(S)-carvone, menthone, isomenthone, menthol, neomenthol, (S,E)-nerolidol, 8-epicedrol, bisabolol, germacrene A, germacrene B, germacrene C, germacrene D, valencene, patchoulol, santalene and δ-cadinene.

The method may further comprise converting the terpene or terpenoid into a terpene derivative, such as myrcenol and dihydromyrcenyl acetate obtained from myrcene; fenchyl and borneol derivatives obtained from fenchol; nootkatone obtained from valencene or (−)-beta-pinene; linalyl and lavandulyl esters obtained from linalool such as linalyl formate, linalyl acetate, linalyl propionate, linalyl butyrate, linalyl isobutyrate and lanvandulyl acetate; citronellyl and dihydromyrcenyl esters obtained from citronellol such as citronellyl formate, citronellyl acetate, citronellyl propionate, citronellyl isobutyrate, citronellyl isovalerate, citronellyl tiglate, citronellic acid nitrile (or citronellyl nitrile); geranyl esters obtained from geraniol such as geranyl formate, geranyl acetate, geranyl propionate, geranyl isobutyrate, neryl acetate, methyl geranate (or geranic acid methyl esther) and geranic acid nitrile (or geranonitrile). Preferably, the terpene derivative is a terpene ester, more preferably is a geranyl ester.

Methods for obtaining terpene derivatives from terpenes or terpenoids are well known by the skilled person. For example, such methods are disclosed in Common Fragrance and Flavor Materials: Preparation, Properties and Uses, 5th ed. H. Surburg and J. Panten, John Wiley & Sons, 2006.

Conditions suitable to produce the terpene or terpenoid may be easily determined by the skilled person according to the *Deinococcus* bacterium used in the present invention. In particular, the carbon source may be selected from the group consisting of C5 sugars such as xylose and arabinose, C6 sugars such as glucose, cellobiose, saccharose and starch. When the *Deinococcus* bacterium exhibits cellulolytic or xylanolytic activity, more complex carbon sources can be used such as cellulosic or lignocellulosic biomass. Temperature conditions can also be adapted depending on the use of mesophilic or thermophilic *Deinococcus* bacteria.

In another aspect, the present invention also relates to a method of producing a terpene derivative, in particular a terpene derivative as described above, comprising (i) culturing a recombinant *Deinococcus* bacterium according to the invention under conditions suitable to produce a terpene or terpenoid and optionally recovering said terpene or terpenoid, and (iii) converting said terpene or terpenoid into a terpene derivative, and optionally (iv) recovering the terpene derivative. Step (iii) may be a chemical or enzymatic conversion.

Preferably, the terpene or terpenoid is geraniol and/or geranic acid and the terpene derivative is a geranyl ester.

The inventors found that non-modified *Deinococcus* bacteria are able to convert geraniol to geranial and geranic acid. Thus, in a particular aspect, the present invention relates to the use of a recombinant *Deinococcus* bacterium of the invention for producing geraniol, geranial and/or geranic acid. The present invention also relates to a method of producing geraniol, geranial and/or geranic acid comprising (i) culturing a recombinant *Deinococcus* bacterium according to the invention under conditions suitable to produce geraniol, geranial and/or geranic acid and optionally (ii) recovering geraniol, geranial and/or geranic acid.

Preferably, the recombinant *Deinococcus* bacteria comprises a gene encoding a heterologous geraniol synthase, and optionally exhibits an enhanced MEP pathway, optionally with an improved DXP synthase and/or a heterologous MEV pathway as disclosed above.

In another aspect, the present invention also relates to a method of producing geranial and/or geranic acid comprising (i) contacting a *Deinococcus* bacterium, preferably a recombinant *Deinococcus* bacterium of the invention, or an extract thereof, with geraniol, and optionally (ii) recovering geranial and/or geranic acid.

In another particular aspect, the present invention relates to a use of a recombinant *Deinococcus* bacterium of the invention for producing a geranyl ester. The present invention also relates to a method of producing a geranyl ester comprising (i) culturing a recombinant *Deinococcus* bacterium according to the invention under conditions suitable to produce geraniol, geranial and/or geranic acid, optionally (ii) recovering geraniol, geranial and/or geranic acid, and (iii) converting geraniol, geranial and/or geranic acid into a geranyl ester, and optionally (iv) recovering the geranyl ester. Step (iii) may be a chemical or enzymatic conversion.

Preferably, the recombinant *Deinococcus* bacteria comprises a gene encoding a heterologous geraniol synthase, an optionally exhibits an enhanced MEP pathway, optionally with an improved DXP synthase and/or a heterologous MEV pathway as disclosed above.

Preferably, the geranyl ester is methyl geranate, geranyl formate, geranyl acetate, geranyl propionate, geranyl isobutyrate, trans-geranyl acetate or neryl acetate. These esters may be produced from geraniol, geranial and/or geranic acid by any method known by the skilled person.

In another aspect, the present invention relates to a use of a recombinant *Deinococcus* bacterium of the invention for producing an apocarotenoid. Preferably, the apocarotenoid is selected from the group consisting of damascones, damascenones and ionones. Examples of damascone, damascenone and ionone include, but are not limited to, β-damascenone, trans-β-damascenone, γ-damascone, α-damascone, trans-α-damascone, cis-α-damascone, cis-beta-damascone, trans-beta-damascone, delta-damascone, trans,trans-delta-damascone, trans-(2,4,4-trimethyl-2-cyclohexenyl)-2-butenone, 1-(2,4,4-trimethyl-2-cyclohexen-1-yl)-2-buten-1-one, 1-(2,4,4-trimethyl-1-cyclohexenyl)-2-butenone, 1-(2,2-dimethyl-6-methylenecyclohexyl)-2-buten-1-one, alpha-ionone, beta-ionone and pseudo-ionone.

Thus, the present invention relates to a method of producing an apocarotenoid, i.e. damascone, damascenone and/or ionone, comprising (i) culturing a recombinant *Deinococcus* bacterium according to the invention under conditions suitable to produce geraniol, geranial and/or geranic acid, optionally (ii) recovering geraniol, geranial and/or geranic acid, and (iii) converting geraniol, geranial and/or geranic acid into said apocarotenoid, and optionally (iv) recovering said apocarotenoid.

Conversion of geraniol, geranial and/or geranic acid into the damascone, damascenone and/or ionone may involve an intermediate conversion of geraniol, geranial and/or geranic acid into a geranyl ester, preferably methyl geranate.

Preferably, the recombinant *Deinococcus* bacteria comprises a gene encoding a heterologous geraniol synthase, an optionally exhibits an enhanced MEP pathway, optionally with an improved DXP synthase and/or a heterologous MEV pathway as disclosed above. Methods for converting geraniol, geranial and/or geranic acid into the damascone, damascenone and/or ionone are well-known by the skilled person.

The present invention also relates to a method of producing an apocarotenoid comprising (i) culturing a recombinant *Deinococcus* bacterium according to the invention under conditions suitable to produce said apocarotenoid, and optionally (ii) recovering said apocarotenoid.

Preferably, the recombinant *Deinococcus* bacterium is a recombinant as described above wherein the gene encoding the lycopene beta-cyclase is inactivated, and further comprising a gene encoding a heterologous carotenoid cleavage dioxygenase (CCD). This recombinant may further comprise a gene encoding a heterologous lycopene epsilon cyclase. Optionally, genes encoding phytoene synthase and phytoene desaturase may also be overexpressed. The recombinant *Deinococcus* bacterium may further exhibit an enhanced MEP pathway, optionally with an improved DXP synthase and/or a heterologous MEV pathway and/or overexpression of FPP synthase as disclosed above.

The present invention also relates to a method of producing an apocarotenoid, i.e. damascone, damascenone and/or ionone, comprising (i) culturing a recombinant *Deinococcus* bacterium according to the invention under conditions suitable to produce β-carotene, (ii) recovering β-carotene, and (iii) converting β-carotene into said apocarotenoid, and optionally (iv) recovering said apocarotenoid.

Conversion of β-carotene into said apocarotenoid, such as damascone, damascenone, speudoionones and/or ionone, may be chemical or enzymatic conversion and is well known by the skilled person.

Preferably, the recombinant *Deinococcus* bacterium is a recombinant as described above exhibiting an enhanced MEP pathway, optionally with an improved DXP synthase and/or a heterologous MEV pathway and/or overexpression of FPP synthase. Optionally, genes encoding phytoene synthase and phytoene desaturase may also be overexpressed.

The present invention also relates to a method of producing an apocarotenoid comprising (i) culturing a recombinant *Deinococcus* bacterium according to claim 13 under conditions suitable to produce lycopene, α-, β-, and/or γ-carotene, (ii) optionally recovering lycopene, α-, β-, and/or γ-carotene, and (iii) chemically or enzymatically converting lycopene, α-, β-, and/or γ-carotene into a apocarotenoid, and optionally (iv) recovering the apocarotenoid Preferably, the recombinant *Deinococcus* bacterium is a recombinant as described above, in particular a recombinant comprising a gene encoding a heterologous CDD. The recombinant may further exhibit an enhanced MEP pathway, optionally with an improved DXP synthase and/or a heterologous MEV pathway and/or overexpression of FPP synthase. Optionally, genes encoding phytoene synthase and phytoene desaturase may also be overexpressed.

Further aspects and advantages of the present invention will be described in the following examples, which should be regarded as illustrative and not limiting.

EXAMPLES

Example 1: Production of Geraniol and Geranic Acid

A *Deinococcus geothermalis* strain was genetically engineered to produce geraniol and geranic acid. A heterologous gene encoding a geraniol synthase (GES) from *Ocimum basilicum* was inserted into chromosome replacing phosphotransacetylase (pta) gene. Expression of GES gene was under the control of a strong constitutive promoter.

To make seed cultures, individual colonies were picked to inoculate 25 ml of CMG2% medium (Peptone 2 g/L; Yeast Extract 5 g/L; Glucose 55 mM (20 g/L); MOPS acid 40 mM; $NH_4Cl$ 20 mM; NaOH 10 mM; KOH 10 mM; $CaCl_2.2H_2O$ 0.5 µM; $Na_2SO_4.10H_2O$ 0.276 mM; $MgCl_2.6H_2O$ 0.528 mM; $(NH_4)_6(Mo_7)O_{24}.4H_2O$ 3 nM; $H_3BO_3$ 0.4 µM; $CoCl_2.6H_2O$ 30 nM; $CuSO_4.5H_2O$ 10 nM; $MnCl_2$ 0.25 µM; $ZnSO_4.7H_2O$ 10 nM; D-Biotin 1 µg/L; Niacin (nicotinic acid) 1 µg/L; B6 vitamin 1 µg/L; B1 vitamin; $FeCl_3$ 20 µM; Sodium Citrate.$2H_2O$ 20 µM; $K_2HPO_4$ 5.7 mM) containing 2% glucose as the main carbon source, and cultured at 37° C. and 250 rpm overnight. Seed from log phase of growth was then inoculated into 25 ml of the same fresh medium at an initial optical density at 600 nm (OD600) of 0.4. This second seed culture was cultured at 37° C. and 250 rpm overnight.

The cultures for geraniol production were performed at 37° C. and 250 rpm for 48 h from log phase of growth inoculated into 25 ml of mineral define medium $(NH_4)_2SO_4$<100 mM; $NaH_2PO_4.H_2O$<10 mM; KCl<10 mM; $Na_2SO_4$<10 mM; Acide citrique<30 mM; $MgCl_2.6H_2O$<10 mM; $CaCl_2.2H_2O$<10 mM; $ZnCl_2$<50 mg/L; $FeSO_4.7H_2O$<50 mg/L; $MnCl_2.4H_2O$<50 mg/L;

CuSO$_4$<50 mg/L; CoCl$_2$.6H$_2$O<50 mg/L; H$_3$BO$_3$<5 mg/L; MES<200 mM; (NH$_4$)$_6$Mo$_7$O$_{24}$.4H$_2$O<0.5 mM; Glucose<30 g/L (166 mM) at an initial optical density at 600 nm (OD600) of 0.4.

Figure 2:
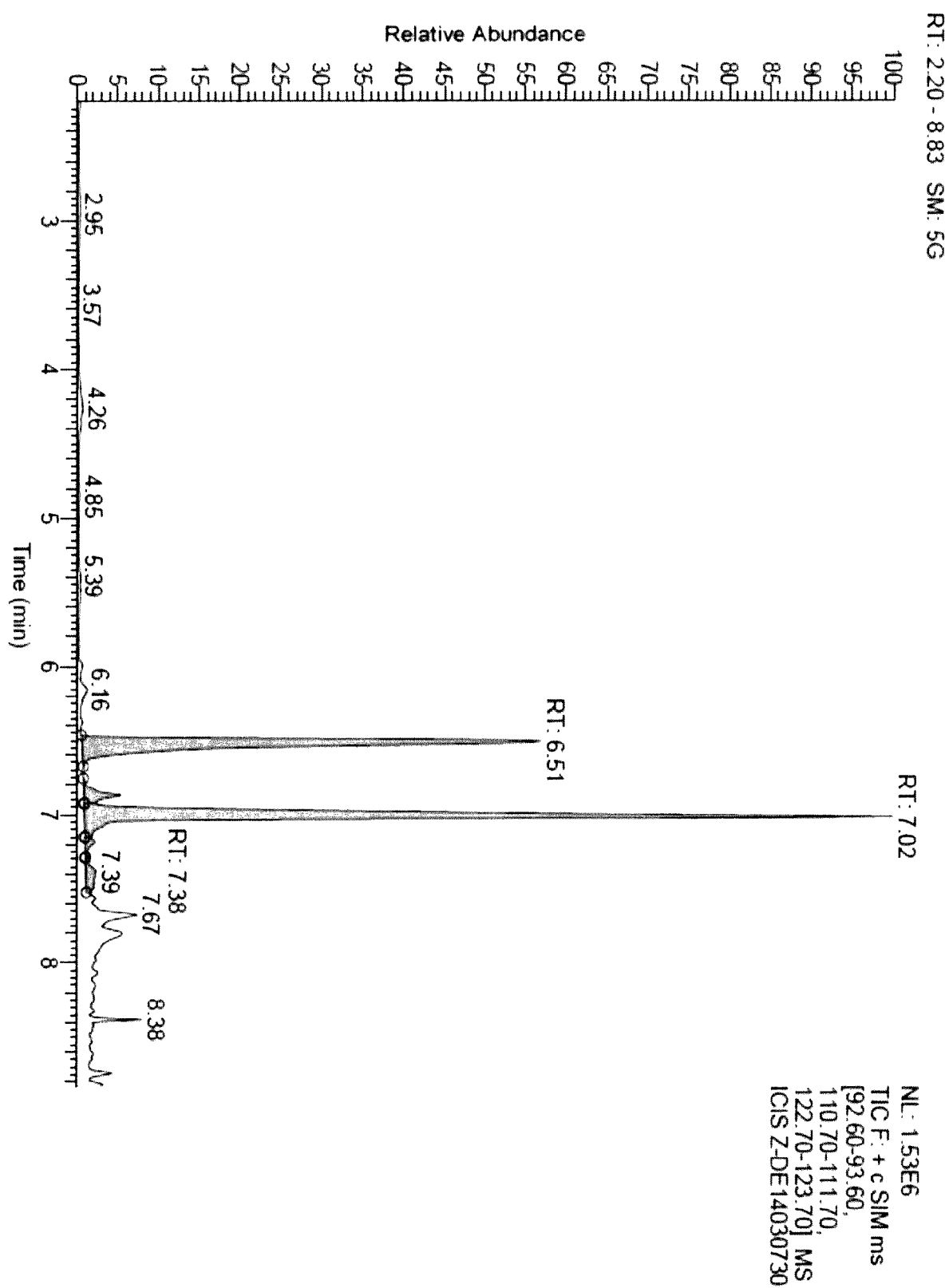
FIG. 2: GCMS analysis of extraction at 48 h of the culture comprising the recombinant *D. geothermalis* bacterium expressing the *Ocimum basilicum* GES.
Figure 3:
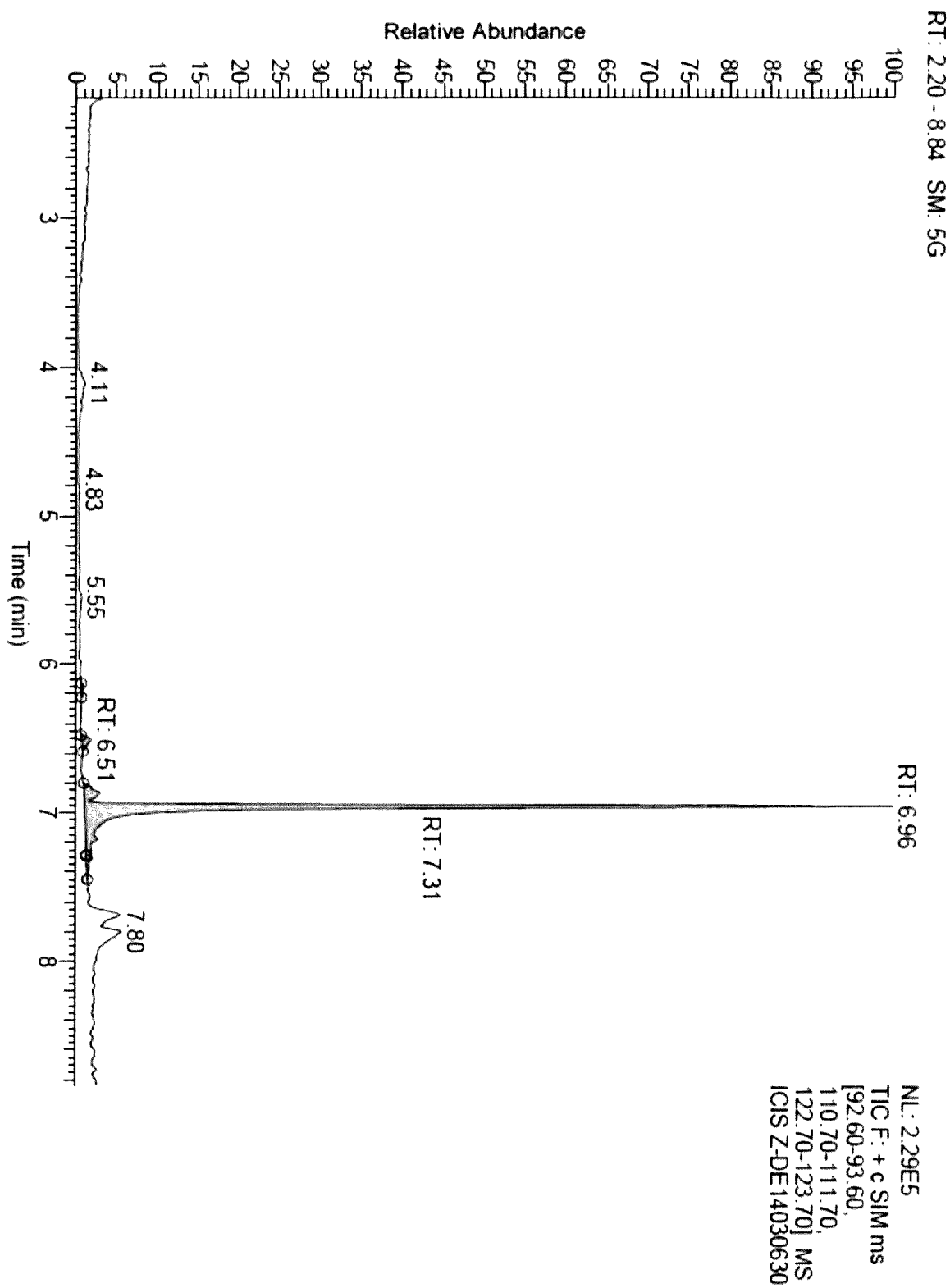
FIG. 3: GCMS analysis of extraction at 72 h of the culture comprising the recombinant *D. geothermalis* bacterium expressing the *Ocimum basilicum* GES.

After 24 H of culture, geraniol was produced (titer: 2.01 mg/L; 1.5 mg/g DCW (dry cell weight); 0.6 mg/g of glucose) (FIG. 1). After 48 H of culture geraniol was produced (titer: 3.9 mg/L; 0.5 mg/g DCW; 0.3 mg/g of glucose) and geranic acid was detected (FIG. 2). After 72 H of culture, a few geraniol remains and a major peak of geranic acid was present (FIG. 3). The extractions were done by mixing 0.5 mL of ethyl acetate with 1 mL of culture and separated by centrifugation. The ethyl acetate phase was analyzed by GC-mass spectrometry (GC-MS).

Figure 4:
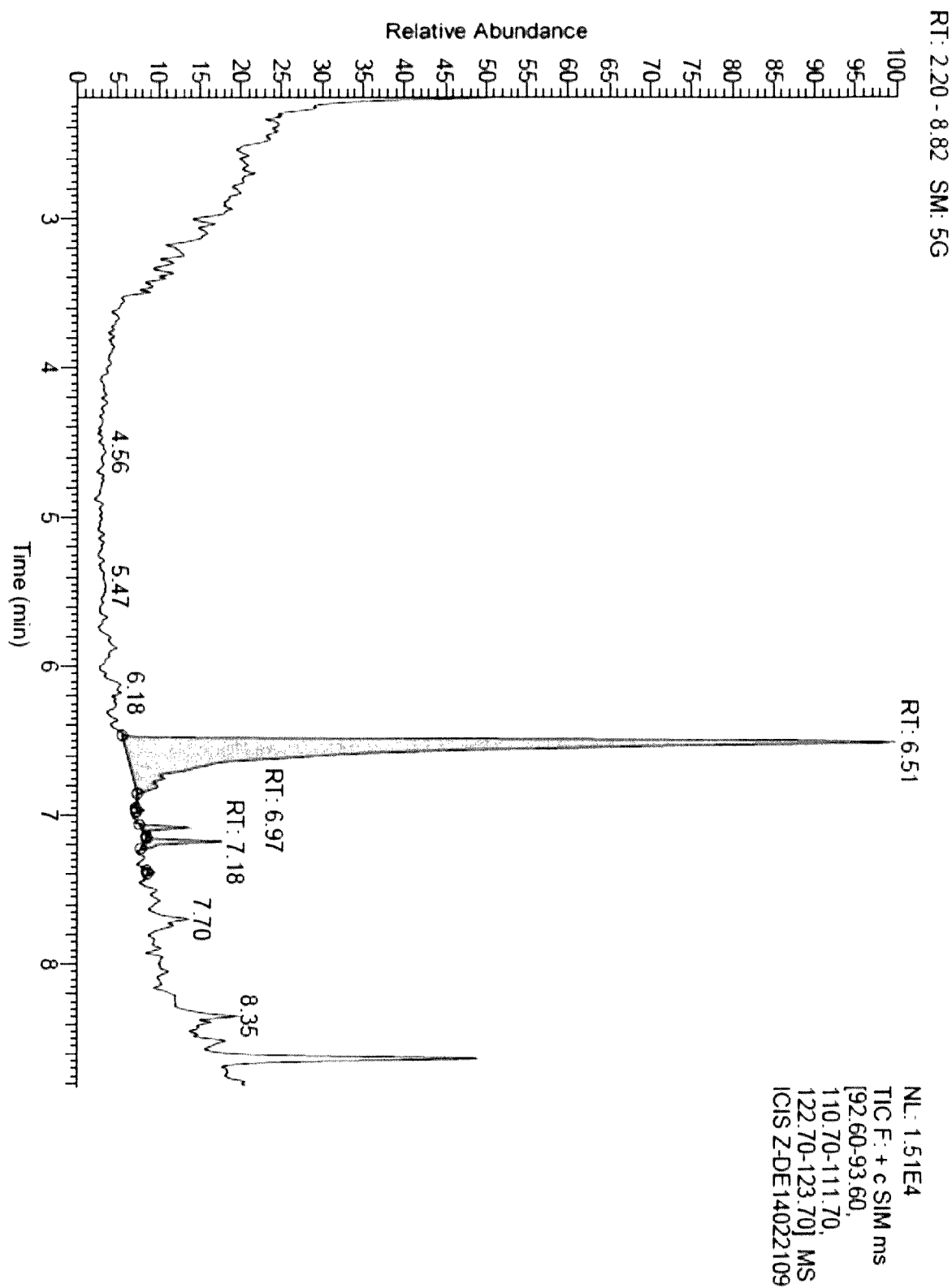
FIG. 4: Retention time of commercial geraniol.

Therefore, the production of geraniol was identified and quantified on a Mass Spectrometer GC. Gas chromatography was performed using GC-MS [Agilent 7890A/5975, column: 0.25 mm×30 m, 0.25 μm (HP-5MS ultra inert)] fitted with a mass spectrometer as detector. GCMS analyze was conducted under electron-impact (EI) mode (70 eV). 1 μL of extract was injected in pulsed splitless mode (50 psi for until 0.75 min). The scan range covered 50-250 m/z. The data were processed using Xcalibur system. Identification were performed using NIST library. The standard curves of geraniol (FIG. 4) were constructed using the same method described as above.

Figure 5:
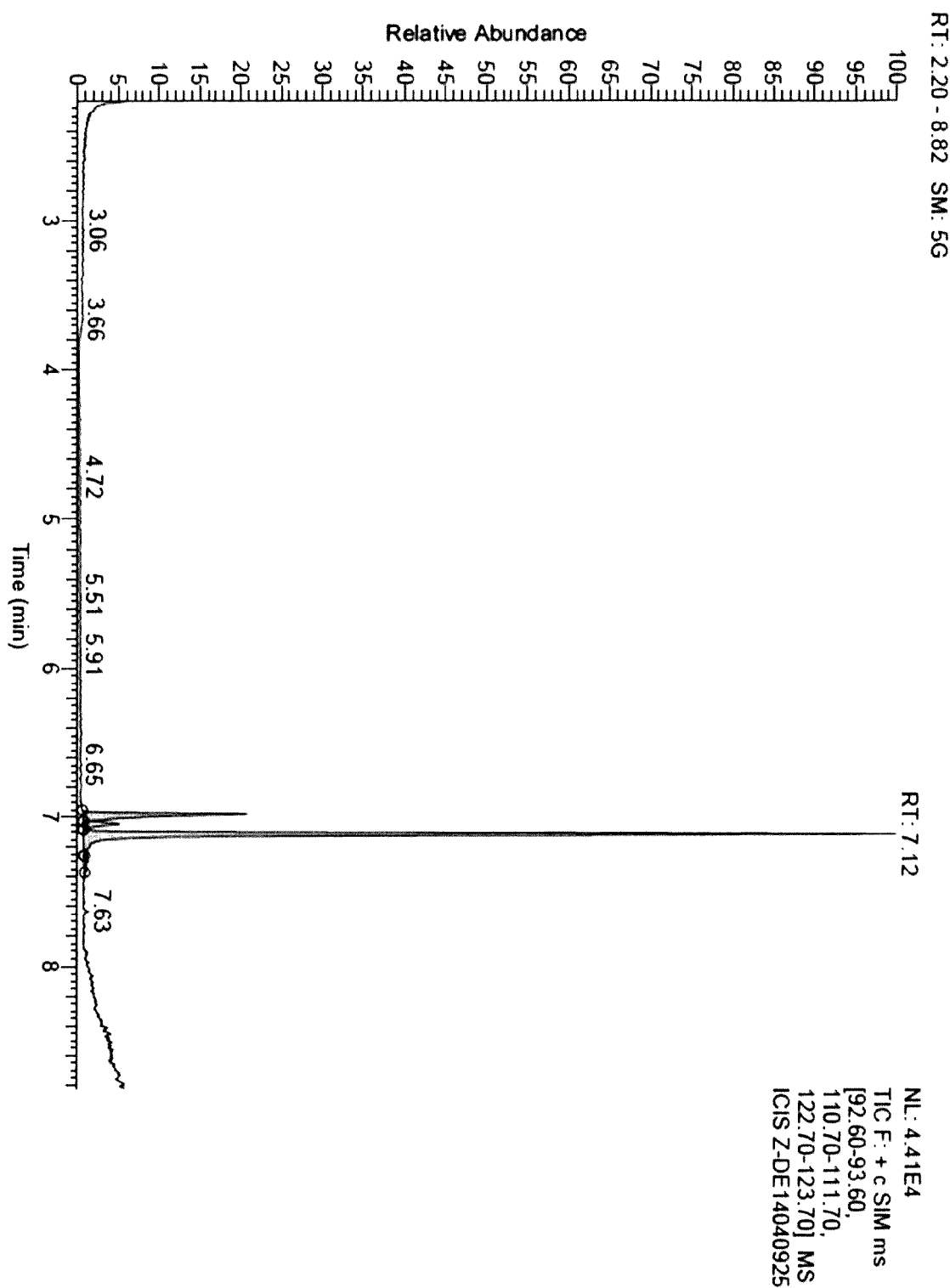
FIG. 5: Retention time of commercial geranic acid.

The production of geranic acid was identified and quantified on high-pressure liquid chromatography. HPLC was performed using an Agilent C18 poroshell column (EC-C18) 4.6*150 mm-2.7 um and a mobile phase Acetonitrile/water (0.1% formic acid). 10 μL of extract was injected. The standard curves of geranic acid (FIG. 5) were constructed using the same method described as above.

Example 2: Production of Lycopene

A *Deinococcus geothermalis* strain was genetically engineered to produce lycopene. The wild-type bacterium comprises related genes for synthesizing the lycopene through a MEP pathway. The recombinant *D. geothermalis* producing lycopene was obtained by disrupting a part of the carotenoid pathway, i.e. the lycopene beta-cyclase (EC 5.5.1.19) (crtIm) gene was knockout. The resulting constructs were checked by sequencing.

To make seed cultures, individual colonies were picked to inoculate 25 ml of CMG2% medium (Peptone 2 g/L; Yeast Extract 5 g/L; Glucose 55 mM (20 g/L); MOPS acid 40 mM; NH$_4$Cl 20 mM; NaOH 10 mM; KOH 10 mM; CaCl$_2$.2H$_2$O 0.5 μM; Na$_2$SO$_4$.10H$_2$O 0.276 mM; MgCl$_2$.6H$_2$O 0.528 mM; (NH$_4$)$_6$(Mo$_7$)O$_{24}$.4H$_2$O 3 nM; H$_3$BO$_3$ 0.4 μM; CoCl$_2$.6H$_2$O 30 nM; CuSO$_4$.5H$_2$O 10 nM; MnCl$_2$ 0.25 μM; ZnSO$_4$.7H$_2$O 10 nM; D-Biotin 1 μg/L; Niacin (nicotinic acid) 1 μg/L; B6 vitamin 1 μg/L; B1 vitamin; FeCl$_3$ 20 μM; Sodium Citrate.2H$_2$O 20 μM; K$_2$HPO$_4$ 5.7 mM) containing 2% glucose as the main carbon source, and cultured at 37° C. and 250 rpm overnight. Seed from log phase of growth was then inoculated into 25 ml of the same fresh medium at an initial optical density at 600 nm (OD600) of 0.4. This second seed culture was cultured at 37° C. or 45° C. and 250 rpm overnight.

The cultures for lycopene production were performed at 37° C. or 45° C. and 250 rpm for 48 h from log phase of growth inoculated into 25 ml of mineral define medium (NH$_4$)$_2$SO$_4$<100 mM; NaH$_2$PO$_4$.H$_2$O<10 mM; KCl<10 mM; Na$_2$SO$_4$<10 mM; Acide citrique<30 mM; MgCl$_2$.6H$_2$O<10 mM; CaCl$_2$.2H$_2$O<10 mM; ZnCl$_2$<50 mg/L; FeSO$_4$.7H$_2$O<50 mg/L; MnCl$_2$.4H$_2$O<50 mg/L; CuSO$_4$<50 mg/L; CoCl$_2$.6H$_2$O<50 mg/L; H$_3$BO$_3$<5 mg/L; MES<200 mM; (NH$_4$)6Mo$_7$O$_{24}$.4H$_2$O<0.5 mM; Glucose<30 g/L (166 mM) at an initial optical density at 600 nm (OD600) of 10.

Figure 6:
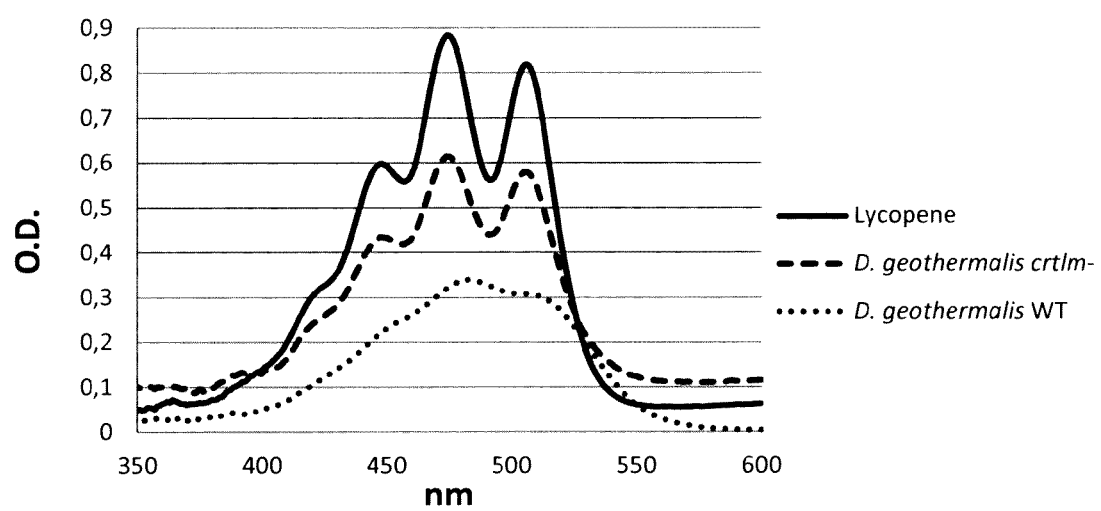
FIG. 6: Difference of acetone extraction absorbance of *D. geothermalis* WT, the recombinant *D. geothermalis* bacterium wherein the crtlm gene was knockout, and lycopene standard.

After 24 h of culture, the lycopene producing strain was at OD600 of 31. The lycopene was produced with a titer of 4.2 mg/L, a yield of 0.5 mg/g DCW (dry cell weight) and 0.3 mg/g of glucose. 1 mL of culture was centrifuged and lycopene extraction was done by mixing 0.9 mL of acetone with pellet. The acetone phase was analyzed by absorbance at OD 472 nm (FIG. 6). Finally the lycopene concentration was determined by the dilution of lycopene standard.

Example 3: Overexpression of the FPP Synthase

The farnesyl pyrophosphate synthase (FPPS) gene from *Deinococcus geothermalis* (SEQ ID NO: 46) was inserted in the genome of the recombinant *D. geothermalis* expressing the GES of *Ocimum basilicum* of example 1 and the recombinant *D. geothermalis* producing lycopene of example 2, under the control of a strong constitutive promoter. The resulting constructs were checked by sequencing.

To make seed cultures, individual colonies were picked to inoculate 25 ml of CMG2% medium (Peptone 2 g/L; Yeast Extract 5 g/L; Glucose 55 mM (20 g/L); MOPS acid 40 mM; NH$_4$Cl 20 mM; NaOH 10 mM; KOH 10 mM; CaCl$_2$.2H$_2$O 0.5 μM; Na$_2$SO$_4$.10H$_2$O 0.276 mM; MgCl$_2$.6H$_2$O 0.528 mM; (NH$_4$)$_6$(Mo$_7$)O$_{24}$.4H$_2$O 3 nM; H$_3$BO$_3$ 0.4 μM; CoCl$_2$.6H$_2$O 30 nM; CuSO$_4$.5H$_2$O 10 nM; MnCl$_2$ 0.25 μM; ZnSO$_4$.7H$_2$O 10 nM; D-Biotin 1 μg/L; Niacin (nicotinic acid) 1 μg/L; B6 vitamin 1 μg/L; B1 vitamin; FeCl$_3$ 20 μM; Sodium Citrate.2H$_2$O 20 μM; K$_2$HPO$_4$ 5.7 mM) containing 2% glucose as the main carbon source, and cultured at 37° C. and 250 rpm overnight. Seed from log phase of growth was then inoculated into 25 ml of the same fresh medium at an initial optical density at 600 nm (OD600) of 0.4. This second seed culture was cultured at 37° C. and 250 rpm overnight.

The cultures for geraniol production were performed at 37° C. or 45° C. and 250 rpm for 24 H and 48 h from log phase of growth inoculated into 25 ml of mineral define medium (NH$_4$)$_2$SO$_4$<100 mM; NaH$_2$PO$_4$.H$_2$O<10 mM; KCl<10 mM; Na$_2$SO$_4$<10 mM; Acide citrique<30 mM; MgCl$_2$.6H$_2$O<10 mM; CaCl$_2$.2H$_2$O<10 mM; ZnCl$_2$<50 mg/L; FeSO$_4$.7H$_2$O<50 mg/L; MnCl$_2$.4H$_2$O<50 mg/L; CuSO$_4$<50 mg/L; CoCl$_2$.6H$_2$O<50 mg/L; H$_3$BO$_3$<5 mg/L; MES<200 mM; (NH$_4$)$_6$Mo$_7$O$_{24}$.4H$_2$O<0.5 mM; Glucose<30 g/L (166 mM) at an initial optical density at 600 nm (OD600) of 0.4.

The cultures for lycopene production were performed following the same protocole as described above. The differences being the initial optical density at 600 nm (OD600) of 10.

Figure 7:
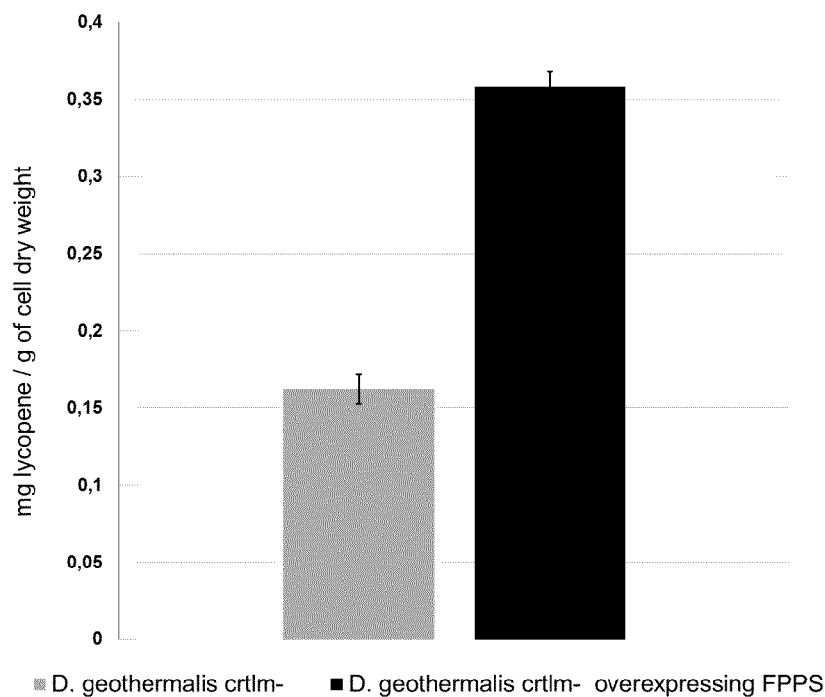
FIG. 7: Lycopene production of the recombinant *D. geothermalis* bacterium wherein the crtlm gene was knockout with and without overexpression of the FPP synthase.
Figure 8:
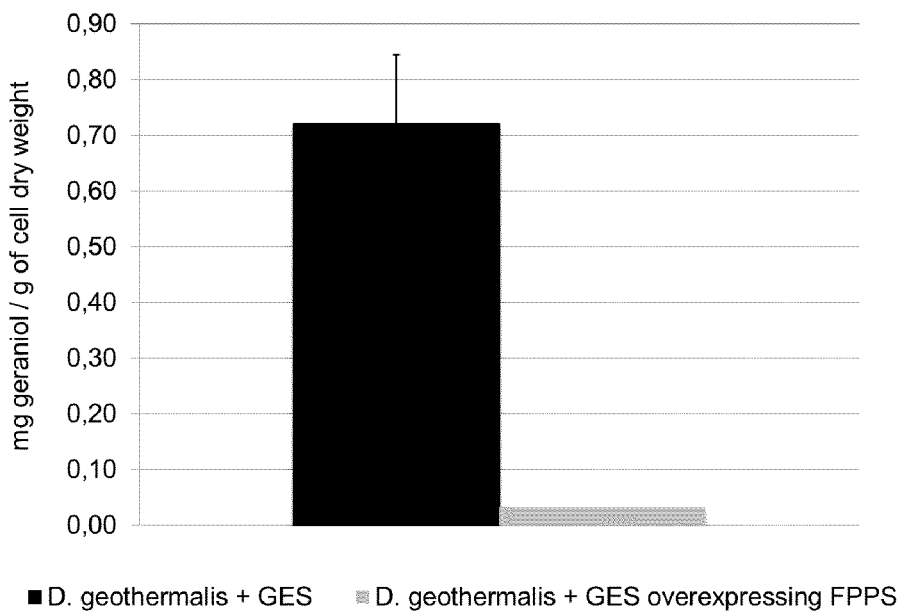
FIG. 8: Geraniol production of the recombinant *D. geothermalis* bacterium expressing the GES of *Ocimum basilicum* with and without overexpression of the FPP synthase.

The inventors observed that overexpression of FPP synthase resulted in a significant increase in lycopene production (FIG. 7). On the contrary, the geraniol production was dramatically reduced (FIG. 8).

Example 4: Overexpression of MEP Enzymes

The 1-Deoxy-D-xylulose 5-phosphate synthase (DXS) gene (SEQ ID NO: 3), the 1-deoxy-D-xylulose 5-phosphate reductoisomerase (DXR) gene (SEQ ID NO: 36), the 2-C-methyl-D-erythritol-4-phosphate cytidyltransferase (IspD) gene (SEQ ID NO: 19), the 4-diphosphocytidyl-2-C-methyl-D-erythritol kinase (IspE) gene (SEQ ID NO: 40), the 2-C-methyl-D-erythritol-2,4-cyclodiphosphate synthase (IspF) gene (SEQ ID NO: 23), (E)-4-hydroxy-3-methylbut-2-enyl-diphosphate synthase (IspG) gene (SEQ ID NO: 27), the 4-hydroxy-3-methylbut-2-enyl diphosphate reductase (IspH) gene (SEQ ID NO: 44) or the 4-hydroxy-3-methylbut-2-enyl-diphosphatereductase (IDI) gene (SEQ ID NO: 31) from *Deinococcus yunweiensis*, was inserted into the chromosome of the recombinant *D. geothermalis* bacterium expressing the GES of *Ocimum basilicum* as described in example 1, under the control of a strong constitutive promoter. The resulting constructs were checked by sequencing.

To make seed cultures, individual colonies were picked to inoculate 25 ml of CMG2% medium (Peptone 2 g/L; Yeast Extract 5 g/L; Glucose 55 mM (20 g/L); MOPS acid 40 mM; $NH_4Cl$ 20 mM; NaOH 10 mM; KOH 10 mM; $CaCl_2.2H_2O$ 0.5 µM; $Na_2SO_4.10H_2O$ 0.276 mM; $MgCl_2.6H_2O$ 0.528 mM; $(NH_4)_6(Mo_7)O_{24}.4H_2O$ 3 nM; $H_3BO_3$ 0.4 µM; $CoCl_2.6H_2O$ 30 nM; $CuSO_4.5H_2O$ 10 nM; $MnCl_2$ 0.25 µM; $ZnSO_4.7H_2O$ 10 nM; D-Biotin 1 µg/L; Niacin (nicotinic acid) 1 µg/L; B6 vitamin 1 µg/L; B1 vitamin; $FeCl_3$ 20 µM; Sodium Citrate.$2H_2O$ 20 µM; $K_2HPO_4$ 5.7 mM) containing 2% glucose as the main carbon source, and cultured at 37° C. and 250 rpm overnight. Seed from log phase of growth was then inoculated into 25 ml of the same fresh medium at an initial optical density at 600 nm (OD600) of 0.4. This second seed culture was cultured at 37° C. and 250 rpm overnight.

The cultures for geraniol production were performed at 37° C. and 250 rpm for 48 h from log phase of growth inoculated into 25 ml of mineral define medium $(NH_4)_2SO_4$<100 mM; $NaH_2PO_4.H_2O$<10 mM; KCl<10 mM; $Na_2SO_4$<10 mM; Acide citrique<30 mM; $MgCl_2.6H_2O$<10 mM; $CaCl_2.2H_2O$<10 mM; $ZnCl_2$<50 mg/L; $FeSO_4.7H_2O$<50 mg/L; $MnCl_2.4H_2O$<50 mg/L; $CuSO_4$<50 mg/L; $CoCl_2.6H_2O$<50 mg/L; $H_3BO_3$<5 mg/L; MES<200 mM; $(NH_4)_6Mo_7O_{24}.4H_2O$<0.5 mM; Glucose<30 g/L (166 mM) at an initial optical density at 600 nm (OD600) of 0.4.

Figure 9:
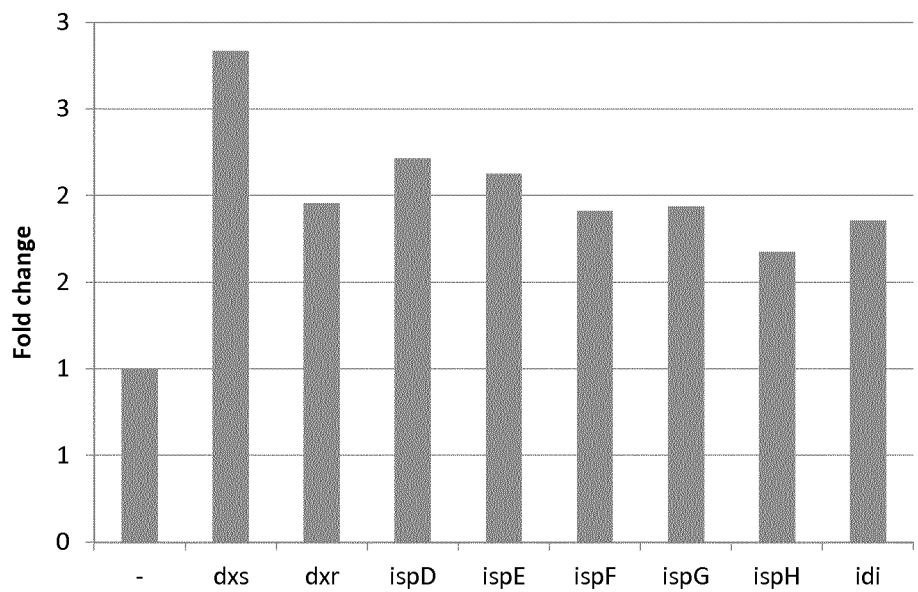
FIG. 9: Geraniol production of recombinant *D. geothermalis* bacteria expressing the GES of *Ocimum basilicum* and overexpressing *D. yunweiensis* DXS, DXR, IspD, IspE, IspF, IspG, IspH or IDI.

The inventors observed that overexpression of at least one MEP enzyme resulted in a significant increase in geraniol production used herein as marker for isoprenoid production (FIG. 9).

Example 5: Improved DXS Enzyme from *Deinococcus yunweiensis*

The 1-Deoxy-D-xylulose 5-phosphate synthase (DXS) gene from *Deinococcus yunweiensis* (SEQ ID NO:3) was inserted into the chromosome, replacing the endogenous dxs gene, of the recombinant *D. geothermalis* bacterium expressing the GES of *Ocimum basilicum* as described in example 1, under the control of a strong constitutive promoter. Site directed mutagenesis was realized to obtain R238C mutant (SEQ ID NO: 13 and 14). The resulting constructs were checked by sequencing.

To make seed cultures, individual colonies were picked to inoculate 25 ml of CMG2% medium (Peptone 2 g/L; Yeast Extract 5 g/L; Glucose 55 mM (20 g/L); MOPS acid 40 mM; $NH_4Cl$ 20 mM; NaOH 10 mM; KOH 10 mM; $CaCl_2.2H_2O$ 0.5 µM; $Na_2SO_4.10H_2O$ 0.276 mM; $MgCl_2.6H_2O$ 0.528 mM; $(NH_4)_6(Mo_7)O_{24}.4H_2O$ 3 nM; $H_3BO_3$ 0.4 µM; $CoCl_2.6H_2O$ 30 nM; $CuSO_4.5H_2O$ 10 nM; $MnCl_2$ 0.25 µM; $ZnSO_4.7H_2O$ 10 nM; D-Biotin 1 µg/L; Niacin (nicotinic acid) 1 µg/L; B6 vitamin 1 µg/L; B1 vitamin; $FeCl_3$ 20 µM; Sodium Citrate.$2H_2O$ 20 µM; $K_2HPO_4$ 5.7 mM) containing 2% glucose as the main carbon source, and cultured at 37° C. and 250 rpm overnight. Seed from log phase of growth was then inoculated into 25 ml of the same fresh medium at an initial optical density at 600 nm (OD600) of 0.4. This second seed culture was cultured at 37° C. and 250 rpm overnight.

The cultures for geraniol production were performed at 37° C. and 250 rpm for 48 h from log phase of growth inoculated into 25 ml of mineral define medium $(NH_4)_2SO_4$<100 mM; $NaH_2PO_4.H_2O$<10 mM; KCl<10 mM; $Na_2SO_4$<10 mM; Acide citrique<30 mM; $MgCl_2.6H_2O$<10 mM; $CaCl_2.2H_2O$<10 mM; $ZnCl_2$<50 mg/L; $FeSO_4.7H_2O$<50 mg/L; $MnCl_2.4H_2O$<50 mg/L; $CuSO_4$<50 mg/L; $CoCl_2.6H_2O$<50 mg/L; $H_3BO_3$<5 mg/L; MES<200 mM; $(NH_4)_6Mo_7O_{24}.4H_2O$<0.5 mM; Glucose<30 g/L (166 mM) at an initial optical density at 600 nm (OD600) of 0.4.

Figure 10:
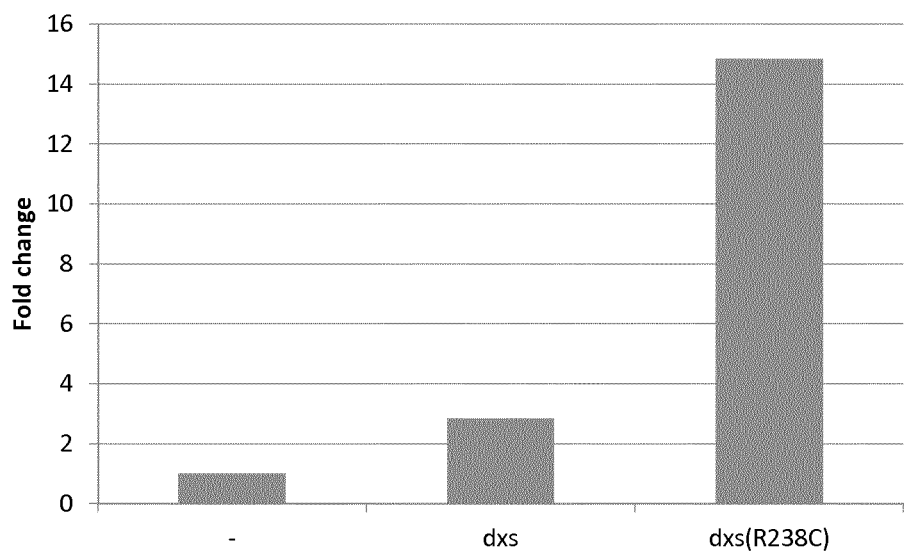
FIG. 10: Geraniol production of recombinant *D. geothermalis* bacteria expressing the GES of *Ocimum basilicum* and the wild-type DXS enzyme from *D. yunweiensis* or the mutant R238C from *D. yunweiensis*.

As shown in FIG. 10, improvement of the DXS by introduction of the mutation R238C results in a dramatic increase of geraniol production used herein as marker for isoprenoid production.

Example 6: Improved DXS Enzyme from *Deinococcus radiopugnans*

A gene encoding 1-Deoxy-D-xylulose 5-phosphate synthase (DXS) from *Deinococcus radiopugnans* (SEQ ID NO: 52) or encoding R244C mutant of said enzyme (SEQ ID NO: 8) was inserted into the chromosome, replacing the endogenous dxs gene, of the recombinant *D. geothermalis* bacterium expressing the GES of *Ocimum basilicum* as described in example 1, under the control of a strong constitutive promoter. The resulting constructs were checked by sequencing. Seed cultures and cultures for geraniol production were performed as detailed in example 5.

Figure 11:
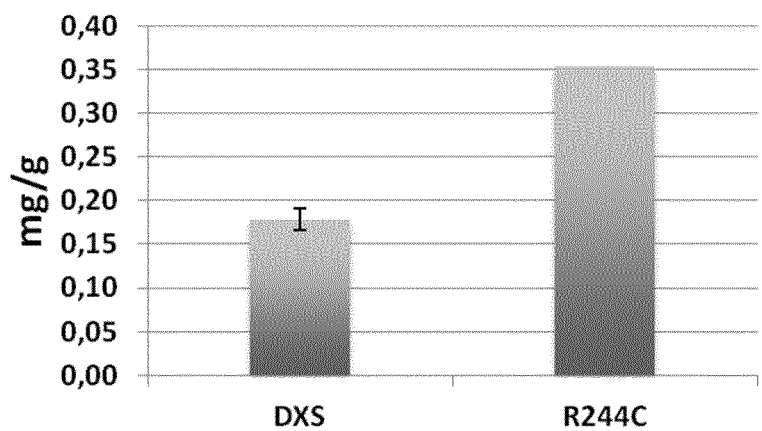
FIG. 11: Geraniol production of recombinant *D. geothermalis* bacteria expressing the GES of *Ocimum basilicum* and the wild-type DXS enzyme from *D. radiopugnans* or the mutant R244C.

As shown in FIG. 11, improvement of the DXS from *Deinococcus radiopugnans* by introduction of the mutation R244C results in a dramatic increase of geraniol production used herein as marker for isoprenoid production.

Example 7: K170G Mutant of *D. geothermalis* Farnesyl Pyrophosphate Synthase

The *D. geothermalis* farnesyl pyrophosphate synthase (FPPS) gene or the gene encoding the K170G mutant of said enzyme obtained by site directed mutagenesis, was inserted in the recombinant *D. geothermalis* bacterium expressing the GES of *Ocimum basilicum* as described in example 1, into chromosome replacing the endogenous gene encoding FPPS. Both wild-type and mutated version of *D. geothermalis* FPPS gene was under the control of a constitutive promoter. The resulting constructs were checked by sequencing. Seed cultures and cultures for geraniol production were performed as detailed in example 5.

Figure 12:
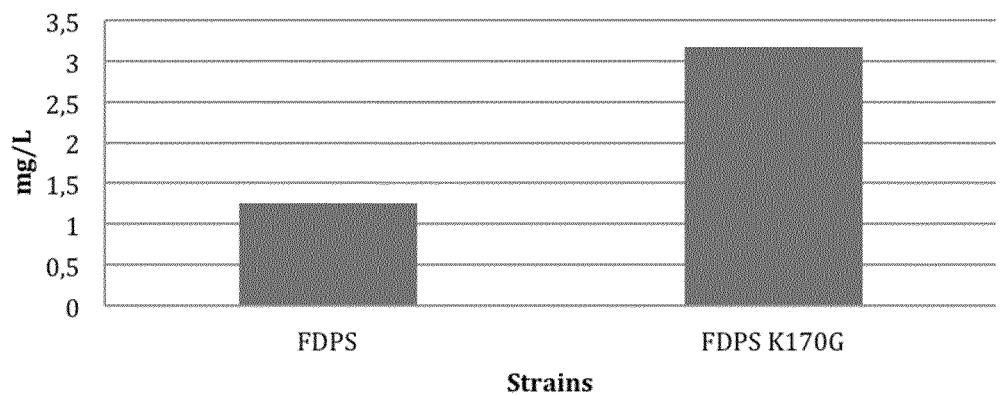
FIG. 12: Geraniol production of recombinant *D. geothermalis* bacteria expressing the GES of *Ocimum basilicum* and the K170G mutant of the *D. geothermalis* FPPS.

As shown in FIG. 12, the mutation K170G of *D. geothermalis* FPPS resulted in a redirection of the carbon flux through GPP and a significant increase in geraniol production.

Example 8: Overexpression of MEP Enzymes in Combination with Improved DXS Enzyme The gene encoding the R238C mutant of DXS enzyme of *Deinococcus yunweinensis* was inserted into chromosome replacing amylase (amy) gene of the recombinant *D. geothermalis* expressing the GES of *Ocimum basilicum* of example 1, under the control of a constitutive promoter. The gene encoding the K170G mutant of *D. geothermalis* farnesyl pyrophosphate synthase (FPPS) gene was also inserted into chromosome replacing the endogenous ispA gene.

Overexpression of FDPS gene was under the control of a constitutive promoter. The resulting constructs were checked by sequencing.

Each of the following MEP pathways genes from *Deinococcus yunweiensis* was expressed under the control of a strong constitutive promoter in the *D. geothermalis* strain expressing *D. geothermalis* FDPS (K170G mutant) and *D. yunweiensis* DXS (R238C mutant): dxr gene (SEQ ID NO: 36), ispD gene (SEQ ID NO: 19), ispE gene (SEQ ID NO: 40), ispF gene (SEQ ID NO: 23), ispG gene (SEQ ID NO: 27) and idi gene (SEQ ID NO: 31). The resulting constructs were checked by sequencing. Seed cultures and cultures for geraniol production were performed as detailed in example 5.

Figure 13:
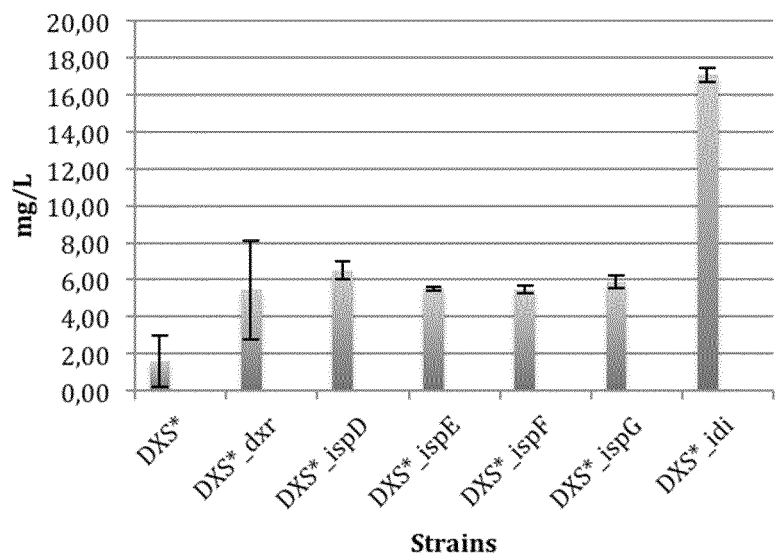
FIG. 13: Geraniol production of recombinant *D. geothermalis* bacteria expressing the GES of *Ocimum basilicum* and a mutated DXS and overexpressing DXR, IspD, IspE, IspF, IspG, IspH or IDI from *D. yunweiensis*.

As shown in FIG. 13, overexpression of mutated DXS and IDI resulted in a dramatic increase in geraniol production by comparison with the other combinations.

Example 9: Production of Bisabolol

A *Deinococcus geothermalis* strain was genetically engineered to produce bisabolol. A heterologous gene encoding a (+)-epi-alpha-bisabolol synthase from *Streptomyces citricolor* was inserted into chromosome replacing phosphotransacetylase (pta) gene. Expression of epi-alpha-bisabolol synthase gene was under the control of a constitutive promoter.

To make seed cultures, individual colonies were picked to inoculate 25 ml of CMG2% medium (Peptone 2 g/L; Yeast Extract 5 g/L; Glucose 55 mM (20 g/L); MOPS acid 40 mM; $NH_4Cl$ 20 mM; NaOH 10 mM; KOH 10 mM; $CaCl_2.2H_2O$ 0.5 µM; $Na_2SO_4.10H_2O$ 0.276 mM; $MgCl_2.6H_2O$ 0.528 mM; $(NH_4)_6(Mo_7)O_{24}.4H_2O$ 3 nM; $H_3BO_3$ 0.4 µM; $CoCl_2.6H_2O$ 30 nM; $CuSO_4.5H_2O$ 10 nM; $MnCl_2$ 0.25 µM; $ZnSO_4.7H_2O$ 10 nM; D-Biotin 1 µg/L; Niacin (nicotinic acid) 1 µg/L; B6 vitamin 1 µg/L; B1 vitamin; $FeCl_3$ 20 µM; Sodium Citrate.$2H_2O$ 20 µM; $K_2HPO_4$ 5.7 mM) containing 2% glucose as the main carbon source, and cultured at 37° C. and 250 rpm overnight. Seed from log phase of growth was then inoculated into 25 ml of the same fresh medium at an initial optical density at 600 nm (OD600) of 0.4. This second seed culture was cultured at 37° C. and 250 rpm overnight. The cultures for bisabolol production were performed at 37° C. and 250 rpm for 48 h from log phase of growth inoculated into 25 ml of mineral define medium $(NH_4)_2SO_4$<100 mM; $NaH_2PO_4.H_2O$<10 mM; KCl<10 mM; $Na_2SO_4$<10 mM; Acide citrique<30 mM; $MgCl_2.6H_2O$<10 mM; $CaCl_2.2H_2O$<10 mM; $ZnCl_2$<50 mg/L; $FeSO_4.7H_2O$<50 mg/L; $MnCl_2.4H_2O$<50 mg/L; $CuSO_4$<50 mg/L; $CoCl_2.6H_2O$<50 mg/L; $H_3BO_3$<5 mg/L; MES<200 mM; $(NH_4)_6Mo_7O_{24}.4H_2O$<0.5 mM; Glucose<30 g/L (166 mM) at an initial optical density at 600 nm (OD600) of 0.4.

The production of bisabolol was identified and quantified on a Mass Spectrometer GC as detailed in example 1 for geraniol.

Figure 14:
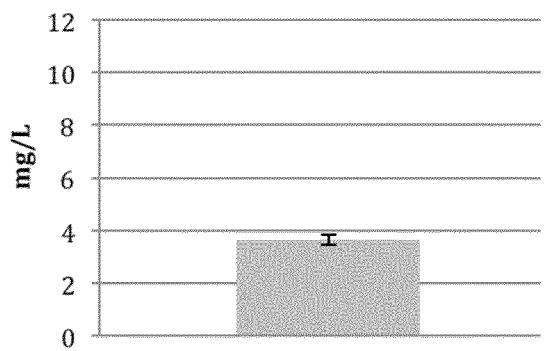
FIG. 14: Bisabolol production of the recombinant *D. geothermalis* bacterium expressing the (+)-epi-alpha-bisabolol synthase from *Streptomyces citricolor*. The wild-type bacterium does not produce bisabolol (data not shown).

As shown in FIG. 14, the expression of bisabolol synthase from *Streptomyces citricolor* in *D. geothermalis* resulted in a bisabolol production (3.6 mg/L).

Example 10: Improved Production of Lycopene

A *Deinococcus geothermalis* strain was genetically engineered to produce lycopene as previously described in example 2. The gene encoding the R238C mutant of DXS enzyme of *D. yunweiensis* and the gene encoding IDI of *D. yunweiensis* were introduced into chromosome of the strain *D. geothermalis* crtlm-, under the control of a constitutive promoter. Seed cultures and cultures for lycopene production were performed as detailed in example 2.

Figure 15:
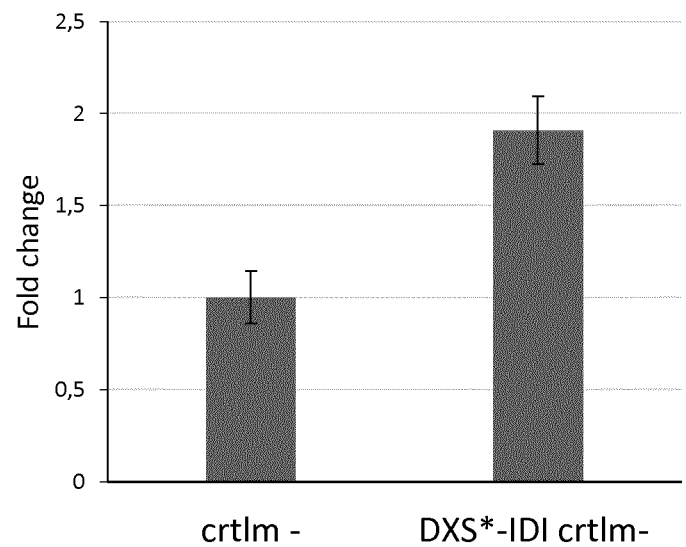
FIG. 15: Lycopene (carotenoid) production of the recombinant *D. geothermalis* bacterium wherein the crtlm gene was knockout with and without overexpression mutant DXS and IDI from *D. yunweiensis*.

As shown in FIG. 15, the lycopene production is two-fold higher when the strain *D. geothermalis* crtlm-overexpresses IDI and mutant DXS.

Example 11: Expression in *D. geothermalis* of GES of Different Origins

A *Deinococcus geothermalis* strain was genetically engineered as described in example 1 by inserting a heterologous gene encoding a geraniol synthase (GES) from *Phyla dulcis* or *Cicer arietinum* into chromosome replacing phosphotransacetylase (pta) gene. Expression of GES gene was under the control of a strong constitutive promoter. The resulting constructs were checked by sequencing. Seed cultures and cultures for geraniol production were performed as detailed in example 1.

Figure 16:
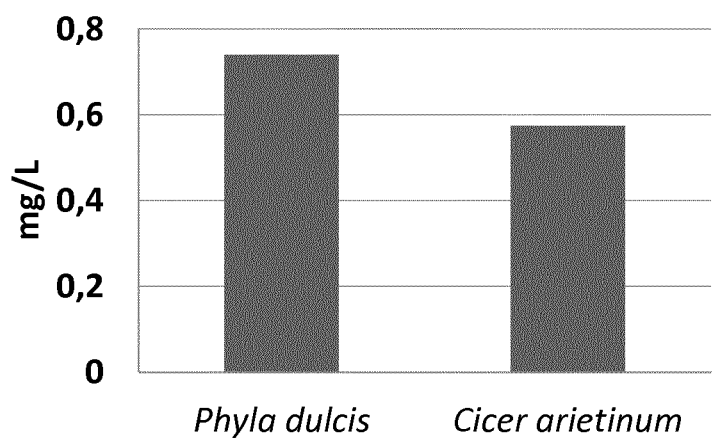
FIG. 16: Geraniol production of the recombinant *D. geothermalis* bacterium expressing the GES of *Phyla dulcis* or *Cicer arietinum* with and without overexpression of the endogenous FPP synthase.

As shown in FIG. 16, the expression of GES of *Phyla dulcis* or *Cicer arietinum* also resulted in production of geraniol.

Example 12: Carotenoid Production

An expression cassette comprising the farnesyl pyrophosphate synthase (FPPS) gene from *Deinococcus geothermalis* (SEQ ID NO: 46) under the control of a strong promoter was inserted in the genome of *D. geothermalis* strain. The resulting constructs were checked by sequencing.

To make seed cultures, individual colonies were picked to inoculate 25 ml of CMG2% medium (Peptone 2 g/L; Yeast Extract 5 g/L; Glucose 55 mM (20 g/L); MOPS acid 40 mM; $NH_4Cl$ 20 mM; NaOH 10 mM; KOH 10 mM; $CaCl_2.2H_2O$ 0.5 µM; $Na_2SO_4.10H_2O$ 0.276 mM; $MgCl_2.6H_2O$ 0.528 mM; $(NH_4)_6(Mo_7)O_{24}.4H_2O$ 3 nM; $H_3BO_3$ 0.4 µM; $CoCl_2.6H_2O$ 30 nM; $CuSO_4.5H_2O$ 10 nM; $MnCl_2$ 0.25 µM; $ZnSO_4.7H_2O$ 10 nM; D-Biotin 1 µg/L; Niacin (nicotinic acid) 1 µg/L; B6 vitamin 1 µg/L; B1 vitamin; $FeCl_3$ 20 µM; Sodium Citrate.$2H_2O$ 20 µM; $K_2HPO_4$ 5.7 mM) containing 2% glucose as the main carbon source, and cultured at 45° C. and 250 rpm overnight. Seed from log phase of growth was then inoculated into 25 ml of the same fresh medium at an initial optical density at 600 nm (OD600) of 0.4. This second seed culture was cultured at 45° C. and 250 rpm overnight.

The cultures for carotenoid production were performed at 45° C. and 250 rpm for 48 h from log phase of growth inoculated into 25 ml of mineral define medium $(NH_4)_2SO_4$<100 mM; $NaH_2PO_4.H_2O$<10 mM; KCl<10 mM; $Na_2SO_4$<10 mM; Acide citrique<30 mM; $MgCl_2.6H_2O$<10 mM; $CaCl_2.2H_2O$<10 mM; $ZnCl_2$<50 mg/L; $FeSO_4.7H_2O$<50 mg/L; $MnCl_2.4H_2O$<50 mg/L; $CuSO_4$<50 mg/L; $CoCl_2.6H_2O$<50 mg/L; $H_3BO_3$<5 mg/L; MES<200 mM; $(NH_4)_6Mo_7O_{24}.4H_2O$<0.5 mM; Glucose<30 g/L (166 mM) at an initial optical density at 600 nm (OD600) of 0.4.

25 mL of culture was centrifuged and carotenoid extraction was done by mixing 25 mL of ethanol with pellet. Spectra of the deinoxanthin were obtained by measuring the absorbance between 350 nm and 600 nm and were normalized by the dry cell weight (DCW) (FIG. 17), the grey spectrum corresponding to a deinoxanthin standard (purified deinoxanthin extracted from *D. radiodurans*).

Figure 17:
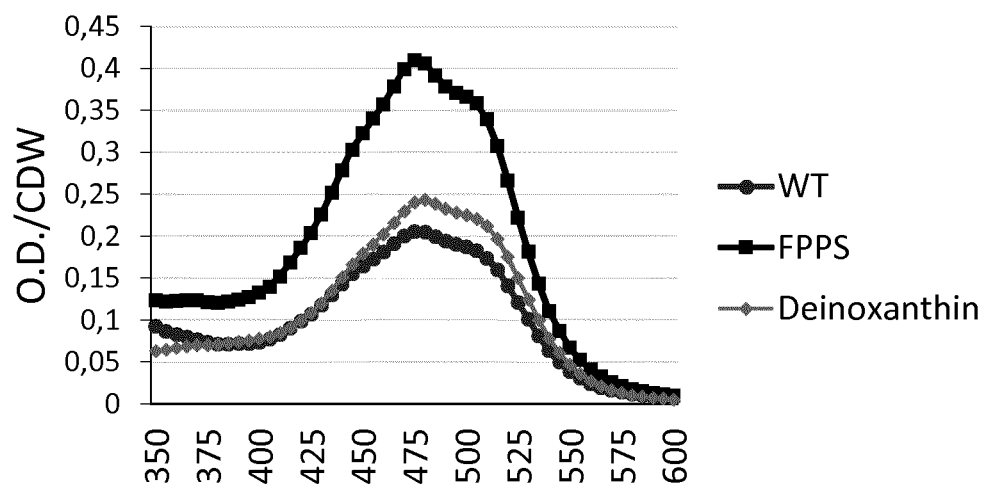
FIG. 17: Spectra of the deinoxanthin obtained by measuring the absorbance between 350 nm and 600 nm and normalizing said absorbances by the dry cell weight (DCW) for the wild-type bacterium and the bacterium overexpressing FPPS. The grey spectrum corresponding to a deinoxanthin standard (purified deinoxanthin extracted from *D. radiodurans*).
Figure 18:
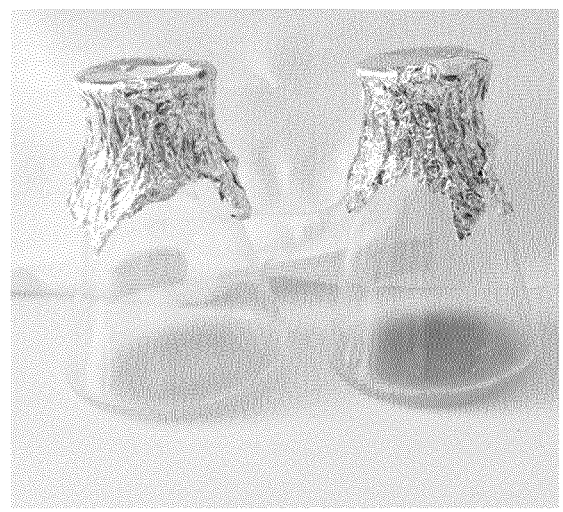
FIG. 18: Pictures of the cultures of the wild-type *D. geothermalis* bacterium and the *D. geothermalis* bacterium overexpressing endogenous FPPS.

As shown in FIGS. 17 and 18, the overexpression of the endogenous farnesyl pyrophosphate synthase (FPPS) of *D. geothermalis* resulted in a dramatic increase of the deinoxanthin production by a factor two compared to the wild type strain (WT). This increased deinoxanthin production was correlated with a darker pink color of the *D. geothermalis* over-expressing the FPPS compared to the wild-type strain (FIG. 18).

Example 13: Production of Cineol

A *Deinococcus geothermalis* strain was genetically engineered to produce cineole. A heterologous gene encoding a 1,8 cineole synthase (CnsA) from *Streptomyces clavuligerus* was inserted into chromosome replacing phosphotransacetylase (pta) gene. Expression of 1,8 cineole synthase gene was under the control of a constitutive promoter. The *D. geothermalis* K170G mutant of farnesyl pyrophosphate synthase (FPPS) gene was inserted into chromosome replacing the endogenous fdps. Overexpression of FDPS gene was under the control of a constitutive promoter. The resulting constructs were checked by sequencing. Seed cultures and cultures for cineole production were performed as detailed in example 1. After 24 H or 48 H of growth, 1 mL of culture was extracted by 0.5 mL of ethyl acetate. The organic phase was analyzed by GCMS. The production of cineole was identified and quantified on a Mass Spectrometer GC as detailed in example 1 for geraniol.

Figure 19:
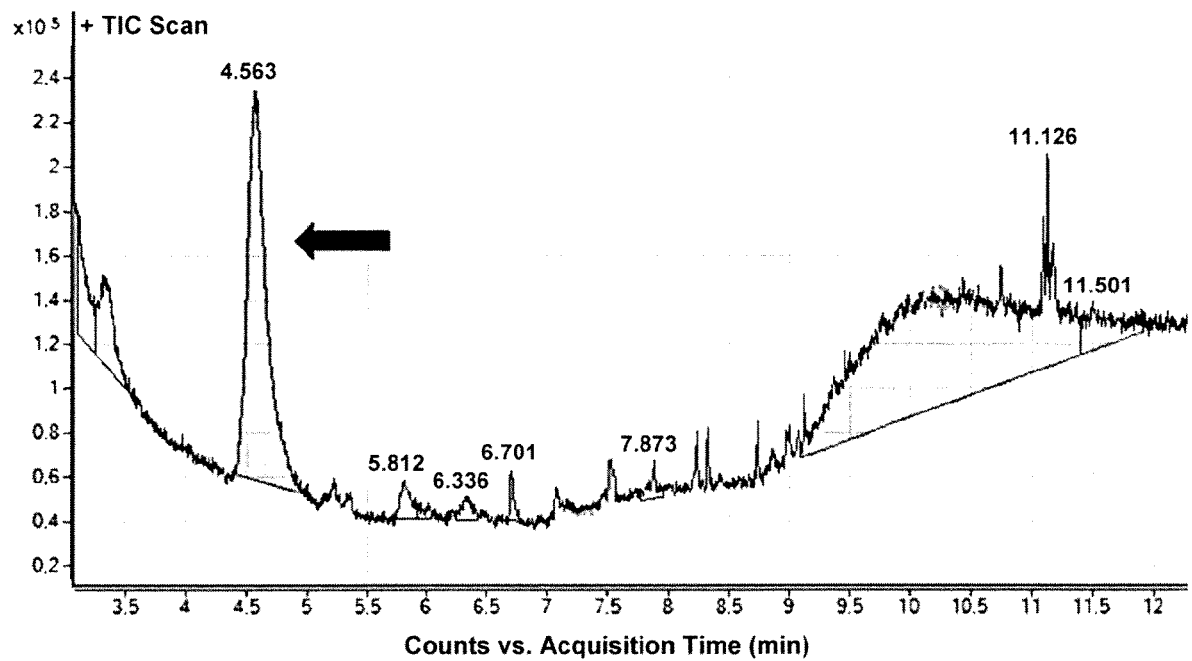
FIG. 19: Cineol production of the recombinant *D. geothermalis* bacterium expressing the 1,8 cineole synthase gene from *Streptomyces clavuligerus*. Cineol is indicated by the arrow. The wild-type bacterium does not produce cineole (data not shown).

As shown in FIG. 19, the insertion of 1,8 cineole synthase resulted in a cineole production by the recombinant *D. geothermalis*.

Example 14: Production of Limonene

A *Deinococcus geothermalis* strain was genetically engineered to produce limonene. A heterologous gene encoding the limonene synthase (LS; GenBank: AAD50304.1) gene from *Mentha longifolia*. The *M. longifolia* LS cDNA fused to GFP was inserted into chromosome replacing phosphotransacetylase (pta) gene. Overexpression of LS gene was under the control of a constitutive promoter. The *D. geothermalis* K170G mutant of farnesyl pyrophosphate synthase (FPPS) gene was inserted into chromosome replacing the endogenous fdps. Overexpression of FDPS gene was under the control of a constitutive promoter. The resulting constructs were checked by sequencing. Seed cultures and cultures for limonene production were performed as detailed in example 1. After 24 H or 48 H of growth, 1 mL of culture was extracted by 0.5 mL of ethyl acetate. The organic phase was analyzed by GCMS. The production of limonene was identified and quantified on a Mass Spectrometer GC as detailed in example 1 for geraniol.

Figure 20:
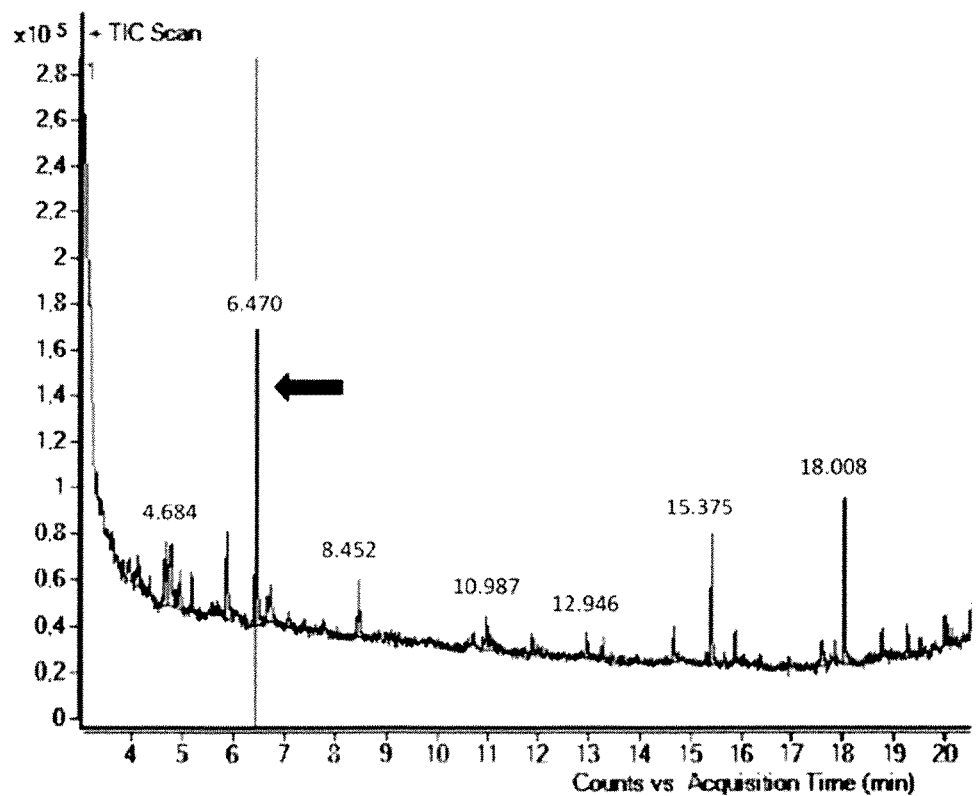
FIG. 20: Limonene production of the recombinant *D. geothermalis* bacterium expressing the limonene synthase gene from *Mentha longifolia*. Limonene is indicated by the arrow. The wild-type bacterium does not produce limonene (data not shown).

As shown in FIG. 20, the insertion of limonene synthase resulted in a limonene production by the recombinant *D. geothermalis*.

Example 15: Production of Linalool

A *Deinococcus geothermalis* strain was genetically engineered to produce linalool. A heterologous gene encoding the linalool synthase (LIS) gene from *Perilla frutescens*. The LIS cDNA fused to GFP was inserted into chromosome replacing phosphotransacetylase (pta) gene. Overexpression of LIS gene was under the control of a constitutive promoter. The *D. geothermalis* K170G mutant of farnesyl pyrophosphate synthase (FPPS) gene was inserted into chromosome replacing the endogenous fdps. Overexpression of FDPS gene was under the control of a constitutive promoter. The resulting constructs were checked by sequencing. Seed cultures and cultures for linalool production were performed as detailed in example 1. The production of linalool was identified and quantified on a Mass Spectrometer GC as detailed in example 1 for geraniol.

Figure 21:
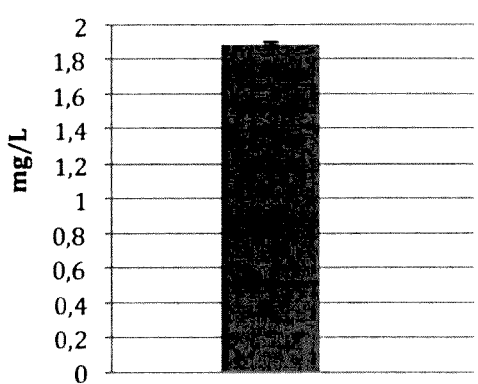
FIG. 21: Linalool production (mg/L) of the recombinant *D. geothermalis* bacterium expressing the linalool synthase of *Perilla frutescens*. The wild-type bacterium does not produce linalool (data not shown).

As shown in FIG. 21, the insertion of linalool synthase resulted in a linalool production by the recombinant *D. geothermalis*.

REFERENCES

Attia et al. Arch Biochem Biophys. 2012 Nov. 1; 527(1): 37-44
Blanchard and Karst, Gene. 1993 Mar. 30; 125(2):185-9.
Brown et al. J. Bacteriol. 2010 vol. 192, no 9, 2424-2433
Carter et al., Phytochemistry, 2003, 64:425-433
Degenhardt and Gershenzon. Planta. 2000 April; 210(5): 815-22.
Del Terra et al. Phytochemistry. 2013 May; 89:6-14.
Herrero et al. Metab Eng 2008, 10:78-86
Lecointe, et al. 2004. Mol Microbiol 53: 1721-1730.
Lois et al. PNAS, USA 1998; 95:2105-2110.
Martin et al. BMC Plant Biol. 2010 Oct. 21; 10:226.
Meima et al. 2001. J Bacteriol 183: 3169-3175.
Sivy et al. Biosci Biotechnol Biochem. 2011; 75(12):2376-83
Aharoni et al., 2004. The Plant cell, 16(11), pp. 3110-31.
Chen et al, 2003. The Plant Cell, 15(2), pp. 481-494.
Crowell et al., 2002. Archives of biochemistry and biophysics, 405(1), pp. 112-21.
Dong et al., 2013. Metabolic engineering, 20C, pp. 198-211.
Dudareva et al., 1996. The Plant cell, 8(7), pp. 1137-48.
Feinberg and Vogelstein, 1983, Anal. Biochem. 132:6-13
Fischer et al., 2011. Biotechnology and Bioengineering, Vol. 108, No. 8, pp. 1883-1892.
Galata et al., Phytochemistry 102, 64-73 (2014)
Herrero et al 2008. Metabolic engineering, 10(2), pp. 78-86.
Hess et al., 2013. PloS one, 8(6), p. e66104.
Iijima, et al., 2004. Plant physiology, 136(3), pp. 3724-36.
Iijima, et al, 2004. Plant. 134(January), pp. 370-379.
Jia, et al., 1999. Archives of biochemistry and biophysics, 372(1), pp. 143-9.
Landmann, et al., 2007. Archives of biochemistry and biophysics, 465(2), pp. 417-29.
Lehning, et al 1999. Plant, Cell & Environment. Volume 22, Issue 5, pages 495-504
Liu, J. et al., 2013. Journal of biotechnology, 168(4), pp. 446-451.
Lv, et al., 2013. Applied microbiology and biotechnology, 97(6), pp. 2357-65.
Masumoto et al., Phytochemistry 71 (10), 1068-1075 (2010)
Miller, et al, 2001. Planta, 213(3), pp. 483-487.
Nakano, et al, 2011. Chem Bio Chem, 12(16), pp. 2403-7.
Nakano, et al, Chem Bio Chem 2011, 12, 1988-1991
Nakano, et al, 2011. Chem bio chem. October 17; 12(15): 2271-5.
Pichersky et al, 1995. Archives of biochemistry and biophysics, 316(2), pp. 803-807.
Rico, et al, 2010. Applied and environmental microbiology, 76(19), pp. 6449-54.
Sharkey et al, 2005. Plant Physiol. 137(2), pp. 700-12.
Sitrit et al., 2004. Plant Science, 167(6), pp. 1257-1262.
Sugiura, et al., 2011. Bioscience, Biotechnology, and Biochemistry, 75(7), pp. 1245-1248.
Whited et al. Ind Biotechnol 2010; 6:152-63.
Yang, et al., 2012. Bioresource Technology, 104(C), pp. 642-647.
Yang, et al., 2012. PloS one, 7(4), p. e33509.
Yang, et al., 2005. Phytochemistry, 66(3), pp. 285-93.
Zhou, et al., 2013. Journal of biotechnology, 169, pp. 42-50.

The invention claimed is:

1. A method of producing a terpene or terpenoid comprising (i) culturing a recombinant *Deinococcus* bacterium that is genetically modified to overexpress a native, homologous or heterologous dxs gene encoding 1-deoxyxylulose 5-phosphate synthase (DXS) and to overexpress a native, homologous or heterologous idi gene encoding isopentenyl pyrophosphatase isomerase (IPP isomerase), under conditions suitable to produce the terpene or terpenoid and optionally (ii) recovering the terpene or terpenoid, wherein the 1-deoxyxylulose 5-phosphate synthase has at least 90% sequence identity to the polypeptide of SEQ ID NO: 4, is a mutant DXS enzyme comprising a cysteine at position corresponding to position 244 of SEQ ID NO: 52, is a R244C mutant of the DXP synthase from *D. radiopugnans* (SEQ ID NO: 8), is a R238C mutant of the DXP synthase from *D. yunweiensis* (SEQ ID NO: 14) or is a R241C mutant of the DXP synthase from *D. geothermalis* (SEQ ID NO: 56).

2. The method of claim 1, wherein the recombinant *Deinococcus* bacterium expresses a DXS enzyme which is a mutant DXS enzyme comprising a cysteine at position corresponding to position 244 of SEQ ID NO: 52.

3. The method of claim 1, wherein the recombinant *Deinococcus* bacterium expresses a gene encoding the R244C mutant of the DXP synthase from *D. radiopugnans* (SEQ ID NO: 8), a gene encoding the R238C mutant of the DXP synthase from *D. yunweiensis* (SEQ ID NO: 14) or a gene encoding the R241C mutant of the DXP synthase from *D. geothermalis* (SEQ ID NO: 56).

4. The method of claim 1, wherein the recombinant *Deinococcus* bacterium overexpresses a native, homologous or heterologous gene encoding farnesyl diphosphate synthase (FPP synthase).

5. The method of claim 4, wherein the gene encoding FPP synthase encodes a polypeptide selected from the group consisting of:
a) a polypeptide comprising the amino acid sequence of SEQ ID NO: 47;
b) a polypeptide having an amino acid sequence having at least 60% sequence identity to SEQ ID NO: 47; and
c) a polypeptide encoded by a nucleotide sequence having at least 60% sequence identity to SEQ ID NO: 46.

6. The method of claim 4, wherein the FPP synthase further exhibits dimethylallyltransferase activity and/or geranylgeranyl diphosphate synthase activity.

7. The method of claim 1, wherein, in the recombinant *Deinococcus* bacterium, at least one gene selected from the group consisting of native, homologous or heterologous dxr, ispD, ispE, ispF, ispG and ispH genes, is overexpressed.

8. The method of claim 1, wherein the recombinant *Deinococcus* bacterium further comprises a gene encoding a heterologous terpene synthase.

9. The method of claim 8, wherein the heterologous terpene synthase is selected from the group consisting of monoterpene synthases, diterpene synthases, triterpene synthases and sesquiterpene synthases.

10. The method of claim 8, wherein the heterologous terpene synthase is a monoterpene synthase, a cineole synthase, a limonene synthase or a linalool synthase.

11. The method of claim 8, wherein the heterologous terpene synthase is a sesquiterpene synthase.

12. The method of claim 1, wherein, in the recombinant *Deinococcus* bacterium, a gene encoding a lycopene beta-cyclase is inactivated.

13. The method of claim 1, wherein the terpene or terpenoid is selected from monoterpenes, diterpenes, triterpenes, sesquiterpenes and carotenoids.

14. The method of claim 1, wherein the terpene or terpenoid is a sesquiterpene.

15. The method of claim 1, wherein the terpene or terpenoid is a carotenoid.

16. The method of claim 15, wherein the carotenoid is lycopene or any other carotenoid compound derived from lycopene.

17. The method of claim 15, wherein the carotenoid is deinoxanthine.

18. A recombinant *Deinococcus* bacterium comprising genetic modifications to overexpress a native, homologous or heterologous dxs gene encoding 1-deoxyxylulose 5-phosphate synthase (DXS) and to overexpress a native, homologous or heterologous idi gene encoding isopentenyl pyrophosphatase isomerase (IPP isomerase), wherein the 1-deoxyxylulose 5-phosphate synthase has at least 90% sequence identity to the polypeptide of SEQ ID NO: 4.

19. The method of claim 1, wherein the recombinant *Deinococcus* bacterium expresses a 1-deoxyxylulose 5-phosphate synthase having at least 90% sequence identity to the polypeptide of SEQ ID NO: 4.

* * * * *

UNITED STATES PATENT AND TRADEMARK OFFICE
CERTIFICATE OF CORRECTION

PATENT NO. : 10,900,060 B2
APPLICATION NO. : 15/317994
DATED : January 26, 2021
INVENTOR(S) : Nicolas Chabot et al.

Page 1 of 1

It is certified that error appears in the above-identified patent and that said Letters Patent is hereby corrected as shown below:

In the Specification

Column 9,
Lines 15-28,
"The team "IspH" or "IDS" refers to the enzyme 4-hydroxy-3-methylbut-2-enyl diphosphate reductase, also named hydroxymethylbutenyl pyrophosphate reductase, (EC 1.17.1.2) encoded by the ispH gene that converts 1-hydroxy-2-methyl-2-(E)-butenyl 4-diphosphate (HMBPP) into isopentenyl diphosphate (IPP) and dimethylallyl diphosphate (DMAPP).
The term ""IspH" or "IDS" refers to the enzyme 4-hydroxy-3-methylbut-2-enyl diphosphate reductase, also named hydroxymethylbutenyl pyrophosphate reductase, (EC 1.17.1.2) encoded by the ispH gene that converts 1-hydroxy-2-methyl-2-(E)-butenyl 4-diphosphate (HMBPP) into isopentenyl diphosphate (IPP) and dimethylallyl diphosphate (DMAPP)." should read
--The term "IspG" or "HDS" refers to the enzyme 4-hydroxy-3-methylbut-2-en-1-yl diphosphate synthase (EC 1.17.7.1) encoded by the ispG gene that is involved in conversion of 2C-methyl-D-erythritol 2,4-cyclodiphosphate (cMEPP) into 1-hydroxy-2-mefhyl-2-(E)-butenyl 4-diphosphate (HMBPP).
The term "IspH" or "IDS" refers to the enzyme 4-hydroxy-3-methylbut-2-enyl diphosphate reductase, also named hydroxymethylbutenyl pyrophosphate reductase, (EC 1.17.1.2) encoded by the ispH gene that converts 1-hydroxy-2-methyl-2-(E)-butenyl 4-diphosphate (HMBPP) into isopentenyl diphosphate (IPP) and dimethylallyl diphosphate (DMAPP).--

Column 25,
Line 48, "*Fragariaxananassa.*" should read --*Fragaria x ananassa.*--

Signed and Sealed this
Ninth Day of November, 2021

Drew Hirshfeld
*Performing the Functions and Duties of the*
*Under Secretary of Commerce for Intellectual Property and*
*Director of the United States Patent and Trademark Office*